(12) United States Patent
Wang et al.

(10) Patent No.: US 11,597,948 B2
(45) Date of Patent: Mar. 7, 2023

(54) USE OF ANP32 PROTEIN IN MAINTAINING THE POLYMERASE ACTIVITY OF INFLUENZA VIRUS IN HOSTS

(71) Applicant: Harbin Veterinary Research Institute, Chinese Academy of Agricultural Sciences (China Animal Health and Epidemiology Center, Harbin), Heilongjiang (CN)

(72) Inventors: Xiaojun Wang, Heilongjiang (CN); Haili Zhang, Heilongjiang (CN); Zhenyu Zhang, Heilongjiang (CN)

(73) Assignee: Harbin Veterinary Research Institute, Chinese Academy of Agricultural Sciences (China Animal Health and Epidemiology Center, Harbin), Heilongjiang (CN)

( * ) Notice: Subject to any disclaimer, the term of this patent is extended or adjusted under 35 U.S.C. 154(b) by 0 days.

(21) Appl. No.: 16/755,840

(22) PCT Filed: Feb. 26, 2019

(86) PCT No.: PCT/CN2019/076171
§ 371 (c)(1),
(2) Date: Apr. 13, 2020

(87) PCT Pub. No.: WO2019/165957
PCT Pub. Date: Sep. 6, 2019

(65) Prior Publication Data
US 2021/0054411 A1   Feb. 25, 2021

(30) Foreign Application Priority Data
Mar. 2, 2018   (CN) .................. 201810177710.X

(51) Int. Cl.
| | | |
|---|---|---|
| C12N 15/87 | (2006.01) | |
| C07K 14/435 | (2006.01) | |
| C12N 15/113 | (2010.01) | |

(52) U.S. Cl.
CPC ............ *C12N 15/87* (2013.01); *C07K 14/435* (2013.01); *C12N 15/1132* (2013.01)

(58) Field of Classification Search
CPC ... C07K 14/435; C12N 15/87; C12N 15/1132
See application file for complete search history.

(56) References Cited

FOREIGN PATENT DOCUMENTS

| | | |
|---|---|---|
| CN | 105505880 A | 4/2016 |
| WO | WO 2020/109780 A2 | 6/2020 |
| WO | WO 2020/109780 A3 | 6/2020 |

OTHER PUBLICATIONS

Dao et al, Highly polarized C-terminal transition state of the leucine-rich repeat domain of PP32 is governed by local stability, PNAS, 2015, E2298-E2306.*

(Continued)

*Primary Examiner* — Li N Komatsu
(74) *Attorney, Agent, or Firm* — Knobbe Martens Olson & Bear LLP

(57) ABSTRACT

The present invention provides a recombinant sequence information of a key host factor ANP32A/B which is necessary for the replication of influenza virus in a host. More specifically, the present invention relates to a 129-130 motif and a 149 site of the host factor ANP32A/B protein, which are key active sites for exerting its ability to promote the replication of influenza virus, and are also potential targeting sites of anti-influenza drugs.

1 Claim, 29 Drawing Sheets

Specification includes a Sequence Listing.

(56) References Cited

OTHER PUBLICATIONS

Dao et al, Capping motifs stabilize the leucine-rich repeat protein PP32 and rigidity adjacent repeats, Protein Science, 2014, 23, pp. 801-811.*
Tochio et al, Solution Structure of Histone Chaperone ANP32B: Interaction with Core Histones H3—H4 through Its Acidic Concave Domain, J. Mol. Biol., 2010, 401, pp. 97-114.*
Long et al. "Species difference in ANP32A underlies influenza A virus polymerase host", Nature, vol. 529, pp. 101-104, Jan. 1, 2016.
Office Action in corresponding Japanese Application No. 2020-542488 dated Dec. 6, 2021.
Sequence of "Acidic leucine-rich nuclear phosphoprotein 32 family member B", ID No. AN32B_HUMAN, Accession No. Q92688, Aug. 1996.
Stallert et al. "A natural variant in ANP32B impairs influenza virus replication in human cells", Journal of General Virology, Sep. 15, 2021, vol. 102 No. 9, pp. 1-12.
Supplementary European Search Report for corresponding European Patent Application No. 19759957.4, dated Nov. 29, 2021.
Watanabe et al. "Influenza Virus-Host Interactome Screen as a Platform for Antiviral Drug Development", Cell Host and Microbe, vol. 16, pp. 795-805, Nov. 20, 2014.
Zhang et al. "Fundamental Contribution and Host Range Determination of ANP32A and ANP32B in Influenza A Virus Polymerase Activity", Journal of Virology, vol. 93 No. 13, Jul. 2019, pp. 1-17.
Domingues et al. "Functional Insight into ANP32A-Dependent Influenza A Virus Polymerase Host Restriction". Cell Reports, vol. 20, pp. 2358-2546, Sep. 12, 2017.
Watanabe et al. "Influenza Virus-Host Interactome Screen as a Platform for Antiviral Drug Development". Cell Host & Microbe, vol. 16, pp. 795-805, Dec. 10, 2014.
Long et al. "Species difference in ANP32A under lies influenza A virus polymerase host restriction". Nature, vol. 529, Jan. 7, 2016.
Office Action in Japanese Patent Application No. 2020-542488, dated Apr. 20, 2021.
Long, Jason S. et al., "Species difference in ANP32A underlies influenza A virus polymerase host restriction" Nature, Jan. 2016, vol. 529.
Watanabe, Tokiko et al., "Influenza Virus-Host Interactome Screen as a Platform for Antiviral Drug Development" Cell Host & Microbe, Dec. 2014, pp. 795-805, vol. 16.
International Search Report for PCT/CN2019/076171 dated Apr. 26, 2019.

* cited by examiner

Fig. 23 — influence of point mutation at position 129 of chANP32A on H7N9 polymerase activity Fig. 24 — influence of point mutation at position 129 of chANP32A on the activity of WSN polymerase

SEQUENCE LISTING

```
<160> NUMBER OF SEQ ID NOS: 436

<210> SEQ ID NO 1
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 1
ggcagcggag actacaagga tgacgatgac aag                              33

<210> SEQ ID NO 2
<211> LENGTH: 8
<212> TYPE: DNA
<213> ORGANISM: Artificial Sequence
<220> FEATURE:
<223> OTHER INFORMATION: artificially synthesized sequence

<400> SEQUENCE: 2 gcggccgc                                                           8

<210> SEQ ID NO 3
<211> LENGTH: 6
<212> TYPE: DNA
<213> ORGANISM: Artificial Sequence
<220> FEATURE:
<223> OTHER INFORMATION: artificially synthesized sequence

<400> SEQUENCE: 3 ctcgag                                                             6

<210> SEQ ID NO 4
<211> LENGTH: 83
<212> TYPE: DNA
<213> ORGANISM: Artificial Sequence
```

```
<220> FEATURE:
<223> OTHER INFORMATION: artificially synthesized sequence

<400> SEQUENCE: 4
aaagaattcg agctcgcggc cgcatgggca gcggagacta caaggatgac gatgacaagt    60
gactcgagct agcagatctt ttt                                           83

<210> SEQ ID NO 5
<211> LENGTH: 83
<212> TYPE: DNA
<213> ORGANISM: Artificial Sequence
<220> FEATURE:
<223> OTHER INFORMATION: artificially synthesized sequence

<400> SEQUENCE: 5
aaaaagatct gctagctcga gtcacttgtc atcgtcatcc ttgtagtctc cgctgcccat    60
gcggccgcga gctcgaattc ttt                                           83

<210> SEQ ID NO 6
<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 6
tcttaagtac aatcaacgt                                                19

<210> SEQ ID NO 7
<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 7
gcctacattt attaaactg                                                19

<210> SEQ ID NO 8
<211> LENGTH: 421
<212> TYPE: DNA
<213> ORGANISM: Artificial Sequence
<220> FEATURE:
<223> OTHER INFORMATION: artificially synthesized sequence

<400> SEQUENCE: 8
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccgt cttaagtaca atcaacgtgt tttagagcta gaaatagcaa   360
gttaaaataa ggctagtccg ttatcaactt gaaaaagtgg caccgagtcg gtgcttttt    420 t                                                                   421

<210> SEQ ID NO 9
<211> LENGTH: 33
<212> TYPE: DNA
<213> ORGANISM: Artificial Sequence
<220> FEATURE:
```

<223> OTHER INFORMATION: artificially synthesized sequence

<400> SEQUENCE: 9
cgggtccggt tcctcagctc cggtgtttcg tcc					33

<210> SEQ ID NO 10
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 10
ggagctgagg aaccggaccc gttttagagc tag					33

<210> SEQ ID NO 11
<211> LENGTH: 22
<212> TYPE: DNA
<213> ORGANISM: Artificial Sequence
<220> FEATURE:
<223> OTHER INFORMATION: artificially synthesized sequence

<400> SEQUENCE: 11
gggcagacgg attcatttag ag					22

<210> SEQ ID NO 12
<211> LENGTH: 22
<212> TYPE: DNA
<213> ORGANISM: Artificial Sequence
<220> FEATURE:
<223> OTHER INFORMATION: artificially synthesized sequence

<400> SEQUENCE: 12
ttctcggtag tcgttcaggt tg					22

<210> SEQ ID NO 13
<211> LENGTH: 23
<212> TYPE: DNA
<213> ORGANISM: Artificial Sequence
<220> FEATURE:
<223> OTHER INFORMATION: artificially synthesized sequence

<400> SEQUENCE: 13
gcggaaagtt aagtttgaag agg					23

<210> SEQ ID NO 14
<211> LENGTH: 23
<212> TYPE: DNA
<213> ORGANISM: Artificial Sequence
<220> FEATURE:
<223> OTHER INFORMATION: artificially synthesized sequence

<400> SEQUENCE: 14
gcggaaagtt aagtttgaag agg					23

<210> SEQ ID NO 15
<211> LENGTH: 22
<212> TYPE: DNA
<213> ORGANISM: Artificial Sequence
<220> FEATURE:
<223> OTHER INFORMATION: artificially synthesized sequence

<400> SEQUENCE: 15
ggcagacgga ttcatttaga gc					22

```
<210> SEQ ID NO 16
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 16
ctttggtaag tttgcgattg a                                        21

<210> SEQ ID NO 17
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 17
ctgccccagc ttacctactt g                                        21

<210> SEQ ID NO 18
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 18
atcctcatcg tcctcgtctt c                                        21

<210> SEQ ID NO 19
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 19
catctgctgg aaggtggaca a                                        21

<210> SEQ ID NO 20
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 20
cgacatccgt aaggacctgt a                                        21

<210> SEQ ID NO 21
<211> LENGTH: 12
<212> TYPE: DNA
<213> ORGANISM: Artificial Sequence
<220> FEATURE:
<223> OTHER INFORMATION: artificially synthesized sequence

<400> SEQUENCE: 21
agcaaaagca gg                                                  12

<210> SEQ ID NO 22
<211> LENGTH: 37
<212> TYPE: DNA
<213> ORGANISM: Artificial Sequence
<220> FEATURE:
<223> OTHER INFORMATION: artificially synthesized sequence
```

<400> SEQUENCE: 22
ttcgagctcg cggccgcatg gagagaataa aagaact					37

<210> SEQ ID NO 23
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 23
atctgctagc tcgagctaat tgatggccat ccgaa					35

<210> SEQ ID NO 24
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 24
ttcgagctcg cggccgcatg gatgtcaatc cgactct					37

<210> SEQ ID NO 25
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 25
atctgctagc tcgagttatt tttgccgtct gagtt					35

<210> SEQ ID NO 26
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 26
ttcgagctcg cggccgcatg gaagactttg tgcgac					36

<210> SEQ ID NO 27
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 27
atctgctagc tcgagctact tcagtgcatg tgtga					35

<210> SEQ ID NO 28
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 28
ttcgagctcg cggccgcatg gcgtctcaag gcaccaa					37

<210> SEQ ID NO 29
<211> LENGTH: 35

<210> SEQ ID NO 29
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 29
atctgctagc tcgagtcaac tgtcatactc ctctg                       35

<210> SEQ ID NO 30
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 30
ttcgagctcg cggccgcatg gaaagaataa aagaac                      36

<210> SEQ ID NO 31
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 31
atctgctagc tcgagctatt cgacactaat tgatg                       35

<210> SEQ ID NO 32
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 32
ttcgagctcg cggccgcatt tgaatggatg tcaatccgac                  40

<210> SEQ ID NO 33
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 33
atctgctagc tcgagtcatg aaggacaagc taaattca                    38

<210> SEQ ID NO 34
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 34
ttcgagctcg cggccgcctg attcaaaatg gaagatt                     37

<210> SEQ ID NO 35
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 35
atctgctagc tcgagttttt ggacagtatg gatagcaaa                              39

<210> SEQ ID NO 36
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 36
ttcgagctcg cggccgctca ctcacagagt gacatcga                               38

<210> SEQ ID NO 37
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 37
atctgctagc tcgagttctt taattgtcgt actcct                                 36

<210> SEQ ID NO 38
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 38
ttcgagctcg cggccgcatg gaaagaataa aagaac                                 36

<210> SEQ ID NO 39
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 39
atctgctagc tcgagttaat tgatggccat ccgaat                                 36

<210> SEQ ID NO 40
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 40
ttcgagctcg cggccgcatg gatgtcaatc cgactttt                               37

<210> SEQ ID NO 41
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 41
atctgctagc tcgagctatt tttgccgtct gagctc                                 36

<210> SEQ ID NO 42
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 42
ttcgagctcg cggccgcatg gaagactttg tgcgac                          36

<210> SEQ ID NO 43
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 43
atctgctagc tcgagctatc ttagtgcatg tgtga                           35

<210> SEQ ID NO 44
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 44
ttcgagctcg cggccgcatg gcgtctcaag gcacca                          36

<210> SEQ ID NO 45
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 45
atctgctagc tcgagtcaat tgtcatactc ctctgc                          36

<210> SEQ ID NO 46
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 46
ttcgagctcg cggccgcatg gagagaataa aagaatt                         37

<210> SEQ ID NO 47
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 47
atctgctagc tcgagctaat tgatggccat ccgaa                           35

<210> SEQ ID NO 48
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 48
ttcgagctcg cggccgcatg gatgtcaatc cgacttt                         37

```
<210> SEQ ID NO 49
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 49
atctgctagc tcgagctatt tttgccgtct gagctc                         36

<210> SEQ ID NO 50
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 50
ttcgagctcg cggccgcatg aagactttg tgcgacaa                        38

<210> SEQ ID NO 51
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 51
atctgctagc tcgagctatt tcagtgcatg tgtgagg                        37

<210> SEQ ID NO 52
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 52
ttcgagctcg cggccgcatg gcgtctcaag gcaccaaac                      39

<210> SEQ ID NO 53
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 53
atctgctagc tcgagttaat tgtcatactc ctctgc                         36

<210> SEQ ID NO 54
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 54
ttcgagctcg cggccgcatg gagagaataa aagaatt                        37

<210> SEQ ID NO 55
<211> LENGTH: 36
<212> TYPE: DNA
<213> ORGANISM: Artificial Sequence
<220> FEATURE:
<223> OTHER INFORMATION: artificially synthesized sequence
```

<400> SEQUENCE: 55
atctgctagc tcgagctaat tgatggccat ccgaat                                36

<210> SEQ ID NO 56
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 56
ttcgagctcg cggccgcatg gatgtcaatc cgacttt                               37

<210> SEQ ID NO 57
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 57
atctgctagc tcgagtcact gttttttgccg tctgag                               36

<210> SEQ ID NO 58
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 58
ttcgagctcg cggccgcatg gaagattttg tgcgacaa                              38

<210> SEQ ID NO 59
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 59
atctgctagc tcgagctatt tcagtgcatg tgtga                                 35

<210> SEQ ID NO 60
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 60
ttcgagctcg cggccgcagc aaaagcaggg tagataat                              38

<210> SEQ ID NO 61
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 61
atctgctagc tcgagagtag aaacaagggt attttc                                37

<210> SEQ ID NO 62

```
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 62
ttcgagctcg cggccgcatg gagagaataa aagaact                               37

<210> SEQ ID NO 63
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 63
atctgctagc tcgagttaat tgatggccat ccgaat                                36

<210> SEQ ID NO 64
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 64
ttcgagctcg cggccgcatg gatgtcaatc cgactct                               37

<210> SEQ ID NO 65
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 65
atctgctagc tcgagctatt tttgccgtct gagc                                  34

<210> SEQ ID NO 66
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 66
ttcgagctcg cggccgcatg gaagactttg tgcgaca                               37

<210> SEQ ID NO 67
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 67
atctgctagc tcgagttact tcagtgcatg tgtaagg                               37

<210> SEQ ID NO 68
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 68
```
ttcgagctcg cggccgcatg gcgtctcaag gcaccaaa        38

<210> SEQ ID NO 69
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 69
atctgctagc tcgagttaac tgtcaaattc ctcagc        36

<210> SEQ ID NO 70
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 70
ttcgagctcg cggccgcatg gcgtctcaag gcac        34

<210> SEQ ID NO 71
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 71
atctgctagc tcgagtcaat tgtcatactc ct        32

<210> SEQ ID NO 72
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 72
ttcgagctcg cggccgcatg gaagactttg tgcg        34

<210> SEQ ID NO 73
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 73
atctgctagc tcgagctatc ttagtgcatg tg        32

<210> SEQ ID NO 74
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 74
ttcgagctcg cggccgcatg gatgtcaatc cga        33

<210> SEQ ID NO 75
<211> LENGTH: 33
<212> TYPE: DNA

```
<213> ORGANISM: Artificial Sequence
<220> FEATURE:
<223> OTHER INFORMATION: artificially synthesized sequence

<400> SEQUENCE: 75
atctgctagc tcgagctatt tttgccgtct gag                                33

<210> SEQ ID NO 76
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 76
ttcgagctcg cggccgcatg gaaagaataa aaga                               34

<210> SEQ ID NO 77
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 77
atctgctagc tcgagttaat tgatgaccat ccg                                33

<210> SEQ ID NO 78
<211> LENGTH: 14
<212> TYPE: DNA
<213> ORGANISM: Artificial Sequence
<220> FEATURE:
<223> OTHER INFORMATION: artificially synthesized sequence

<400> SEQUENCE: 78
agcaaaagca gggg                                                     14

<210> SEQ ID NO 79
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 79
gtatactaat aattaaaaac acccttgttt ctact                              35

<210> SEQ ID NO 80
<211> LENGTH: 1971
<212> TYPE: DNA
<213> ORGANISM: Artificial Sequence
<220> FEATURE:
<223> OTHER INFORMATION: artificially synthesized sequence

<400> SEQUENCE: 80
cggagtactg gtcgacctcc gaagttgggg gggagcaaaa gcagggatg gaagacgcca    60 aaaacataaa gaaaggcccg gcgccattct atccgctgga agatggaacc gctggagagc  120
aactgcataa ggctatgaag agatacgccc tggttcctgg aacaattgct ttacagatg   180 cacatatcga ggtggacatc acttacgctg agtacttcga aatgtccgtt cggttggcag  240
aagctatgaa acgatatggg ctgaatacaa atcacagaat cgtcgtatgc agtgaaaact  300
ctcttcaatt ctttatgccg gtgttgggcg cgttattta t cggagttgca gttgcgcccg  360
cgaacgacat ttataatgaa cgtgaattgc tcaacagtat gggcatttcg cagcctaccg  420
```

```
tggtgttcgt ttccaaaaag gggttgcaaa aaattttgaa cgtgcaaaaa aagctcccaa      480
tcatccaaaa aattattatc atggattcta aaacggatta ccaggatttt cagtcgatgt      540
acacgttcgt cacatctcat ctacctcccg gttttaatga atacgatttt gtgccagagt     600
ccttcgatag ggacaagaca attgcactga tcatgaactc ctctggatct actggtctgc      660
ctaaaggtgt cgctctgcct catagaactg cctgcgtgag attctcgcat gccagagatc      720
ctatttttgg caatcaaatc attccggata ctgcgatttt aagtgttgtt ccattccatc      780
acggttttgg aatgtttact acactcggat atttgatatg tggatttcga gtcgtcttaa      840
tgtatagatt tgaagaagag ctgtttctga ggagccttca ggattacaag attcaaagtg      900
cgctgctggt gccaacccta ttctccttct tcgccaaaag cactctgatt gacaaatacg      960
atttatctaa tttacacgaa attgcttctg gtggcgctcc cctctctaag gaagtcgggg     1020
aagcggttgc caagaggttc catctgccag gtatcaggca aggatatggg ctcactgaga     1080
ctacatcagc tattctgatt acacccgagg gggatgataa accgggcgcg gtcggtaaag     1140
ttgttccatt ttttgaagcg aaggttgtgg atctggatac cgggaaaacg ctgggcgtta     1200
atcaaagagg cgaactgtgt gtgagaggtc ctatgattat gtccggttat gtaaacaatc     1260
cggaagcgac caacgccttg attgacaagg atggatggct acattctgga gacatagctt     1320
actgggacga agacgaacac ttcttcatcg ttgaccgcct gaagtctctg attaagtaca     1380
aaggctatca ggtggctccc gctgaattgg aatccatctt gctccaacac cccaacatct     1440
tcgacgcagg tgtcgcaggt cttcccgacg atgacgccgg tgaacttccc gccgccgttg     1500
ttgttttgga gcacggaaag acgatgacgg aaaaagagat cgtggattac gtcgccagtc     1560
aagtaacaac cgcgaaaaag ttgcgcggag gagttgtgtt tgtggacgaa gtaccgaaag     1620
gtcttaccgg aaaactcgac gcaagaaaaa tcagagagat cctcataaag gccaagaagg     1680
gcggaaagat cgccgtgtaa gtatactaat aattaaaaac cccttgtttt ctactaataa     1740
cccggcggcc caaaatgccg actcggagcg aaagatatac ctcccccggg gccgggaggt     1800
cgcgtcaccg accacgccgc cggcccaggc gacgcgcgac acggacacct gtccccaaaa     1860
acgccaccat cgcagccaca cacggagcgc ccggggccct ctggtcaacc ccaggacaca     1920
cgcgggagca gcgccgggcc ggggacgccc tcccggccgc ccgtgccaca c              1971
```

<210> SEQ ID NO 81
<211> LENGTH: 24
<212> TYPE: DNA
<213> ORGANISM: Artificial Sequence
<220> FEATURE:
<223> OTHER INFORMATION: artificially synthesized sequence

<400> SEQUENCE: 81
catttcgcag cctaccgtgg tgtt                                              24

<210> SEQ ID NO 82
<211> LENGTH: 16
<212> TYPE: DNA
<213> ORGANISM: Artificial Sequence
<220> FEATURE:
<223> OTHER INFORMATION: artificially synthesized sequence

<400> SEQUENCE: 82
agtagaaaca agggtg                                                       16

<210> SEQ ID NO 83

```
<211> LENGTH: 20
<212> TYPE: DNA
<213> ORGANISM: Artificial Sequence
<220> FEATURE:
<223> OTHER INFORMATION: artificially synthesized sequence

<400> SEQUENCE: 83 ttttttttttt ttttttttttt                                            20

<210> SEQ ID NO 84
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 84
gattaccagg gatttcagtc g                                            21

<210> SEQ ID NO 85
<211> LENGTH: 20
<212> TYPE: DNA
<213> ORGANISM: Artificial Sequence
<220> FEATURE:
<223> OTHER INFORMATION: artificially synthesized sequence

<400> SEQUENCE: 85 gacacccttta ggcagaccag                                             20

<210> SEQ ID NO 86
<211> LENGTH: 583
<212> TYPE: DNA
<213> ORGANISM: Artificial Sequence
<220> FEATURE:
<223> OTHER INFORMATION: artificially synthesized sequence

<400> SEQUENCE: 86
gtgtggcacg ggcggccggg agggcgtccc cggcccggcg ctgctcccgc gtgtgtcctg    60
gggttgacca gagggccccg ggcgctccgt gtgtggctgc gatggtggcg tttttgggga   120
caggtgtccg tgtcgcgcgt cgcctgggcc ggcggcgtgg tcggtgacgc gacctcccgg   180
ccccggggga ggtatatctt tcgctccgag tcggcatttt gggccgccgg gttattggaa   240
gagccagatc ttcaatttca gcattccag gatttctgct ttctcgcacc tgatccatca    300 ttgcttttttg tgctgctgtt tgaaatttcc ctttgaggat gttgcacatt ctctcatatg   360
caatccttgt tcttcgtcca ttctcgcctc tccagaagtt ccggtcatta atgcctcgct   420
ttatcatccg aattagttcc attaccatcg tcccgactcc ctttattgct gcaccagcag   480
ctccagatct ggctcttctg gccggcatgg tcccagcctc ctcgctggcg ccggctgggc    540
aacattccga ggggaccgtc ccctcggtaa tggcgaatgg gac                       583

<210> SEQ ID NO 87
<211> LENGTH: 2341
<212> TYPE: DNA
<213> ORGANISM: Artificial Sequence
<220> FEATURE:
<223> OTHER INFORMATION: artificially synthesized sequence

<400> SEQUENCE: 87
agcaaaagca ggtcaaatat attcaatatg gagagaataa agaactgag agatctaatg     60 tcgcagtccc gcactcgcga gatactcact aagaccactg tggaccatat ggccataatc   120
aaaaagtaca catcaggaag gcaagagaag aaccccgcac tcagaatgaa gtggatgatg   180
```

```
gcaatgagat acccaattac agcagacaag agaataatgg acatgattcc agagaggaat      240
gaacaaggac aaaccctctg gagcaaaaca aacgatgctg gatcagaccg agtgatggta      300
tcacctctgg ccgtaacatg gtggaatagg aatggcccaa caacaagtac agttcattac      360
cctaaggtat ataaaactta tttcgaaaag gtcgaaaggt tgaaacatgg taccttcggc      420
cctgtccact tcagaaatca agttaaaata aggaggagag ttgatacaaa ccctggccat      480
gcagatctca gtgccaagga ggcacaggat gtgattatgg aagttgtttt cccaaatgaa      540
gtgggggcaa gaatactgac atcagagtca caactggcaa taacaaaaga gaagaaagaa      600
gagctccagg attgtaaaat tgctcccttg atggtggcgt acatgctaga aagagaattg      660
gtccgtaaaa caaggtttct cccagtagcc ggcggaacag gcagtgttta tattgaagtg      720
ttgcacttaa cccaagggac gtgctgggag cagatgtaca ctccaggagg agaagtgaga      780
aatgatgatg ttgaccaaag tttgattatc gctgctagaa acatagtaag aagagcagca      840
gtgtcagcag acccattagc atctctcttg gaaatgtgcc acagcacaca gattggagga      900
gtaaggatgg tggacatcct tagacagaat ccaactgagg aacaagccgt agacatatgc      960
aaggcagcaa tagggttgag gattagctca tctttcagtt ttggtgggtt cactttcaaa     1020
aggacaagcg gatcatcagt caagaaagaa gaagaagtgc taacgggcaa cctccaaaca     1080
ctgaaaataa gagtacatga agggtatgaa gaattcacaa tggttgggag aagagcaaca     1140
gctattctca gaaaggcaac caggagattg atccagttga tagtaagcgg gagagacgag     1200
cagtcaattg ctgaggcaat aattgtggcc atggtattct cacaagagga ttgcatgatc     1260
aaggcagtta ggggcgatct gaactttgtc aatagggcaa accagcgact gaaccccatg     1320
caccaactct tgaggcattt ccaaaaagat gcaaaagtgc tttccagaa ctggggaatt     1380 gaatccatcg acaatgtgat gggaatgatc ggaatactgc ccgacatgac cccaagcatg     1440
gagatgtcgc tgagagggat aagagtcagc aaaatgggag tagatgaata ctccagcacg     1500
gagagagtgg tagtgagtat tgaccgattt ttaagggtta gagatcaaag agggaacgta     1560
ctattgtctc ccgaagaagt cagtgaaacg caaggaactg agaagttgac aataacttat     1620
tcgtcatcaa tgatgtggga gatcaatggc cctgagtcag tgctagtcaa cacttatcaa     1680
tggataatca ggaactggga aattgtgaaa attcaatggt cacaagatcc cacaatgtta     1740
tacaacaaaa tggaatttga accatttcag tctcttgtcc ctaaggcaac cagaagccgg     1800
tacagtggat tcgtaaggac actgttccag caaatgcggg atgtgcttgg acatttgac     1860 actgtccaaa taataaaact tctccccttt gctgctgctc caccagaaca gagtaggatg     1920 caatttttcct cattgactgt gaatgtgaga ggatcagggt tgaggatact ggtaagaggc     1980
aattctccag tattcaatta caacaaggca accaaacgac ttacagttct tggaaaggat     2040
gcaggtgcat tgactgaaga tccagatgaa ggcacatctg gggtggagtc tgctgtcctg     2100
agaggatttc tcattttggg caaagaagac aagagatatg cccagcatt aagcatcaat     2160 gaactgagca atcttgcaaa aggagagaag gctaatgtgc taattgggca agggacgta     2220 gtgttggtaa tgaaacgaaa acgggactct agcatactta ctgacagcca gacagcgacc     2280
aaaagaattc ggatggccat caattagtgt cgaattgttt aaaaacgacc ttgtttctac     2340
t                                                                    2341
```

<210> SEQ ID NO 88
<211> LENGTH: 2341
<212> TYPE: DNA

<213> ORGANISM: Artificial Sequence
<220> FEATURE:
<223> OTHER INFORMATION: artificially synthesized sequence

<400> SEQUENCE: 88

```
agcaaaagca ggcaaaccat ttgaatggat gtcaatccga ctctactttt cctaaaaatt      60
ccagcgcaaa atgccataag caccacattc ccttatactg gagatcctcc atacagccat     120
ggaacaggaa caggatacac catggacaca gtaaacagaa cacaccaata ctcagaaaag     180
ggaaagtgga cgacaaacac agagactggt gcaccccagc tcaacccgat tgatggacca     240
ctacctgagg ataatgaacc aagtgggtat gcacaaacag actgtgttct agaggctatg     300
gctttccttg aagaatccca cccgggaata tttgagaatt catgccttga acaatggaa      360
gttgttcaac aaacaagggt agataaacta actcaaggtc gccagactta tgattggaca     420
ttaaacagaa atcaaccggc agcaactgca ttggccaaca ccatagaagt ctttagatcg     480
aatggcctaa cagctaatga gtcaggaagg ctaatagatt tcttaaagga tgtaatggaa     540
tcaatgaaca aagaggaaat agagataaca acccactttc aaagaaaaag gagagtaaga     600
gacaacatga ccaagaagat ggtcacgcaa agaacaatag gaagaaaaa caaagactg      660
aataagagag gctatctaat aagagcactg acattaaata cgatgaccaa agatgcagag     720
agaggcaagt taaaagaag ggctatcgca cacctgggga tgcagattag aggtttcgta     780
tactttgttg aaactttagc taggagcatt tgcgaaaagc ttgaacagtc tgggctccca     840
gtaggggca atgaaaagaa ggccaaactg gcaaatgttg tgagaaagat gatgactaat     900
tcacaagaca cagagatttc tttcacaatc actgggaca acactaagtg gaatgaaaat     960
caaaatcctc gaatgttcct ggcgatgatt acatatatca ccagaaatca acccgagtgg    1020
ttcagaaaca tcctgagcat ggcacccata atgttctcaa acaaaatggc aagactaggg    1080
agagggtaca tgttcgagag taaaagaatg aagattcgaa cacaaatacc agcagaaatg    1140
ctagcaagca ttgacctgaa gtacttcaat gaatcaacaa agaagaaat tgagaaaata    1200
aggcctcttc taatagatgg cacagcatca ctgagtcctg gatgatgat gggcatgttc    1260
aacatgctaa gtacggtctt gggagtctcg atactgaatc ttggacaaaa gaaatacacc    1320
aagacaatat actggtggga tgggctccaa tcatccgacg attttgctct catagtgaat    1380
gcaccaaacc atgagggaat acaagcagga gtggacagat tctacaggac ctgcaagtta    1440
gtgggaatca acatgagcaa aaagaagtcc tatataaata gacagggac atttgaattc    1500
acaagctttt tttatcgcta tggatttgtg gctaattta gcatggagct acccagcttt    1560
ggagtgtctg gagtaaatga atcagctgac atgagtattg gagtaacagt gataaagaac    1620
aacatgataa acaatgacct tggacctgca acggcccaga tggctcttca attgttcatc    1680
aaagactaca gatacacata taggtgccat agggagacg cacaaattca gacgagaaga    1740
tcatttgagt taaagaagct gtgggatcaa acccaatcaa aggtagggct attagtatca    1800
gatggaggac caaacttata caatatacgg aatcttcaca ttcctgaagt ctgcttaaaa    1860
tgggagctaa tggatgatga ttatcgggga agactttgta atcccctgaa tccctttgtc    1920
agtcataaag agattgattc tgtaaacaat gctgtggtaa tgccagccca tggtccagcc    1980
aaaagcatgg aatatgatgc cgttgcaact acacattcct ggattcccaa gaggaatcgt    2040
tctattctca acacaagcca aaggggaatt cttgaggatg aacagatgta ccagaagtgc    2100
tgcaatctat tcgagaaatt ttttcccagc agttcatata ggaaccggt tggaatttct    2160
agcatggtgg aggccatggt gtctagggcc cggattgatg ccagggtcga cttcgagtct    2220
```

```
ggacggatca agaaagaaga gttctctgag atcatgaaga tctgttccac cattgaagaa    2280
ctcagacggc aaaaataatg aatttaactt gtccttcatg aaaaaatgcc ttgtttctac    2340
t                                                                   2341
```

<210> SEQ ID NO 89
<211> LENGTH: 2233
<212> TYPE: DNA
<213> ORGANISM: Artificial Sequence
<220> FEATURE:
<223> OTHER INFORMATION: artificially synthesized sequence

<400> SEQUENCE: 89

```
agcaaaagca ggtactgatc caaaatggaa gactttgtgc gacaatgctt caatccaatg      60
atcgtcgagc ttgcggaaaa ggcaatgaaa gaatatgggg aagatccgaa aatcgaaact     120
aacaagtttg ctgcaatatg cacacatttg gaagtttgtt tcatgtattc ggatttccat     180
ttcatcgacg aacggggtga atcaataatt gtagaatctg cgacccgaat gcactattg     240 aagcaccgat ttgagataat tgaaggaaga gaccgaatca tggcctggac agtggtgaac     300
agtatatgta acacaacagg ggtagagaag cctaaatttc ttcctgattt gtatgattac     360
aaagagaacc ggttcattga aattggagta acacggaggg aagtccacat atattaccta     420
gagaaagcca acaaaataaa atctgagaag acacacattc acatcttttc attcactgga     480
gaggagatgg ccaccaaagc ggactacacc cttgacgagg agagcagggc aagaatcaaa     540
actaggcttt tcactataag acaagaaatg gccagtagga gtctatggga ttccttcgt     600 cagtccgaaa gaggcgaaga gacaattgaa gaaaatttg agattacagg aactatgcgc     660
aagcttgccg accaaagtct cccaccgaac ttctccagcc ttgaaaactt tagagcctat     720
gtagatggat tcgagccgaa cggctgcatt gagggcaagc tttcccaaat gtcaaaagaa     780
gtgaacgcca aaattgaacc attcttgagg acgacaccac gccccctcag attgcctgat     840
gggcctcttt gccatcagcg gtcaaagttc ctactgatgg atgctctgaa attaagtatt     900
gaagacccga gtcacgaggg ggagggaata ccactatatg atgcaatcaa atgcatgaag     960
acattctttg gctggaaaga gcctaacata gtcaaaccac atgagaaagg cataaatccc    1020
aattacctca tggcttggaa gcaggtgcta acagagctac aggacattga aaatgaagag    1080
aagatcccaa ggacaaagaa catgaagaga acaagccaat gaagtgggc actcggtgaa    1140 aatatggcac cagaaaaagt agactttgat gactgcaaag atgttggaga ccttaaacag    1200
tatgacagta tgagccaga gcccagatct ctagcaagct gggtccaaaa tgaattcaat    1260
aaggcatgtg aattgactga ttcaagctgg ataagaacttg atgaataggg aagatgtt    1320 gccccgattg aacatatcgc aagcatgagg aggaactatt ttacagcaga agtgtcccac    1380
tgcagggcta ctgaatacat aatgaaggga gtgtacataa atacggcctt gctcaatgca    1440
tcctgtgcag ccatggatga cttcagctg atcccaatga taagcaaatg taggaccaaa    1500
gaaggaagac ggaaaacaaa cctgtatggg ttcattataa aaggaaggtc tcatttgaga    1560
aatgatactg atgtggtgaa ctttgtaagt atggagttct cactcactga cccgagactg    1620
gagccacaca aatgggaaaa atactgtgtt cttgaaatag agacatgct cttgaggact    1680 gcgataggcc aagtgtcgag gcccatgttc ctatatgtga aaccaatgg aacctccaag    1740 atcaagatga atggggcat ggaaatgagg cgctgcctc ttcagtctct tcagcagatt    1800
gagagcatga ttgaggccga gtcttctgtc aaagagaaag acatgaccaa ggaattcttt    1860
```

| | |
|---|---:|
| gaaaacaaat cggaaacatg ccaatcgga gagtcaccca ggggagtgga ggaaggctct | 1920 |
| attgggaaag tatgcaggac cttactggca aaatctgtat tcaacagtct atatgcgtct | 1980 |
| ccacaacttg aggggttttc ggctgaatcg agaaaattgc ttctcattgt tcaggcactt | 2040 |
| agggacaacc tggaacctgg aaccttcgat cttgggggc tatatgaagc aatcgaggag | 2100 |
| tgcctgatta atgatccctg ggttttgctt aatgcatctt ggttcaactc cttcctcaca | 2160 |
| catgcactga agtagttgtg gcaatgctac tatttgctat ccatactgtc caaaaagta | 2220 |
| ccttgtttct act | 2233 |

<210> SEQ ID NO 90
<211> LENGTH: 1565
<212> TYPE: DNA
<213> ORGANISM: Artificial Sequence
<220> FEATURE:
<223> OTHER INFORMATION: artificially synthesized sequence

<400> SEQUENCE: 90

| | |
|---|---:|
| agcaaaagca gggtagataa tcactcactg agtgacatcg aagtcatggc gtctcaaggc | 60 |
| accaaacgat catatgaaca aatggagact ggtggggagc gccaggatgc cacagaaatc | 120 |
| agagcatctg tcgaagaat gattggtgga atcgggagat tctacatcca aatgtgcact | 180 |
| gaactcaaac tcagtgatta tgatggacga ctaatccaga atagcataac aatagagagg | 240 |
| atggtgcttt ctgcttttga tgagagaaga aataaatacc tagaagagca tcccagtgct | 300 |
| gggaaggacc ctaagaaaac aggaggaccc atatatagaa gagtagacgg aaagtggatg | 360 |
| agagaactca tcctttatga caaagaagaa ataaggagag tttggcgcca agcaaacaat | 420 |
| ggcgaagatg caacagcagg tcttactcat atcatgattt ggcattccaa cctgaatgat | 480 |
| gccacatatc agagaacaag agcgcttgtt cgcaccggaa tggatcccag aatgtgctct | 540 |
| ctaatgcaag gttcaacact tcccagaagg tctggtgccg caggtgctgc ggtgaaagga | 600 |
| gttgaacaa tagcaatgga gttaatcaga atgatcaaac gtggaatcaa tgaccgaaat | 660 |
| ttctggaggg gtgaaaatgg acgaaggaca agggttgctt atgaaagaat gtgcaatatc | 720 |
| ctcaaaggaa aatttcaaac agctgcccag agggcaatga tggatcaagt aagagaaagt | 780 |
| cgaaacccag gaaacgctga gattgaagac ctcattttcc tggcacggtc agcactcatt | 840 |
| ctgagggat cagttgcaca taaatcctgc ctgcctgctt gtgtgtatgg cttgcagta | 900 |
| gcaagtgggc atgactttga aagggaaggg tactcactgg tcgggataga cccattcaaa | 960 |
| ttactccaaa acagccaagt ggtcagcctg atgagaccaa atgaaaaccc agctcacaag | 1020 |
| agtcaattgg tgtggatggc atgccactct gctgcatttg aagatttaag agtatcaagt | 1080 |
| ttcataagag gaaagaaagt gattccaaga ggaaagcttt ccacaagagg gtccagatt | 1140 |
| gcttcaaatg agaatgtgga aaccatgaac tccaataccc tggaactgag aagcagatac | 1200 |
| tgggccataa ggaccaggag tggaggaaat accaatcaac aaaaggcatc cgcaggccag | 1260 |
| atcagtgtgc agcctacatt ctcagtgcag cggaatctcc cttttgaaag caaccgtt | 1320 |
| atggcagcat tcagcgggaa caatgaagga cggacatccg acatgcgaac agaagttata | 1380 |
| agaatgatgg aaagtgcaaa gccagaagat ttgtccttcc aggggcgggg agtcttcgag | 1440 |
| ctctcggacg aaaaggcaac gaacccgatc gtgccttcct ttgacatgag taatgaaggg | 1500 |
| tcttatttct tcggagacaa tgcagaggag tatgacagtt gaggaaaaat acccttgttt | 1560 |
| ctact | 1565 |

<210> SEQ ID NO 91
<211> LENGTH: 1777
<212> TYPE: DNA
<213> ORGANISM: Artificial Sequence
<220> FEATURE:
<223> OTHER INFORMATION: artificially synthesized sequence

<400> SEQUENCE: 91

| | | | | | |
|---|---|---|---|---|---|
| agcaaaagca | ggggaaaaca | aaagcaacaa | aaatgaaggc | aatactagta | gttctgctat | 60 |
| atacatttgc | aaccgcaaat | gcagacacat | tatgtatagg | ttatcatgcg | aacaattcaa | 120 |
| cagacactgt | agacacagta | ctagaaaaga | atgtaacagt | aacacactct | gttaacattc | 180 |
| tagaagacaa | gcataacggg | aaactatgca | aactaagagg | ggtagcccca | ttgcatttgg | 240 |
| gtaaatgtaa | cattgctggc | tggatcctgg | gaaatccaga | gtgtgaatca | ctctccacag | 300 |
| caagctcatg | gtcctacatt | gtggaaacat | ctagttcaga | caatgaacg | tgttacccag | 360 |
| gagatttcat | cgattatgag | gagctaagag | agcaattgag | ctcagtgtca | tcatttgaaa | 420 |
| ggtttgagat | attccccaag | acaagttcat | ggcccaatca | tgactcgaac | aaaggtgtaa | 480 |
| cggcagcatg | tcctcatgct | ggagcaaaaa | gcttctacaa | aaatttaata | tggctagtta | 540 |
| aaaaaggaaa | ttcataccca | aagctcagca | atcctacat | taatgataaa | gggaaagaag | 600 |
| tcctcgtgct | atggggcatt | caccatccat | ctactagtgc | tgaccaacaa | agtctctatc | 660 |
| agaatgcaga | tgcatatgtt | tttgtggggt | catcaagata | cagcaagaag | ttcaagccgg | 720 |
| aaatagcaat | aagacccaaa | gtgagggatc | gagaagggag | aatgaactat | tactggacac | 780 |
| tagtagagcc | gggagacaaa | ataacattcg | aagcaactgg | aaatctagta | gtaccgagat | 840 |
| atgcattcgc | aatggaaaga | aatgctggat | ctggtattat | catttcagat | acaccagtcc | 900 |
| acgattgcaa | tacaacttgt | cagacaccca | agggtgctat | aaacaccagc | ctcccatttc | 960 |
| agaatataca | tccgatcaca | attggaaaat | gtccaaaata | tgtaaaaagc | acaaaattga | 1020 |
| gactggccac | aggattgagg | aatgtcccgt | ctattcaatc | tagaggccta | tttggggcca | 1080 |
| ttgccggttt | cattgaaggg | gggtggacag | ggatggtaga | tggatggtac | ggttatcacc | 1140 |
| atcaaaatga | gcaggggtca | ggatatgcag | ccgacctgaa | gagcacacag | aatgccattg | 1200 |
| acgagattac | taacaaagta | aattctgtta | ttgaaaagat | gaatacacag | ttcacagcag | 1260 |
| taggtaaaga | gttcaaccac | ctggaaaaaa | gaatagagaa | tttaaataaa | aaagttgatg | 1320 |
| atggtttcct | ggacatttgg | acttacaatg | ccgaactgtt | ggttctattg | gaaaatgaaa | 1380 |
| gaactttgga | ctaccacgat | tcaaatgtga | agaacttata | tgaaaaggta | agaagccagc | 1440 |
| taaaaaacaa | tgccaaggaa | attggaaacg | gctgctttga | attttaccac | aaatgcgata | 1500 |
| acacgtgcat | ggaaagtgtc | aaaaatggga | cttatgacta | cccaaaatac | tcagaggaag | 1560 |
| caaaattaaa | cagagaagaa | atagatgggg | taaagctgga | atcaacaagg | atttaccaga | 1620 |
| ttttggcgat | ctattcaact | gtcgccagtt | cattggtact | ggtagtctcc | ctgggggcaa | 1680 |
| tcagtttctg | gatgtgctct | aatgggtctc | tacagtgtag | aatatgtatt | taacattagg | 1740 |
| atttcagaag | catgagaaaa | acaccccttgt | ttctact | | | 1777 |

<210> SEQ ID NO 92
<211> LENGTH: 1458
<212> TYPE: DNA
<213> ORGANISM: Artificial Sequence
<220> FEATURE:
<223> OTHER INFORMATION: artificially synthesized sequence

<400> SEQUENCE: 92

| | |
|---|---|
| agcaaaagca ggagtttaaa atgaatccaa accaaaagat aataaccatt ggttcggtct | 60 |
| gtatgacaat tggaatggct aacttaatat tacaaattgg aaacataatc tcaatatgga | 120 |
| ttagccactc aattcaactt gggaatcaaa atcagattga acatgcaat caaagcgtca | 180 |
| ttacttatga aaacaacact tgggtaaatc agacatatgt taacatcagc aacaccaact | 240 |
| tgctgctgg acagtcaatg gtttccgtga aattagcggg caattcctct ctctgccctg | 300 |
| ttagtggatg ggctatatac agtaaagaca acagtgtaag aatcggttcc aaggggatg | 360 |
| tgtttgtcat aagggaacca ttcatatcat gctccccctt ggaatgcaga accttcttct | 420 |
| tgactcaagg ggccttgcta aatgacaaac attccaatgg aaccattaaa gacaggagcc | 480 |
| catatcgaac cctaatgagc tgtcctattg gtgaagttcc ctctccatac aactcaagat | 540 |
| ttgagtcagt cgcttggtca gcaagtgctt gtcatgatgg catcaattgg ctaacaattg | 600 |
| gaatttctgg cccagacaat ggggcagtgg ctgtgttaaa gtacaacggc ataataacag | 660 |
| acactatcaa gagttggaga aacaatatat tgagaacaca agagtctgaa tgtgcatgtg | 720 |
| taaatggttc ttgctttact gtaatgaccg atggaccaag taatgacag gcctcataca | 780 |
| agatcttcag aatagaaaag ggaaagatag tcaaatcagt cgaaatgaat gctcctaatt | 840 |
| atcactatga ggaatgctcc tgttatcctg attctagtga atcacatgt gtgtgcaggg | 900 |
| ataactggca tggctcgaat cgaccgtggg tgtctttcaa ccagaatctg aatatcaga | 960 |
| taggatacat atgcagtggg atttttcggag acaatccacg ccctaatgat aagacaggca | 1020 |
| gttgtggtcc agtatcgtct aatggagcaa atggagtaaa aggattttca ttcaaatacg | 1080 |
| gcaatggtgt ttggataggg agaactaaaa gcattagttc aagaaacggt tttgagatga | 1140 |
| tttgggatcc gaacggatgg actgggacag acaataactt ctcaataaag caagatatcg | 1200 |
| taggaataaa tgagtggtca ggatatagcg ggagttttgt tcagcatcca gaactaacag | 1260 |
| ggctggattg tataagacct tgcttctggg ttgaactaat cagagggcga cccaaagaga | 1320 |
| acacaatctg gactagcggg agcagcatat ctttttgtgg tgtaaacagt gacactgtgg | 1380 |
| gttggtcttg gccagacggt gctgagttgc catttaccat tgacaagtaa tttgttcaaa | 1440 |
| aaactccttg tttctact | 1458 |

<210> SEQ ID NO 93
<211> LENGTH: 1027
<212> TYPE: DNA
<213> ORGANISM: Artificial Sequence
<220> FEATURE:
<223> OTHER INFORMATION: artificially synthesized sequence

<400> SEQUENCE: 93

| | |
|---|---|
| agcaaaagca ggtagatatt taaagatgag tcttctaacc gaggtcgaaa cgtacgttct | 60 |
| ttctatcatc ccgtcaggcc ccctcaaagc cgagatcgcg cagagactgg aaagtgtctt | 120 |
| tgcaggaaag aacacagatc ttgaggctct catggaatgg ctaaagacaa gaccaatctt | 180 |
| gtcacctctg actaagggaa ttttaggatt tgtgttcacg ctcaccgtgc ccagtgagcg | 240 |
| aggactgcag cgtagacgct ttgtccaaaa tgcccctaaat gggaatgggg acccgaacaa | 300 |
| catggataga gcagtaaaac tatacaagaa gctcaaaaga gaaataacgt tccatggggc | 360 |
| caaggaggtg tcactaagct attcaactgg tgcacttgcc agttgcatgg gcctcatata | 420 |
| caacaggat ggaacagtga ccacagaagc tgcttttggt ctagtgtgtg ccacttgtga | 480 |
| acagattgct gattcacagc atcggtctca cagacagatg gctactacca ccaatccact | 540 |
| aatcaggcat gaaaacagaa tggtgctggc tagcactacg gcaaaggcta tggaacagat | 600 |

| | | |
|---|---|---|
| ggctggatcg agtgaacagg cagcggaggc catggaggtt gctaatcaga ctaggcagat | 660 | |
| ggtacatgca atgagaacta ttgggactca tcctagctcc agtgctggtc tgaaagatga | 720 | |
| ccttcttgaa aatttgcagg cctaccagaa gcgaatggga gtgcagatgc agcgattcaa | 780 | |
| gtgatcctct cgtcattgca gcaaatatca ttgggatctt gcacctgata ttgtggatta | 840 | |
| ctgatcgtct ttttttcaaa tgtatttatc gtcgctttaa atacggtttg aaaagagggc | 900 | |
| cttctacgga aggagtgcct gagtccatga gggaagaata tcaacaggaa cagcagagtg | 960 | |
| ctgtggatgt tgacgatggt cattttgtca acatagagct agagtaaaaa actaccttgt | 1020 | |
| ttctact | 1027 | |

<210> SEQ ID NO 94
<211> LENGTH: 890
<212> TYPE: DNA
<213> ORGANISM: Artificial Sequence
<220> FEATURE:
<223> OTHER INFORMATION: artificially synthesized sequence

<400> SEQUENCE: 94

| | | |
|---|---|---|
| agcaaaagca gggtgacaaa gacataatgg actccaacac catgtcaagc tttcaggtag | 60 | |
| actgtttcct ttggcatatc cgcaagcgat ttgcagacaa tggattgggt gatgccccat | 120 | |
| tccttgatcg gctccgccga gatcaaaagt ccttaaaagg aagaggcaac acccttggcc | 180 | |
| tcgatatcga aacagccact cttgttggga aacaaatcgt ggaatggatc ttgaaagagg | 240 | |
| aatccagcga gacacttaga atgacaattg catctgtacc tacttcgcgc tacctttctg | 300 | |
| acatgaccct cgaggaaatg tcacgagact ggttcatgct catgcctagg caaaagataa | 360 | |
| taggccctct ttgcgtgcga ttggaccagg cgatcatgga aaagaacata gtactgaaag | 420 | |
| cgaacttcag tgtaatcttt aaccgattag agaccttgat actactaagg gctttcactg | 480 | |
| aggagggagc aatagttgga gaaatttcac cattaccttc tcttccagga catacttatg | 540 | |
| aggatgtcaa aaatgcagtt ggggtcctca tcggaggact tgaatggaat ggtaacacgg | 600 | |
| ttcgagtctc tgaaaatata cagagattcg cttggagaaa ctgtgatgag aatgggagac | 660 | |
| cttcactacc tccagagcag aaatgaaaag tggcgagagc aattgggaca gaaatttgag | 720 | |
| gaaataaggt ggttaattga agaaatgcgg cacagattga aagcgacaga aatagtttc | 780 | |
| gaacaaataa catttatgca agccttacaa ctactgcttg aagtagaaca agagataaga | 840 | |
| gctttctcgt ttcagcttat ttaatgataa aaaacaccct tgtttctact | 890 | |

<210> SEQ ID NO 95
<211> LENGTH: 26
<212> TYPE: DNA
<213> ORGANISM: Artificial Sequence
<220> FEATURE:
<223> OTHER INFORMATION: artificially synthesized sequence

<400> SEQUENCE: 95

| | |
|---|---|
| ggccggcatg gtcccagcct cctcgc | 26 |

<210> SEQ ID NO 96
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 96

```
aataacccgg cggcccaaaa tgccgactcg                              30
```

<210> SEQ ID NO 97
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 97

```
gggaccatgc cggccagcaa aagcaggtca aatatat                      37
```

<210> SEQ ID NO 98
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 98

```
ggccgccggg ttattagtag aaacaaggtc gtttttaa                     38
```

<210> SEQ ID NO 99
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 99

```
gggaccatgc cggccagcaa aagcaggcaa accatt                       36
```

<210> SEQ ID NO 100
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 100

```
ggccgccggg ttattagtag aaacaaggca ttttttca                     38
```

<210> SEQ ID NO 101
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 101

```
gggaccatgc cggccagcaa aagcaggtac tgatcca                      37
```

<210> SEQ ID NO 102
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 102

```
ggccgccggg ttattagtag aaacaaggta ctttttggg                    39
```

<210> SEQ ID NO 103
<211> LENGTH: 33
<212> TYPE: DNA
<213> ORGANISM: Artificial Sequence

```
<220> FEATURE:
<223> OTHER INFORMATION: artificially synthesized sequence

<400> SEQUENCE: 103
gggaccatgc cggccagcaa aagcagggta gat                              33

<210> SEQ ID NO 104
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 104
ggccgccggg ttattagtag aaacaagggt atttttc                          37

<210> SEQ ID NO 105
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 105
gggaccatgc cggccagcaa aagcagggga aaa                              33

<210> SEQ ID NO 106
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 106
ggccgccggg ttattagtag aaacaagggt gt                               32

<210> SEQ ID NO 107
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 107
gggaccatgc cggccagcaa aagcaggagt ttaa                             34

<210> SEQ ID NO 108
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 108
ggccgccggg ttattagtag aaacaaggag ttt                              33

<210> SEQ ID NO 109
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 109
gggaccatgc cggccagcaa aagcaggtag ata                              33
```

<210> SEQ ID NO 110
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 110
ggccgccggg ttattagtag aaacaaggta gttt                          34

<210> SEQ ID NO 111
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 111
gggaccatgc cggccagcaa aagcagggtg acaaag                        36

<210> SEQ ID NO 112
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 112
ggccgccggg ttattagtag aaacaagggt gttttttat                     39

<210> SEQ ID NO 113
<211> LENGTH: 27
<212> TYPE: DNA
<213> ORGANISM: Artificial Sequence
<220> FEATURE:
<223> OTHER INFORMATION: artificially synthesized sequence

<400> SEQUENCE: 113
ctaaagctgt cagaggccaa tatagtg                                  27

<210> SEQ ID NO 114
<211> LENGTH: 27
<212> TYPE: DNA
<213> ORGANISM: Artificial Sequence
<220> FEATURE:
<223> OTHER INFORMATION: artificially synthesized sequence

<400> SEQUENCE: 114
tattggcctc tgacagcttt aggcact                                  27

<210> SEQ ID NO 115
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 115
tgccagaggc aaatatagtg ggttcgtg                                 28

<210> SEQ ID NO 116
<211> LENGTH: 28
<212> TYPE: DNA
<213> ORGANISM: Artificial Sequence
<220> FEATURE:
<223> OTHER INFORMATION: artificially synthesized sequence

```
<400> SEQUENCE: 116
cccactatat ttgcctctgg cagcttta                                              28

<210> SEQ ID NO 117
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 117
tgccagaggc agatatagtg ggttcgtg                                              28

<210> SEQ ID NO 118
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 118
cccactatat ctgcctctgg cagcttta                                              28

<210> SEQ ID NO 119
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 119
agtgggttcg tgaggattct attccaacag atg                                        33

<210> SEQ ID NO 120
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 120
catctgttgg aatagaatcc tcacgaaccc act                                        33

<210> SEQ ID NO 121
<211> LENGTH: 29
<212> TYPE: DNA
<213> ORGANISM: Artificial Sequence
<220> FEATURE:
<223> OTHER INFORMATION: artificially synthesized sequence

<400> SEQUENCE: 121
gcagccccgc cgaagcagag taggatgca                                             29

<210> SEQ ID NO 122
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 122
atcctactct gcttcggcgg ggctgctgca                                            30

<210> SEQ ID NO 123
```

<210> SEQ ID NO 123
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 123
gggcaaagaa aataaaagat atgggcca                                    28

<210> SEQ ID NO 124
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 124
ccatatcttt tattttcttt gcccagaatc                                  30

<210> SEQ ID NO 125
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 125
gcggccgcga gctcgaattc tttgccaaaa                                  30

<210> SEQ ID NO 126
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 126
gaggcagatg gggatggact ggaagacgag                                  30

<210> SEQ ID NO 127
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 127
gaattgtgcg gccgcatgga catgaagagg aggatcca                         38

<210> SEQ ID NO 128
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 128
atccccatct gcctcggcat ctgagtcagg tgcttcct                         38

<210> SEQ ID NO 129
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 129
agggtctgag tcagggctt cctgctcatc                                    30

<210> SEQ ID NO 130
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 130
ggcagcggag actacaagga tgacgatgac                                    30

<210> SEQ ID NO 131
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 131
cctgactcag accctgaggt ggatggtgtg gatgaaga                           38

<210> SEQ ID NO 132
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 132
gtagtctccg ctgccatcat cttctccttc atcatctg                           38

<210> SEQ ID NO 133
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 133
gcggccgcga gctcgaattc tttgccaa                                      28

<210> SEQ ID NO 134
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 134
gtgaacttag agttcctcag tttaataaat                                    30

<210> SEQ ID NO 135
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 135
gaattgtgcg gccgcatgga gatgaaaaag cggctcac                           38

<210> SEQ ID NO 136
<211> LENGTH: 38
<212> TYPE: DNA

```
<213> ORGANISM: Artificial Sequence
<220> FEATURE:
<223> OTHER INFORMATION: artificially synthesized sequence

<400> SEQUENCE: 136
gaactctaag ttcacaaaat ctgaagagag cccaacga                              38

<210> SEQ ID NO 137
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 137
aaattcagct gttaagccct caattttttcc                                      30

<210> SEQ ID NO 138
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 138
aagttagaat gtctgaaaag cctggacctc                                       30

<210> SEQ ID NO 139
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 139
ttaacagctg aatttgagaa cctggagttc ctcagcat                              38

<210> SEQ ID NO 140
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 140
cagacattct aactttttca agggttccag ggtattga                              38

<210> SEQ ID NO 141
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 141
tttcaaaggt tccaaggtgc tgatatcttt                                       30

<210> SEQ ID NO 142
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 142
ctcctcctct tcatccacac catccacctc                                       30
```

<210> SEQ ID NO 143
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 143
ttggaacctt tgaaaaagtt gccaaacctg catagtct					38

<210> SEQ ID NO 144
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 144
cacaccatcc acctcagggt ctgagtcagg ggcttcct					38

<210> SEQ ID NO 145
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 145
ctttttcaag ggttccaggg tattgatgtc					30

<210> SEQ ID NO 146
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 146
gaggcagatg gggatggact ggaagacgag					30

<210> SEQ ID NO 147
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 147
gaacccttga aaagttaga atgtctgaaa agcctgga					38

<210> SEQ ID NO 148
<211> LENGTH: 38
<212> TYPE: DNA
<213> ORGANISM: Artificial Sequence
<220> FEATURE:
<223> OTHER INFORMATION: artificially synthesized sequence

<400> SEQUENCE: 148
atccccatct gcctcggcat ctgagtcagg tgcttcct					38

<210> SEQ ID NO 149
<211> LENGTH: 33
<212> TYPE: DNA
<213> ORGANISM: Artificial Sequence
<220> FEATURE:

<223> OTHER INFORMATION: artificially synthesized sequence

<400> SEQUENCE: 149
cctttgaaaa agttaccctg tctgaaaagc ctg                33

<210> SEQ ID NO 150
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 150 caggctttc agacagggta acttttcaa agg                33

<210> SEQ ID NO 151
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 151
aagttagaat gtctgcacag cctggacctc ttt                33

<210> SEQ ID NO 152
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 152
aaagaggtcc aggctgtgca gacattctaa ctt                33

<210> SEQ ID NO 153
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 153
aactgtgagg ttaccatgct gaatgactac cga                33

<210> SEQ ID NO 154
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 154
tcggtagtca ttcagcatgg taacctcaca gtt                33

<210> SEQ ID NO 155
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 155
gaggttacca acctgattaa ctaccgagag agtgtc                36

<210> SEQ ID NO 156
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 156
gacactctct cggtagttaa tcaggttggt aacctc        36

<210> SEQ ID NO 157
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 157
cgagagagtg tcttcaccct cctgccccag ctt        33

<210> SEQ ID NO 158
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 158
aagctggggc aggagggtga agacactctc tcg        33

<210> SEQ ID NO 159
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 159
ttggatggct atgacgctga ggaccaggaa gca        33

<210> SEQ ID NO 160
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 160
tgcttcctgg tcctcagcgt catagccatc caa        33

<210> SEQ ID NO 161
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 161
gcacctgact cagatccgga ggtggatggt gtg        33

<210> SEQ ID NO 162
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 162
cacaccatcc acctccggat ctgagtcagg tgc                33

<210> SEQ ID NO 163
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 163
gaggttacca acctgattga ctaccgagag agt                33

<210> SEQ ID NO 164
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 164
actctctcgg tagtcaatca ggttggtaac ctc                33

<210> SEQ ID NO 165
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 165
gttaccaacc tgaataacta ccgagagagt gtc                33

<210> SEQ ID NO 166
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 166
gacactctct cggtagttat tcaggttggt aac                33

<210> SEQ ID NO 167
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 167
gaggtaacca acctgattga ctaccgagaa aat                33

<210> SEQ ID NO 168
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 168
attttctcgg tagtcaatca ggttggttac ctc                33

<210> SEQ ID NO 169
<211> LENGTH: 33

```
<212> TYPE: DNA
<213> ORGANISM: Artificial Sequence
<220> FEATURE:
<223> OTHER INFORMATION: artificially synthesized sequence

<400> SEQUENCE: 169
gtaaccaacc tgaacaacta ccgagaaaat gtg                                    33

<210> SEQ ID NO 170
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 170
cacattttct cggtagttgt tcaggttggt tac                                    33

<210> SEQ ID NO 171
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 171
gaggtaacca acctgattaa ctaccgagaa aatgtg                                 36

<210> SEQ ID NO 172
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 172
cacattttct cggtagttaa tcaggttggt tacctc                                 36

<210> SEQ ID NO 173
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 173
gaggtaacca acttgattga ttatagagaa aac                                    33

<210> SEQ ID NO 174
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 174
gttttctcta taatcaatca agttggttac ctc                                    33

<210> SEQ ID NO 175
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 175
```
gtaaccaact tgaataacta tagagaaaac gta                               33

<210> SEQ ID NO 176
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 176
tacgttttct ctatagttat tcaagttggt tac                               33

<210> SEQ ID NO 177
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 177
gaggtaacca acttgattaa ctatagagaa aacgta                            36

<210> SEQ ID NO 178
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 178
tacgttttct ctatagttaa tcaagttggt tacctc                            36

<210> SEQ ID NO 179
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 179
gaggtgacga tgctcaataa ctaccgggag agt                               33

<210> SEQ ID NO 180
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 180
actctcccgg tagttattga gcatcgtcac ctc                               33

<210> SEQ ID NO 181
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 181
gtgacgatgc tcatcgacta ccgggagagt gtg                               33

<210> SEQ ID NO 182
<211> LENGTH: 33
<212> TYPE: DNA
<213> ORGANISM: Artificial Sequence

```
<220> FEATURE:
<223> OTHER INFORMATION: artificially synthesized sequence

<400> SEQUENCE: 182
cacactctcc cggtagtcga tgagcatcgt cac                                    33

<210> SEQ ID NO 183
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 183
gaggtgacga tgctcaatga ctaccgggag agtgtg                                 36

<210> SEQ ID NO 184
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 184
cacactctcc cggtagtcat tgagcatcgt cacctc                                 36

<210> SEQ ID NO 185
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 185
gaggtaacca acttggcaga ttatagagaa aac                                    33

<210> SEQ ID NO 186
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 186
gttttctcta taatctgcca agttggttac ctc                                    33

<210> SEQ ID NO 187
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 187
gaggtaacca acttgtgtga ttatagagaa aac                                    33

<210> SEQ ID NO 188
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 188
gttttctcta taatcacaca agttggttac ctc                                    33
```

<210> SEQ ID NO 189
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 189
gaggtaacca acttggacga ttatagagaa aac                          33

<210> SEQ ID NO 190
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 190
gttttctcta taatcgtcca agttggttac ctc                          33

<210> SEQ ID NO 191
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 191
gaggtaacca acttggaaga ttatagagaa aac                          33

<210> SEQ ID NO 192
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 192
gttttctcta taatcttcca agttggttac ctc                          33

<210> SEQ ID NO 193
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 193
gaggtaacca acttgttcga ttatagagaa aac                          33

<210> SEQ ID NO 194
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 194
gttttctcta taatcgaaca agttggttac ctc                          33

<210> SEQ ID NO 195
<211> LENGTH: 33
<212> TYPE: DNA
<213> ORGANISM: Artificial Sequence
<220> FEATURE:
<223> OTHER INFORMATION: artificially synthesized sequence

```
<400> SEQUENCE: 195
gaggtaacca acttgggaga ttatagagaa aac                                33

<210> SEQ ID NO 196
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 196
gttttctcta taatctccca agttggttac ctc                                33

<210> SEQ ID NO 197
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 197
gaggtaacca acttgcacga ttatagagaa aac                                33

<210> SEQ ID NO 198
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 198
gttttctcta taatcgtgca agttggttac ctc                                33

<210> SEQ ID NO 199
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 199
gaggtaacca acttgaagga ttatagagaa aac                                33

<210> SEQ ID NO 200
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 200
gttttctcta taatccttca agttggttac ctc                                33

<210> SEQ ID NO 201
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 201
gaggtaacca acttgctaga ttatagagaa aac                                33

<210> SEQ ID NO 202
```

-continued

```
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 202
gttttctcta taatctagca agttggttac ctc                                33

<210> SEQ ID NO 203
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 203
gaggtaacca acttgatgga ttatagagaa aac                                33

<210> SEQ ID NO 204
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 204
gttttctcta taatccatca agttggttac ctc                                33

<210> SEQ ID NO 205
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 205
gaggtaacca acttgccaga ttatagagaa aac                                33

<210> SEQ ID NO 206
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 206
gttttctcta taatctggca agttggttac ctc                                33

<210> SEQ ID NO 207
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 207
gaggtaacca acttgcaaga ttatagagaa aac                                33

<210> SEQ ID NO 208
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 208
```
gttttctcta taatcttgca agttggttac ctc     33

<210> SEQ ID NO 209
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 209
gaggtaacca acttgagaga ttatagagaa aac     33

<210> SEQ ID NO 210
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 210
gttttctcta taatctctca agttggttac ctc     33

<210> SEQ ID NO 211
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 211
gaggtaacca acttgagcga ttatagagaa aac     33

<210> SEQ ID NO 212
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 212
gttttctcta taatcgctca agttggttac ctc     33

<210> SEQ ID NO 213
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 213
gaggtaacca acttgacaga ttatagagaa aac     33

<210> SEQ ID NO 214
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 214
gttttctcta taatctgtca agttggttac ctc     33

<210> SEQ ID NO 215
<211> LENGTH: 33
<212> TYPE: DNA

<213> ORGANISM: Artificial Sequence
<220> FEATURE:
<223> OTHER INFORMATION: artificially synthesized sequence

<400> SEQUENCE: 215
gaggtaacca acttggtaga ttatagagaa aac                33

<210> SEQ ID NO 216
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 216
gttttctcta taatctacca agttggttac ctc                33

<210> SEQ ID NO 217
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 217
gaggtaacca acttgtggga ttatagagaa aac                33

<210> SEQ ID NO 218
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 218
gttttctcta taatcccaca agttggttac ctc                33

<210> SEQ ID NO 219
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 219
gaggtaacca acttgtacga ttatagagaa aac                33

<210> SEQ ID NO 220
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 220
gttttctcta taatcgtaca agttggttac ctc                33

<210> SEQ ID NO 221
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 221
gtaaccaact tgaatgcata tagagaaaac                30

<210> SEQ ID NO 222
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 222
cgttttctct atatgcattc aagttggtta cc                                    32

<210> SEQ ID NO 223
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 223
gtaaccaact tgaattgtta tagagaaaac                                       30

<210> SEQ ID NO 224
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 224
cgttttctct ataacaattc aagttggtta cct                                   33

<210> SEQ ID NO 225
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 225
gtaaccaact tgaatgaata tagagaaaac                                       30

<210> SEQ ID NO 226
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 226
cgttttctct atattcattc aagttggtta cc                                    32

<210> SEQ ID NO 227
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 227
gtaaccaact tgaatttcta tagagaaaac                                       30

<210> SEQ ID NO 228
<211> LENGTH: 32
<212> TYPE: DNA
<213> ORGANISM: Artificial Sequence
<220> FEATURE:

<223> OTHER INFORMATION: artificially synthesized sequence

<400> SEQUENCE: 228
cgttttctct atagaaattc aagttggtta cc                32

<210> SEQ ID NO 229
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 229
gtaaccaact tgaatggcta tagagaaaac                30

<210> SEQ ID NO 230
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 230
cgttttctct atagccattc aagttggtta cc                32

<210> SEQ ID NO 231
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 231
gtaaccaact tgaatcacta tagagaaaac                30

<210> SEQ ID NO 232
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 232
cgttttctct atagtgattc aagttggtta cc                32

<210> SEQ ID NO 233
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 233
gtaaccaact tgaataagta tagagaaaac                30

<210> SEQ ID NO 234
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 234
cgttttctct atacttattc aagttggtta cc                32

```
<210> SEQ ID NO 235
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 235
gtaaccaact tgaatctata tagagaaaac                                      30

<210> SEQ ID NO 236
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 236
cgttttctct atatagattc aagttggtta cc                                   32

<210> SEQ ID NO 237
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 237
gtaaccaact tgaatatgta tagagaaaac                                      30

<210> SEQ ID NO 238
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 238
cgttttctct atacatattc aagttggtta cc                                   32

<210> SEQ ID NO 239
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 239
gtaaccaact tgaatccata tagagaaaac                                      30

<210> SEQ ID NO 240
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 240
cgttttctct atatggattc aagttggtta cc                                   32

<210> SEQ ID NO 241
<211> LENGTH: 30
<212> TYPE: DNA
<213> ORGANISM: Artificial Sequence
<220> FEATURE:
<223> OTHER INFORMATION: artificially synthesized sequence
```

<400> SEQUENCE: 241
gtaaccaact tgaatcaata tagagaaaac                                             30

<210> SEQ ID NO 242
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 242
cgttttctct atattgattc aagttggtta cc                                          32

<210> SEQ ID NO 243
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 243
gtaaccaact tgaatagata tagagaaaac                                             30

<210> SEQ ID NO 244
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 244
cgttttctct atatctattc aagttggtta cc                                          32

<210> SEQ ID NO 245
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 245
gtaaccaact tgaatagcta tagagaaaac                                             30

<210> SEQ ID NO 246
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 246
cgttttctct atagctattc aagttggtta cc                                          32

<210> SEQ ID NO 247
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 247
gtaaccaact tgaatacata tagagaaaac                                             30

<210> SEQ ID NO 248
<211> LENGTH: 32

```
<212> TYPE: DNA
<213> ORGANISM: Artificial Sequence
<220> FEATURE:
<223> OTHER INFORMATION: artificially synthesized sequence

<400> SEQUENCE: 248
cgttttctct atatgtattc aagttggtta cc                            32

<210> SEQ ID NO 249
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 249
gtaaccaact tgaatgtata tagagaaaac                               30

<210> SEQ ID NO 250
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 250
cgttttctct atatacattc aagttggtta cc                            32

<210> SEQ ID NO 251
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 251
gtaaccaact tgaattggta tagagaaaac                               30

<210> SEQ ID NO 252
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 252
cgttttctct ataccaattc aagttggtta cc                            32

<210> SEQ ID NO 253
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 253
gtaaccaact tgaattacta tagagaaaac                               30

<210> SEQ ID NO 254
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 254
```
cgttttctct atagtaattc aagttggtta cc                                    32

<210> SEQ ID NO 255
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 255
gtaaccaact tgaatatcta tagagaaaac                                       30

<210> SEQ ID NO 256
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 256
cgttttctct atagatattc aagttggtta cc                                    32

<210> SEQ ID NO 257
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 257
tcgcggccgc atggccgccg ccgccgccgc cgccgccgcc ctgaggaacc ggaccccg        58

<210> SEQ ID NO 258
<211> LENGTH: 57
<212> TYPE: DNA
<213> ORGANISM: Artificial Sequence
<220> FEATURE:
<223> OTHER INFORMATION: artificially synthesized sequence

<400> SEQUENCE: 258
ggttcctcag gcggcggcg gcggcggcgg cggcggccat gcggccgcga gctcgaa         57

<210> SEQ ID NO 259
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 259
ccacctggag gccgccgccg ccgccgccgc cgccgccgcc gaacttgtct tggacaat        58

<210> SEQ ID NO 260
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 260
agacaagttc ggcggcggcg gcggcggcgg cggcggcggc ctccaggtgg atcctcct        58

<210> SEQ ID NO 261
<211> LENGTH: 58
<212> TYPE: DNA
<213> ORGANISM: Artificial Sequence

```
<220> FEATURE:
<223> OTHER INFORMATION: artificially synthesized sequence

<400> SEQUENCE: 261
agctgttcga gccgccgccg ccgccgccgc cgccgccgcc gatggaaaaa ttgagggc      58

<210> SEQ ID NO 262
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 262
tttttccatc ggcggcggcg gcggcggcgg cggcggcggc tcgaacagct gccggggt      58

<210> SEQ ID NO 263
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 263
caaatcaaat gccgccgccg ccgccgccgc cgccgccgcc tttgtgaact tagagttc      58

<210> SEQ ID NO 264
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 264
agttcacaaa ggcggcggcg gcggcggcgg cggcggcggc atttgatttg caattgtc      58

<210> SEQ ID NO 265
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 265
aacagctgaa gccgccgccg ccgccgccgc cgccgccgcc aatgtaggct tgatctca      58

<210> SEQ ID NO 266
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 266
agcctacatt ggcggcggcg gcggcggcgg cggcggcggc ttcagctgtt aagccctc      58

<210> SEQ ID NO 267
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 267
cagtttaata gccgccgccg ccgccgccgc cgccgccgcc cccaagctgc ctaaattg      58
```

<210> SEQ ID NO 268
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 268
gcagcttggg ggcggcggcg gcggcggcgg cggcggcggc tattaaactg aggaactc        58

<210> SEQ ID NO 269
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 269
ttcaaatctc gccgccgccg ccgccgccgc cgccgccgcc ctcagtgaaa atagaatc        58

<210> SEQ ID NO 270
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 270
tttcactgag ggcggcggcg gcggcggcgg cggcggcggc gagatttgaa actgagat        58

<210> SEQ ID NO 271
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 271
aaagcttgaa gccgccgccg ccgccgccgc cgccgccgcc gacatgttag ctgaaaaa        58

<210> SEQ ID NO 272
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 272
ctaacatgtc ggcggcggcg gcggcggcgg cggcggcggc ttcaagcttt ttcaattt        58

<210> SEQ ID NO 273
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 273
tggaggtctg gccgccgccg ccgccgccgc cgccgccgcc acacatctaa acttaagt        58

<210> SEQ ID NO 274
<211> LENGTH: 58
<212> TYPE: DNA
<213> ORGANISM: Artificial Sequence
<220> FEATURE:
<223> OTHER INFORMATION: artificially synthesized sequence

```
<400> SEQUENCE: 274
ttagatgtgt ggcggcggcg gcggcggcgg cggcggcggc cagacctcca aagattct      58

<210> SEQ ID NO 275
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 275
tccaaatctc gccgccgccg ccgccgccgc cgccgccgcc aaagatatca gcaccttg      58

<210> SEQ ID NO 276
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 276
tgatatcttt ggcggcggcg gcggcggcgg cggcggcggc gagatttgga agttttc      58

<210> SEQ ID NO 277
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 277
aaataaactg gccgccgccg ccgccgccgc cgccgccgcc aagttagaat gtctgaaa      58

<210> SEQ ID NO 278
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 278
attctaactt ggcggcggcg gcggcggcgg cggcggcggc cagtttattt ccacttaa      58

<210> SEQ ID NO 279
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 279
acctttgaaa gccgccgccg ccgccgccgc cgccgccgcc tttaactgtg aggttacc      58

<210> SEQ ID NO 280
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 280
cacagttaaa ggcggcggcg gcggcggcgg cggcggcggc tttcaaaggt tccaaggt      58

<210> SEQ ID NO 281
```

```
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 281
cctggacctc gccgccgccg ccgccgccgc cgccgccgcc taccgagaga gtgtcttc       58

<210> SEQ ID NO 282
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 282
tctctcggta ggcggcggcg gcggcggcgg cggcggcggc gaggtccagg cttttcag       58

<210> SEQ ID NO 283
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 283
cctgaatgac gccgccgccg ccgccgccgc cgccgccgcc cagcttacct acttggat       58

<210> SEQ ID NO 284
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 284
aggtaagctg ggcggcggcg gcggcggcgg cggcggcggc gtcattcagg ttggtaac       58

<210> SEQ ID NO 285
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 285
gctcctgccc gccgccgccg ccgccgccgc cgccgccgcc gaggaccagg aagcacct       58

<210> SEQ ID NO 286
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 286
cctggtcctc ggcggcggcg gcggcggcgg cggcggcggc gggcaggagc ttgaagac       58

<210> SEQ ID NO 287
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 287
```
ctatgaccga gccgccgccg ccgccgccgc cgccgccgcc gaggtggatg gtgtggat        58

<210> SEQ ID NO 288
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 288
catccacctc ggcggcggcg gcggcggcgg cggcggcggc tcggtcatag ccatccaa        58

<210> SEQ ID NO 289
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 289
ctcagatgcc gccgccgccg ccgccgccgc cgccgccgcc gacgaagaag gagaagat        58

<210> SEQ ID NO 290
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 290
cttcttcgtc ggcggcggcg gcggcggcgg cggcggcggc ggcatctgag tcaggtgc        58

<210> SEQ ID NO 291
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 291
agaggaggag gccgccgccg ccgccgccgc cgccgccgcc gacgatgagg atggtgaa        58

<210> SEQ ID NO 292
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 292
cctcatcgtc ggcggcggcg gcggcggcgg cggcggcggc ctcctcctct tcatccac        58

<210> SEQ ID NO 293
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 293
ggaagacgag gccgccgccg ccgccgccgc cgccgccgcc gatgaagaag atgatgaa        58

<210> SEQ ID NO 294
<211> LENGTH: 58
<212> TYPE: DNA

```
<213> ORGANISM: Artificial Sequence
<220> FEATURE:
<223> OTHER INFORMATION: artificially synthesized sequence

<400> SEQUENCE: 294
cttcttcatc ggcggcggcg cggcggcgg cggcggcggc ctcgtcttcc tcatcttc        58

<210> SEQ ID NO 295
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 295
agaggagttt gccgccgccg ccgccgccgc cgccgccgcc gaagggatg aggacgac         58

<210> SEQ ID NO 296
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 296 catcccttc ggcggcggcg cggcggcgg cggcggcggc aaactcctct tcttcacc         58

<210> SEQ ID NO 297
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 297
tgaagatgta gccgccgccg ccgccgccgc cgccgccgcc gaggaggaag aagaattt        58

<210> SEQ ID NO 298
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 298
cttcctcctc ggcggcggcg cggcggcgg cggcggcggc tacatcttca tcttcatc        58

<210> SEQ ID NO 299
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 299
tgaagtcagt gccgccgccg ccgccgccgc cgccgccgcc gaagatgaag atgaggat        58

<210> SEQ ID NO 300
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 300
cttcatcttc ggcggcggcg cggcggcgg cggcggcggc actgacttca tcgtcgtc        58
```

<210> SEQ ID NO 301
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 301
acttgatgaa gccgccgccg ccgccgccgc cgccgccgcc gaggaagaag gtgggaaa          58

<210> SEQ ID NO 302
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 302
cttcttcctc ggcggcggcg gcggcggcgg cggcggcggc ttcatcaagt ccaaattc          58

<210> SEQ ID NO 303
<211> LENGTH: 57
<212> TYPE: DNA
<213> ORGANISM: Artificial Sequence
<220> FEATURE:
<223> OTHER INFORMATION: artificially synthesized sequence

<400> SEQUENCE: 303
ggatgaagag gccgccgccg ccgccgccgc cgccgccgcc aagagagaaa cagatga           57

<210> SEQ ID NO 304
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 304
tttctctctt ggcggcggcg gcggcggcgg cggcggcggc ctcttcatcc tcatcctc          58

<210> SEQ ID NO 305
<211> LENGTH: 59
<212> TYPE: DNA
<213> ORGANISM: Artificial Sequence
<220> FEATURE:
<223> OTHER INFORMATION: artificially synthesized sequence

<400> SEQUENCE: 305
tgaaaagagg gccgccgccg ccgccgccgc cgccgccgcc gccggcagcg gagactaca         59

<210> SEQ ID NO 306
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 306
ctccgctgcc ggcggcggcg gcggcggcgg cggcggcggc ggccctctttt tcacctttt       58

<210> SEQ ID NO 307
<211> LENGTH: 59
<212> TYPE: DNA
<213> ORGANISM: Artificial Sequence
<220> FEATURE:

<223> OTHER INFORMATION: artificially synthesized sequence

<400> SEQUENCE: 307
tcgcggccgc atggccgccg ccgccgccgc cgccgccgcc ctgcggaaca ggacgccct    59

<210> SEQ ID NO 308
<211> LENGTH: 60
<212> TYPE: DNA
<213> ORGANISM: Artificial Sequence
<220> FEATURE:
<223> OTHER INFORMATION: artificially synthesized sequence

<400> SEQUENCE: 308
tcctgttccg cagggcggcg gcggcggcgg cggcggcggc catgcggccg cgagctcgaa    60

<210> SEQ ID NO 309
<211> LENGTH: 59
<212> TYPE: DNA
<213> ORGANISM: Artificial Sequence
<220> FEATURE:
<223> OTHER INFORMATION: artificially synthesized sequence

<400> SEQUENCE: 309
ggatccactt agaggccgcc gccgccgccg ccgccgccgc cgccgaactt gttcttgac    59

<210> SEQ ID NO 310
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 310
aagaacaagt tcggcggcgg cggcggcggc ggcggcggcg gcctctaagt ggatcctt    58

<210> SEQ ID NO 311
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 311
cagatgttaa ggccgccgcc gccgccgccg ccgccgccgc cgaaggcaaa attgaagg    58

<210> SEQ ID NO 312
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 312
aattttgcct tcggcggcgg cggcggcggc ggcggcggcg gccttaacat ctgagggc    58

<210> SEQ ID NO 313
<211> LENGTH: 59
<212> TYPE: DNA
<213> ORGANISM: Artificial Sequence
<220> FEATURE:
<223> OTHER INFORMATION: artificially synthesized sequence

<400> SEQUENCE: 313
ctgtaggtca tacgccgccg ccgccgccgc cgccgccgcc gcctttgaag agctggaat    59

-continued

```
<210> SEQ ID NO 314
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 314
agctcttcaa aggcggcggc ggcggcggcg gcggcggcgg cgtatgacct acagttgt         58

<210> SEQ ID NO 315
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 315
ttacagatga ggccgccgcc gccgccgccg ccgccgccgc caacgtaggc ttagcctc         58

<210> SEQ ID NO 316
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 316
taagcctacg ttggcggcgg cggcggcggc ggcggcggcg gcctcatctg taaggcct         58

<210> SEQ ID NO 317
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 317
tgagtacaat cgccgccgcc gccgccgccg ccgccgccgc cccaaagtta aacaaact         58

<210> SEQ ID NO 318
<211> LENGTH: 59
<212> TYPE: DNA
<213> ORGANISM: Artificial Sequence
<220> FEATURE:
<223> OTHER INFORMATION: artificially synthesized sequence

<400> SEQUENCE: 318
ttaactttgg ggcggcggcg gcggcggcgg cggcggcggc gattgtactc aagaattcc        59

<210> SEQ ID NO 319
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 319
tgcaaactta gccgccgccg ccgccgccgc cgccgccgcc ctaagtgaca acagagtc         58

<210> SEQ ID NO 320
<211> LENGTH: 58
<212> TYPE: DNA
<213> ORGANISM: Artificial Sequence
<220> FEATURE:
<223> OTHER INFORMATION: artificially synthesized sequence
```

<400> SEQUENCE: 320
ttgtcactta gggcggcggc ggcggcggcg gcggcggcgg ctaagtttgc aactgagg            58

<210> SEQ ID NO 321
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 321
gaagctcgaa gccgccgccg ccgccgccgc cgccgccgcc gaagtgttgg cagaaaag            58

<210> SEQ ID NO 322
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 322
ccaacacttc ggcggcggcg gcggcggcgg cggcggcggc ttcgagcttc ttaagttt            58

<210> SEQ ID NO 323
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 323
aggaggactg gccgccgccg ccgccgccgc cgccgccgcc acgcatctaa atctaagt            58

<210> SEQ ID NO 324
<211> LENGTH: 57
<212> TYPE: DNA
<213> ORGANISM: Artificial Sequence
<220> FEATURE:
<223> OTHER INFORMATION: artificially synthesized sequence

<400> SEQUENCE: 324
tttagatgcg tggcggcggc ggcggcggcg gcggcggcgg ccagtcctcc tgagact            57

<210> SEQ ID NO 325
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 325
tccaaacctc gccgccgccg ccgccgccgc cgccgccgcc aaagatcttg gtacaata            58

<210> SEQ ID NO 326
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 326
ccaagatctt tggcggcggc ggcggcggcg gcggcggcgg cgaggtttgg acacttt             58

<210> SEQ ID NO 327
<211> LENGTH: 58

-continued

```
<212> TYPE: DNA
<213> ORGANISM: Artificial Sequence
<220> FEATURE:
<223> OTHER INFORMATION: artificially synthesized sequence

<400> SEQUENCE: 327
ggcaacaaaa tagccgccgc cgccgccgcc gccgccgccg ccaagttaga aaacctga       58

<210> SEQ ID NO 328
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 328
ttttctaact tggcggcggc ggcggcggcg gcggcggcgg ctattttgtt gccactta       58

<210> SEQ ID NO 329
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 329
acctctgaaa gccgccgccg ccgccgccgc cgccgccgcc ttcaattgcg aggtaacc       58

<210> SEQ ID NO 330
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 330
cgcaattgaa ggcggcggcg gcggcggcgg cggcggcggc tttcagaggt tctattgt       58

<210> SEQ ID NO 331
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 331
tttagatctt gccgccgccg ccgccgccgc cgccgccgcc tatagagaaa acgtattc       58

<210> SEQ ID NO 332
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 332
tttctctata ggcggcggcg gcggcggcgg cggcggcggc aagatctaaa ctcttcag       58

<210> SEQ ID NO 333
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 333
```
acttgaatga tgccgccgcc gccgccgccg ccgccgccgc ccaactcaca tacctcga    58

<210> SEQ ID NO 334
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 334
atgtgagttg ggcggcggcg gcggcggcgg cggcggcggc atcattcaag ttggttac    58

<210> SEQ ID NO 335
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 335
gctcctccca gccgccgccg ccgccgccgc cgccgccgcc gatgacaaag aagcacca    58

<210> SEQ ID NO 336
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 336
tctttgtcat cggcggcggc ggcggcggcg gcggcggcgg ctgggaggag cttgaata    58

<210> SEQ ID NO 337
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 337
ctacgatcgg gccgccgccg ccgccgccgc cgccgccgcc gagggctacg tggagggc    58

<210> SEQ ID NO 338
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 338
cgtagccctc ggcggcggcg gcggcggcgg cggcggcggc ccgatcgtag ccatcgag    58

<210> SEQ ID NO 339
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 339
ctctgatgca gccgccgccg ccgccgccgc cgccgccgcc gaggaagatg aagatgtc    58

<210> SEQ ID NO 340
<211> LENGTH: 58
<212> TYPE: DNA
<213> ORGANISM: Artificial Sequence

```
<220> FEATURE:
<223> OTHER INFORMATION: artificially synthesized sequence

<400> SEQUENCE: 340
catcttcctc ggcggcggcg gcggcggcgg cggcggcggc tgcatcagag tctggtgc        58

<210> SEQ ID NO 341
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 341
agacgatgag gccgccgccg ccgccgccgc cgccgccgcc aaagatcggg atgacaaa       58

<210> SEQ ID NO 342
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 342
cccgatcttt ggcggcggcg gcggcggcgg cggcggcggc ctcatcgtct aagccctc       58

<210> SEQ ID NO 343
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 343
atctctagtg gccgccgccg ccgccgccgc cgccgccgcc tctgatgcag agggctac       58

<210> SEQ ID NO 344
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 344
ctgcatcaga ggcggcggcg gcggcggcgg cggcggcggc cactagagat aagacatc       58

<210> SEQ ID NO 345
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 345
agcaccggac gccgccgccg ccgccgccgc cgccgccgcc gacgacgagg aggaagat       58

<210> SEQ ID NO 346
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 346
cctcgtcgtc ggcggcggcg gcggcggcgg cggcggcggc gtccggtgct tctttgtc       58
```

<210> SEQ ID NO 347
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 347
ggaaggctta gccgccgccg ccgccgccgc cgccgccgcc gagtatgacg atgatgct      58

<210> SEQ ID NO 348
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 348
cgtcatactc ggcggcggcg gcggcggcgg cggcggcggc taagccttcc acgtagcc      58

<210> SEQ ID NO 349
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 349
agacgaagag gccgccgccg ccgccgccgc cgccgccgcc gatgaagagg atgaggag      58

<210> SEQ ID NO 350
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 350
cctcttcatc ggcggcggcg gcggcggcgg cggcggcggc ctcttcgtct tcatcttc      58

<210> SEQ ID NO 351
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 351
ggtagtagaa gccgccgccg ccgccgccgc cgccgccgcc ggagaagagg aggacgta      58

<210> SEQ ID NO 352
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 352
cctcttctcc ggcggcggcg gcggcggcgg cggcggcggc ttctactacc tgagcatc      58

<210> SEQ ID NO 353
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 353
ggaagaggaa gccgccgccg ccgccgccgc cgccgccgcc gaggaggatg aggaaggc    58

<210> SEQ ID NO 354
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 354
catcctcctc ggcggcggcg gcggcggcgg cggcggcggc ttcctcttcc tcctcctc    58

<210> SEQ ID NO 355
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 355
cggagaggaa gccgccgccg ccgccgccgc cgccgccgcc gacgtagatg atgatgaa    58

<210> SEQ ID NO 356
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 356
catctacgtc ggcggcggcg gcggcggcgg cggcggcggc ttcctctccg cttacgtc    58

<210> SEQ ID NO 357
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 357
taatgatggt gccgccgccg ccgccgccgc cgccgccgcc cccgatgaag aacgggga    58

<210> SEQ ID NO 358
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 358
cttcatcggg ggcggcggcg gcggcggcgg cggcggcggc accatcatta tagccttc    58

<210> SEQ ID NO 359
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 359
tgaagaagaa gccgccgccg ccgccgccgc cgccgccgcc cgagaacccg aagacgaa    58

<210> SEQ ID NO 360

```
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 360
cgggttctcg gcggcggcg gcggcggcgg cggcggcggc ttcttcttca tcttcatc        58

<210> SEQ ID NO 361
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 361
gaagaggaaa gccgccgccg ccgccgccgc cgccgccgcc gccggcagcg gagactac        58

<210> SEQ ID NO 362
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 362
ctccgctgcc ggcggcggcg gcggcggcgg cggcggcggc ggctttcctc ttctgtcc        58

<210> SEQ ID NO 363
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 363
ttatctctag tgaaagcccg ggatgacaaa gaa        33

<210> SEQ ID NO 364
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 364
ttctttgtca tcccgggctt tcactagaga taa        33

<210> SEQ ID NO 365
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 365
tctctagtga aagatgccga tgacaaagaa gca        33

<210> SEQ ID NO 366
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 366
```
tgcttctttg tcatcggcat ctttcactag aga                             33

<210> SEQ ID NO 367
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 367
ctagtgaaag atcgggccga caaagaagca ccg                             33

<210> SEQ ID NO 368
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 368
cggtgcttct ttgtcggccc gatctttcac tag                             33

<210> SEQ ID NO 369
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 369
gtgaaagatc gggatgccaa agaagcaccg gac                             33

<210> SEQ ID NO 370
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 370
gtccggtgct tctttggcat cccgatcttt cac                             33

<210> SEQ ID NO 371
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 371
aaagatcggg atgacgccga agcaccggac tct                             33

<210> SEQ ID NO 372
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 372
agagtccggt gcttcggcgt catcccgatc ttt                             33

<210> SEQ ID NO 373
<211> LENGTH: 33
<212> TYPE: DNA

```
<213> ORGANISM: Artificial Sequence
<220> FEATURE:
<223> OTHER INFORMATION: artificially synthesized sequence

<400> SEQUENCE: 373
gatcgggatg acaaagccgc accggactct gat                                    33

<210> SEQ ID NO 374
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 374
atcagagtcc ggtgcggctt tgtcatcccg atc                                    33

<210> SEQ ID NO 375
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 375
tgatctcagt ttcaaatgcc cccaaggccc ctaaattgaa aaagcttgaa ctcagtga         58

<210> SEQ ID NO 376
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 376 aagcttttc aatttagggg ccttgggggc atttgaaact gagatcaagc ctacattt          58

<210> SEQ ID NO 377
<211> LENGTH: 57
<212> TYPE: DNA
<213> ORGANISM: Artificial Sequence
<220> FEATURE:
<223> OTHER INFORMATION: artificially synthesized sequence

<400> SEQUENCE: 377
agctgaaaaa gccccaaatg ccacacatgc caacgccagt ggaaataaac tgaaaga          57

<210> SEQ ID NO 378
<211> LENGTH: 58
<212> TYPE: DNA
<213> ORGANISM: Artificial Sequence
<220> FEATURE:
<223> OTHER INFORMATION: artificially synthesized sequence

<400> SEQUENCE: 378
ttatttccac tggcgttggc atgtgtggca tttggggctt tttcagctaa catgtcca         58

<210> SEQ ID NO 379
<211> LENGTH: 57
<212> TYPE: DNA
<213> ORGANISM: Artificial Sequence
<220> FEATURE:
<223> OTHER INFORMATION: artificially synthesized sequence

<400> SEQUENCE: 379
gaacctttga aaaggccga atgtgccaaa agcgccgacc tctttaactg tgaggtt          57
```

<210> SEQ ID NO 380
<211> LENGTH: 57
<212> TYPE: DNA
<213> ORGANISM: Artificial Sequence
<220> FEATURE:
<223> OTHER INFORMATION: artificially synthesized sequence

<400> SEQUENCE: 380
ttaaagaggt cggcgctttt ggcacattcg gcctttttca aaggttccaa ggtgctg    57

<210> SEQ ID NO 381
<211> LENGTH: 20
<212> TYPE: DNA
<213> ORGANISM: Artificial Sequence
<220> FEATURE:
<223> OTHER INFORMATION: artificially synthesized sequence

<400> SEQUENCE: 381
ccaacctgaa cgactaccga                                              20

<210> SEQ ID NO 382
<211> LENGTH: 20
<212> TYPE: DNA
<213> ORGANISM: Artificial Sequence
<220> FEATURE:
<223> OTHER INFORMATION: artificially synthesized sequence

<400> SEQUENCE: 382
ctctcggtag tcattcaggt                                              20

<210> SEQ ID NO 383
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 383
tctcggtagt cgttcaggtg ttttagagct agaaat                            36

<210> SEQ ID NO 384
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 384
acctgaacga ctaccgagac ggtgtttcgt cctttc                            36

<210> SEQ ID NO 385
<211> LENGTH: 80
<212> TYPE: DNA
<213> ORGANISM: Artificial Sequence
<220> FEATURE:
<223> OTHER INFORMATION: artificially synthesized sequence

<400> SEQUENCE: 385
tgagttgcgg gaggagcttg aacacatttt ctcggtagtt aatcaggttg gttacctcgc    60
aattgaaaag gtctaagctc                                              80

<210> SEQ ID NO 386
<211> LENGTH: 39
<212> TYPE: DNA

```
<213> ORGANISM: Artificial Sequence
<220> FEATURE:
<223> OTHER INFORMATION: artificially synthesized sequence

<400> SEQUENCE: 386
tctcggtagt cattcaggtg ttttagagct agaaatagc                    39

<210> SEQ ID NO 387
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 387
acctgaatga ctaccgagac ggtgtttcgt cctttc                       36

<210> SEQ ID NO 388
<211> LENGTH: 80
<212> TYPE: DNA
<213> ORGANISM: Artificial Sequence
<220> FEATURE:
<223> OTHER INFORMATION: artificially synthesized sequence

<400> SEQUENCE: 388
taagctgggg caggagcttg aagacactct ctcggtagtt aatcaggttg gtaacctcac    60
agttaaagag gtccaggctt                                         80

<210> SEQ ID NO 389
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 389
ccaaagttaa acaaacttaa gaagcttgaa ctaagc                       36

<210> SEQ ID NO 390
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 390
ttagtcatca tcttctccct catcttcagg ttct                         34

<210> SEQ ID NO 391
<211> LENGTH: 29
<212> TYPE: DNA
<213> ORGANISM: Artificial Sequence
<220> FEATURE:
<223> OTHER INFORMATION: artificially synthesized sequence

<400> SEQUENCE: 391
agctgcctaa attgaaaaag cttgaactc                               29

<210> SEQ ID NO 392
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 392
```

-continued ttaatcatct ctccttcat catctgtttc tctc    34

<210> SEQ ID NO 393
<211> LENGTH: 31
<212> TYPE: DNA
<213> ORGANISM: Artificial Sequence
<220> FEATURE:
<223> OTHER INFORMATION: artificially synthesized sequence

<400> SEQUENCE: 393
ctaaccggat taactaccga gaaactgtct t    31

<210> SEQ ID NO 394
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 394
tcggtagtta atccggttag tgacctcaca    30

<210> SEQ ID NO 395
<211> LENGTH: 262
<212> TYPE: PRT
<213> ORGANISM: Gallus gallus

<400> SEQUENCE: 395

Met Glu Met Lys Lys Arg Leu Thr Leu Glu Leu Arg Asn Lys Lys Pro
1               5                   10                  15

Gly Glu Val Lys Glu Leu Val Leu Asp Asn Cys Arg Ser Asp Asp Gly
            20                  25                  30

Lys Ile Val Gly Leu Ser Ser Asp Phe Glu Asn Leu Glu Phe Leu Ser
        35                  40                  45

Met Ile Asn Val Asn Leu Leu Ser Ile Ser Asn Leu Pro Lys Leu Asn
    50                  55                  60

Lys Leu Arg Lys Leu Glu Leu Ser Asp Asn Arg Ile Ser Gly Gly Leu
65                  70                  75                  80

Glu Val Leu Ala Glu Arg Thr Pro Asn Leu Thr His Leu Asn Leu Ser
                85                  90                  95

Gly Asn Lys Ile Lys Asp Ile Asn Thr Leu Glu Pro Leu Lys Lys Leu
            100                 105                 110

Pro Asn Leu His Ser Leu Asp Leu Phe Asn Cys Glu Val Thr Met Leu
        115                 120                 125

Ile Asn Tyr Arg Glu Ser Val Phe Thr Leu Leu Pro Gln Leu Thr Tyr
    130                 135                 140

Leu Asp Gly Phe Asp Ala Asp Glu Gln Glu Ala Pro Asp Ser Asp Pro
145                 150                 155                 160

Glu Ala Asp Gly Asp Gly Leu Glu Asp Glu Tyr Glu Asn Gly Glu Gly
                165                 170                 175

Glu Glu Glu Glu Asp Asp Glu Glu Asp Leu Asp Glu Glu Val
            180                 185                 190

Ile Asp Glu Glu Asp Asp Glu Asp Asp Leu Glu Gly Glu Glu
        195                 200                 205

Glu Asp Gly Val Asp Glu Glu Glu Asp Glu Glu Asp Gly Glu
    210                 215                 220

Asp Glu Glu Asp Asp Glu Ala Asp Asp Leu Pro Arg Gly Glu Lys
225                 230                 235                 240

Arg Lys Arg Asn Leu Glu Asp Glu Gly Glu Glu Asp Pro Glu Asp Glu
            245                 250                 255

Glu Asp Asp Glu Asp Asp
            260

<210> SEQ ID NO 396
<211> LENGTH: 251
<212> TYPE: PRT
<213> ORGANISM: Homo sapiens

<400> SEQUENCE: 396

Met Asp Met Lys Arg Arg Ile His Leu Glu Leu Arg Asn Arg Thr Pro
1               5                   10                  15

Ala Ala Val Arg Glu Leu Val Leu Asp Asn Cys Lys Ser Asn Asp Gly
            20                  25                  30

Lys Ile Glu Gly Leu Thr Ala Glu Phe Val Asn Leu Glu Phe Leu Ser
        35                  40                  45

Leu Ile Asn Val Gly Leu Ile Ser Val Ser Asn Leu Pro Lys Leu Pro
    50                  55                  60

Lys Leu Lys Lys Leu Glu Leu Ser Glu Asn Arg Ile Phe Gly Gly Leu
65                  70                  75                  80

Asp Met Leu Ala Glu Lys Leu Pro Asn Leu Thr His Leu Asn Leu Ser
                85                  90                  95

Gly Asn Lys Leu Lys Asp Ile Ser Thr Leu Glu Pro Leu Lys Lys Leu
            100                 105                 110

Glu Cys Leu Lys Ser Leu Asp Leu Phe Asn Cys Glu Val Thr Asn Leu
        115                 120                 125

Asn Asp Tyr Arg Glu Ser Val Phe Lys Leu Leu Pro Gln Leu Thr Tyr
    130                 135                 140

Leu Asp Gly Tyr Asp Arg Glu Asp Gln Glu Ala Pro Asp Ser Asp Ala
145                 150                 155                 160

Glu Val Asp Gly Val Asp Glu Glu Asp Glu Glu Gly Glu Asp
            165                 170                 175

Glu Glu Asp Glu Asp Asp Glu Asp Gly Glu Glu Glu Glu Phe Asp Glu
            180                 185                 190

Glu Asp Asp Glu Asp Glu Asp Val Glu Gly Asp Glu Asp Asp Glu
            195                 200                 205

Val Ser Glu Glu Glu Glu Phe Gly Leu Asp Glu Glu Asp Glu Asp
            210                 215                 220

Glu Asp Glu Asp Glu Glu Glu Gly Gly Lys Gly Glu Lys Arg
225                 230                 235                 240

Lys Arg Glu Thr Asp Asp Glu Gly Glu Asp Asp
            245                 250

<210> SEQ ID NO 397
<211> LENGTH: 261
<212> TYPE: PRT
<213> ORGANISM: Sus scrofa

<400> SEQUENCE: 397

Met Asp Met Lys Lys Arg Ile His Leu Glu Leu Arg Asn Arg Thr Pro
1               5                   10                  15

Ala Ala Val Arg Glu Leu Val Leu Asp Asn Cys Lys Ser Ser Asp Gly
            20                  25                  30

Lys Ile Glu Gly Leu Thr Ala Glu Phe Val Asn Leu Glu Phe Leu Ser
        35                  40                  45

```
Leu Ile Asn Val Gly Leu Ile Ser Val Ser Asn Leu Pro Lys Leu Pro
 50                  55                  60
Lys Leu Lys Lys Leu Glu Leu Ser Asp Asn Arg Ile Tyr Gly Gly Leu
 65                  70                  75                  80
Asp Met Leu Ala Glu Lys Leu Pro Asn Leu Thr His Leu Asn Leu Ser
                 85                  90                  95
Gly Asn Lys Leu Lys Asp Ile Ser Thr Leu Glu Pro Leu Lys Lys Leu
                100                 105                 110
Glu Cys Leu Lys Ser Leu Asp Leu Phe Asn Cys Glu Val Thr Asn Leu
                115                 120                 125
Asn Asp Tyr Arg Glu Ser Val Phe Lys Leu Leu Pro Gln Leu Ser Tyr
                130                 135                 140
Leu Asp Gly Tyr Asp Arg Asp Asp Gly Glu Ala Pro Asp Ser Asp Ala
145                 150                 155                 160
Glu Val Asp Gly Val Asp Glu Glu Asp Glu Glu Gly Glu Asp
                    165                 170                 175
Glu Asp Lys Glu Glu Glu Asp Gly Glu Glu Glu Phe Asp Asp
                180                 185                 190
Glu Glu Asp Glu Asp Glu Asp Val Glu Gly Glu Asp
                195                 200                 205
Asp Glu Val Ser Gly Glu Glu Glu Phe Gly His Asp Gly Glu Val
210                 215                 220
Asp Glu Asp Glu Asp Glu Asp Glu Asp Glu Asp Glu Glu
225                 230                 235                 240
Glu Glu Glu Asn Glu Lys Gly Glu Lys Arg Lys Arg Glu Thr Asp Asp
                245                 250                 255
Glu Gly Glu Asp Asp
                260

<210> SEQ ID NO 398
<211> LENGTH: 52
<212> TYPE: PRT
<213> ORGANISM: Gallus gallus

<400> SEQUENCE: 398

Lys Lys Leu Pro Asn Leu His Ser Leu Asp Leu Phe Asn Cys Glu Val
 1               5                  10                  15
Thr Met Leu Ile Asn Tyr Arg Glu Ser Val Phe Thr Leu Leu Pro Gln
                 20                  25                  30
Leu Thr Tyr Leu Asp Gly Phe Asp Ala Asp Glu Gln Glu Ala Pro Asp
                 35                  40                  45
Ser Asp Pro Glu
     50

<210> SEQ ID NO 399
<211> LENGTH: 52
<212> TYPE: PRT
<213> ORGANISM: Homo sapiens

<400> SEQUENCE: 399

Lys Lys Leu Glu Cys Leu Lys Ser Leu Asp Leu Phe Asn Cys Glu Val
 1               5                  10                  15
Thr Asn Leu Asn Asp Tyr Arg Glu Ser Val Phe Lys Leu Leu Pro Gln
                 20                  25                  30
Leu Thr Tyr Leu Asp Gly Tyr Asp Arg Glu Asp Gln Glu Ala Pro Asp
                 35                  40                  45
```

Ser Asp Ala Glu
    50

<210> SEQ ID NO 400
<211> LENGTH: 52
<212> TYPE: PRT
<213> ORGANISM: Sus scrofa

<400> SEQUENCE: 400

Lys Lys Leu Glu Cys Leu Lys Ser Leu Asp Leu Phe Asn Cys Glu Val
1               5                   10                  15

Thr Asn Leu Asn Asp Tyr Arg Glu Ser Val Phe Lys Leu Leu Pro Gln
            20                  25                  30

Leu Ser Tyr Leu Asp Gly Tyr Asp Arg Asp Gly Glu Ala Pro Asp
        35                  40                  45

Ser Asp Ala Glu
    50

<210> SEQ ID NO 401
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 401
gaggtaacca acctgaacga ctaccgagaa aatgtg                          36

<210> SEQ ID NO 402
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 402
gaggtaacca acctgattaa ctaccgagaa aatgtg                          36

<210> SEQ ID NO 403
<211> LENGTH: 12
<212> TYPE: PRT
<213> ORGANISM: Artificial Sequence
<220> FEATURE:
<223> OTHER INFORMATION: artificially synthesized sequence

<400> SEQUENCE: 403

Glu Val Thr Asn Leu Ile Asn Tyr Arg Glu Asn Val
1               5                   10

<210> SEQ ID NO 404
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 404
gaggttacca acctgaatga ctaccgagag agtgtc                          36

<210> SEQ ID NO 405
<211> LENGTH: 36
<212> TYPE: DNA
<213> ORGANISM: Artificial Sequence
<220> FEATURE:

-continued

<223> OTHER INFORMATION: artificially synthesized sequence

<400> SEQUENCE: 405
gaggttacca atctgaatga ctaccgagag agtgtc                36

<210> SEQ ID NO 406
<211> LENGTH: 12
<212> TYPE: PRT
<213> ORGANISM: Artificial Sequence
<220> FEATURE:
<223> OTHER INFORMATION: artificially synthesized sequence

<400> SEQUENCE: 406

Glu Val Thr Asn Leu Asn Asp Tyr Arg Glu Asn Val
1               5                   10

<210> SEQ ID NO 407
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 407
gaggttacca acctgattaa ctaccgagag agtgtc                36

<210> SEQ ID NO 408
<211> LENGTH: 141
<212> TYPE: PRT
<213> ORGANISM: Gallus gallus

<400> SEQUENCE: 408

Leu Pro Lys Leu Asn Lys Leu Lys Leu Glu Leu Ser Asp Asn Arg
1               5                   10                  15

Val Ser Gly Gly Leu Glu Val Leu Ala Glu Lys Cys Pro Asn Leu Thr
            20                  25                  30

His Leu Asn Leu Ser Gly Asn Lys Ile Lys Asp Leu Gly Thr Ile Glu
        35                  40                  45

Pro Leu Lys Lys Leu Glu Asn Leu Lys Ser Leu Asp Leu Phe Asn Cys
    50                  55                  60

Glu Val Thr Asn Leu Asn Asp Tyr Arg Glu Asn Val Phe Lys Leu Leu
65                  70                  75                  80

Pro Gln Leu Thr Tyr Leu Asp Gly Tyr Asp Arg Asp Lys Glu Ala
                85                  90                  95

Pro Asp Ser Asp Ala Glu Gly Tyr Val Glu Gly Leu Asp Asp Glu Glu
            100                 105                 110

Glu Asp Glu Asp Val Leu Ser Leu Val Lys Asp Arg Asp Asp Lys Glu
        115                 120                 125

Ala Pro Asp Ser Asp Ala Glu Gly Tyr Val Glu Gly Leu
    130                 135                 140

<210> SEQ ID NO 409
<211> LENGTH: 137
<212> TYPE: PRT
<213> ORGANISM: Anas platyrhynchos

<400> SEQUENCE: 409

Leu Pro Lys Leu Asn Lys Leu Lys Leu Glu Leu Ser Asp Asn Arg
1               5                   10                  15

Ile Ser Gly Gly Leu Glu Val Leu Ala Glu Lys Cys Pro Asn Leu Thr
            20                  25                  30

```
His Leu Asn Leu Ser Gly Asn Lys Ile Lys Asp Leu Gly Thr Ile Glu
        35                  40                  45

Pro Leu Lys Lys Leu Glu Asn Leu Lys Ser Leu Asp Leu Phe Asn Cys
    50                  55                  60

Glu Val Thr Asn Leu Asn Asp Tyr Arg Glu Asn Val Phe Lys Leu Leu
65                  70                  75                  80

Pro Gln Leu Thr Tyr Leu Asp Gly Tyr Asp Arg Asp Lys Glu Ala
            85                  90                  95

Pro Asp Ser Asp Ala Glu Gly Tyr Val Glu Gly Leu Asp Glu Glu
            100                 105                 110

Glu Asp Glu Asp Val Lys Asp Arg Asp Lys Glu Ala Pro Asp Ser
            115                 120                 125

Asp Ala Glu Gly Tyr Val Glu Gly Leu
            130                 135

<210> SEQ ID NO 410
<211> LENGTH: 141
<212> TYPE: PRT
<213> ORGANISM: Meleagris gallopavo

<400> SEQUENCE: 410

Leu Pro Lys Leu Asn Lys Leu Lys Lys Leu Glu Leu Ser Asp Asn Arg
1               5                   10                  15

Val Ser Gly Gly Leu Glu Val Leu Ala Glu Lys Cys Pro Asn Leu Thr
            20                  25                  30

His Leu Asn Leu Ser Gly Asn Lys Ile Lys Asp Leu Gly Thr Ile Glu
        35                  40                  45

Pro Leu Lys Lys Leu Glu Asn Leu Lys Ser Leu Asp Leu Phe Asn Cys
    50                  55                  60

Glu Val Thr Asn Leu Asn Asp Tyr Arg Glu Asn Val Phe Lys Leu Leu
65                  70                  75                  80

Pro Gln Leu Thr Tyr Leu Asp Gly Tyr Asp Arg Asp Lys Glu Ala
            85                  90                  95

Pro Asp Ser Asp Ala Glu Gly Tyr Val Glu Gly Leu Asp Glu Glu
            100                 105                 110

Glu Asp Glu Asp Val Leu Ser Leu Val Lys Asp Arg Asp Lys Glu
            115                 120                 125

Ala Pro Asp Ser Asp Ala Glu Gly Tyr Val Glu Gly Leu
        130                 135                 140

<210> SEQ ID NO 411
<211> LENGTH: 141
<212> TYPE: PRT
<213> ORGANISM: Taeniopygia guttata

<400> SEQUENCE: 411

Leu Pro Lys Leu Asn Lys Leu Lys Lys Leu Glu Leu Gly Asp Asn Arg
1               5                   10                  15

Ile Ser Gly Gly Leu Glu Val Leu Ala Glu Lys Cys Pro Asn Leu Thr
            20                  25                  30

His Leu Asn Leu Ser Gly Asn Lys Leu Lys Asp Leu Gly Thr Ile Glu
        35                  40                  45

Pro Leu Lys Lys Leu Glu Asn Leu Lys Ser Leu Asp Leu Phe Asn Cys
    50                  55                  60

Glu Val Thr Asn Leu Asn Asp Tyr Arg Glu Asn Val Phe Lys Leu Leu
65                  70                  75                  80
```

```
Pro Gln Leu Thr Tyr Leu Asp Gly Tyr Asp Arg Asp Lys Glu Ala
                 85                  90                  95

Pro Asp Ser Asp Ala Glu Gly Tyr Val Glu Leu Asp Asp Lys Glu
            100                 105                 110

Glu Asp Glu Asp Val Leu Ser Leu Val Lys Asp Arg Asp Asp Lys Glu
        115                 120                 125

Ala Pro Asp Ser Asp Ala Glu Gly Tyr Val Glu Gly Leu
    130                 135                 140

<210> SEQ ID NO 412
<211> LENGTH: 130
<212> TYPE: PRT
<213> ORGANISM: Homo sapiens

<400> SEQUENCE: 412

Phe Val Asn Leu Glu Phe Leu Ser Leu Ile Asn Val Gly Leu Ile Ser
1               5                   10                  15

Val Ser Asn Leu Pro Lys Leu Pro Lys Leu Lys Leu Glu Leu Ser
            20                  25                  30

Glu Asn Arg Ile Phe Gly Gly Leu Asp Met Leu Ala Glu Lys Leu Pro
        35                  40                  45

Asn Leu Thr His Leu Asn Leu Ser Gly Asn Lys Leu Lys Asp Ile Ser
    50                  55                  60

Thr Leu Glu Pro Leu Lys Lys Leu Glu Cys Leu Lys Ser Leu Asp Leu
65                  70                  75                  80

Phe Asn Cys Glu Val Thr Asn Leu Asn Asp Tyr Arg Glu Ser Val Phe
                85                  90                  95

Lys Leu Leu Pro Gln Leu Thr Tyr Leu Asp Gly Tyr Asp Arg Glu Asp
            100                 105                 110

Gln Glu Ala Pro Asp Ser Asp Ala Glu Val Asp Gly Val Asp Glu Glu
        115                 120                 125

Glu Glu
    130

<210> SEQ ID NO 413
<211> LENGTH: 130
<212> TYPE: PRT
<213> ORGANISM: Gallus gallus

<400> SEQUENCE: 413

Phe Glu Asn Leu Glu Phe Leu Ser Met Ile Asn Val Asn Leu Leu Ser
1               5                   10                  15

Ile Ser Asn Leu Pro Lys Leu Asn Lys Leu Arg Lys Leu Glu Leu Ser
            20                  25                  30

Asp Asn Arg Ile Ser Gly Gly Leu Glu Val Leu Ala Glu Arg Thr Pro
        35                  40                  45

Asn Leu Thr His Leu Asn Leu Ser Gly Asn Lys Ile Lys Asp Ile Asn
    50                  55                  60

Thr Leu Glu Pro Leu Lys Lys Leu Pro Asn Leu His Ser Leu Asp Leu
65                  70                  75                  80

Phe Asn Cys Glu Val Thr Met Leu Ile Asn Tyr Arg Glu Ser Val Phe
                85                  90                  95

Thr Leu Leu Pro Gln Leu Thr Tyr Leu Asp Gly Phe Asp Ala Asp Glu
            100                 105                 110

Gln Glu Ala Pro Asp Ser Asp Pro Glu Ala Asp Gly Asp Gly Leu Glu
        115                 120                 125
```

Asp Glu
    130

<210> SEQ ID NO 414
<211> LENGTH: 130
<212> TYPE: PRT
<213> ORGANISM: Anas platyrhynchos

<400> SEQUENCE: 414

Phe Glu Asn Leu Glu Phe Leu Ser Met Ile Asn Ile Asn Leu Leu Ser
1               5                   10                  15

Val Ser Asn Leu Pro Lys Leu Asn Lys Leu Arg Lys Leu Glu Leu Ser
            20                  25                  30

Asp Asn Arg Ile Ser Gly Gly Leu Glu Val Leu Ala Glu Arg Thr Pro
        35                  40                  45

Asn Leu Thr His Leu Asn Leu Ser Gly Asn Lys Ile Lys Asp Ile Asn
    50                  55                  60

Thr Leu Glu Pro Leu Lys Lys Leu Pro Asn Leu His Ser Leu Asp Leu
65                  70                  75                  80

Phe Asn Cys Glu Val Thr Met Leu Ile Asn Tyr Arg Glu Ser Val Phe
                85                  90                  95

Thr Leu Leu Pro Gln Leu Thr Tyr Leu Asp Gly Phe Asp Ala Asp Asp
            100                 105                 110

Gln Glu Ala Pro Asp Ser Asp Pro Glu Ala Asp Gly Asp Gly Leu Glu
        115                 120                 125

Asp Glu
    130

<210> SEQ ID NO 415
<211> LENGTH: 122
<212> TYPE: PRT
<213> ORGANISM: Meleagris gallopavo

<400> SEQUENCE: 415

Met Ile Asn Val Asn Leu Leu Ser Ile Ser Asn Leu Pro Lys Leu Asn
1               5                   10                  15

Lys Leu Arg Lys Leu Glu Leu Ser Asp Asn Arg Ile Ser Gly Gly Leu
            20                  25                  30

Glu Val Leu Ala Glu Arg Thr Pro Asn Leu Thr His Leu Asn Leu Ser
        35                  40                  45

Gly Asn Lys Ile Lys Asp Ile Asn Thr Leu Glu Pro Leu Lys Lys Leu
    50                  55                  60

Pro Asn Leu His Ser Leu Asp Leu Phe Asn Cys Glu Val Thr Met Leu
65                  70                  75                  80

Ile Asn Tyr Arg Glu Ser Val Phe Thr Leu Leu Pro Gln Leu Thr Tyr
                85                  90                  95

Leu Asp Gly Phe Asp Ala Asp Glu Gln Glu Ala Pro Asp Ser Asp Pro
            100                 105                 110

Glu Ala Asp Gly Asp Gly Leu Glu Asp Glu
        115                 120

<210> SEQ ID NO 416
<211> LENGTH: 160
<212> TYPE: PRT
<213> ORGANISM: Gallus gallus

<400> SEQUENCE: 416

Phe Glu Glu Leu Glu Phe Leu Ser Thr Ile Asn Val Gly Leu Ala Ser
1               5                   10                  15

Val Ala Asn Leu Pro Lys Leu Asn Lys Leu Lys Leu Glu Leu Ser
            20                  25                  30

Asp Asn Arg Val Ser Gly Gly Leu Glu Val Leu Ala Glu Lys Cys Pro
            35                  40                  45

Asn Leu Thr His Leu Asn Leu Ser Gly Asn Lys Ile Lys Asp Leu Gly
        50                  55                  60

Thr Ile Glu Pro Leu Lys Lys Leu Glu Asn Leu Lys Ser Leu Asp Leu
65                  70                  75                  80

Phe Asn Cys Glu Val Thr Asn Leu Asn Asp Tyr Arg Glu Asn Val Phe
                85                  90                  95

Lys Leu Leu Pro Gln Leu Thr Tyr Leu Asp Gly Tyr Asp Arg Asp Asp
                100                 105                 110

Lys Glu Ala Pro Asp Ser Asp Ala Glu Gly Tyr Val Glu Gly Leu Asp
            115                 120                 125

Asp Glu Glu Glu Asp Asp Val Leu Ser Leu Val Lys Asp Arg Asp
        130                 135                 140

Asp Lys Glu Ala Pro Asp Ser Asp Ala Glu Gly Tyr Val Glu Gly Leu
145                 150                 155                 160

<210> SEQ ID NO 417
<211> LENGTH: 130
<212> TYPE: PRT
<213> ORGANISM: Canis familiaris

<400> SEQUENCE: 417

Phe Glu Glu Leu Glu Phe Leu Ser Thr Ile Asn Val Gly Leu Thr Ser
1               5                   10                  15

Val Ala Asn Leu Pro Lys Leu Asn Lys Leu Lys Leu Glu Leu Ser
            20                  25                  30

Asp Asn Arg Ile Ser Gly Gly Leu Glu Val Leu Ala Glu Lys Cys Pro
            35                  40                  45

Asn Leu Thr His Leu Asn Leu Ser Gly Asn Lys Ile Lys Asp Leu Ser
        50                  55                  60

Thr Ile Glu Pro Leu Lys Lys Leu Glu Asn Leu Lys Ser Leu Asp Leu
65                  70                  75                  80

Phe Asn Cys Glu Val Thr Asn Leu Asn Asp Tyr Arg Glu Asn Val Phe
                85                  90                  95

Lys Leu Leu Pro Gln Leu Thr Tyr Leu Asp Gly Tyr Asp Arg Asp Asp
                100                 105                 110

Lys Glu Ala Pro Asp Ser Asp Ala Glu Gly Tyr Val Glu Gly Leu Asp
            115                 120                 125

Asp Asp
    130

<210> SEQ ID NO 418
<211> LENGTH: 130
<212> TYPE: PRT
<213> ORGANISM: Equus caballus

<400> SEQUENCE: 418

Phe Glu Glu Leu Glu Phe Leu Ser Thr Ile Asn Val Gly Leu Thr Ser
1               5                   10                  15

Val Ala Asn Leu Pro Lys Leu Asn Lys Leu Lys Leu Glu Leu Ser
            20                  25                  30

-continued

Asp Asn Arg Ile Ser Gly Gly Leu Glu Val Leu Ala Glu Lys Cys Pro
                35                  40                  45

Asn Leu Thr His Leu Asn Leu Ser Gly Asn Lys Ile Lys Asp Leu Ser
         50                  55                  60

Thr Ile Glu Pro Leu Lys Lys Leu Glu Asn Leu Lys Ser Leu Asp Leu
 65                  70                  75                  80

Phe Asn Cys Glu Val Thr Asn Leu Asn Asp Tyr Arg Glu Asn Val Phe
                 85                  90                  95

Lys Leu Leu Pro Gln Leu Thr Tyr Leu Asp Gly Tyr Asp Arg Asp Asp
                100                 105                 110

Lys Glu Ala Pro Asp Ser Asp Ala Glu Gly Tyr Val Glu Gly Leu Asp
            115                 120                 125

Asp Asp
    130

<210> SEQ ID NO 419
<211> LENGTH: 130
<212> TYPE: PRT
<213> ORGANISM: Homo sapiens

<400> SEQUENCE: 419

Phe Glu Glu Leu Glu Phe Leu Ser Thr Ile Asn Val Gly Leu Thr Ser
 1               5                  10                  15

Ile Ala Asn Leu Pro Lys Leu Asn Lys Leu Lys Lys Leu Glu Leu Ser
                20                  25                  30

Asp Asn Arg Val Ser Gly Gly Leu Glu Val Leu Ala Glu Lys Cys Pro
                35                  40                  45

Asn Leu Thr His Leu Asn Leu Ser Gly Asn Lys Ile Lys Asp Leu Ser
         50                  55                  60

Thr Ile Glu Pro Leu Lys Lys Leu Glu Asn Leu Lys Ser Leu Asp Leu
 65                  70                  75                  80

Phe Asn Cys Glu Val Thr Asn Leu Asn Asp Tyr Arg Glu Asn Val Phe
                 85                  90                  95

Lys Leu Leu Pro Gln Leu Thr Tyr Leu Asp Gly Tyr Asp Arg Asp Asp
                100                 105                 110

Lys Glu Ala Pro Asp Ser Asp Ala Glu Gly Tyr Val Glu Gly Leu Asp
            115                 120                 125

Asp Glu
    130

<210> SEQ ID NO 420
<211> LENGTH: 130
<212> TYPE: PRT
<213> ORGANISM: Mus musculus

<400> SEQUENCE: 420

Phe Glu Glu Leu Glu Phe Leu Ser Thr Ile Asn Val Gly Leu Thr Ser
 1               5                  10                  15

Val Ala Asn Leu Pro Lys Leu Asn Lys Leu Lys Lys Leu Glu Leu Ser
                20                  25                  30

Asp Asn Arg Ile Ser Gly Gly Leu Glu Val Leu Ala Glu Lys Cys Pro
                35                  40                  45

Asn Leu Thr His Leu Asn Leu Ser Gly Asn Lys Ile Lys Asp Leu Ser
         50                  55                  60

Thr Val Glu Pro Leu Lys Lys Leu Glu Asn Leu Lys Ser Leu Asp Leu
 65                  70                  75                  80

Phe Asn Cys Glu Val Thr Asn Leu Asn Asp Tyr Arg Glu Asn Val Phe
                85                  90                  95

Lys Leu Leu Pro Gln Leu Thr Tyr Leu Asp Gly Tyr Asp Arg Asp Asp
            100                 105                 110

Lys Glu Ala Ser Asp Ser Asp Ala Glu Gly Tyr Val Glu Gly Leu Asp
        115                 120                 125

Glu Glu
    130

<210> SEQ ID NO 421
<211> LENGTH: 130
<212> TYPE: PRT
<213> ORGANISM: Sus scrofa

<400> SEQUENCE: 421

Phe Glu Glu Leu Glu Phe Leu Ser Thr Ile Asn Val Gly Leu Thr Ser
1               5                   10                  15

Val Ala Asn Leu Pro Lys Leu Asn Lys Leu Lys Lys Leu Glu Leu Ser
            20                  25                  30

Asp Asn Arg Ile Ser Gly Gly Leu Glu Val Leu Ala Glu Lys Cys Pro
        35                  40                  45

Asn Leu Thr His Leu Asn Leu Ser Gly Asn Lys Ile Lys Asp Leu Ser
    50                  55                  60

Thr Val Glu Pro Leu Lys Lys Leu Glu Asn Leu Lys Ser Leu Asp Leu
65                  70                  75                  80

Phe Asn Cys Glu Val Thr Asn Leu Asn Asp Tyr Arg Glu Asn Val Phe
                85                  90                  95

Lys Leu Leu Pro Gln Leu Thr Tyr Leu Asp Gly Tyr Asp Arg Asp Asp
            100                 105                 110

Lys Glu Ala Ser Asp Ser Asp Ala Glu Gly Tyr Val Glu Gly Leu Asp
        115                 120                 125

Asp Asp
    130

<210> SEQ ID NO 422
<211> LENGTH: 130
<212> TYPE: PRT
<213> ORGANISM: Homo sapiens

<400> SEQUENCE: 422

Phe Val Asn Leu Glu Phe Leu Ser Leu Ile Asn Val Gly Leu Ile Ser
1               5                   10                  15

Val Ser Asn Leu Pro Lys Leu Pro Lys Leu Lys Lys Leu Glu Leu Ser
            20                  25                  30

Glu Asn Arg Ile Phe Gly Gly Leu Asp Met Leu Ala Glu Lys Leu Pro
        35                  40                  45

Asn Leu Thr His Leu Asn Leu Ser Gly Asn Lys Leu Lys Asp Ile Ser
    50                  55                  60

Thr Leu Glu Pro Leu Lys Lys Leu Glu Cys Leu Lys Ser Leu Asp Leu
65                  70                  75                  80

Phe Asn Cys Glu Val Thr Asn Leu Asn Asp Tyr Arg Glu Ser Val Phe
                85                  90                  95

Lys Leu Leu Pro Gln Leu Thr Tyr Leu Asp Gly Tyr Asp Arg Glu Asp
            100                 105                 110

Gln Glu Ala Pro Asp Ser Asp Ala Glu Val Asp Gly Val Asp Glu Glu
        115                 120                 125

Glu Glu
    130

<210> SEQ ID NO 423
<211> LENGTH: 130
<212> TYPE: PRT
<213> ORGANISM: Canis familiaris

<400> SEQUENCE: 423

Phe Val Asn Leu Glu Phe Leu Ser Leu Ile Asn Val Gly Leu Ile Ser
1               5                   10                  15

Val Ser Asn Leu Pro Lys Leu Pro Lys Leu Lys Lys Leu Glu Leu Ser
            20                  25                  30

Asp Asn Arg Ile Phe Gly Gly Leu Asp Met Leu Ala Glu Lys Leu Pro
        35                  40                  45

Asn Leu Thr His Leu Asn Leu Ser Gly Asn Lys Leu Lys Asp Ile Ser
    50                  55                  60

Thr Leu Glu Pro Leu Lys Lys Leu Glu Tyr Leu Lys Ser Leu Asp Leu
65                  70                  75                  80

Phe Asn Cys Glu Val Thr Asn Leu Asn Asp Tyr Arg Glu Ser Val Phe
                85                  90                  95

Lys Leu Leu Pro Gln Leu Thr Tyr Leu Asp Gly Tyr Asp Arg Glu Asp
            100                 105                 110

Arg Glu Ala Pro Asp Ser Asp Ala Glu Val Asp Gly Val Asp Glu Glu
        115                 120                 125

Glu Glu
    130

<210> SEQ ID NO 424
<211> LENGTH: 130
<212> TYPE: PRT
<213> ORGANISM: Equus caballus

<400> SEQUENCE: 424

Phe Val Asn Leu Glu Phe Leu Ser Leu Ile Asn Val Gly Leu Ile Ser
1               5                   10                  15

Val Ser Asn Leu Pro Lys Leu Pro Lys Leu Lys Lys Leu Glu Leu Ser
            20                  25                  30

Asp Asn Arg Ile Phe Gly Gly Leu Asp Met Leu Ala Glu Lys Leu Pro
        35                  40                  45

Asn Leu Thr His Leu Asn Leu Ser Gly Asn Lys Leu Lys Asp Ile Ser
    50                  55                  60

Thr Leu Glu Pro Leu Lys Lys Leu Asp Cys Leu Lys Ser Leu Asp Leu
65                  70                  75                  80

Phe Asn Cys Glu Val Thr Asn Leu Asn Asp Tyr Arg Glu Ser Val Phe
                85                  90                  95

Lys Leu Leu Pro Gln Leu Thr Tyr Leu Asp Gly Tyr Asp Arg Glu Asp
            100                 105                 110

Gln Glu Ala Pro Asp Ser Asp Ala Glu Val Asp Gly Val Asp Glu Glu
        115                 120                 125

Glu Glu
    130

<210> SEQ ID NO 425
<211> LENGTH: 130
<212> TYPE: PRT
<213> ORGANISM: Mus musculus

<400> SEQUENCE: 425

```
Phe Val Asn Leu Glu Phe Leu Ser Leu Ile Ser Val Gly Leu Phe Ser
1               5                   10                  15
Val Ser Asp Leu Pro Lys Leu Pro Lys Leu Lys Lys Leu Glu Leu Ser
            20                  25                  30
Glu Asn Arg Ile Phe Gly Gly Leu Asp Arg Leu Ala Glu Leu Pro
        35                  40                  45
Ser Leu Thr His Leu Asn Leu Ser Gly Asn Asn Leu Lys Asp Ile Ser
    50                  55                  60
Thr Leu Glu Pro Leu Lys Arg Leu Asp Cys Leu Lys Ser Leu Asp Leu
65                  70                  75                  80
Phe Gly Cys Glu Val Thr Asn Arg Ser Asp Tyr Arg Glu Thr Val Phe
                85                  90                  95
Arg Leu Leu Pro Gln Leu Ser Tyr Leu Asp Gly Tyr Asp Arg Glu Asp
            100                 105                 110
Gln Glu Ala Pro Asp Ser Asp Val Glu Val Asp Ser Val Glu Glu Ala
            115                 120                 125
Pro Asp
    130
```

<210> SEQ ID NO 426
<211> LENGTH: 130
<212> TYPE: PRT
<213> ORGANISM: Sus scrofa

<400> SEQUENCE: 426

```
Phe Val Asn Leu Glu Phe Leu Ser Leu Ile Asn Val Gly Leu Ile Ser
1               5                   10                  15
Val Ser Asn Leu Pro Lys Leu Pro Lys Leu Lys Lys Leu Glu Leu Ser
            20                  25                  30
Asp Asn Arg Ile Tyr Gly Gly Leu Asp Met Leu Ala Glu Lys Leu Pro
        35                  40                  45
Asn Leu Thr His Leu Asn Leu Ser Gly Asn Lys Leu Lys Asp Ile Ser
    50                  55                  60
Thr Leu Glu Pro Leu Lys Lys Leu Glu Cys Leu Lys Ser Leu Asp Leu
65                  70                  75                  80
Phe Asn Cys Glu Val Thr Asn Leu Asn Asp Tyr Arg Glu Ser Val Phe
                85                  90                  95
Lys Leu Leu Pro Gln Leu Ser Tyr Leu Asp Gly Tyr Asp Arg Asp Asp
            100                 105                 110
Gly Glu Ala Pro Asp Ser Asp Ala Glu Val Asp Gly Val Asp Glu Glu
            115                 120                 125
Glu Asp
    130
```

<210> SEQ ID NO 427
<211> LENGTH: 4
<212> TYPE: PRT
<213> ORGANISM: Artificial Sequence
<220> FEATURE:
<223> OTHER INFORMATION: artificially synthesized sequence

<400> SEQUENCE: 427

```
Lys Arg Lys Arg
1
```

<210> SEQ ID NO 428

```
<211> LENGTH: 9
<212> TYPE: PRT
<213> ORGANISM: Artificial Sequence
<220> FEATURE:
<223> OTHER INFORMATION: artificially synthesized sequence

<400> SEQUENCE: 428

Asp Met Lys Arg Arg Ile His Leu Glu
1               5

<210> SEQ ID NO 429
<211> LENGTH: 9
<212> TYPE: PRT
<213> ORGANISM: Artificial Sequence
<220> FEATURE:
<223> OTHER INFORMATION: artificially synthesized sequence

<400> SEQUENCE: 429

Ala Ala Ala Ala Ala Ala Ala Ala Ala
1               5

<210> SEQ ID NO 430
<211> LENGTH: 10
<212> TYPE: PRT
<213> ORGANISM: Artificial Sequence
<220> FEATURE:
<223> OTHER INFORMATION: artificially synthesized sequence

<400> SEQUENCE: 430

Leu Arg Asn Arg Thr Pro Ala Ala Val Arg
1               5                   10

<210> SEQ ID NO 431
<211> LENGTH: 10
<212> TYPE: PRT
<213> ORGANISM: Artificial Sequence
<220> FEATURE:
<223> OTHER INFORMATION: artificially synthesized sequence

<400> SEQUENCE: 431

Ala Ala Ala Ala Ala Ala Ala Ala Ala Ala
1               5                   10

<210> SEQ ID NO 432
<211> LENGTH: 9
<212> TYPE: PRT
<213> ORGANISM: Artificial Sequence
<220> FEATURE:
<223> OTHER INFORMATION: artificially synthesized sequence

<400> SEQUENCE: 432

Asp Met Lys Lys Arg Ile His Leu Glu
1               5

<210> SEQ ID NO 433
<211> LENGTH: 10
<212> TYPE: PRT
<213> ORGANISM: Artificial Sequence
<220> FEATURE:
<223> OTHER INFORMATION: artificially synthesized sequence

<400> SEQUENCE: 433

Leu Arg Asn Arg Thr Pro Ser Asp Val Lys
1               5                   10

<210> SEQ ID NO 434
<211> LENGTH: 10
```

```
<212> TYPE: PRT
<213> ORGANISM: Artificial Sequence
<220> FEATURE:
<223> OTHER INFORMATION: artificially synthesized sequence

<400> SEQUENCE: 434

Leu Pro Lys Leu Pro Lys Leu Lys Lys Leu
1               5                   10

<210> SEQ ID NO 435
<211> LENGTH: 9
<212> TYPE: PRT
<213> ORGANISM: Artificial Sequence
<220> FEATURE:
<223> OTHER INFORMATION: artificially synthesized sequence

<400> SEQUENCE: 435

Leu Pro Asn Leu Thr His Leu Asn Leu
1               5

<210> SEQ ID NO 436
<211> LENGTH: 15
<212> TYPE: PRT
<213> ORGANISM: Artificial Sequence
<220> FEATURE:
<223> OTHER INFORMATION: artificially synthesized sequence

<400> SEQUENCE: 436

Leu Glu Pro Leu Lys Lys Leu Glu Cys Leu Lys Ser Leu Asp Leu
1               5                   10                  15
```

USE OF ANP32 PROTEIN IN MAINTAINING THE POLYMERASE ACTIVITY OF INFLUENZA VIRUS IN HOSTS

CROSS REFERENCE TO RELATED APPLICATIONS

This application is a U.S. National Phase Application of PCT International Application Number PCT/CN2019/076171, filed on Feb. 26, 2019, designating the United States of America and published in the Chinese language, which is an International Application of and claims the benefit of priority to Chinese Patent Application No. 201810177710.X, filed on Mar. 2, 2018. The disclosures of the above-referenced applications are hereby expressly incorporated by reference in their entireties.

SEQUENCE LISTING

The present application is being filed along with a Sequence Listing in electronic format. The Sequence Listing is provided as a file entitled SeqList-CSPT083-001APC, created Dec. 19, 2022, which is approximately 137,567 bytes in size. The information in the electronic format of the Sequence Listing is incorporated herein by reference in its entirety.

TECHNICAL FIELD

The present invention relates to key host factors necessary for influenza virus replication in a host. More specifically, it relates to the key host factors ANP32A and ANP32B necessary for influenza virus replication in hosts.

BACKGROUND

Influenza is one of the most serious human infectious diseases caused by influenza virus. A global influenza epidemic will infect about 20%-40% of the population (Basler C F, et al. Sequence of the 1918 pandemic influenza virus nonstructural gene (NS) segment and characterization of recombinant viruses bearing the 1918 NS genes[J]. Proc Natl Acad Sci USA, 2001, 98(5):2746-2751.), and will pose a huge threat to human life, health and social life. Influenza virus is an enveloped RNA virus belonging to the family of orthomyxoviridae, and is a spherical or polymorphic particle with a diameter of 80-120 nm. Influenza viruses can be classified into type A, B, C, and D, wherein influenza A virus is the main virus responsible for seasonal influenza and historical influenza pandemics due to its rapid mutation and evolution, variable antigens, strong infectivity and pathogenicity, and rapid spread (Hardelid P, al. Excess mortality monitoring in England and Wales during the influenza A(H1N1) 2009 pandemic[J]. Epidemiol Infect, 2011,139(9): 1431-1439; Yang L, et al. Excess mortality associated with the 2009 pandemic of influenza A(H1N1) in Hong Kong[J]. Epidemiol Infect, 2012,140(9):1542-1550). The influenza A virus caused four global influenza pandemics in 1918, 1957, 1968, and 2009. The rapid and widespread spread of the virus in the population may be related to its increased adaptability and replication capacity in the host, while the specific and efficient replication in the host and its adaptability to the host are mainly determined by RNA-dependent RNA polymerases (Eisfeld A J, et al. At the centre: influenza A virus ribonucleoproteins. [J]. Nat Rev Microbiol. 2015 January; 13(1):28-41.).

The genome of influenza virus contains eight fragments of negative-strand RNA, encoding a total of 11 proteins, wherein the RNA polymerase is a heteromultimer consisting of PB1, PB2 and PA encoded by the first three sequences (Area E, et al. 3D structure of the influenza virus polymerase complex: localization of subunit domains[J]. Proc Natl Acad Sci USA, 2004,101(1):308-313; Eisfeld A J, et al. At the centre: influenza A virus ribonucleoproteins. [J]. Nat Rev Microbiol. 2015 January; 13(1):28-41). RNA polymerase is the material basis for the transcription and replication of influenza virus in host cells, and has an important influence on the pathogenicity and host range of the virus (Neumann G, et al. Host range restriction and pathogenicity in the context of influenza pandemic[J]. Emerg Infect Dis, 2006, 12(6):881-886.). Various factors that interact with influenza virus polymerase and subunits thereof in the host cell, such as RNA helicase DDX, importin a, etc., have influence on the assembly and activity of influenza virus polymerase trimers (Bortz E, et al. Host- and strain-specific regulation of influenza virus polymerase activity by interacting cellular proteins[J]. MBio, 2011, 2(4); Gabriel G, et al. Differential use of importin-alpha isoforms governs cell tropism and host adaptation of influenza virus[J]. Nat Commun, 2011, 2:156.). Therefore, the interaction of influenza virus polymerase with host proteins is an important factor in determining the virulence and host range of the virus.

The cross-species spread of influenza virus and its host restriction mechanism have always been the focus of research in the field. The host protein ANP32 (acidic nuclear phosphoprotein) is thought to be involved in the synthesis of viral RNA in infected cells. Previous studies have focused on the role of the protein in cellular physiological activities such as intracellular transport, cell death pathways, and regulation of transcription, etc., as well as the correlation of ANP32 protein with tumors and nervous system diseases. The members of ANP32 protein family are numerous and structurally similar, consisting of a spherical amino-terminus rich in leucine repeats (LRRs) and an extended carboxyl terminus rich in acidic amino acids (LCAR) (Reilly P T, et al. Cracking the ANP32 whips: important functions, unequal requirement, and hints at disease implications[J]. Bioessays, 2014, 36(11):1062-1071.). The protein family is found in animals, plants and protista, but not found in yeast and other fungi, which indicates that the protein family originates from eukaryotes and is lost in fungi due to certain reasons. It has been reported that this family has 8 members in humans, 3 of which are more conservative in vertebrates, including ANP32A, ANP32B and ANP32E, and the most widely studied are ANP32A and ANP32B. The amino acid sequence homology of ANP32A and ANP32B protein is 70%. The existence of the LRRs region at the amino terminal of the ANP32 protein makes the protein hydrophobic, which helps ANP32 protein to bind to other proteins and play different biological roles; the carboxyl terminal is rich in acidic amino acids and contains a nuclear localization signal, KRKR(SEQ ID NO:427), which makes the protein capable of interacting with the basic proteins in the nucleus and shuttling in the karyoplasm (Matsubae, Masami, et al. "Characterization of the nuclear transport of a novel leucine-rich acidic nuclear protein-like protein." Febs Letters 468.2-3(2000):171-175, Matsuoka, K., et al. "A Nuclear Factor Containing the Leucine-Rich Repeats Expressed in Murine Cerebellar Neurons." Proceedings of the National Academy of Sciences of the United States of America 91.21(1994): 9670.). The protein can also be expressed on the cell surface and even secreted outside of the cell. These characteristics allow the ANP32 protein to participate in a variety of biological processes in cytoplasm and nucleus. It was reported in the papers that ANP32A and ANP32B function as transcriptional regulators in the nucleus: ① as a component of the inhibitor of the histone acetyltransferase (INHAT) complex, involved in regulating transcription (Kadota, S, et al. "pp32, an INHAT component, is a transcription machinery recruiter for maximal induction of IFN-stimulated genes." Journal of Cell Science 124.Pt 6(2011): 892.); ② as the ligand of mRNA binding protein HuR and nuclear export factor CRM1, may accelerate the nuclear export of mRNA chain rich in adenosine (Brennan C M, et al. Protein Ligands to Hur Modulate Its Interaction with Target Mrnas in Vivo[J]. Journal of Cell Biology, 2000, 151(1):1.), and this function can control both the mRNA of the cell host (Fries, Barbara, et al. "Analysis of Nucleocytoplasmic Trafficking of the HuR Ligand APRIL and Its Influence on CD83 Expression." Journal of Biological Chemistry 282.7(2007):4504-15.), and the mRNA of the virus (Bodem, J, et al. "Foamy virus nuclear RNA export is distinct from that of other retroviruses." Journal of Virology 85.5(2011):2333-2341.). In addition, ANP32 protein can also play an important role in the cytoplasm, for example, ANP32A can bind to microtubule-associated proteins (Ulitzur, N, M, et al. "Mapmodulin: a possible modulator of the interaction of microtubule-associated proteins with microtubules." Proceedings of the National Academy of Sciences of the United States of America 94.10(1997):5084.), which affects the transport and signal transmission of intracellular materials, maintains the cell morphology and the spatial distribution of organelles, etc.; ANP32 protein can activate apoptotic bodies, and regulate the cell death pathways (Pan, Wei, et al. "PHAPI/pp32 Suppresses Tumorigenesis by Stimulating Apoptosis." Journal of Biological Chemistry 284.11(2009): 6946.).

After Shapira screened the host protein ANP32A through the yeast two-hybrid method in 2009 and initially discovered that it was associated with influenza virus infection, scientists have successively conducted researches on the interaction between this protein family and influenza virus. In 2011, Bradel-Tretheway et al. discovered that ANP32A and ANP32B bond to influenza virus polymerase through proteomics; in 2014, Watanabe et al. demonstrated that ANP32A and ANP32B can affect vRNA synthesis after the influenza virus infected cells through RANi library screening; in 2015, Sugiyama et al. found that ANP32A and ANP32B can promote the synthesis of cRNA-vRNA in influenza virus replication, and demonstrated that ANP32 protein interacted with influenza virus polymerase trisubunit (PB2/PB1/PA) polymer through biological techniques such as CO-IP, and had nothing to do with NP protein (Sugiyama K, et al. pp32 and APRIL are host cell-derived regulators of influenza virus RNA synthesis from cRNA[J]. Elife, 2015, 4; Watanabe T, et al. Influenza virus-host interactome screen as a platform for antiviral drug development[J]. Cell Host Microbe, 2014, 16(6):795-805.). Subsequently, the British scholar Wendy S. Barclay's research team revealed for the first time that the activity of avian influenza virus RNA polymerase in mammalian cells is related to the species-specificity of ANP32A (Long J S, et al. Species difference in ANP32A underlies influenza A virus polymerase host restriction[J]. Nature, 2016,529(7584):101-104.). Study found that compared to mammals, avian-derived ANP32A contains a sequence of 33 amino acid inserted between the LRRs and LCAR region. This characteristic of sequence determines the characteristic that avian-derived ANP32A specifically activates the polymerase activity of avian-derived influenza virus. Avian-derived influenza virus (H5N1/H7N9) can make the polymerase more adaptive to mammalian ANP32A only after obtaining mutations in PB2 E627K. Therefore, it is inferred that ANP32A is an important host protein that supports influenza virus replication, but the specific molecular mechanism of its interaction with polymerase remains to be further explored.

The harm of seasonal influenza and global pandemic influenza has attracted widespread attention from the society. At present, preliminary success has been made on anti-influenza virus drugs. However, due to the clinical widespread use of existing drugs, influenza viruses are constantly mutating, and have developed different degrees of resistance to these drugs, which makes development and screening of new anti-influenza virus drugs increasingly important. The present invention demonstrates that ANP32A and ANP32B are common host proteins used by influenza viruses in cells of different species of animals, and that both or either of the two proteins are necessary for the replication of influenza viruses in the host. Furthermore, the present invention also finds the key amino acid positions in the two proteins, and the mutation of the key amino acids makes the influenza virus almost impossible to replicate. This discovery can provide a direct basis for the further design of anti-influenza drugs or anti-influenza animals.

SUMMARY OF THE INVENTION

In one aspect of the invention, it relates to a mutated ANP32 protein having one or more mutations selected from the group consisting of:
  the amino acid at position 129 is substituted with isoleucine I, lysine K, aspartic acid D, valine V, proline P, tryptophan W, histidine H, arginine R, glutamine Q, glycine G, or glutamic acid E,
  the amino acid at position 130 is substituted with asparagine N, phenylalanine F, lysine K, leucine L, valine V, proline P, isoleucine I, methionine M, tryptophan W, histidine H, arginine R, glutamine Q, or tyrosine Y,
  the amino acid at position 149 is substituted with alanine A,
  the amino acid at position 151 is substituted with alanine A, and
  the amino acids at positions 60 and 63, positions 87, 90, 93 and 95, positions 112, 115 and 118 are substituted with alanine,
  when the ANP32 protein is chicken ANP32B protein, duck ANP32B protein or turkey ANP32B protein, the amino acid at position 129 is not isoleucine I and the amino acid at position 130 is not asparagine N,
  when the ANP32 protein is murine ANP32A, the amino acid at position 130 is not alanine A,
  wherein, when the ANP32 protein is an ANP32A protein, the amino acid positions correspond to the amino acid positions of a chicken ANP32A protein of GenBank No. XP_413932.3;
  when the ANP32 protein is an ANP32B protein, the amino acid positions correspond to the amino acid positions of a human ANP32B protein of GenBank No. NP_006392.1,
  wherein, preferably, the amino acids at positions 87, 90, 93 and 95 are from the mammalian ANP32B protein.

In one aspect of the invention, it relates to a mutated ANP32 protein, wherein one or more of the amino acid segments selected from the group consisting of the following are deleted or substituted with alanine: amino acids at positions 61-70, amino acids at positions 71-80, amino acids at positions 81-90, amino acids at positions 91-100, amino acids at positions 101-110, amino acids at positions 111-120, amino acids at positions 121-130, amino acids at positions 131-140, amino acids at positions 141-150, amino acids at positions 151-160, wherein, when the ANP32 protein is an ANP32A protein, the amino acid positions correspond to the amino acid positions of a chicken ANP32A protein of GenBank No. XP_413932.3;

when the ANP32 protein is an ANP32B protein, the amino acid positions correspond to the amino acid positions of a human ANP32B protein of GenBank No. NP_006392.1.

In one aspect of the invention, it relates to a mutated ANP32 protein, wherein when the ANP32 protein is a human ANP32B protein, one or more of the amino acid segments selected from the group consisting of the following are deleted or substituted with alanine: amino acids at positions 21-30, amino acids at positions 41-50, amino acids at positions 51-60 or amino acids at positions 161-170, and the amino acid positions correspond to the amino acid positions of the human ANP32B protein of GenBank No. NP_006392.1.

In one aspect of the invention, it relates to a mutated ANP32 protein, wherein when the ANP32 protein is a chicken ANP32B protein, one or more of the amino acid segments selected from the group consisting of the following are deleted or substituted with alanine: amino acids at positions 161-170, amino acids at positions 171-180 or amino acids at positions 191-200, and the amino acid positions correspond to the amino acid positions of the chicken ANP32B protein of GenBank No. XP_413932.3.

In an embodiment of the present invention, the ANP32 protein is selected from ANP32A or ANP32B, preferably derived from chicken, human, zebra finch, duck, turkey, pig, mouse or horse, more preferably derived from chicken or human, most preferably is human ANP32B, or chicken ANP32A In one aspect of the present invention, it relates to a use of ANP32 protein in maintaining the polymerase activity of influenza virus. Preferably, the ANP32 protein is an avian-derived ANP32 protein, and the influenza virus is selected from avian-derived or mammal-derived influenza virus; alternatively, the ANP32 protein is a mammal-derived ANP32 protein, and the influenza virus is a mammal-derived influenza virus; preferably, the influenza virus is selected from a human, canine, avian, or equine influenza virus, and preferably, the ANP32 protein is selected from ANP32A protein and ANP32B protein, more preferably, the ANP32 protein is derived from chicken, human, zebra finch, duck, turkey, pig, mouse or horse, and preferably, the ANP32 protein is not a chicken-derived ANP32B or mouse-derived ANP32A.

In one aspect of the present invention, it relates to a use of ANP32 protein in reducing the polymerase activity of influenza virus. Preferably, the influenza virus is selected from human, canine, avian, or equine influenza virus; preferably, the ANP32 protein is selected from ANP32A protein and ANP32B protein, more preferably, the ANP32 protein is derived from chicken, human, zebra finch, duck, turkey, pig, mouse or horse, and more preferably, the ANP32 protein is a mutated ANP32 protein as defined in claim 1, or ANP32 protein is a chicken-derived ANP32B protein or mouse-derived ANP32A protein.

In one aspect of the invention, it relates to a method of reducing the polymerase activity of influenza virus, including subjecting the ANP32 protein to one or more mutations selected from the group consisting of:

the amino acid at position 129 is substituted with isoleucine I, lysine K, aspartic acid D, valine V, proline P, tryptophan W, histidine H, arginine R, glutamine Q, glycine G, or glutamic acid E, the amino acid at position 130 is substituted with asparagine N, phenylalanine F, lysine K, leucine L, valine V, proline P, isoleucine I, methionine M, tryptophan W, histidine H, arginine R, glutamine Q, or tyrosine Y, the amino acid at position 149 is substituted with alanine A, the amino acid at position 151 is substituted with alanine A, and the amino acids at positions 60 and 63, positions 87, 90, 93 and 95, positions 112, 115 and 118 are substituted with alanine, when the ANP32 protein is a chicken ANP32B protein, duck ANP32B protein or turkey ANP32B protein, the amino acid at position 129 is not isoleucine and the amino acid at position 130 is not asparagine N, when the ANP32 protein is murine ANP32A, the amino acid at position 130 is not alanine A, wherein, when the ANP32 protein is an ANP32A protein, the amino acid positions correspond to the amino acid positions of a chicken ANP32A protein of GenBank No. XP_413932.3;

when the ANP32 protein is an ANP32B protein, the amino acid positions correspond to the amino acid positions of a human ANP32B protein of GenBank No. NP_006392.1, wherein, preferably, the amino acids at positions 87, 90, 93 and 95 are from the mammalian ANP32B protein.

In an embodiment of the present invention, wherein the polymerase activity of influenza virus is lost, wherein the ANP32 protein is subjected to one or more mutations selected from the group consisting of:

the amino acid at position 129 is substituted with isoleucine I, lysine K or aspartic acid D, the amino acid at position 130 is substituted with asparagine N, phenylalanine F or lysine K, the amino acids at positions 87, 90, 93 and 95, positions 112, 115 and 118 are substituted with alanine.

In one aspect of the invention, it relates to a method of reducing the polymerase activity of influenza virus, including one or more of the amino acid segments of ANP32 protein selected from the group consisting of: amino acids at positions 61-70, amino acids at positions 71-80, amino acids at positions 81-90, amino acids at positions 91-100, amino acids at positions 101-110, amino acids at positions 111-120, amino acids at positions 121-130, amino acids at positions 131-140, amino acids at positions 141-150, amino acids at positions 151-160, are deleted or substituted with alanine, wherein, when the ANP32 protein is an ANP32A protein, the amino acid positions correspond to the amino acid positions of a chicken ANP32A protein of GenBank No. XP_413932.3;

when the ANP32 protein is an ANP32B protein, the amino acid positions correspond to the amino acid positions of a human ANP32B protein of GenBank No. NP_006392.1.

In an embodiment of the present invention, wherein the polymerase activity of influenza virus is lost, wherein one or more of the amino acid segments of ANP32 protein selected from the group consisting of: amino acids at positions 71-80, amino acids at positions 81-90, amino acids at positions 91-100, amino acids at positions 101-110, amino acids at positions 111-120, amino acids at positions 121-130, amino acids at positions 131-140, amino acids at positions 141-150, amino acids at positions 151-160, are deleted or substituted with alanine.

In one aspect of the invention, it relates to a method of reducing the polymerase activity of influenza virus, including deleting or substituting one or more of the amino acid segments of human ANP32B protein selected from the group consisting of: amino acids at positions 21-30, amino acids at positions 41-50, amino acids at positions 51-60 or amino acids at positions 161-170 with alanine, the amino acid positions correspond to the amino acid positions of the human ANP32B protein of GenBank No. NP_006392.1.

In one aspect of the invention, it relates to a method of reducing the polymerase activity of influenza virus, including deleting or substituting one or more of the amino acid segments of chicken ANP32A protein selected from the group consisting of: amino acids at positions 161-170, amino acids at positions 171-180 or amino acids at positions 191-200 with alanine, the amino acid positions correspond to the amino acid positions of the chicken ANP32A protein of GenBank No. XP_413932.3.

In an embodiment of the present invention, wherein the polymerase activity of influenza virus is lost,
wherein, one or more of the amino acid segments of chicken ANP32A protein selected from the group consisting of: amino acids at positions 161-170, amino acids at positions 171-180 are deleted or substituted with alanine.

In an embodiment of the present invention, wherein the ANP32 protein is selected from ANP32A or ANP32B, preferably derived from chicken, human, zebra finch, duck, turkey, pig, mouse or horse, and more preferably derived from chicken or human. Most preferably, it is a human ANP32B, or chicken ANP32A; preferably, the influenza virus is selected from human, canine, avian or equine influenza virus.

In one aspect of the present invention, it relates to a use of one or more of the amino acid segments of ANP32 protein in maintaining the polymerase activity of influenza virus, wherein the amino acid segment is selected from the group consisting of:
amino acids at positions 61-70, amino acids at positions 71-80, amino acids at positions 81-90, amino acids at positions 91-100, amino acids at positions 101-110, amino acids at positions 111-120, amino acids at position 121-130, amino acids at positions 131-140, amino acids at positions 141-150, amino acid at positions 151-160, amino acids at positions 161-170 of chicken ANP32A protein, amino acids at positions 171-180 of chicken ANP32A protein, amino acids at positions 191-200 of chicken ANP32A protein, amino acids at positions 21-30 of human ANP32B protein, amino acids at positions 41-50 of human ANP32B protein, amino acids at positions 51-60 of human ANP32B protein or amino acids at positions 161-170 of human ANP32B protein,
wherein, when the ANP32 protein is an ANP32A protein, the amino acid positions correspond to the amino acid positions of a chicken ANP32A protein of GenBank No. XP_413932.3;
when the ANP32 protein is an ANP32B protein, the amino acid positions correspond to the amino acid positions of a human ANP32B protein of GenBank No. NP_006392.1,
preferably, the ANP32 protein is an avian-derived ANP32 protein, and the influenza virus is selected from an avian-derived or mammal-derived influenza virus;
alternatively, the ANP32 protein is a mammal-derived ANP32 protein, and the influenza virus is a mammal-derived influenza virus.

In one aspect of the present invention, it relates to the use of one or more of the amino acid segments of ANP32 protein in reducing the activity of influenza virus polymerase, wherein the amino acid segment is selected from the group consisting of:
amino acids at positions 61-70, amino acids at positions 71-80, amino acids at positions 81-90, amino acids at positions 91-100, amino acids at positions 101-110, amino acids at positions 111-120, amino acids at position 121-130, amino acids at positions 131-140, amino acids at positions 141-150, amino acid at positions 151-160, amino acids at positions 161-170 of chicken ANP32A protein, amino acids at positions 171-180 of chicken ANP32A protein, amino acids at positions 191-200 of chicken ANP32A protein, amino acids at positions 21-30 of human ANP32B protein, amino acids at positions 41-50 of human ANP32B protein, amino acids at positions 51-60 of human ANP32B protein or amino acids at positions 161-170 of human ANP32B protein,
wherein, when the ANP32 protein is an ANP32A protein, the amino acid positions correspond to the amino acid positions of a chicken ANP32A protein of GenBank No. XP_413932.3;
when the ANP32 protein is an ANP32B protein, the amino acid positions correspond to the amino acid positions of a human ANP32B protein of GenBank No. NP_006392.1,
preferably, wherein the ANP32 protein is selected from ANP32A or ANP32B, preferably derived from chicken, human, zebra finch, duck, turkey, pig, mouse or horse, more preferably derived from chicken or human, most preferably is human ANP32B or chicken ANP32A; preferably, the influenza virus is selected from human, canine, avian or equine influenza virus.

In one aspect of the present invention, it relates to a kit comprising at least one reagent or a set of reagents, wherein the at least one reagent or set of reagents is used to determine the type of amino acid at one or more positions of an ANP32 protein selected from the group consisting of: amino acid at position 129, amino acid at position 130, amino acid at position 149, amino acid at position 151, amino acid at position 60, amino acid at position 63, amino acid at position 87, amino acid at position 90, amino acid at position 93, amino acid at position 95, amino acid at position 112, amino acid at position 115, or amino acid at position 118, wherein
when the amino acid at position 129 is isoleucine I, lysine K, aspartic acid D, valine V, proline P, tryptophan W, histidine H, arginine R, glutamine Q, glycine G, or glutamic acid E,
the amino acid at position 130 is asparagine N, phenylalanine F, lysine K, leucine L, valine V, proline P, isoleucine I, methionine M, tryptophan W, histidine H, arginine R, glutamine Q, or tyrosine Y,
the amino acid at position 149 is alanine A,
the amino acid at position 151 is alanine A,
the amino acids at positions 60 and 63, at positions 87, 90, 93 and 95, at positions 112, 115, and 118 are alanine, the ability of the ANP32 protein to support the activity of influenza polymerase is decreased,
wherein, when the ANP32 protein is an ANP32A protein, the amino acid positions correspond to the amino acid positions of a chicken ANP32A protein of GenBank No. XP_413932.3;
when the ANP32 protein is an ANP32B protein, the amino acid positions correspond to the amino acid positions of a human ANP32B protein of GenBank No. NP_006392.1, wherein, preferably, the amino acids at positions 87, 90, 93 and 95 are from the mammalian ANP32B protein.

In one aspect of the present invention, it relates to an oligonucleotide primer for determining the type of amino acid of ANP32 protein selected from the group consisting of: amino acid at position 129, amino acid at position 130, amino acid at position 149, amino acid at position 151, amino acid at position 60, amino acid at position 63, amino acid at position 87, amino acid at position 90, amino acid at position 93, amino acid at position 95, amino acid at position 112, amino acid at position 115, and amino acid at position 118,
wherein
when the amino acid at position 129 is isoleucine I, lysine K, aspartic acid D, valine V, proline P, tryptophan W, histidine H, arginine R, glutamine Q, glycine G, or glutamic acid E,
the amino acid at position 130 is asparagine N, phenylalanine F, lysine K, leucine L, valine V, proline P, isoleucine I, methionine M, tryptophan W, histidine H, arginine R, glutamine Q, or tyrosine Y,
the amino acid at position 149 is alanine A,
the amino acid at position 151 is alanine A,
the amino acids at positions 60, 63, or the amino acids at positions 87, 90, 93 and 95, or the amino acids at positions 112, 115 and 118 are alanine,
the ability of ANP32 protein to support the activity of influenza polymerase is decreased,
wherein, when the ANP32 protein is an ANP32A protein, the amino acid positions correspond to the amino acid positions of a chicken ANP32A protein of GenBank No. XP_413932.3;
when the ANP32 protein is an ANP32B protein, the amino acid positions correspond to the amino acid positions of a human ANP32B protein of GenBank No. NP_006392.1,
wherein, preferably, the amino acids at positions 87, 90, 93 and 95 are from the mammalian ANP32B protein.

In an embodiment of the present invention, the oligonucleotide primer is preferably at least 20 bases in length. For example at least 21, 22, 23, 24, 25, 26, 27, 28, 29, 30, 31, 32, 33, 34 or 35 bases in length.

In an embodiment of the present invention, the oligonucleotide sequence is selected from SEQ ID NOs: 155-156, 163-166, 167-256, and 375-380.

In an embodiment of the present invention, the ANP32 protein is selected from ANP32A or ANP32B, preferably derived from chicken, human, zebra finch, duck, turkey, pig, mouse or horse, more preferably derived from chicken or human. Most preferably, the ANP32 protein is human ANP32B, or chicken ANP32A.

In one aspect of the present invention, it relates to a method of producing an animal, including the step of subjecting the ANP32 protein in the animal to one or more mutations selected from the group consisting of:
the amino acid at position 129 is substituted with isoleucine I, lysine K, aspartic acid D, valine V, proline P, tryptophan W, histidine H, arginine R, glutamine Q, glycine G, or glutamic acid E,
the amino acid at position 130 is substituted with asparagine N, phenylalanine F, lysine K, leucine L, valine V, proline P, isoleucine I, methionine M, tryptophan W, histidine H, arginine R, glutamine Q, or tyrosine Y,
the amino acid at position 149 is substituted with alanine A,
the amino acid at position 151 is substituted with alanine A, and
the amino acids at positions 60 and 63, positions 87, 90, 93 and 95, positions 112, 115 and 118 are substituted with alanine,
the amino acids at positions 61-70, amino acids at positions 71-80, amino acids at positions 81-90, amino acids at positions 91-100, amino acids at positions 101-110, amino acids at positions 111-120, amino acid at position 121-130, amino acids at positions 131-140, amino acids at positions 141-150, amino acids at positions 151-160, amino acids at positions 161-170 of chicken ANP32A protein, amino acids at positions 171-180 of chicken ANP32A protein, amino acids at positions 191-200 of chicken ANP32A protein, amino acids at positions 21-30 of human ANP32B protein, amino acids at positions 41-50 of human ANP32B protein, amino acids at positions 51-60 of human ANP32B protein or amino acids at positions 161-170 of human ANP32B protein are substituted with alanine,
wherein, when the ANP32 protein is chicken ANP32B protein, duck ANP32B protein or turkey ANP32B protein, the amino acid at position 129 is not isoleucine I and the amino acid at position 130 is not asparagine N,
wherein, when the ANP32 protein is murine ANP32A, the amino acid at position 130 is not alanine A,
wherein, when the ANP32 protein is an ANP32A protein, the amino acid positions correspond to the amino acid positions of a chicken ANP32A protein of GenBank No. XP_413932.3;
when the ANP32 protein is an ANP32B protein, the amino acid positions correspond to the amino acid positions of a human ANP32B protein of GenBank No. NP_006392.1,
wherein, preferably, the amino acids at positions 87, 90, 93 and 95 are from the mammalian ANP32B protein.

In an embodiment of the present invention, the animal is selected from chicken, human, zebra finch, duck, turkey, pig, mouse or horse.

In one aspect of the present invention, it relates to the use of ANP32 protein or amino acid(s) thereof as a target in preparing a medicament for treating a disease caused by an influenza virus infection, wherein the amino acid(s) is (are) selected from the amino acid(s) located at the following positions or segments,
wherein the amino acid(s) is (are) selected from one or more of the following amino acids: amino acid at position 129, amino acid at position 130, amino acid at position 149, amino acid at position 150, amino acids at positions 60 and 63, amino acids at positions 87, 90, 93 and 95, amino acids at positions 112, 115 and 118, amino acids at positions 61-70, amino acids at positions 71-80, amino acids at positions 81-90, amino acids at positions 91-100, amino acids at positions 101-110, amino acids at positions 111-120, amino acids at position 121-130, amino acids at positions 131-140, amino acids at positions 141-150, amino acids at positions 151-160, amino acid at positions 161-170 of chicken ANP32A protein, amino acids at positions 171-180 of chicken ANP32A protein, amino acids at positions 191-200 of chicken ANP32A protein, amino acids at positions 21-30 of human ANP32B protein, amino acids at positions 41-50 of human ANP32B protein, amino acids at positions 51-60 of human ANP32B protein or amino acids at positions 161-170 of human ANP32B protein, preferably, the amino acids at positions 87, 90, 93 and 95 are from the ANP32B protein of mammal. Preferably, the ANP32 protein is ANP32A or ANP32B protein, preferably derived from chicken, human, zebra finch, duck, turkey, pig, mouse or horse; preferably, the influenza virus is selected from human, canine, avian or equine influenza virus.

In one aspect of the present invention, it relates a method of screening for a candidate drug for treating an influenza virus infection, including the following steps:

(1) knocking out the ANP32A and/or ANP32B protein from a cell line containing ANP32A and/or ANP32B protein, to obtain a cell line in which ANP32A protein and ANP32B protein are knocked out, (2) transfecting the knockout cell line obtained in step (1) with a plasmid encoding ANP32A and/or ANP32B protein and a plasmid encoding influenza virus polymerase, (3) contacting the knockout cell line with a candidate, wherein the contacting can be performed simultaneously with or separately from the transfection of step (2), wherein that the cell line treated in step (3) does not express influenza virus polymerase or has reduced expression of influenza virus polymerase compared to a cell line containing ANP32A and/or ANP32B, indicates that the candidate is a candidate drug for treating influenza virus infection.

In one embodiment, wherein the ANP32A and/or ANP32B protein is derived from chicken, human, zebra finch, duck, turkey, pig, mouse or horse; preferably, the influenza virus is selected from human, canine, avian or equine influenza virus.

BRIEF DESCRIPTION OF THE DRAWINGS

FIG. 7 shows the detection of activity of different polymerases on 293T wild-type and knockout cell lines.

FIG. 11 shows the influence of ANP32 protein of different species on the replication of different influenza viruses.

FIG. 12 shows the detection of $H1N1_{SC09}$ influenza virus.

FIG. 13 shows the detection of WSN influenza virus.

FIG. 15 shows the ANP32B sequences alignment, truncation and fragment interchange.

FIG. 16 shows the ANP32B point mutation.

FIG. 17 shows the influence of single point mutation on position 129 or 130 of huANP32B on $H1N1_{SC09}$ polymerase activity.

FIG. 18 shows the influence of single point mutation of huANP32B on $H7N9_{AH13}$ polymerase activity.

FIG. 21 shows the influence of chANP32A point mutation and chANP32B point mutation on $H7N9_{AH13}$ polymerase activity.

FIG. 22 shows the influence of point mutant at position 129 of chANP32A on $H7N9_{ZJ13}$ polymerase activity.

FIG. 23 shows the influence of point mutant at position 129 of chANP32A on $H7N9_{AH13}$ polymerase activity.

FIG. 24 shows the influence of point mutant at position 129 of chANP32A on the activity of WSN polymerase.

FIG. 25 shows the influence of point mutant at position 130 of chANP32A on $H7N9_{ZJ13}$ polymerase activity.

FIG. 26 shows the influence of point mutant at position 130 of chANP32A on $H7N9_{AH13}$ polymerase activity.

FIG. 29 shows the influence of chANP32A truncated mutant on $H7N9_{ZJ13}$ polymerase activity.

FIG. 30 shows the influence of chANP32A point mutant on $H7N9_{AH13}$ polymerase activity.

FIG. 36 shows the alignment of amino acid sequences of avian-derived ANP32A proteins, wherein chANP32A 60-200 is shown in SEQ ID NO:408, dkANP32A 50-186 is shown in SEQ ID NO:409, tyANP32A 59-199 is shown in SEQ ID NO:410, zfANP32A 60-200 is shown in SEQ ID NO:411. FIG. 37 shows the alignment of amino acid sequences between avian-derived ANP32B protein and huANP32B protein, wherein huANP32B 41-170 is shown in SEQ ID NO:412, chANP32B 41-170 is shown in SEQ ID NO:413, dkANP32B 55-184 is shown in SEQ ID NO:414, and tyANP32B 1-122 is shown in SEQ ID NO:415.

FIG. 38 shows the alignment of amino acid sequences between chicken ANP32A protein and mammalian ANP32A protein, wherein chANP32A 41-200 is shown in SEQ ID NO:416, dogANP32A 41-170 is shown in SEQ ID NO:417, eqANP32A 41-170 is shown in SEQ ID NO:418, huANP32A 41-170 is shown in SEQ ID NO:419, muANP32A 41-170 is shown in SEQ ID NO:420, and pgANP32A 41-170 is shown in SEQ ID NO:421.

FIG. 39 shows the alignment of amino acid sequences of mammalian ANP32B protein, wherein huANP32B 41-170 is shown in SEQ ID NO:422, dogANP32B 48-177 is shown in SEQ ID NO:423, eqANP32B 41-170 is shown in SEQ ID NO:424, muANP32B 41-170 is shown in SEQ ID NO:425, and pgANP32B 41-170 is shown in SEQ ID NO:426).

SPECIFIC MODE FOR CARRYING OUT THE INVENTION

The present invention is described in detail below with reference to the examples and the accompanying drawings. It will be understood by those skilled in the art that the following examples are for illustrative purposes and should not be construed as limiting the present invention in any way. The protection scope of the present invention is defined by the appended claims.

Example 1. Construction of ANP32 Protein Expression Vector

The nucleotide sequences of ANP32 proteins from chicken, human, zebra finch, duck, turkey, pig, mouse, horse, etc. are as follows:

chicken ANP32A (chANP32A) (*Gallus gallus*, XM_413932.5), human ANP32A (huANP32A) (*Homo sapiens*, NM_006305.3), zebra finch ANP32A (zfANP32A) (*Taeniopygia guttata*, XM_012568610.1), duck ANP32A (dkANP32A) (*Anas platyrhynchos*, XM_005022967.1), turkey ANP32A (tyANP32A) (*Meleagris gallopavo*, XM_010717616.1), pig ANP32A (pgANP32A) (*Sus scrofa*, XM_003121759.6), murine ANP32A (muANP32A) (*Mus musculus*, NM_009672.3), equine ANP32A (eqANP32A) (*Equus caballus*, XM_001495810.5), chicken ANP32B (chANP32B) (*Gallus gallus*, NM_001030934.1), human ANP32B (huANP32B) (*Homo sapiens*, NM_006401.2).

The amino acid sequences of ANP32 proteins from chicken, human, zebra finch, duck, turkey, pig, mouse, horse, etc. are as follows:

chicken ANP32A (chANP32A) (*Gallus gallus*, XP_413932.3), human ANP32A (huANP32A) (*Homo sapiens*, NP_006296.1), zebra finch ANP32A (zfANP32A) (*Taeniopygia guttata*, XP_012424064.1), duck ANP32A (dkANP32A) (*Anas platyrhynchos*, XP_005023024.1), turkey ANP32A (tyANP32A) (*Meleagris gallopavo*, XP_010715918.1), pig ANP32A (pgANP32A) (*Sus scrofa*, XP_003121807.3), mouse ANP32A (muANP32A) (*Mus musculus*, NP_033802.2), equine ANP32A (eqANP32A) (*Equus caballus*, XP_001495860.2), chicken ANP32B (chANP32B) (*Gallus gallus*, NP_001026105.1), human ANP32B (huANP32B) (*Homo sapiens*, NP_006392.1).

First, a PCAGGS-Flag recombinant plasmid was constructed. A start codon (ATG) was introduced at the N-terminus of the Flag-tag (GGCAGCGGAGACTACAAGGATGACGATGACAAG, SEQ ID NO:1), and a stop codon (TGA) was introduced at the C-terminus; NotI (GCGGCCGC, SEQ ID NO:2) restriction site was introduced upstream of the start codon, and XhoI (CTCGAG, SEQ ID NO:3) restriction site was introduced downstream of the stop codon, and a 15 bp homologous arm (underlined) of PCAGGS vector was introduced at the outer ends of the two restriction sites, and two primers Flag-S (SEQ ID NO: 4) and Flag-A (SEQ ID NO: 5) complementary to the Flag-tag gene fragment were synthesized.

```
Flag-S: SEQ ID NO: 4
5-AAAGAATTCGAGCTCGCGGCCGCATGGGCAGCGGAGACTACAAGGAT
GACGATGACAAGTGACTCGAGCTAGCAGATCTTTTT-3

Flag-A: SEQ ID NO: 5
5-AAAAAGATCTGCTAGCTCGAGTCACTTGTCATCGTCATCCTTGTAGT
CTCCGCTGCCCATGCGGCCGCGAGCTCGAATTCTTT-3
```

Figure 1:
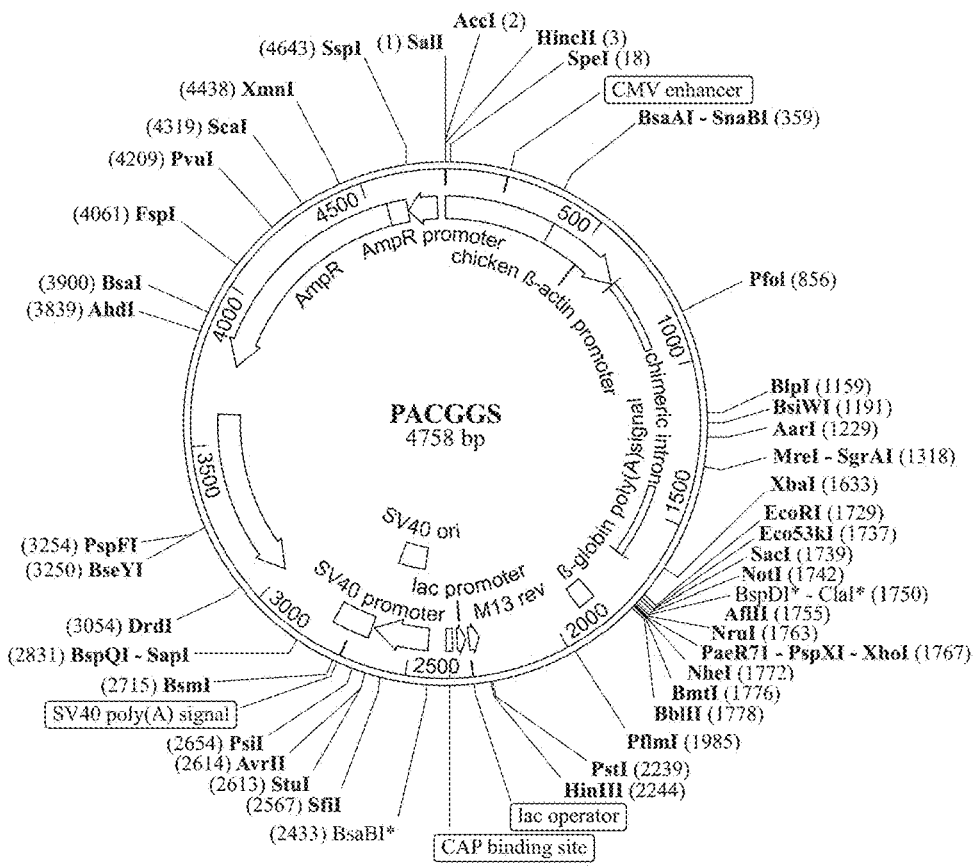
FIG. 1 shows the map of PCAGGS vector.

The designed upstream and downstream primers Flag-S and Flag-A were diluted respectively to 100 uM (diluted with TE buffer); 10 ul of each diluted primers were taken and then mixed uniformly, and placed at 95° C. for 5 min; the PCR instrument was turned off, and the temperature was naturally reduced to room temperature (about 2 h), and the obtained product is an annealed synthetic sample. Commercially available PCAGGS vector (see FIG. 1, purchased from Fenghui Bio, product number V00514, cat # JM004, <<www.fenghbio.cn>>) was subjected to double enzyme digestion by Thermo rapid restriction endonuclease Not I and Xho I under a water bath condition at 37° C. for 1.5 h, and the enzyme digested fragments were recovered by using a gel recovery kit (OMEGA, cat # D2500-01), and the obtained product is recovered for future use. The PCAGGS double-enzyme digested product and the annealed synthetic sample were ligated by In-Fusion ligase (purchased from Clontech, cat #639648) according to the instructions, and then transformed into DH5a competent cells. The next day, a single clone was selected and sequenced, and the plasmid which was verified correct by sequencing was named as PCAGGS-Flag plasmid which was used as a control plasmid for subsequent experiments and was extracted in large-scale for later use.

Figure 2:
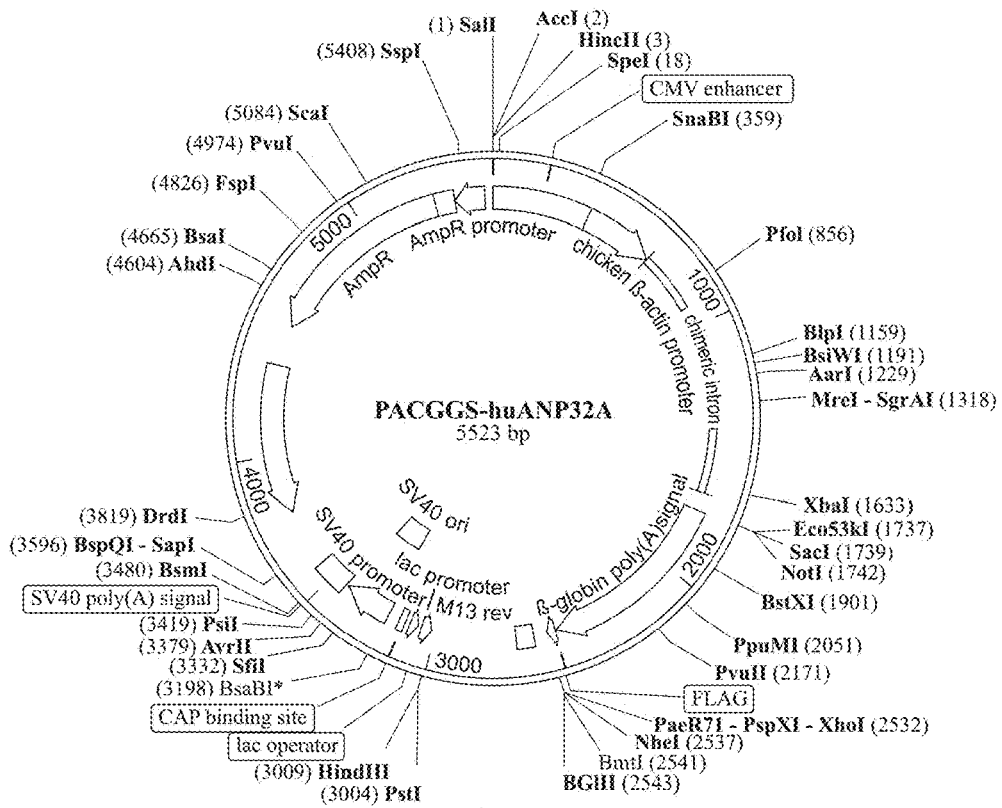
FIG. 2 shows the map of PCAGGS-huANP32A vector.

According to the nucleotide sequences of ANP32A and ANP32B of each species mentioned above, the sequences of ANP32A and ANP32B of each species mentioned above were synthesized respectively. During the synthesis, the stop codon was removed at the C-terminus of the gene fragment and the a Flag-tag (SEQ ID NO: 1) was added in tandem; a stop codon (TGA) was added at the end of the Flag-tag; Not I (SEQ ID NO: 2) and Xho I (SEQ ID NO: 3) restriction sites were introduced at both ends of the synthesized fragment. The PCAGGS-Flag vector was digested by Thermo rapid restriction endonucleases Not I and Xho I at 37° C. for 1.5 h, and the digested fragments were recovered using a gel recovery kit (OMEGA, cat # D2500-01). The PCAGGS-Flag double-digested product and each gene fragment were ligated by In-Fusion ligase (purchased from Clontech, cat #639648) according to the instructions, and then transformed into DH5a competent cells. The next day, a single clone was selected and sequenced, and the fragment was finally inserted into the PCAGGS vector. For example, the plasmid map of PCAGGS-huANP32A is shown in FIG. 2. The plasmid maps of ANP32A and ANP32B genes of other species are similar to that of FIG. 2, and only the corresponding gene sequences are replaced. For example, the plasmid map of PCAGGS-huANP32B is a sequence in which huANP32A is replaced by huANP32B.

Figure 3:
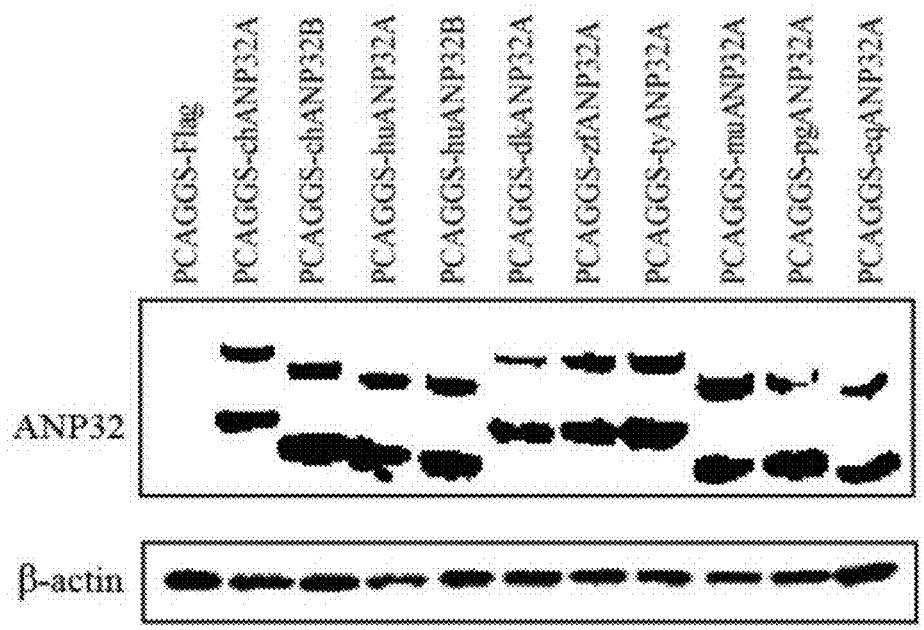
FIG. 3 shows the detection of expression of ANP32 protein from various species.

After the recombinant plasmids were sequenced correctly, 1 µg of the recombinant plasmids were respectively transfected into 293T cells by lipofectamine 2000 reagent, and the cell lysate was taken after 48 hours; the protein expression was detected by Flag-antibody (purchased from Sigma, cat # F1804-1MG) by utilizing western blotting; intracellular β-actin was used as an internal control gene; the antibody Monoclonal Anti-β-Actin antibody produced in mouse (purchased from Sigma, cat # A1978-200UL) was used and the result was shown in FIG. 3 showing that ANP32A and ANP32B proteins from various species were well expressed.

Example 2: Construction of a Cell Line

We performed the construction of cell line by using CRISPR-Cas9 technology. According to NCBI published reference nucleotide sequences of human ANP32A (NM_006305.3) and human ANP32B (NM_006401.2), sgRNAs for the two proteins were designed by using the online software <<http://crispr.mit.edu/>> (see Table 1 for sequences).

TABLE 1

| sgRNA sequences | |
|---|---|
| primer name | primer sequence (5'-3') |
| human ANP32A-sgRNA, SEQ ID NO:6 | TCTTAAGTACAATCAACGT |
| human ANP32B-sgRNA, SEQ ID NO:7 | GCCTACATTTATTAAACTG |

The pMD18T-U6 recombinant plasmid, which contains a human U6 promoter sequence+sgRNA sequence (huANP32A or huANP32B)+sgRNA scaffold sequence+TTTTTT, was constructed as follows.

First, a gene fragment is synthesized, wherein the fragment contains a human U6 promoter sequence+huANP32A-sgRNA sequence+sgRNA scaffold sequence+TTTTTT, and the sequence is SEQ ID NO: 8. The synthesized fragment was directly ligated into a pMD-18T vector (TaKaRa, Cat. No. D101A), and a pMD18T-U6-huANPsgRNA-1 recombinant plasmid (containing huANP32AsgRNA) was successfully constructed. Using this plasmid as a template, sgRNA primers for huANP32B were designed, and amplified by KOD-FX Neo high-efficiency DNA polymerase (Cat. No.: KFX-201, purchased from Toyobo) using the overlapping PCR method (the reaction condition and reaction system were based on the instructions of said polymerase; unless otherwise specified, except for the quantitative PCR reaction, KOD-FX Neo high-efficiency DNA polymerase was used in the PCR reactions of the following examples, and the reaction system and reaction condition were based on the instructions of said polymerase), to construct a plasmid containing sgRNA of huANP32B; and the primer sequences were shown in Table 2, and the PCR system and procedure were performed with reference to the KOD-FX Neo instructions. The obtained PCR product was digested with Dpn I in a 37° C. constant temperature water bath for 30 minutes, and then 5 ul of the digested product was taken to be transformed into 20 ul of DH5α competent cells; the next day, a single clone was picked for sequencing, and the plasmid which was verified correct by sequencing, namely pMD18T-U6-huANPsgRNA-2 (containing huANP32BsgRNA), was used for subsequent transfection experiment.

TABLE 2

| primer sequences | |
|---|---|
| primer name | primer sequence (5'-3') |
| huANP32B-sgRNA-F, SEQ ID NO: 9 | CGGGTCCGGTTCCTCAGCTCCGGTGTTTCGTCC |
| huANP32B-sgRNA-R, SEQ ID NO: 10 | GGAGCTGAGGAACCGGACCCGTTTTAGAGCTAG |

1 ug of eukaryotic plasmid pMJ920 (Addge plasmid #42234) expressing Cas9-GFP protein and pMD18T-U6-huANPsgRNA-1 or pMD18T-U6-huANPsgRNA-2 recombinant plasmids were taken respectively, and mixed with lipofectamine 2000 at a ratio of 1:2.5, and then transfected into 293T cells. After 48 hours, GFP-positive cells were screened by an ultra-speed flow cytometry sorting system, and plated in a 96-well plate at a single cell/well for about 10 days; single-cell clones were picked for expansion and culture, and then cellular RNA was extracted according to the procedure using a SimplyP total RNA extraction Kit (purchased from Bioflux, cat # BSC52M1), and cDNA was synthesized using a reverse transcription Kit of Takara Co., Ltd (PrimeScript™ RT reagent Kit with gDNA Eraser (Perfect read Time), Cat.RR047A); and sgRNA-targeting fragments of huANP32A and huANP32B were amplified by KOD Fx Neo polymerase using the cDNA as the template, and the amplification primers were shown in Table 3, wherein the size of huANP32A amplified fragment was 390 bp, and the size of huANP32B amplified fragment was 362 bp. Single-cell clones that were verified as gene deletion by sequencing were subject to western blotting and fluorescent quantitative identification. The huANP32A and huANP32B double-knockout cell lines were obtained after the first round of obtaining the huANP32B single-knockout cell line, followed by another round of knockout screening, and the transfection system and screening steps were as described above.

TABLE 3 the primer sequences for identification of huANP32A and huANP32B knockout cell line

| primer name | primer sequence (5'-3') |
|---|---|
| QhuANP32A-F180, SEQ ID NO: 11 | GGGCAGACGGATTCATTTAGAG |
| QhuANP32A-R570, SEQ ID NO: 12 | TTCTCGGTAGTCGTTCAGGTTG |
| QhuANP32B-F312, SEQ ID NO: 13 | GCGGAAAGTTAAGTTTGAAGAGG |
| QhuANP32B-R674, SEQ ID NO: 14 | GCGGAAAGTTAAGTTTGAAGAGG |

Figure 4:
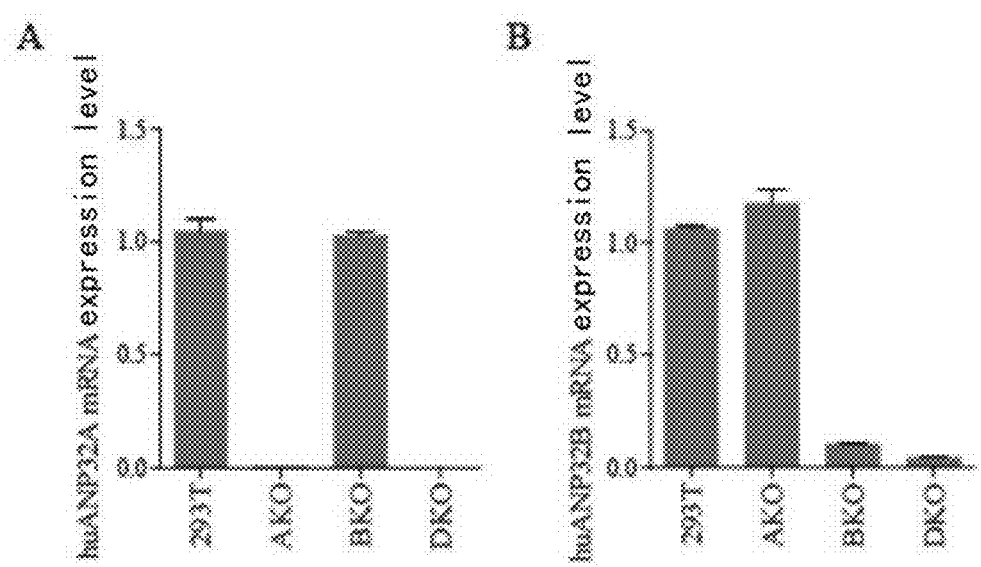
FIG. 4 shows the detection of the knockout cell line by fluorescent quantitative PCR: A is the quantitative detection of huANP32A on each cell line, and B is the quantitative detection of huANP32B on each cell line.
Figure 5:
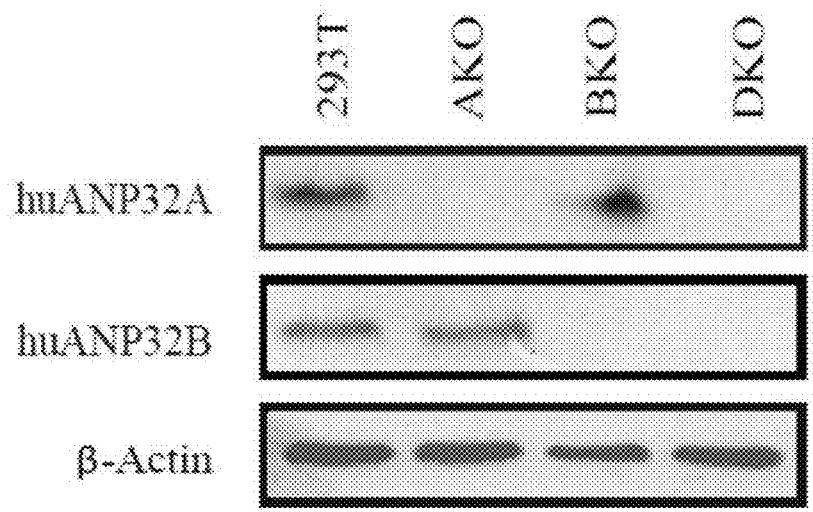
FIG. 5 shows the detection of endogenous ANP32 protein in 293T wild-type and knockout cell lines.

Anti-PHAP1 antibody (purchased from Abcam, cat # ab51013) and Anti-PHAPI2/APRIL antibody [EPR14588] (purchased from Abcam, cat # ab200836) were used in Western blotting; β-actin was used as the internal control gene, and the antibody of Monoclonal Anti-β-Actin antibody produced in mouse (purchased from Sigma, cat # A1978-200UL) was used, and the results were shown in FIG. 4. The primers for the fluorescent quantitative identification of the knockout cell line were shown in Table 4; β-actin was used as an internal control gene; the results of the fluorescent PCR identification were shown in FIG. 5. Based on the above, we successfully constructed a huANP32A single-knockout cell line (AKO), a huANP32B single-knockout cell line (BKO), and a huANP32A and ANP32B double-knockout cell line (DKO), which were used for subsequent experiments. Fluorescent quantitative PCR was performed using SYBR®Premix Ex Taq™ II (Tli RnaseH plus) (Cat. # RR820A) produced by TAKARA according to the instructions (the subsequent fluorescent quantitative PCR was also performed using the kit produced by TAKARA).

TABLE 4 the primer sequences for fluorescence quantitation of huANP32A and huANP32B

| primer name | primer sequence (5'-3') |
|---|---|
| qhu32A-F1, SEQ ID NO: 15 | GGCAGACGGATTCATTTAGAGC |
| qhu32A-R, SEQ ID NO: 16 | CTTTGGTAAGTTTGCGATTGA |
| qhu32B-F, SEQ ID NO: 17 | CTGCCCCAGCTTACCTACTTG |
| qhu32B-R, SEQ ID NO: 18 | ATCCTCATCGTCCTCGTCTTC |
| actin-F, SEQ ID NO: 19 | CATCTGCTGGAAGGTGGACAA |
| actin-R, SEQ ID NO: 20 | CGACATCCGTAAGGACCTGTA |

Example 3: Detection of Influenza Polymerase Activity

The influenza polymerase reporter system involved in the present invention includes influenza polymerases PB2, PB1 and PA proteins, and a nuclear protein NP. These proteins are derived from human influenza H1N1 subtype A/Sichuan/01/2009 ($H1N1_{SC09}$) and A/WSN/1933(WSN), human influenza H7N9 subtype A/Anhui/01/2013 ($H7N9_{AH13}$), and canine influenza H3N2 subtype A/canine/Guangdong/1/2011 ($H3N2_{GD11}$), avian influenza H9N2 subtype A/chicken/Zhejiang/B2013/2012 ($H9N2_{ZJ12}$) and H7N9 subtype A/chicken/Zhejiang/DTID-ZJU01/2013 ($H7N9_{ZJ13}$), equine influenza A/equine/Jilin/1/1989 ($H3N8_{JL89}$) and A/equine/Xinjiang/3/2007 ($H3N8_{XJ07}$) The sequences of PB2, PB1, PA and NP proteins of these influenza subtypes are shown in Table 5.

TABLE 5

The nucleotide sequences of PB2, PB1, PA and NP proteins

NP of human $H1N1_{sc09}$ (Genebank: GQ166225.1)
PA of human $H1N1_{sc09}$ (Genebank: GQ166226.1)
PB1 of human $H1N1_{sc09}$ (Genebank: GQ166227.1)
PB2 of human $H1N1_{sc09}$ (Genebank: GQ166228.1)
PB2 of human $H1N1_{WSN}$ (Genebank: CY034139.1)
PB1 of human $H1N1_{WSN}$ (Genebank: CY034138.1)
PA of human $H1N1_{WSN}$ (Genebank: CY034137.1)
NP of human $H1N1_{WSN}$ (Genebank: CY034135.1)
PB2 of human $H7N9_{AH13}$ (Genebank: EPI439504)
PB1 of human $H7N9_{AH13}$ (Genebank: EPI439508)
PA of human $H7N9_{AH13}$ (Genebank: EPI439503)
NP of human $H7N9_{AH13}$ (Genebank: EPI439505)
PB2 of canine $H3N2_{GD11}$ (Genebank: JX195347.1)
PB1 of canine $H3N2_{GD11}$ (Genebank: JX195346.1)
PA of canine $H3N2_{GD11}$ (Genebank: JX195340.1)
NP of canine $H3N2_{GD11}$ (Genebank: JX195341.1)
PB2 of avian $H9N2_{ZJ12}$ (Genebank: KP865886.1)
PB1 of avian $H9N2_{ZJ12}$ (Genebank: KP865839.1)
PA of avian $H9N2_{ZJ12}$ (Genebank: KP865793.1)
NP of avian $H9N2_{ZJ12}$ ( Genebank: KP865771.1)
PB2 of equine $H3N8_{JL89}$ (Genebank: KF285454.1)
PB1 of equine $H3N8_{JL89}$ (Genebank: KF285455.1)
PA of equine $H3N8_{JL89}$ (Genebank: KF285456.1)
NP of equine $H3N8_{JL89}$ (Genebank: M63786.1)
PB2 of equine $H3N8_{XJ07}$ (Genebank: EU794556.1)
PB1 of equine $H3N8_{XJ07}$ (Genebank: EU794557.1)
PA of equine $H3N8_{XJ07}$ (Genebank: EU794558.1)
NP of equine $H3N8_{XJ07}$ (Genebank: EU794560.1)
PB2 of avian $H7N9_{ZJ13}$ (Genebank: KC899666.1)
PB1 of avian $H7N9_{ZJ13}$ (Genebank: KC899667.1)
PA of avian $H7N9_{ZJ13}$ (Genebank: KC899668.1)
NP of avian $H7N9_{ZJ13}$ (Genebank: KC899670.1)

A plasmid containing the above-mentioned proteins of each influenza virus subtype was constructed, for example, $H1N1_{SC09}$ polymerase contained PB2, PB1 and PA proteins and a nuclear protein NP derived from human influenza H1N1 subtype A/Sichuan/01/2009 ($H1N1_{SC09}$), and was named as the $H1N1_{SC09}$ polymerase reporter system; plasmids were constructed with the vector PCAGGS for PB2, PB1, PA and NP, respectively, and were named as PB2 plasmid, PB1 plasmid, PA plasmid, and NP plasmid. The same is for others.

Taking the $H1N1_{SC09}$ polymerase reporter system as an example, the construction process was as follows:

mRNA of $H1N1_{SC09}$ strain (Master's thesis of Zhang Qianyi, "Establishment of reverse genetic operating system for H1N1 influenza virus A/Sichuan/01/2009 strain", Gansu Agricultural University, 2011) was extracted according to the operation manual of QIAamp Viral RNA Mini Kit (purchased from QIAGEN, cat #52904), and then cDNA was synthesized according to the instruction of M-MLV reverse transcriptase kit (purchased from Invitrogen, cat #28025-013) using Uni12 (AGCAAAAGCAGG, SEQ ID NO:21) as reverse transcription primer. Based on the sequence information of each gene fragment, PCR primers were designed (see Table 7); a 15 bp PCAGGS homologous arm was respectively introduced at both ends; the gene of interest was synthesized using KOD FX Neo high-efficiency polymerase; and then the amplified fragment of each gene of $H1N1_{SC09}$ and the double-digested PCAGGS vector in Example 1 were ligated at room temperature for 30 minutes using the seamless cloning kit, ClonExpress II One Step Cloning Kit (purchased from Vazyme, cat # C112-01) according to the instructions; the ligation product was transformed into 20 ul DH5α competent cells, and the next day a single clone was picked for sequencing. The plasmid which were verified correct by sequencing were respectively named as PB2 plasmid, PB1 plasmid, PA plasmid and NP plasmid, and used for subsequent experiments. The same is for others. See Table 6 for the sources of other various strains.

TABLE 6

| | |
|---|---|
| Human H1N1 WSN | Neumann G; Watanabe T; Ito H; Watanabe S; Goto H; Gao P; Hughes M; Perez D R; Donis R; Hoffmann E; Hobom G; Kawaoka Y. Generation of influenza A viruses entirely from cloned cDNAs. [J]. Proceedings of the National Academy of Sciences of the United States of America, 1999, 96(16): 9345-50 |
| human A/Anhui/01/2013 (H7N9$_{AH13}$) | Zhang, Q., Shi, J., Deng, G., Guo, J., Zeng, X., He, X., Kong, H., Gu, C., Li, X., Liu, J., et al. (2013). H7N9 influenza viruses are transmissible in ferrets by respiratory droplet. Science. 341(6144), 410-414 |
| canine influenza H3N2 subtype A/canine/ Guangdong/ 1/2011 (H3N2$_{GD11}$) | Su S, Li H T, Zhao F R, et al. Avian-origin H3N2 canine influenza virus circulating in farmed dogs in Guangdong, China[J]. Infection Genetics & Evolution, 2013, 14(2): 444-449 |
| avian influenza H9N2 subtype A/chicken/ Zhejiang/ B2013/2012 (H9N2$_{ZJ12}$) | Teng Q, Xu D, Shen W, et al. A Single Mutation at Position 190 in Hemagglutinin Enhances Binding Affinity for Human Type Sialic Acid Receptor and Replication of H9N2 Avian Influenza Virus in Mice[J], Journal of Virology, 2016, 90(21): 9806 |
| avian H7N9 subtype A/chicken/ Zhejiang/ DTID-ZJU01/ 2013(H7N9$_{ZJ13}$) | Li C, Li C, Zhang A J, et al. Avian influenza A H7N9 virus induces severe pneumonia in mice without prior adaptation and responds to a combination of zanamivir and COX-2 inhibitor[J]. Plos One, 2014, 9(9): e107966 |
| equine A/equine/Jilin/1/ 1989 (H3N8$_{JL89}$) | Zhang Xiang, Guo Wei, Wang Xiaojun. Construction of Two-way Transcription/Expression Vector and Its Application in Reverse Genetic System of Equine Influenza Virus [J]. Chinese Journal of Preventive Veterinary Medicine, 2016, 38 (11): 860-864 |
| equine A/equine/ Xinjiang/3/2007 (H3N8$_{XJ07}$) | master's thesis Dai Lingli. Sequence analysis of HA gene of equine influenza virus A/Equine/Xinjiang/3/07 (H3N8) and establishment of two PCR detection methods [D]. Chinese Academy of Agricultural Sciences, 200 |

TABLE 7

Polymerase construction primers:

| primer name | primer sequence |
|---|---|
| H1N1 SC09-PB2-F SEQ ID NO: 22 | TTCGAGCTCGCGGCCGCATGGAGAGAATAAAAGAACT |
| H1N1 SC09-PB2-R SEQ ID NO: 23 | ATCTGCTAGCTCGAGCTAATTGATGGCCATCCGAA |
| H1N1 SC09-PB1-F SEQ ID NO: 24 | TTCGAGCTCGCGGCCGCATGGATGTCAATCCGACTCT |
| H1N1 SC09-PB1-R SEQ ID NO: 25 | ATCTGCTAGCTCGAGTTATTTTTGCCGTCTGAGTT |
| H1N1 SC09-PA-F SEQ ID NO: 26 | TTCGAGCTCGCGGCCGCATGGAAGACTTTGTGCGAC |
| H1N1 SC09-PA-R SEQ ID NO: 27 | ATCTGCTAGCTCGAGCTACTTCAGTGCATGTGTGA |
| H1N1 SC09-NP-F SEQ ID NO: 28 | TTCGAGCTCGCGGCCGCATGGCGTCTCAAGGCACCAA |
| H1N1 SC09-NP-R SEQ ID NO: 29 | ATCTGCTAGCTCGAGTCAACTGTCATACTCCTCTG |
| H1N1 WSN-PB2-F SEQ ID NO: 30 | TTCGAGCTCGCGGCCGCATGGAAAGAATAAAAGAAC |
| H1N1 WSN-PB2-R SEQ ID NO: 31 | ATCTGCTAGCTCGAGCTATTCGACACTAATTGATG |
| H1N1 WSN-PB1-F SEQ ID NO: 32 | TTCGAGCTCGCGGCCGCATTTGAATGGATGTCAATCCGAC |
| H1N1 WSN-PB1-R SEQ ID NO: 33 | ATCTGCTAGCTCGAGTCATGAAGGACAAGCTAAATTCA |
| H1N1 WSN-PA-F SEQ ID NO: 34 | TTCGAGCTCGCGGCCGCCTGATTCAAAATGGAAGATT |
| H1N1 WSN-PA-R SEQ ID NO: 35 | ATCTGCTAGCTCGAGTTTTTGGACAGTATGGATAGCAAA |
| H1N1 WSN-NP-F SEQ ID NO: 36 | TTCGAGCTCGCGGCCGCTCACTCACAGAGTGACATCGA |
| H1N1 WSN-NP-R SEQ ID NO: 37 | ATCTGCTAGCTCGAGTTCTTTAATTGTCGTACTCCT |
| H7N9 AH13-PB2-F SEQ ID NO: 38 | TTCGAGCTCGCGGCCGCATGGAAAGAATAAAAGAAC |
| H7N9 AH13-PB2-R SEQ ID NO: 39 | ATCTGCTAGCTCGAGTTAATTGATGGCCATCCGAAT |
| H7N9 AH13-PB1-F SEQ ID NO: 40 | TTCGAGCTCGCGGCCGCATGGATGTCAATCCGACTTT |
| H7N9 AH13-PB 1-R SEQ ID NO: 41 | ATCTGCTAGCTCGAGCTATTTTTGCCGTCTGAGCTC |

TABLE 7-continued

| Polymerase construction primers: | |
|---|---|
| primer name | primer sequence |
| H7N9 AH13-PA-F SEQ ID NO: 42 | TTCGAGCTCGCGGCCGCATGGAAGACTTTGTGCGAC |
| H7N9 AH13-PA-R SEQ ID NO: 43 | ATCTGCTAGCTCGAGCTATCTTAGTGCATGTGTGA |
| H7N9 AH13-NP-F SEQ ID NO: 44 | TTCGAGCTCGCGGCCGCATGGCGTCTCAAGGCACCA |
| H7N9 AH13-NP-R SEQ ID NO: 45 | ATCTGCTAGCTCGAGTCAATTGTCATACTCCTCTGC |
| H3N2 GD12-PB2-F SEQ ID NO: 46 | TTCGAGCTCGCGGCCGCATGGAGAGAATAAAAGAATT |
| H3N2 GD12-PB2-R SEQ ID NO: 47 | ATCTGCTAGCTCGAGCTAATTGATGGCCATCCGAA |
| H3N2 GD12-PB1-F SEQ ID NO: 48 | TTCGAGCTCGCGGCCGCATGGATGTCAATCCGACTTT |
| H3N2 GD12-PB1-R SEQ ID NO: 49 | ATCTGCTAGCTCGAGCTATTTTTGCCGTCTGAGCTC |
| H3N2 GD12-PA-F SEQ ID NO: 50 | TTCGAGCTCGCGGCCGCATGGAAGACTTTGTGCGACAA |
| H3N2 GD12-PA-R SEQ ID NO: 51 | ATCTGCTAGCTCGAGCTATTTCAGTGCATGTGTGAGG |
| H3N2 GD12-NP-F SEQ ID NO: 52 | TTCGAGCTCGCGGCCGCATGGCGTCTCAAGGCACCAAAC |
| H3N2 GD12-NP-R SEQ ID NO: 53 | ATCTGCTAGCTCGAGTTAATTGTCATACTCCTCTGC |
| H3N8 JL89-PB2-F SEQ ID NO: 54 | TTCGAGCTCGCGGCCGCATGGAGAGAATAAAAGAATT |
| H3N8 JL89-PB2-R SEQ ID NO: 55 | ATCTGCTAGCTCGAGCTAATTGATGGCCATCCGAAT |
| H3N8 JL89-PB1-F SEQ ID NO: 56 | TTCGAGCTCGCGGCCGCATGGATGTCAATCCGACTTT |
| H3N8 JL89-PB1-R SEQ ID NO: 57 | ATCTGCTAGCTCGAGTCACTGTTTTTGCCGTCTGAG |
| H3N8 JL89-PA-F SEQ ID NO: 58 | TTCGAGCTCGCGGCCGCATGGAAGATTTTGTGCGACAA |
| H3N8 JL89-PA-R SEQ ID NO: 59 | ATCTGCTAGCTCGAGCTATTTCAGTGCATGTGTGA |
| H3N8 JL89-NP-F SEQ ID NO: 60 | TTCGAGCTCGCGGCCGCAGCAAAAGCAGGGTAGATAAT |
| H3N8 JL89-NP-R SEQ ID NO: 61 | ATCTGCTAGCTCGAGAGTAGAAACAAGGGTATTTTTC |
| H3N8 XJ07-PB2-F SEQ ID NO: 62 | TTCGAGCTCGCGGCCGCATGGAGAGAATAAAAGAACT |
| H3N8 XJ07-PB2-R SEQ ID NO: 63 | ATCTGCTAGCTCGAGTTAATTGATGGCCATCCGAAT |
| H3N8 XJ07-PB1-F SEQ ID NO: 64 | TTCGAGCTCGCGGCCGCATGGATGTCAATCCGACTCT |
| H3N8 XJ07-PB1-R SEQ ID NO: 65 | ATCTGCTAGCTCGAGCTATTTTTGCCGTCTGAGC |
| H3N8 XJ07-PA-F SEQ ID NO: 66 | TTCGAGCTCGCGGCCGCATGGAAGACTTTGTGCGACA |
| H3N8 XJ07-PA-R SEQ ID NO: 67 | ATCTGCTAGCTCGAGTTACTTCAGTGCATGTGTAAGG |
| H3N8 XJ07-NP-F SEQ ID NO: 68 | TTCGAGCTCGCGGCCGCATGGCGTCTCAAGGCACCAAA |
| H3N8 XJ07-NP-R SEQ ID NO: 69 | ATCTGCTAGCTCGAGTTAACTGTCAAATTCCTCAGC |
| H9N2 ZJ12-NP-F SEQ ID NO: 70 | TTCGAGCTCGCGGCCGCATGGCGTCTCAAGGCAC |
| H9N2 Z112-NP-R SEQ ID NO: 71 | ATCTGCTAGCTCGAGTCAATTGTCATACTCCT |
| H9N2 Z112-PA-F SEQ ID NO: 72 | TTCGAGCTCGCGGCCGCATGGAAGACTTTGTGCG |
| H9N2 Z112-PA-R SEQ ID NO: 73 | ATCTGCTAGCTCGAGCTATCTTAGTGCATGTG |
| H9N2 Z112-PB1-F SEQ ID NO: 74 | TTCGAGCTCGCGGCCGCATGGATGTCAATCCGA |
| H9N2 Z112-PB1-R SEQ ID NO: 75 | ATCTGCTAGCTCGAGCTATTTTTGCCGTCTGAG |
| H9N2 ZI12-PB2-F SEQ ID NO: 76 | TTCGAGCTCGCGGCCGCATGGAAAGAATAAAAGA |
| H9N2 Z112-PB2-R SEQ ID NO: 77 | ATCTGCTAGCTCGAGTTAATTGATGACCATCCG |

We constructed a reporter plasmid (pMD18T-vLuc) for detecting the activity of polymerase; the reporter plasmid uses the pMD18T plasmid as the backbone and contains the sequence of interest; the sequence of interest is characterized in that the 5' end non-coding region (sequence: agcaaaagcagggg, SEQ ID NO:78) and the 3' end non-coding region (sequence: gtatactaataattaaaaacacccttgtttctact, SEQ ID NO:79) of HA gene of H3N8$_{JL89}$ strain were introduced into both ends of the protein coding sequence of Firefly luciferase; a human polI promoter was introduced into the 3'end of the sequence, and a murine pol I terminator sequence was introduced into the 5'end of the sequence. The sequence of interest is as follows: murine pol I terminator sequence (bold underlined)+5' non-coding region (red italics) of HA gene+gene sequence of Firefly luciferase+3' non-coding region (green italics) of HA gene+human polI promoter (bold underlined), SEQ ID NO: 80. The synthesized fragment was directly ligated into the pMD18-T vector, obtaining the reporter plasmid pMD18T-vLuc.

After co-transfecting this reporter plasmid and the influenza polymerase system into 293T, the polymerase complex can recognize the non-coding sequences of the virus at both ends of Firefly luciferase, thereby starting the synthesis of Firefly luciferase gene vRNA, cRNA and mRNA. In order to make the polymerase system more stable and stringent, we introduced a polymerase dual fluorescence reporter system, wherein *Renilla* luciferase (pRL-TK) was further added as an internal control into the above influenza polymerase reporter system, and we established a stable transfection system: taking a 12-well plate as an example, adding PB1 plasmid (80 ng), PB2 plasmid (80 ng), PA plasmid (40 ng), NP plasmid (160 ng), pMD18T-vLuc plasmid (80 ng) and pRL-TK plasmid (10 ng, Promega cat # E2241, GenBank number: AF025846) into each well, and then transfecting with the transfection reagent lipo2000. After 24 hours of transfection, the cell supernatant was discarded; the cells were lysed by 100 ul of cell lysis buffer/well (passive lysis buffer, derived from the dual luciferase kit (Promega)), and then measured by the dual luciferase kit (Promega) using Centro. XS LB 960 luminometer (Berthold technologies). *Renilla* luciferase was used as an internal control, and the ratio can represent the activity of the polymerase.

Figure 6:
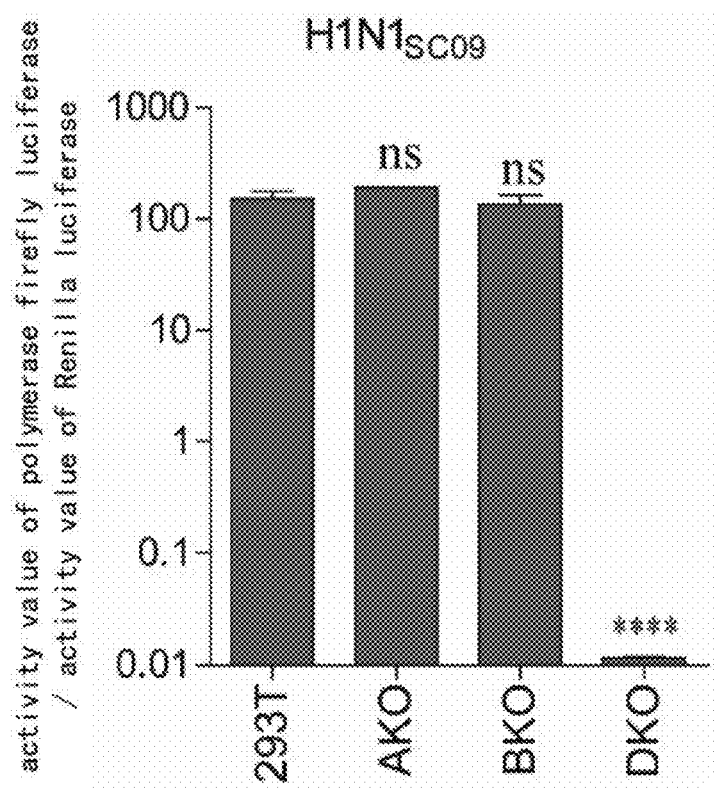
FIG. 6 shows the detection of activity of $H1N1_{SC09}$ polymerase on 293T wild-type and knockout cell lines.
Figure 7A:
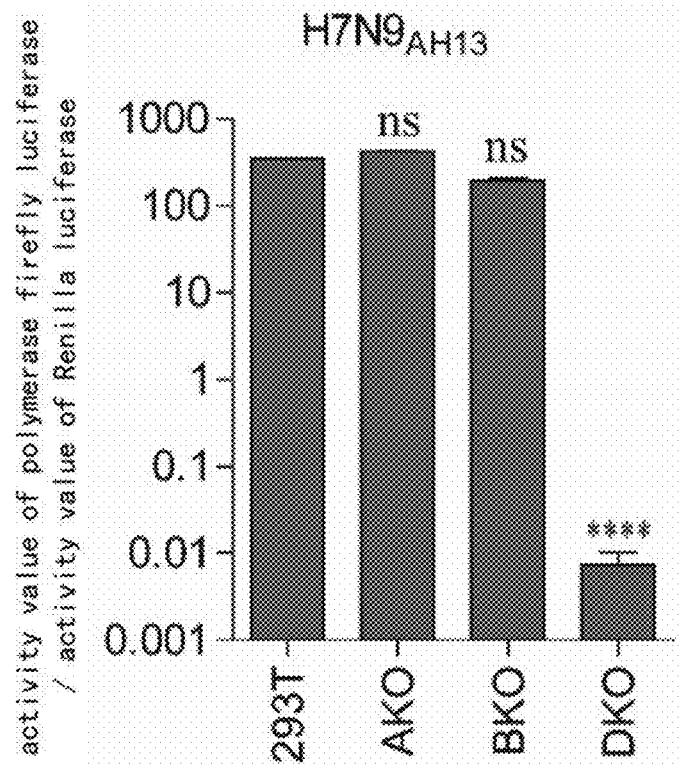
FIG. 7A is the detection of activity of $H7N9_{AH13}$ polymerase on 293T wild-type and knockout cell lines.
Figure 7B:
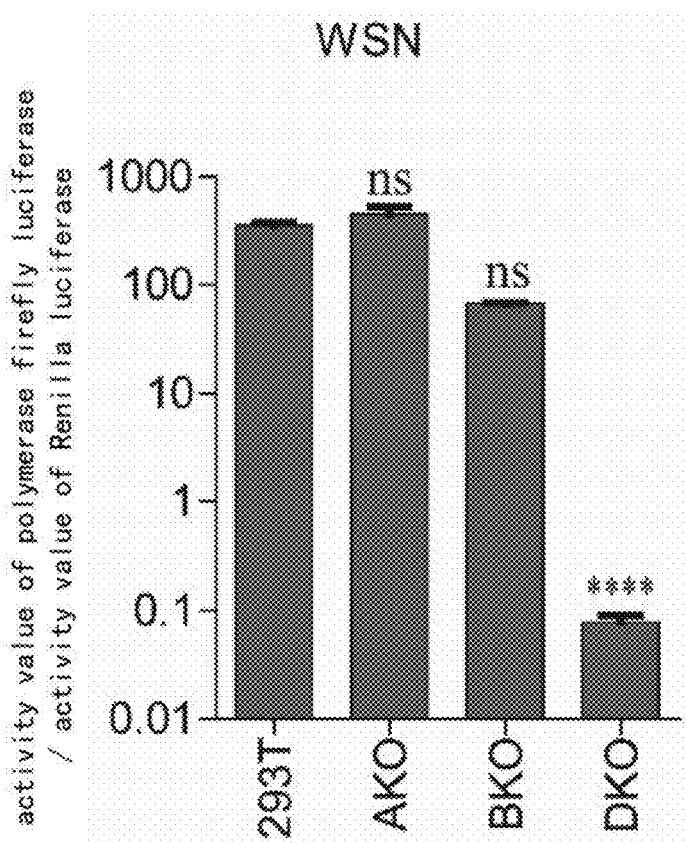
FIG. 7B is the detection of activity of WSN polymerase on 293T wild-type and knockout cell lines.
Figure 7C:
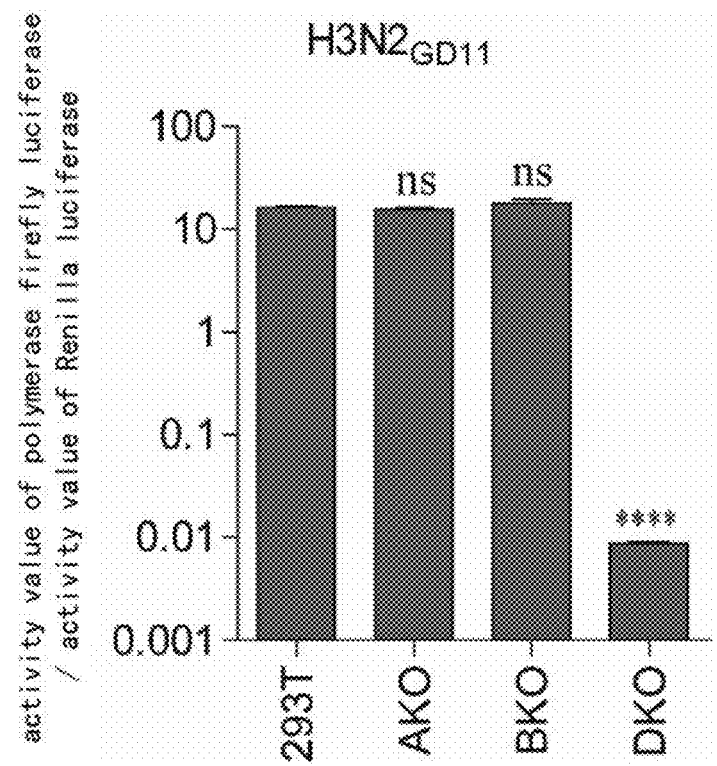
FIG. 7C is the detection of activity of $H3N2_{GD11}$ polymerase on 293T wild-type and knockout cell lines.
Figure 7D:
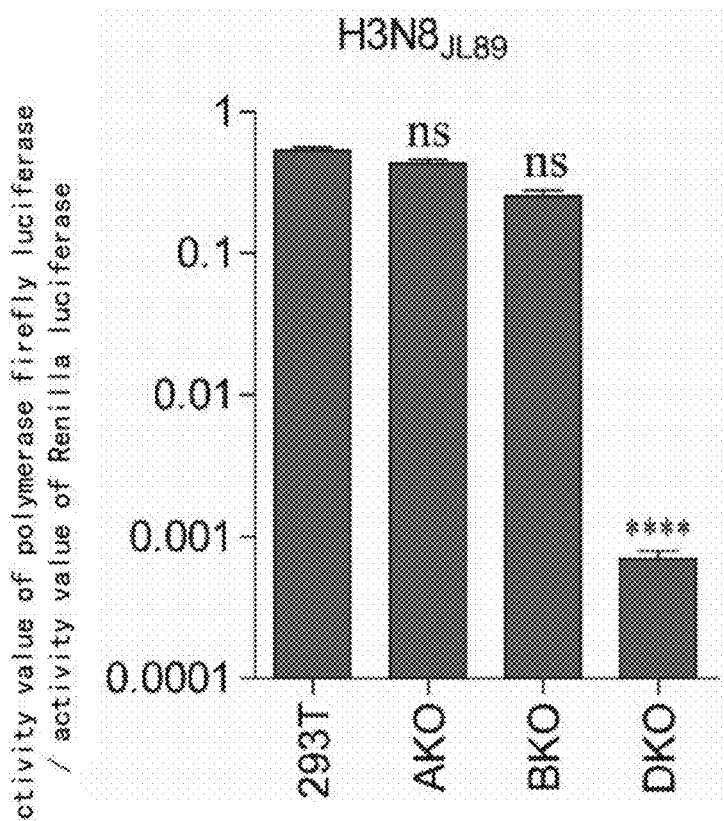
FIG. 7D is the detection of activity of $H3N8_{JL89}$ polymerase on 293T wild-type and knockout cell lines.
Figure 7E:
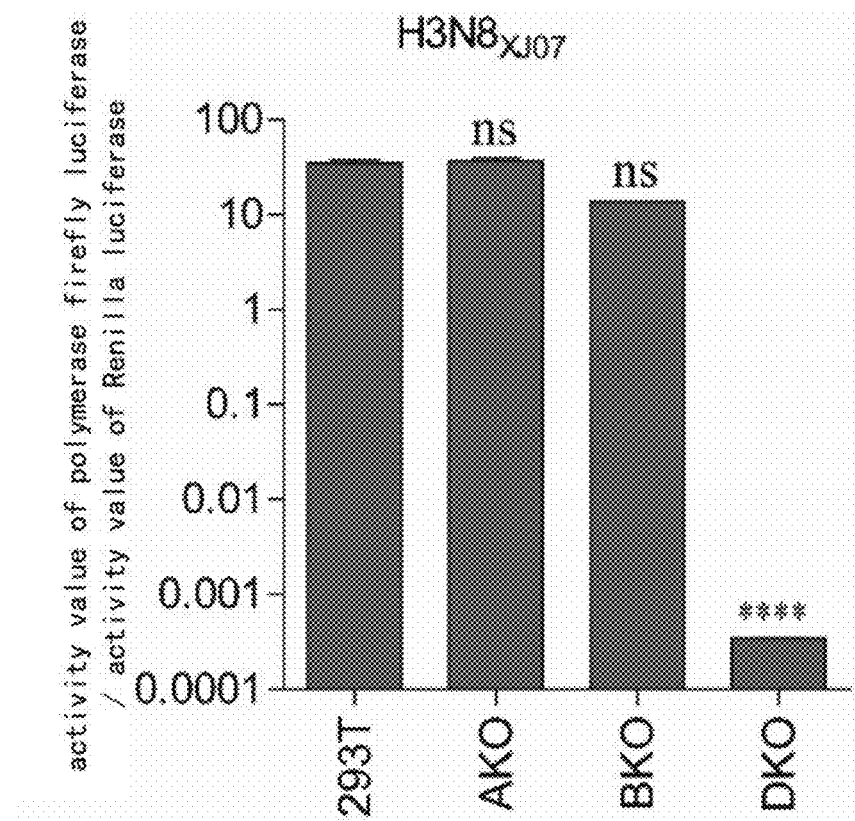
FIG. 7E is the detection of activity of $H3N8_{XJ07}$ polymerase on 293T wild-type and knockout cell lines.

We transfected the H1N1$_{SC09}$ polymerase into the cell lines AKO, BKO, DKO constructed in Example 2 and wild-type 293T cell by the above system; each group was set up with triplicate wells and then detected 24 hours after transfection, the activity of H1N1$_{SC09}$ polymerase in AKO and BKO was not different from that of wild-type 293T cells, while the activity of H1N1$_{SC09}$ polymerase in DKO cells decreased by more than 10,000 times, see FIG. 6. The results were processed by the biological software GraphPad Prism 5 (<<https://www.graphpad.com>>) and analyzed by one-way ANOVA and Dunnett's t-test; the difference between each experimental group and the control group is shown in the chart: ns means no difference, * means P<0.05,  means P<0.01, * means P<0.001, **** means P<0.0001. The symbols ns, *, , * and **** in other figures relating to the detection of polymerase activity have the same meanings as above, and processed as above.

H7N9$_{AH13}$, WSN, H3N2$_{GD11}$, H3N8$_{JL89}$, H3N8$_{XJ07}$ polymerase were transfected into different cell lines AKO, BKO, DKO and wild-type 293T cells in the same way as H1N1$_{SC09}$ polymerase; the result is that the activity in AKO and BKO was not different from that in wild-type 293T cells, while the activity in DKO cells decreased by about 10,000 times; the results are shown in FIG. 7A-E.

The huANP32A and huANP32B expression plasmids constructed in Example 1 PCAGGS-huANP32A and PCAGGS-huANP32B were co-transfected with H1N1$_{SC09}$ polymerase into DKO cells; the specific transfection system was: taking a 12-well plate as an example, each well was added with H1N1$_{SC09}$ PB1 plasmid (80 ng), PB2 plasmid (80 ng), PA plasmid (40 ng), NP plasmid (160 ng), pMD18T-vLuc plasmid (80 ng), pRL-TK plasmid (10 ng) and different doses of ANP32A and ANP32B proteins, and the specific doses of ANP32A and ANP32B protein plasmids were respectively selected from the following doses: 0 pg, 10 pg, 100 pg, 1 ng, 5 ng, 10 ng, 20 ng, 100 ng, 500 ng, 1 ug, and a PCAGGS-Flag empty vector control was set at the same time; the total amount of plasmid was made up by the PCAGGS-Flag empty vector, and each group was provided with triplicate wells. Cells were lysed 24 h after transfection, and the polymerase activity was detected as described above.

Figure 8:
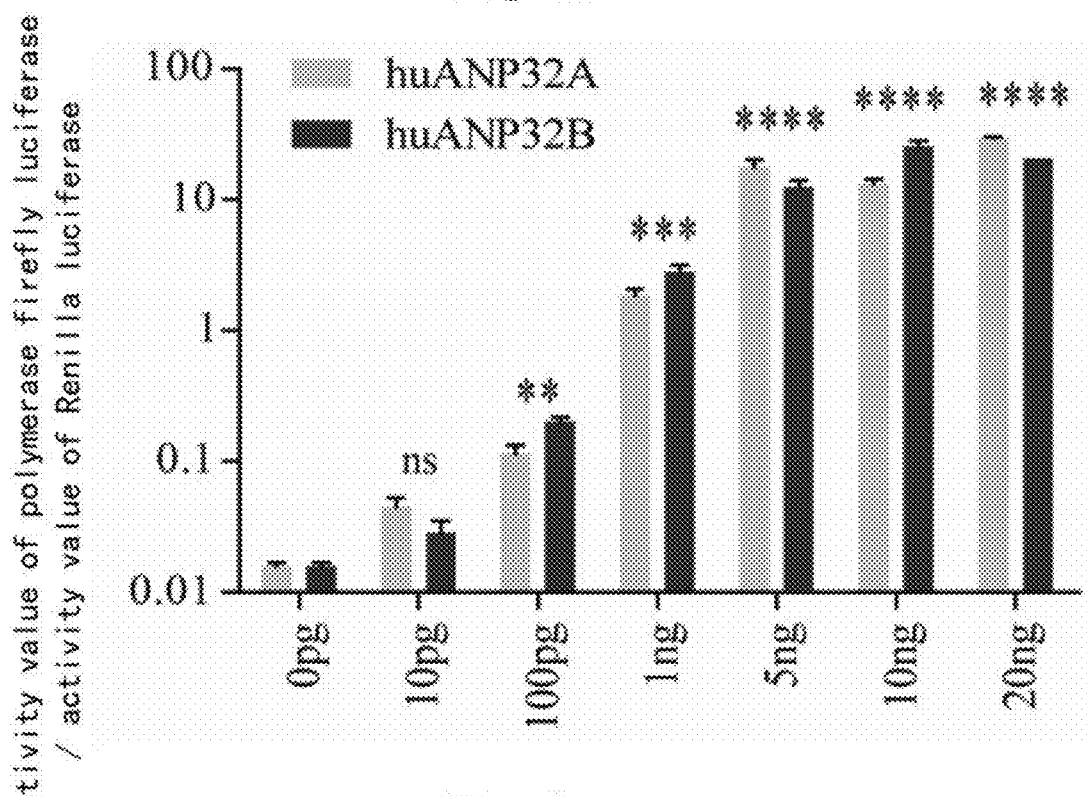
FIG. 8 shows the activity assay of $H1N1_{SC09}$ polymerase on DKO cell line when supplemented with different doses of huANP32A or huANP32B.
Figure 9:
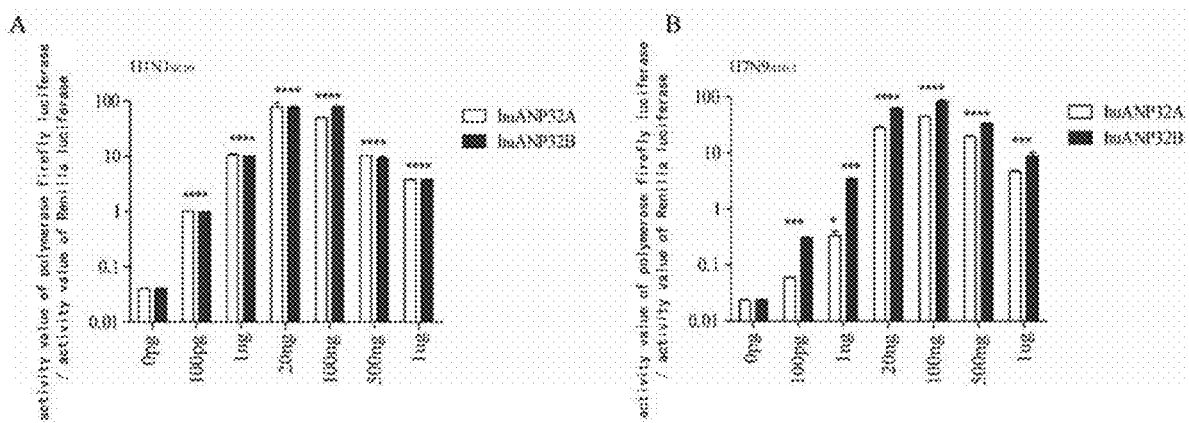
FIG. 9 shows that the activity of $H1N1_{SC09}$ polymerase (A) and $H7N9_{AH13}$ polymerase (B) on DKO cells is inhibited when supplemented with excessive huANP32A or huANP32B.

The results showed that the supplementation of huANP32A and ANP32B proteins can restore the activity of polymerase in a dose-dependent manner, reaching a plateau phase at 20 ng, and the activity of the polymerase can be restored by about 3000 times. The activity curves of huANP32A and huANP32B proteins have the same trend, and there was no additive effect during the plateau phase, as shown in FIG. 8. Therefore, the polymerase was dose-dependent on huANP32A and ANP32B proteins, and the dose requirement was low. Whereas, the activity of polymerase was inhibited when the amount of the huANP32A and huANP32B proteins was excessive, as shown in FIG. 9A. DKO cells were co-transfected with the huANP32A and huANP32B expression plasmids constructed in Example 1 at different doses described above as well as H7N9$_{AH13}$ polymerase, and the result was similar to H1N1$_{SC09}$, as shown in FIG. 9B.

Figure 10:
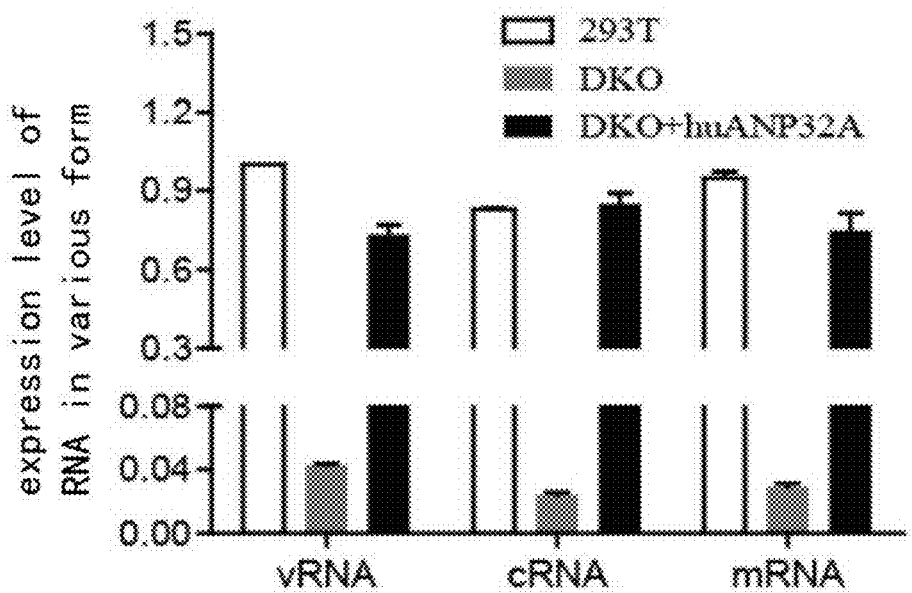
FIG. 10 shows the influence of huANP32A on the RNA synthesis of $H1N1_{SC09}$ influenza virus by fluorescent quantitative detection.

Example 4: Fluorescent Quantitative Detection of the Influence of ANP32 Protein on RNA Synthesis of Influenza Virus Real-time PCR was used to detect the differences in the synthesis of cRNA, vRNA and mRNA of influenza virus on wild-type 293T and the double-knockout cell line DKO. First, wild-type 293T and double-knockout cell line DKO cell were plated in a 12-well plate, and the 293T cells were transfected with the H1N1$_{SC09}$ polymerase dual fluorescence reporter system of Example 3. The transfection system was: PB1 plasmid (80 ng), PB2 plasmid (80 ng), PA plasmid (40 ng), NP plasmid (160 ng), pMD 18T-vLuc plasmid (80 ng), pRL-TK plasmid (10 ng), and empty vector PCAGGS-Flag plasmid (20 ng); the DKO cells were transfected with H1N1$_{SC09}$ polymerase dual fluorescence reporter system of Example 3. The transfection system was: PB1 plasmid (80 ng), PB2 plasmid (80 ng), PA plasmid (40 ng), NP plasmid (160 ng), pMD18T-vLuc plasmid (80 ng), pRL-TK plasmid (10 ng), and PCAGGS-huANP32A plasmid (20 ng), while the empty vector PCAGGS-Flag plasmid (20 ng) was set as a negative control. After 24 h, total cellular RNA was extracted, and reverse transcription was performed using particular primers (see Table 8) to synthesize the first cDNAs of cRNA, vRNA and mRNA, respectively, followed by fluorescent quantitative PCR using specific primers (see Table 9); using random primers (contained in the kit) as reverse transcription primers for internal control gene β-actin, and the fluorescent quantitative primers of β-actin were shown in Table 4 of Example 2. The results showed that compared to the wild type, the synthesis of viral cRNA, vRNA and mRNA was significantly reduced (about 30-50 times) on the double-knockout cell line, indicating that RNA of influenza virus was hardly replicated in cell lines lacking ANP32A and ANP32B. When human ANP32A was supplemented to the double-knockout cell line, the replication and synthesis of RNA could be restored, as shown in FIG. 10. The above experimental procedure was repeated with the huANP32B plasmid instead of the huANP32A plasmid; it was found that human ANP32B also had the same function (data is similar to DKO+huANP32A in FIG. 10). This showed that the ANP32A and ANP32B proteins were involved in the synthesis and replication of influenza virus RNA and played a decisive role therein.

TABLE 8

Reverse transcription primers

| primer name | primer sequence |
|---|---|
| Luc-vRNA, SEQ ID NO: 81 | CATTTCGCAGCCTACCGTGGTGT T |
| Luc-cRNA, SEQ ID NO: 82 | AGTAGAAACAAGGGTG |
| Luc-mRNA, SEQ ID NO: 83 | oligo-dT20 |

TABLE 9 fluorescent quantitative PCR primers

| primer name | primer sequence |
|---|---|
| Luc-F, SEQ ID NO: 84 | GATTACCAGGGATTTCAGTCG |
| Luc-R, SEQ ID NO: 85 | GACACCTTTAGGCAGACCAG |

Example 5: Influence of ANP32 Protein on the Replication of Influenza Virus

Figure 11A:
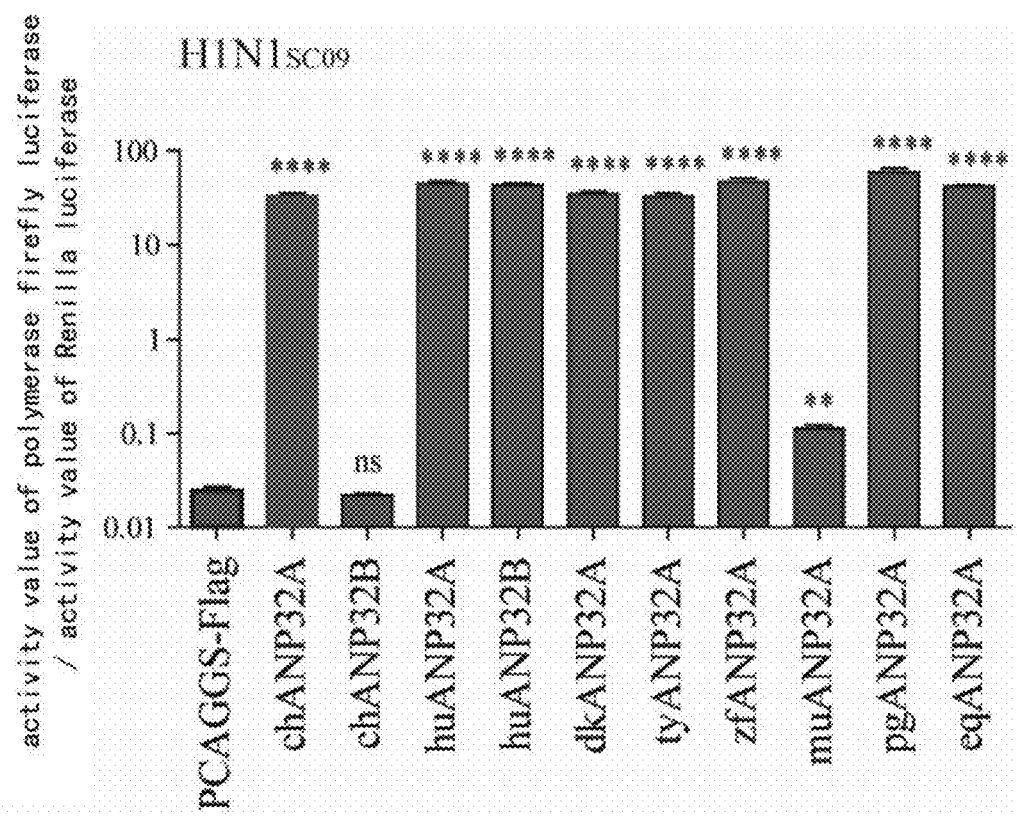
FIG. 11A shows the influence of ANP32 protein of different species on the replication of $H1N1_{SC09}$ influenza virus.

Double-knockout cell lines (DKO) were plated in a 12-well plate at $3 \times 10^5$/well; after 20 hours, the ANP32A and ANP32B protein plasmids of different species constructed in Example 1 were co-transfected with 6 plasmids of the H1N1$_{SC09}$polymerase reporter system. The transfection system was: PB1 plasmid (80 ng), PB2 plasmid (80 ng), PA plasmid (40 ng), NP plasmid (160 ng), pMD 18T-vLuc plasmid (80 ng), pRL-TK plasmid (10 ng), and ANP32A or ANP32B protein plasmid (20 ng), and the empty vector PCAGGS-Flag (20 ng) was set as a negative control, and each group was provided with triplicate wells. 24 h after transfection, the cells were lysed as described in Example 3 to detect the activity of polymerase, showing that: compared to the empty vector, avian ANP32A such as chANP32A, dkANP32A, zfANP32A, tyANP32A, mammalian ANP32 such as huANP32A, pgANP32A, eqANP32A, huANP32B all supported the activity of H1N1$_{SC09}$ polymerase, whereas the two proteins chANP32B and muANP32A did not have the ability to support the activity of H1N1$_{SC09}$ polymerase, as shown in FIG. 11A.

Figure 11B:
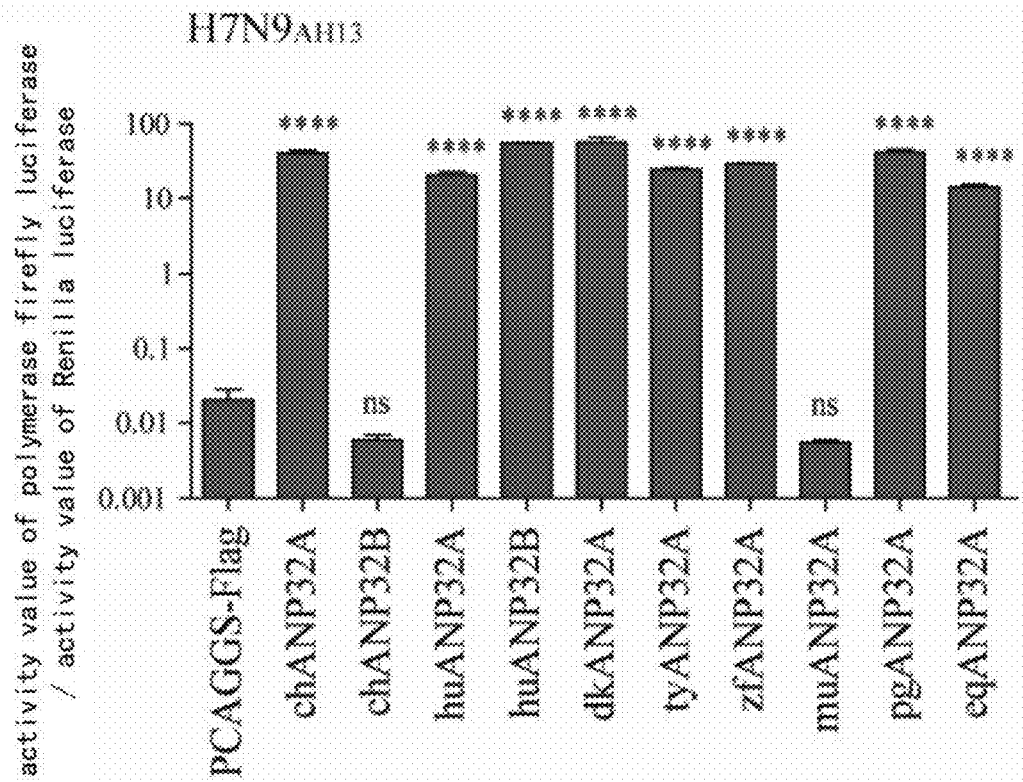
FIG. 11B shows the influence of ANP32 protein of different species on the replication of $H7N9_{AH13}$ influenza virus.

The above experiment was repeated with the H7N9$_{AH13}$ polymerase reporter system instead of the H1N1$_{SC09}$ polymerase reporter system, and the result showed that: compared to the empty vector, avian ANP32A such as chANP32A, dkANP32A, zfANP32A, tyANP32A, mammalian ANP32 such as huANP32A, pgANP32A, eqANP32A, huANP32B all supported the activity of H7N9$_{AH13}$ polymerase, whereas the two proteins chANP32B and muANP32A did not have the ability to support the activity of H7N9$_{AH13}$ polymerase, as shown in FIG. 11B.

Figure 11C:
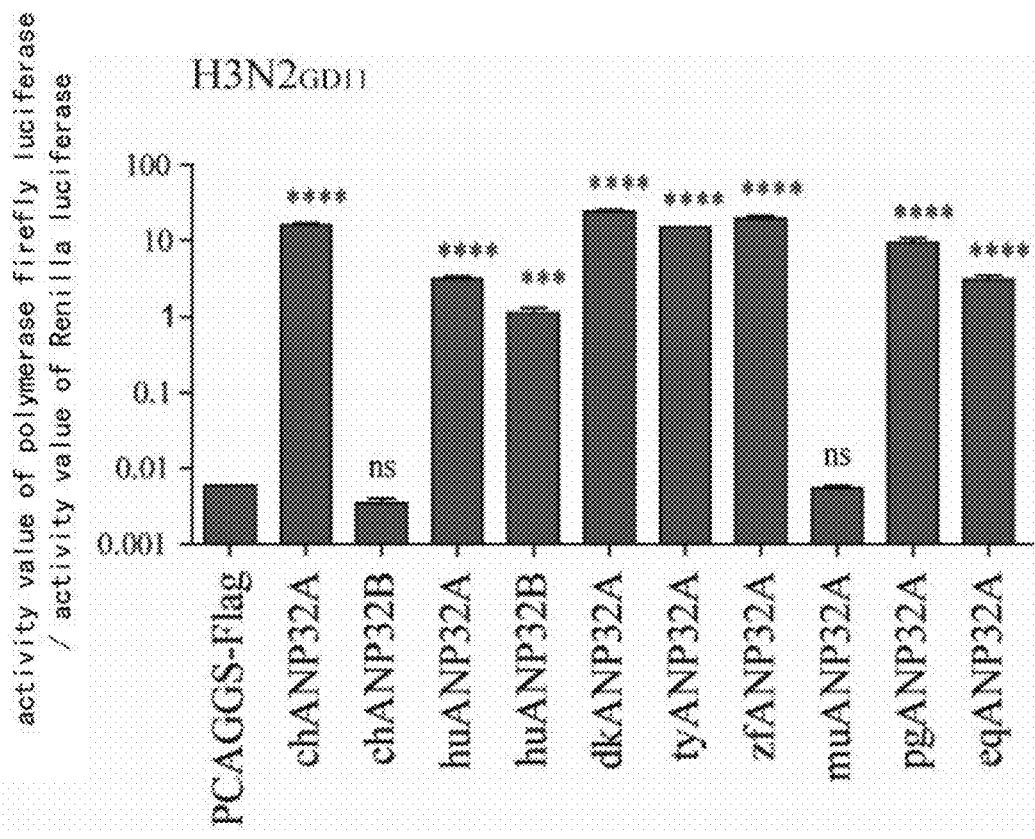
FIG. 11C shows the influence of ANP32 protein of different species on the replication of $H3N2_{GD11}$ influenza virus.

The above experiment was repeated with the H3N2$_{GD11}$ polymerase reporter system instead of the H1N1$_{SC09}$ polymerase reporter system, and the result showed that: compared to the empty vector, avian ANP32A such as chANP32A, dkANP32A, zfANP32A, tyANP32A, mammalian ANP32 such as huANP32A, pgANP32A, eqANP32A, huANP32B all supported the activity of H3N2$_{GD11}$ polymerase, whereas the two proteins chANP32B and muANP32A did not have the ability to support the activity of H3N2$_{GD11}$ polymerase, as shown in FIG. 11C.

Figure 11D:
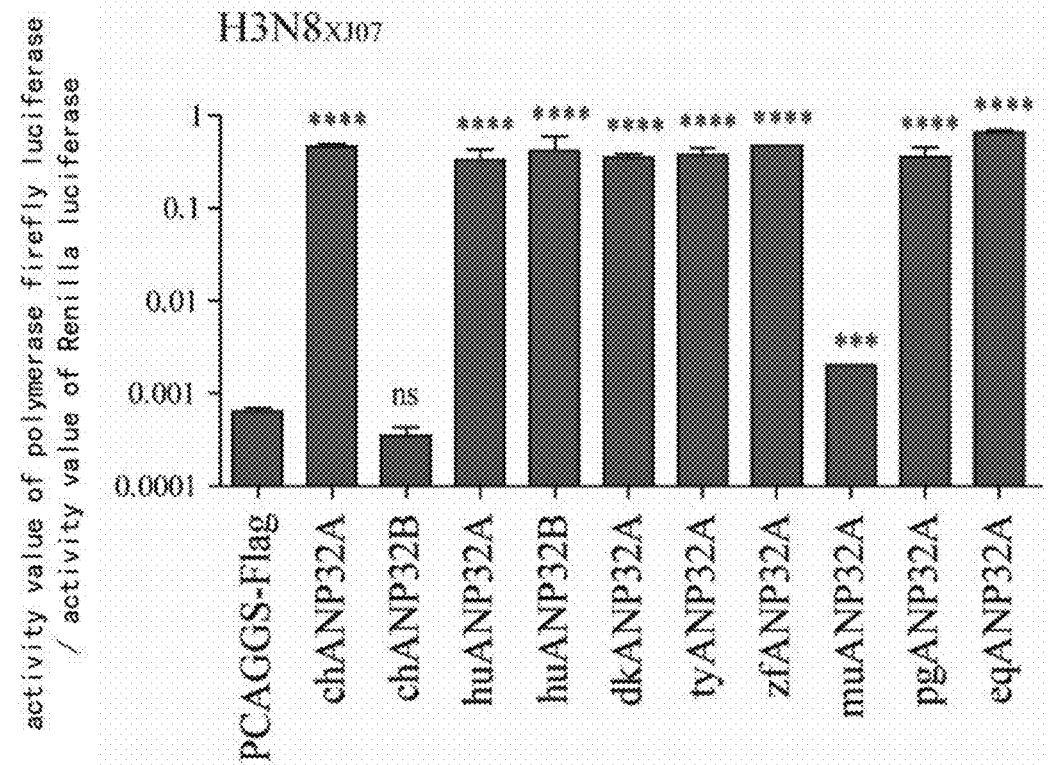
FIG. 11D shows the influence of ANP32 protein of different species on the replication of $H3N8_{XJ07}$ influenza virus.

The above experiment was repeated with the H3N8$_{XJ07}$ polymerase reporter system instead of the H1N1$_{SC09}$ polymerase reporter system, and the result showed that: compared to the empty vector, avian ANP32A such as chANP32A, dkANP32A, zfANP32A, tyANP32A, mammalian ANP32 such as huANP32A, pgANP32A, eqANP32A, huANP32B all supported the activity of H3N8$_{XJ07}$ polymerase, whereas the two proteins chANP32B and muANP32A did not have the ability to support the activity of H3N8$_{XJ07}$ polymerase, as shown in FIG. 11D.

Figure 11E:
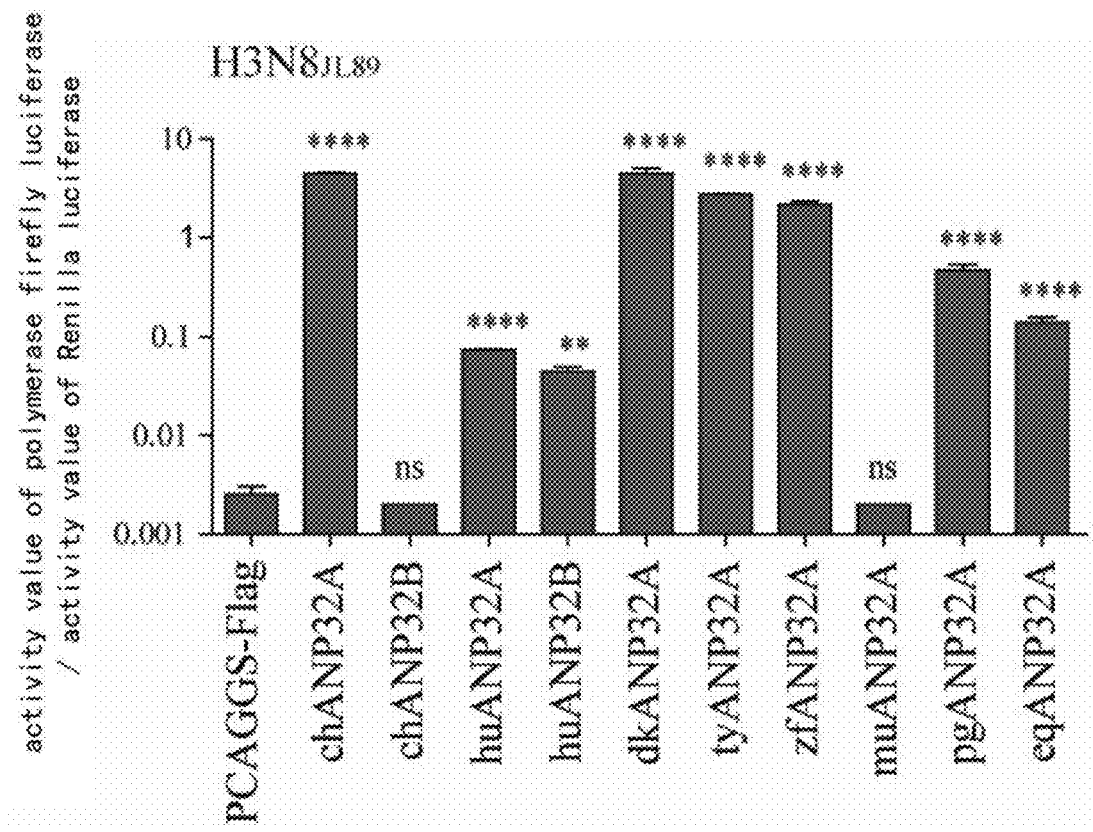
FIG. 11E shows the influence of ANP32 protein of different species on the replication of $H3N8_{JL89}$ influenza virus.

The above experiment was repeated with the H3N8$_{JL89}$ polymerase reporter system instead of the H1N1$_{SC09}$ polymerase reporter system, and the result showed that: compared to the empty vector, avian ANP32A such as chANP32A, dkANP32A, zfANP32A, tyANP32A supported the activity of H3N8$_{JL89}$ polymerase, whereas chANP32B and mammalian ANP32 such as huANP32A, pgANP32A, eqANP32A, huANP32B, muANP32A did not support the activity of H3N8$_{JL89}$ polymerase, as shown in FIG. 11E.

Figure 11F:
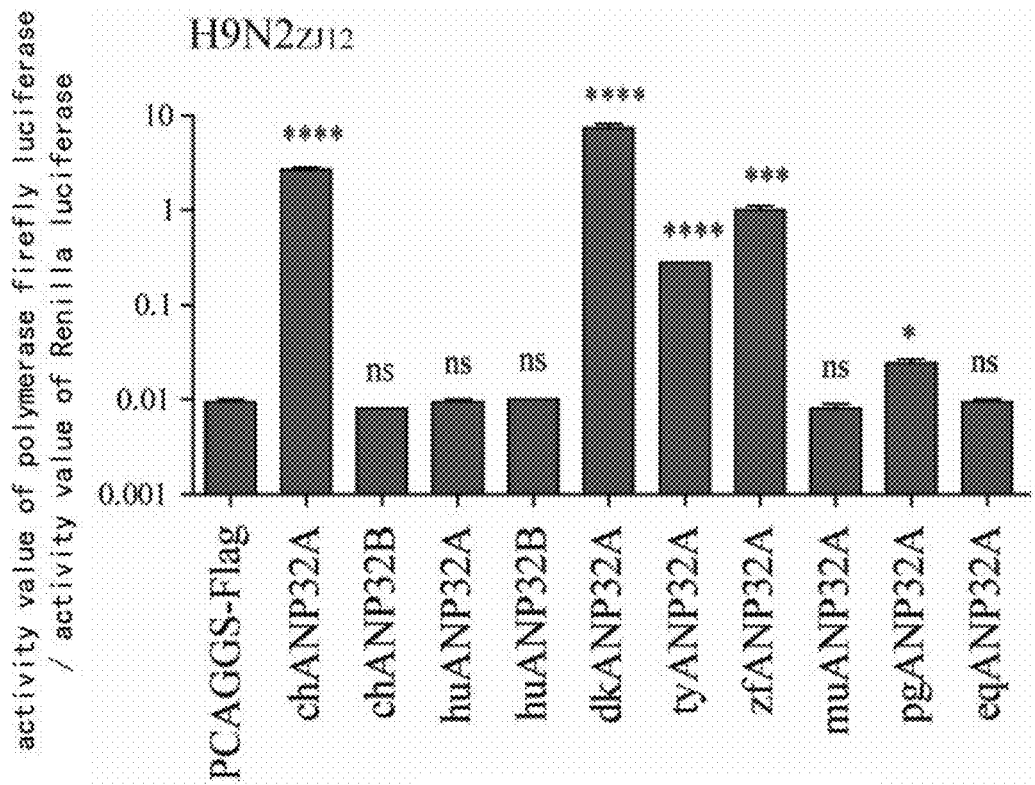
FIG. 11F shows the influence of ANP32 protein of different species on the replication of $H9N2_{ZJ12}$ influenza virus.

The above experiment was repeated with the H9N2$_{ZJ12}$ polymerase reporter system instead of the H1N1$_{SC09}$ polymerase reporter system, and the result showed that: compared to the empty vector, avian ANP32A such as chANP32A, dkANP32A, zfANP32A, tyANP32A supported the activity of H9N2$_{ZJ12}$ polymerase, whereas chANP32B and mammalian ANP32 such as huANP32A, eqANP32A, huANP32B, muANP32A did not support the activity of H9N2$_{ZJ12}$ polymerase, and pgANP32A substantially did not support the activity of H9N2$_{ZJ12}$ polymerase. The results were shown in FIG. 11F.

Figure 11G:
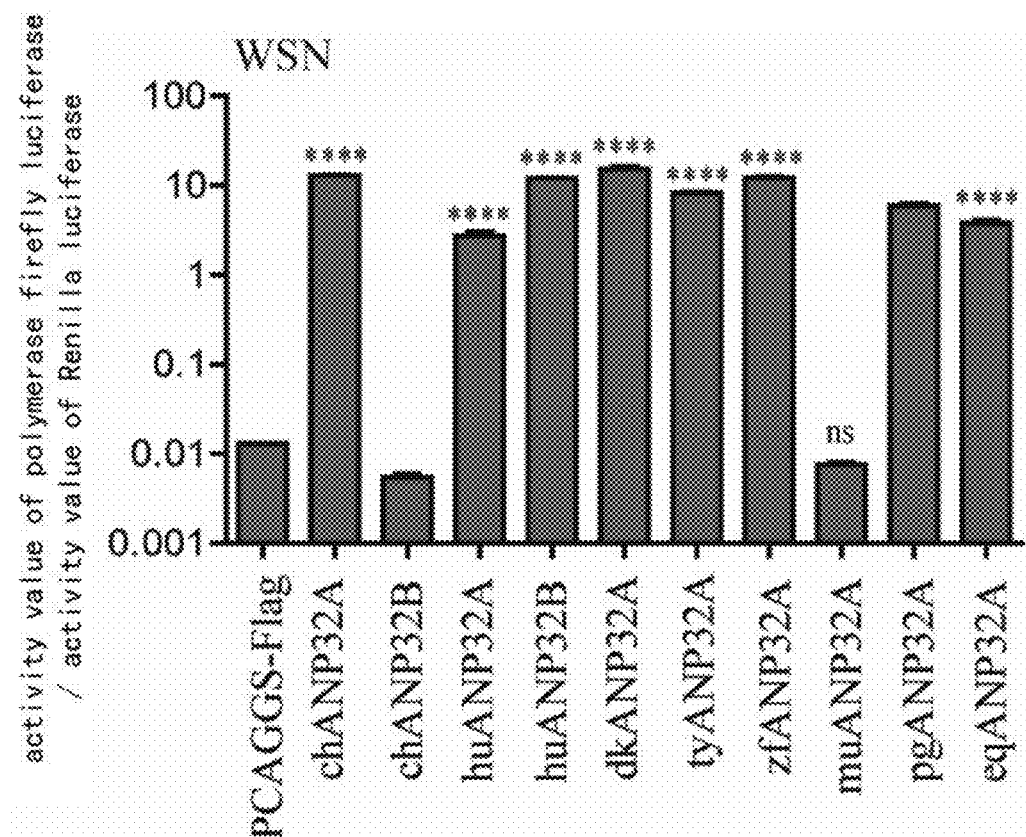
FIG. 11G shows the influence of ANP32 protein of different species on the replication of WSN influenza virus.

The above experiment was repeated with the WSN polymerase reporter system instead of the H1N1$_{SC09}$ polymerase reporter system, and the result showed that: compared to the empty vector, avian ANP32A such as chANP32A, dkANP32A, zfANP32A, tyANP32A, mammalian ANP32 such as huANP32A, pgANP32A, eqANP32A, huANP32B all supported the activity of WSN polymerase, whereas the two proteins chANP32B and muANP32A did not have the ability to support the activity of WSN polymerase, as shown in FIG. 11G.

Example 6: H1N1$_{SC09}$ Influenza Virus Transfected Cell Line

The influence of ANP32A and ANP32B proteins on virus replication was further investigated using the influenza virus reverse genetic system. Eight gene fragments of influenza H1N1$_{SC09}$ (PB2, PB1, PA, NP, HA, NA, M and NS) were ligated into a pBD vector with a double promoter (Journal of Virology, September 2005, p12058-12064, Molecular Basis of Replication of Duck H5N1 influenza Viruses in a Mammalian Mouse Model; "Establishment of reverse genetic operating system for H1N1 influenza virus A/Sichuan/01/2009 strain", Zhang Qianyi et al, Veterinary Science in China, 2011, 41 (05): 448-452).

The steps for constructing the pBD vector were as follows: the Pol-HDVR expression cassette was inserted in reverse orientation into the XbaI cleavage site, using pCI vector (purchased from Promega, Cat. No. E1841, GenBank No. U47120) as the backbone. The sequence of the Pol-HDVR expression cassette is artificially synthesized as SEQ ID NO: 86. That is, the pCI vector was digested with XbaI restriction enzyme (NEB, cat # R0145S), and then the linearized vector was recovered using a gel recovery kit (OMEGA, cat # D2500-01), treated with dephosphorylating enzyme CIAP (purchased from TAKARA, cat # D2250) according to the instructions, and then recovered for use. The artificially synthesized Pol-HDVR expression cassette and the digested fragments of pCI vector have a 15 bp homologous arm on both the left arm and the right arm, then the Pol-HDVR expression cassette fragment and the pCI linearized vector were ligated for 30 min at room temperature by using a seamless cloning Kit of Clonexpress II One Step Cloning Kit (purchased from Vazyme, cat # C112-01) according to the instructions; the ligation product was transformed into 20 ul of DH5α competent cells, and the next day a single clone was picked for sequencing. The plasmid which was verified correct by sequencing was the pBD two-way expression vector.

According to the methods described in Zhang Qianyi et al, "Establishment of reverse genetic operating system for H1N1 influenza virus A/Sichuan/01/2009 strain", Veterinary Science in China, 2011, 41(05): 448-452 and Master's thesis of Zhang Qianyi, "Establishment of reverse genetic operating system for H1N1 influenza virus A/Sichuan/01/2009 strain", Gansu Agricultural University, 2011, the H1N1$_{SC09}$ pBD 8 plasmid system was constructed as follows:

mRNA of H1N1$_{SC09}$ strain was extracted according to the operation manual of QIAamp Viral RNA Kit Manual, and then cDNA was synthesized using Uni12 (AGCAAAAGCAGG SEQ ID NO:21) as a reverse transcription primer according to the instructions of Invitrogen M-MLV Kit. Based on the sequence information of each gene fragment (the sequence of PB2 is SEQ ID NO: 87, the sequence of PB1 is SEQ ID NO: 88, the sequence of PA is SEQ ID NO: 89, the sequence of NP is SEQ ID NO: 90, and the sequence of HA is SEQ ID NO: 91, the sequence of NA is SEQ ID NO: 92, the sequence of M is SEQ ID NO: 93 and the sequence of NS is SEQ ID NO: 94), PCR primers were designed (see Table 10); a 15 bp pBD homologous arm was respectively introduced at both ends; the gene of interest and linearized pBD vector were amplified using KOD FX Neo high-efficiency polymerase; and then the amplified fragment of each gene of H1N1$_{SC09}$ and the linearized pBD vector were ligated at room temperature for 30 minutes by using the seamless cloning kit of ClonExpress II One Step Cloning Kit (purchased from Vazyme, cat # C112-01) according to the instructions; the ligation product was transformed into 20 ul DH5α competent cells, and the next day a single clone was picked for sequencing. The plasmid which were verified correct by sequencing were respectively named as pBD-H1N1$_{SC09}$-PB2 plasmid, pBD-H1N1$_{SC09}$-PB1 plasmid, pBD-H1N1$_{SC09}$-PA plasmid, pBD-H1N1$_{SC09}$-NP plasmid, pBD-H1N1$_{SC09}$-HA plasmid, pBD-H1N1$_{SC09}$-NA plasmid, pBD-H1N1$_{SC09}$-M plasmid and pBD-H1N1$_{SC09}$-NS plasmid for subsequent experiments.

TABLE 10

The primers for constructing H1N1SC09 pBD eight plasmids

| primer name | primer sequence (5'-3') |
|---|---|
| pBD-up, SEQ ID NO: 95 | GGCCGGCATGGTCCCAGCCTCCTCGC |
| pBD-down, SEQ ID NO: 96 | AATAACCCGGCGGCCCAAAATGCCGACTCG |
| pBD-PB2-F, SEQ ID NO: 97 | GGGACCATGCCGGCCAGCAAAAGCAGGTCAAATATAT |
| pBD-PB2-R, SEQ ID NO: 98 | GGCCGCCGGGTTATTAGTAGAAACAAGGTCGTTTTTAA |
| pBD-PB1-F, SEQ ID NO: 99 | GGGACCATGCCGGCCAGCAAAAGCAGGCAAACCATT |
| pBD-PB1-R, SEQ ID NO: 100 | GGCCGCCGGGTTATTAGTAGAAACAAGGCATTTTTTCA |
| pBD-PA-F, SEQ ID NO: 101 | GGGACCATGCCGGCCAGCAAAAGCAGGTACTGATCCA |
| pBD-PA-R, SEQ ID NO: 102 | GGCCGCCGGGTTATTAGTAGAAACAAGGTACTTTTTTGG |
| pBD-NP-F, SEQ ID NO: 103 | GGGACCATGCCGGCCAGCAAAAGCAGGGTAGAT |
| pBD-NP-R, SEQ ID NO: 104 | GGCCGCCGGGTTATTAGTAGAAACAAGGGTATTTTC |
| pBD-HA-F, SEQ ID NO: 105 | GGGACCATGCCGGCCAGCAAAAGCAGGGGAAAA |
| pBD-HA-R, SEQ ID NO: 106 | GGCCGCCGGGTTATTAGTAGAAACAAGGGTGT |
| pBD-NA-F, SEQ ID NO: 107 | GGGACCATGCCGGCCAGCAAAAGCAGGAGTTTAA |
| pBD-NA-R, SEQ ID NO: 108 | GGCCGCCGGGTTATTAGTAGAAACAAGGAGTTT |
| pBD-M-F, SEQ ID NO: 109 | GGGACCATGCCGGCCAGCAAAAGCAGGTAGATA |
| pBD-M-R, SEQ ID NO: 110 | GGCCGCCGGGTTATTAGTAGAAACAAGGTAGTTT |
| pBD-NS-F, SEQ ID NO: 111 | GGGACCATGCCGGCCAGCAAAAGCAGGGTGACAAAG |
| pBD-NS-R, SEQ ID NO: 112 | GGCCGCCGGGTTATTAGTAGAAACAAGGGTGTTTTTAT |

Figure 12A:
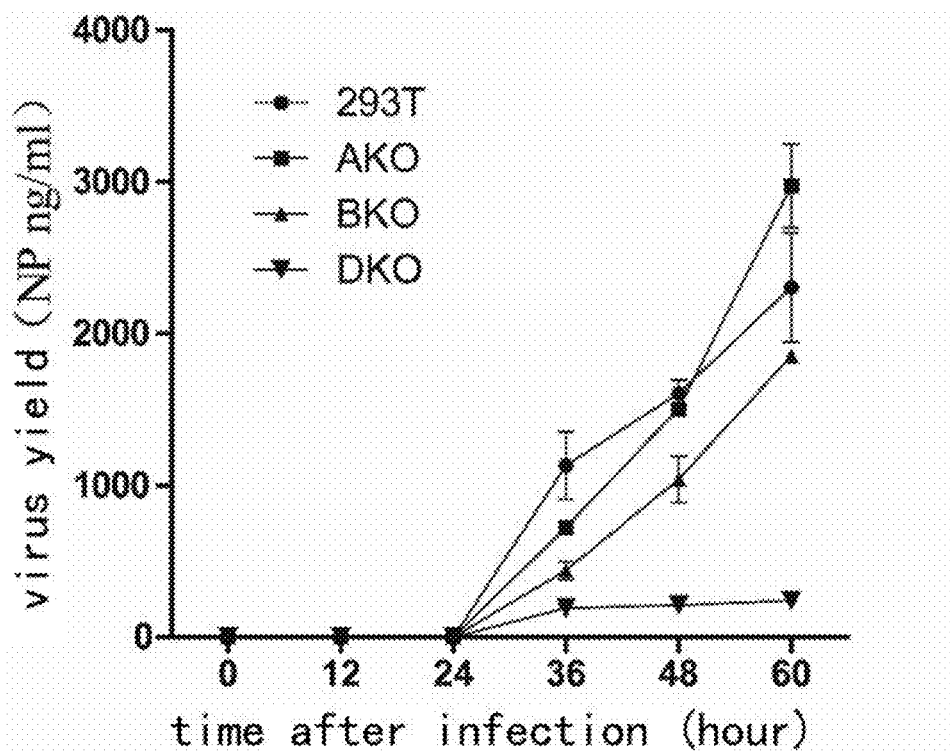
FIG. 12A shows the amount of virus from different cell lines transfected with $H1N1_{SC09}$ influenza virus.

The cell lines AKO, BKO, DKO constructed in Example 2 and wild type 293T cell line were counted respectively and plated in a 6-well plate at 4×10⁵/well. After cultured in an incubator at 37° C. for 20 h, the system of H1N1$_{SC09}$ pBD 8 plasmids was transfected into a wild type 293T cell line and a knockout cell line at 0.5 ug per plasmid; the cell supernatant was collected at 0 h, 12 h, 24 h, 36 h, 48 h and 60 h after transfection, and the virus yield was determined by using an NP double antibody sandwich ELISA method: the 96-well ELISA plate was first coated with NP monoclonal antibody 2B8A11 at 1 ug/well (Wang Yadi, Wen Kun, Qiu Liwen, etc., the establishment of ELISA capture method of influenza A virus nucleocapsid protein and the clinical application thereof, 2009, Guangdong Medicine. 30(5): 703-705) at 4° C. overnight. The plate was rinsed with 1×PBST washing solution for 3 times (5 minutes each time) and shaked, and then patted clean, added with 5% calf serum as a blocking solution, and blocked at 37° C. for 2 hr. The plate was again rinsed with 1×PBST washing solution for 3 times (5 minutes each time) and shaked, and then patted clean; the sample to be tested was added. The sample dilution used for the sample to be tested was 10% fetal bovine serum+0.1% TritonX-100 wherein the NP protein (NP protein construction plasmid pET30a-NP is cited from Master's thesis: Ji Yuanyuan, the establishment of capture ELISA detection method of the equine influenza virus antigen and the primary application thereof [D]. Chinese Academy of Agricultural Sciences, 2011) was used as a standard sample with a 2-fold dilution, and the collected cell supernatant was diluted 5-fold. Each sample was set with 3 gradients, 2 replicate wells. The plate was incubated at 37° C. for 2 h, rinsed with 1×PBST washing solution for 3 times (5 minutes each time), and then patted clean; added with NP monoclonal antibody C16A15 strain (Wang Yadi, Wen Kun, Qiu Liwen, etc., the establishment of ELISA capture method of influenza A virus nucleocapsid protein and the clinical application thereof, 2009, Guangdong Medicine. 30(5): 703-705) by 1 ug/well, incubated at 37° C. for 1 h, discarded, rinsed with 1×PBST washing solution for 5 times (5 minutes each time) and shaked. After the washing, 1:1 mixed AB color developing solution (purchased from Beijing Taitianhe Biotech Co., Ltd., cat # ME142) was added by 100 ul/well, and the color development was performed for 10 min. The color development was stopped by adding 2M $H_2SO_4$ at 50 ul/well, and OD450 nm was detected by using a biotech Ex150 microplate reader. A standard curve was drawn by using the NP protein standard sample and the concentration of the sample to be tested was calculated. The results showed that: compared to 293T cells, the amount of virus in the supernatant of AKO/BKO cells had a similar growth curve after transfection, and almost no virus particles were detected in the supernatant of DKO cells. This indicated that DKO cells did not supported the replication and growth of virus, and the results were shown in FIG. 12A. It was shown that the knockout of ANP32A or ANP32B alone did not affect the replication and growth of the virus.

Figure 12B:
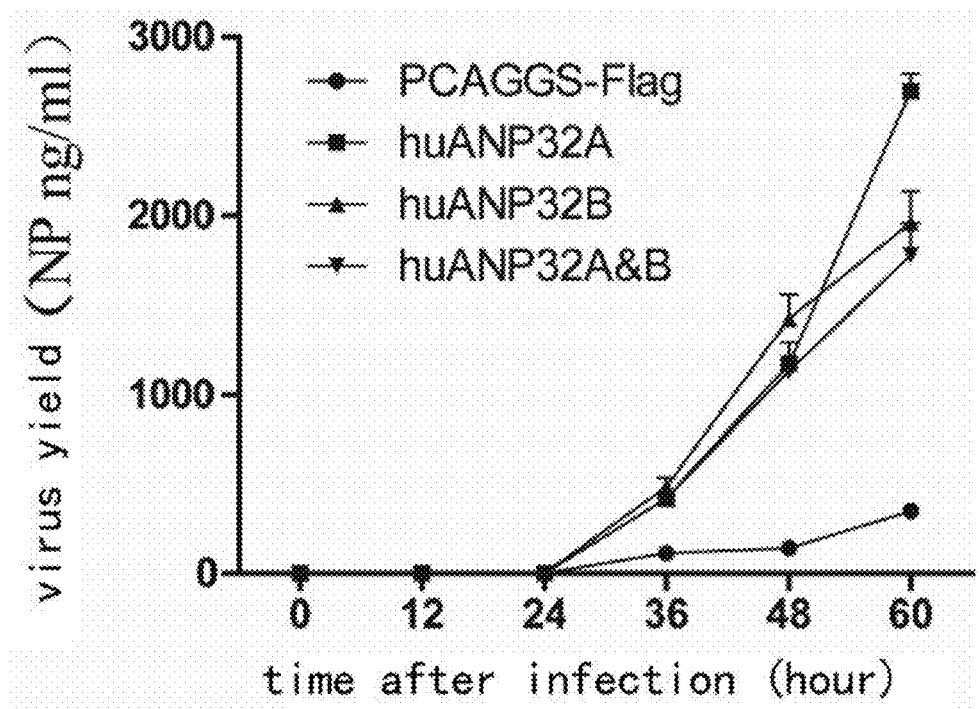
FIG. 12B shows the influence of supplementation with ANP32 protein on the amount of $H1N1_{SC09}$ influenza virus from DKO cells.

The DKO cell lines constructed in Example 2 were counted respectively and plated in a 6-well plate at $3\times10^5$/well. After incubated in an incubator at 37° C. for 20 h, transfection wells were set: 1 ug empty vector PCAGGS-Flag, 1 ug PCAGGS-huANP32A, 1 ug PCAGGS-huANP32B, 0.5 ug PCAGGS-huANP32A+0.5 ug PCAGGS-huANP32B. 24 hours after transfection, the system of $H1N1_{SC09}$ pBD 8 plasmids was transfected into cells of different treatment groups at 0.5 ug of each plasmid; after transfection, the cell supernatant was respectively collected at 0 h, 12 h, 24 h, 36 h, 48 h and 60 h, and virus yield was determined by NP double antibody sandwich ELISA method, in which the specific steps were described above. The results showed that: compared to the empty vector of PCAGGS-Flag, the supplementation of huANP32A, the supplementation of huANP32B, and the simultaneous supplementation of both huANP32A and huANP32B proteins all supported virus replication very well, and the results were shown in FIG. 12B. In summary, the huANP32A or huANP32B proteins was essential in the replication of $H1N1_{SC09}$.

Example 7: The Experiment of H1N1/WSN Influenza Virus Infection

Figure 13A:
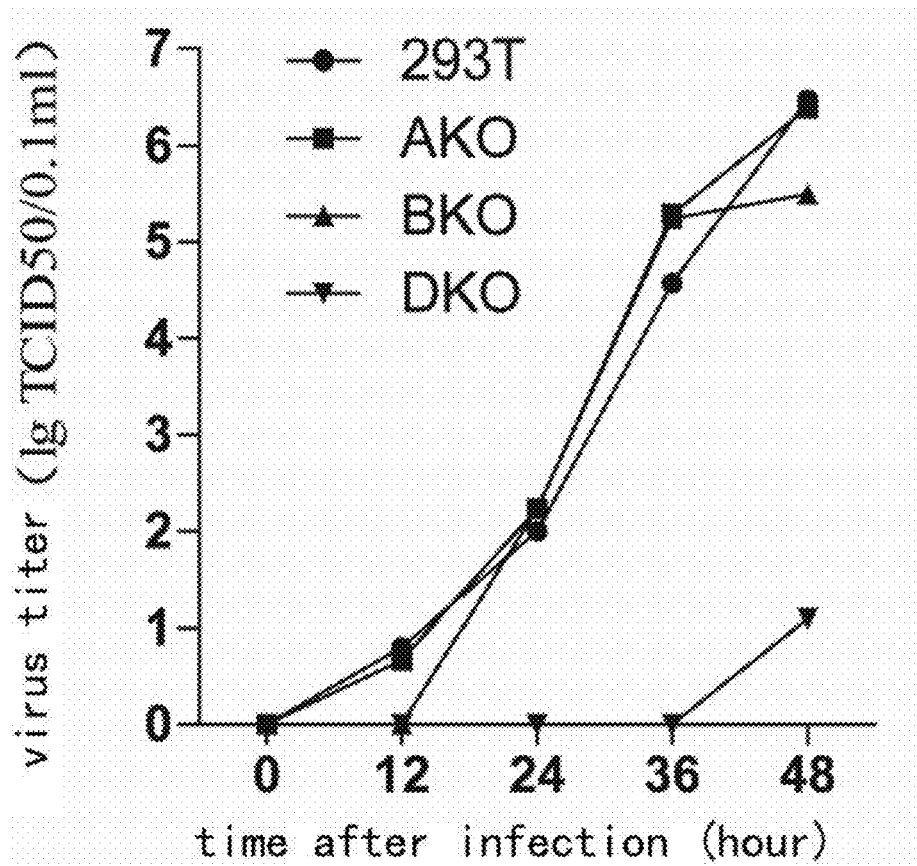
FIG. 13A shows the virus titers of different cell lines transfected with WSN influenza virus.

The cell lines AKO, BKO, DKO constructed in Example 2 and wild type 293T cell line were counted respectively and plated in a 6-well plate at $4\times10^5$/well. After incubated in an incubator at 37° C. for 20 hours, the cells were infected with 0.01 MOI of WSN virus (Neumann G; et al. Generation of influenza A viruses entirely from cloned cDNAs. [J]. Proceedings of the National Academy of Sciences of the United States of America, 1999, 96(16):9345-50); after 2 hours of virus adsorption, the virus-infected solution was discarded and rinsed twice with 1×PBS buffer, and then 2 ml of a cell maintenance solution containing 1% pancreatin (sigma)+1% double antibody (gibco)+0.5% fetal bovine serum (sigma) was added to each well, and cell infection supernatants were taken at 0 h, 12 h, 24 h, 36 h, 48 h after infection and frozen at −80° C. for use. MDCK cells (canine kidney cell line, purchased from China Institute of Veterinary Drug Control) were plated in a 96-well plate at $1.5\times10^4$/well, and the above-obtained supernatant was 10-fold diluted with culture solution DMEM (hyclone) and then added into a 96-well plate at 100 ul/well with 8 replicates per gradient. After 2 hours of virus adsorption, the virus infection solution was discarded and the wells were rinsed twice by 1×PBS buffer, then 100 ul of cell maintenance solution containing 2% fetal bovine serum (sigma)+1% double antibody (gibco)+1% pancreatin (sigma) was added into each well; after 48 hours, the cell lesion was observed and counted; virus TCID50 at different time points of different treatment groups was calculated according to a Reed-Muench method, and finally, the virus growth curve was drawn by Graphpad prism 5 software. The result showed that: the virus growth curves of AKO and BKO cells were consistent with that of wild-type 293T cells, whereas DKO cells hardly supported virus growth. The result was shown in FIG. 13A.

Figure 13B:
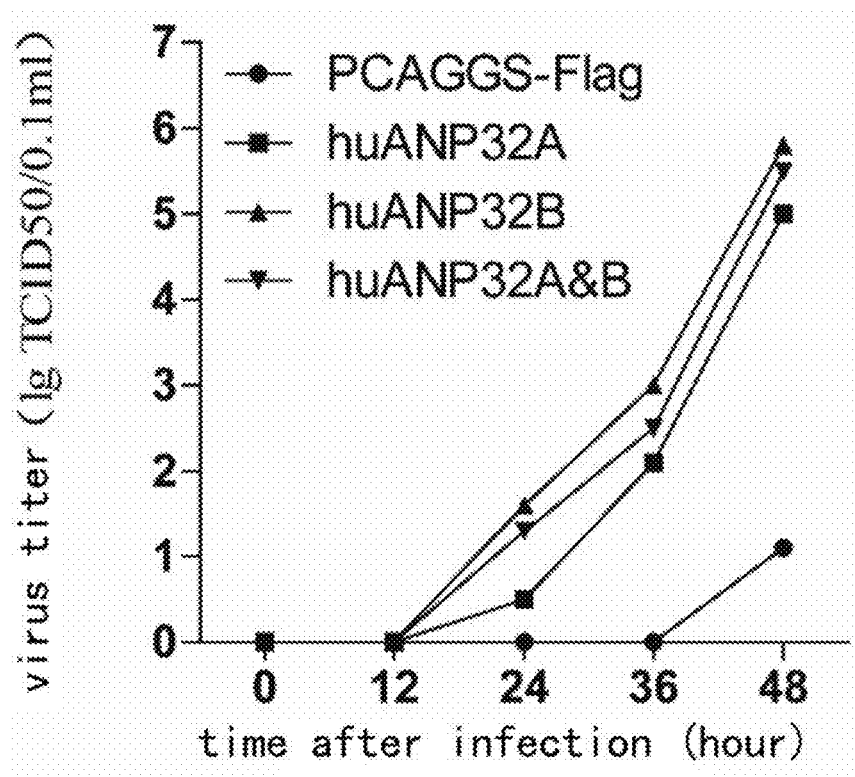
FIG. 13B shows the influence of supplementation with ANP32 protein on the virus titer of WSN influenza virus from DKO cells.

Double-knockout cell lines (DKO) were plated in a 6-well plate at $4\times10^5$/well; 20 hours later, four transfection groups were set: PCAGGS-huANP32A (1 ug) plasmid, PCAGGS-huANP32B (1 ug) plasmid, PCAGGS-huANP32A+PCAGGS-huANP32B (0.5 ug+0.5 ug), and PCAGGS-Flag empty vector (1 ug). After 24 hours of transfection, cells of different treatment groups were infected with 0.01 MOI of WSN virus; after 2 hours of virus adsorption, the virus infection solution was discarded and the wells were rinsed twice with 1×PBS buffer, and then 2 ml of a cell maintenance solution containing 1% pancreatin (sigma)+1% double antibody (gibco)+0.5% fetal bovine serum (sigma) was added to each well, and virus infection supernatants were taken at 0 h, 12 h, 24 h, 36 h, 48 h after infection and frozen at −80° C. for use. MDCK cells were plated in a 96-well plate at $1.5\times10^4$/well, and the above-obtained supernatant was 10-fold diluted and then added into a 96-well plate at 100 ul/well with 8 replicates per gradient. After 2 hours of virus adsorption, the virus infection solution was discarded and rinsed twice by 1×PBS buffer, then the cell maintenance solution was added; after 48 hours, the cell lesion was observed and counted; virus TCID50 at different time points of different treatment groups was calculated according to a Reed-Muench method, and finally, the virus growth curve was drawn by Graphpad prism 5 software. The result showed that: compared with the empty vector, supplementation of huANP32A or huANP32B alone can restore the growth of virus in DKO cells, which was consistent with the virus growth curves of supplementation of both huANP32A and huANP32B. The result was shown in FIG. 13B.

It was shown that the knockout of huANP32A or huANP32B alone did not affect the replication and growth of the virus, and that huANP32A and huANP32B had a functional compensation effect on the replication and growth of influenza virus.

Example 8: Influence of ANP32A and ANP32B Proteins on Polymerase Replication after Mutation of Homologous or Heterologous Virus Construction of Point Mutation Vector of PB2 Gene of H7N9 Subtype Influenza Virus The analysis of some key amino acid sites on PB2 gene of a human-derived H7N9 isolated strain showed that compared with an avian-derived isolates, the human-derived isolates had some reported point mutations related to host adaptability, such as A588V, Q591K, Q591R, V598I, E627K, D701N and the like (Hu et al., 2017, PB2 substitutions V598T/I increase the virulence of H7N9 influenza A virus in mammals. Virology. 501, 92-101.; Mok et al., 2014, Amino acid substitutions in polymerase basic protein 2 gene contribute to the pathogenicity of the novel A/H7N9 influenza virus in mammalian hosts. Journal of virology. 88(6), 3568-3576; Xiao et al., 2016, PB2-588 V promotes the mammalian adaptation of H10N8, H7N9 and H9N2 avian influenza viruses. Sci Rep. 6, 19474.; Yamayoshi et al., 2015, Amino acids substitutions in the PB2 protein of H7N9 influenza A viruses are important for virulence in mammalian hosts[J]. Sci Rep, 2015, 5:8039.; Zhang et al., 2014, The PB2 E627K mutation contributes to the high polymerase activity and enhanced replication of H7N9 influenza virus. J Gen Virol. 95(Pt 4), 779-786.), that is, after the point mutations of A588V, Q591K, Q591R, V598I, E627K or D701N were performed on the avian-derived influenza strain, the strain became adaptive to a human body.

(1) Mutant PB2 Gene and Plasmid Construction

We performed a single point mutation at the above six positions on PB2 of avian H7N9 influenza A/chicken/Zhejiang/DTID-ZJU01/2013(H7N9$_{ZJ13}$); the mutation primers were shown in Table 11 (the underlined parts were mutant bases); the avian H7N9 (H7N9$_{ZJ13}$) PB2 plasmid was used as a template, and KOD-FX Neo high-efficiency DNA polymerase was used for amplification; the obtained PCR product was digested with Dpn I for 30 minutes in a constant temperature water bath at 37° C., then 5 ul of the digested product was transformed into 20 ul of DH5c competent cells; the next day, a single clone was picked for sequencing, and a large amount of plasmid which was verified correct by sequencing was extracted for later use. PB2(A588V), PB2 (Q591K), PB2(Q591R), PB2(V598I), PB2(E627K) and PB2 (D701N) mutant genes were obtained, respectively.

TABLE 11

Mutation primers

| primer name | primer sequence |
|---|---|
| ZJ13-PB2 A588V-S, SEQ ID NO: 113 | CTAAAGCTGTCAGAGGCCAATATAGTG |
| ZJ13-PB2 A588V-A, SEQ ID NO: 114 | TATTGGCCTCTGACAGCTTTAGGCACT |
| ZJ13-PB2 Q591K-S, SEQ ID NO: 115 | TGCCAGAGGCAAATATAGTGGGTTCGTG |
| ZJ13-PB2 Q591K-A, SEQ ID NO: 116 | CCCACTATATTTGCCTCTGGCAGCTTTA |
| ZJ13-PB2 Q591R-S, SEQ ID NO: 117 | TGCCAGAGGCAGATATAGTGGGTTCGTG |
| ZJ13-PB2 Q591R-A, SEQ ID NO: 118 | CCCACTATATCTGCCTCTGGCAGCTTTA |

TABLE 11-continued

Mutation primers

| primer name | primer sequence |
|---|---|
| ZJ13-PB2 V598I-S, SEQ ID NO: 119 | AGTGGGTTCGTGAGGATTCTATTCCAACAGATG |
| ZJ13-PB2 V598I-A, SEQ ID NO: 120 | CATCTGTTGGAATAGAATCCTCACGAACCCACT |
| ZJ13-PB2 E627K-S, SEQ ID NO: 121 | GCAGCCCCGCCGAAGCAGAGTAGGATGCA |
| ZJ13-PB2 E627K-A, SEQ ID NO: 122 | ATCCTACTCTGCTTCGGCGGGGCTGCTGCA |
| ZJ13-PB2 D701N-S, SEQ ID NO: 123 | GGGCAAAGAAAATAAAAGATATGGGCCA |
| ZJ13-PB2 D701N-A, SEQ ID NO: 124 | CCATATCTTTTATTTTCTTTGCCCAGAATC |

(2) Influence of huANP32A and huANP32B on Polymerase Replication

Figure 14:
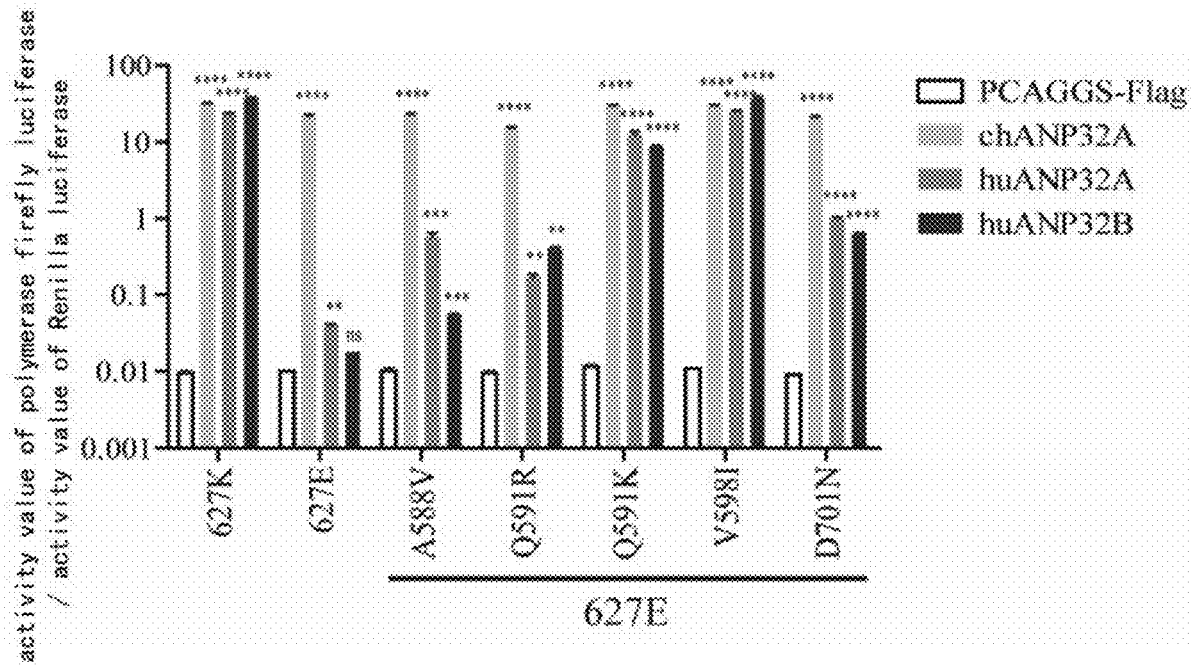
FIG. 14 shows the adaptation of point mutation of PB2 gene of H7N9 subtype influenza virus to ANP32.

Double-knockout cell lines (DKO) were plated in a 12-well plate at 3×10$^5$/well; after 20 hours, the plasmids of PCAGGS-chANP32A, PCAGGS-huANP32A, pCAGGS-huANP32B constructed in Example 1 and the empty vector PCAGGS-Flag were respectively co-transfected with the plasmids of H7N9$_{713}$ polymerase reporter system. The transfection system was: PB1 plasmid (80 ng), PB2 plasmid (80 ng, that is, PB2(A588V), PB2(Q591K), PB2(Q591R), PB2 (V598I), PB2(E627K) and PB2(D701N) were respectively used), PA plasmid (40 ng), NP plasmid (160 ng), pMD18T-vLuc plasmid (80 ng), pRL-TK plasmid (10 ng), and ANP32A protein plasmid (20 ng), and the empty vector PCAGGS-Flag (20 ng) was set as a negative control, and each group was provided with triplicate wells. 24 hours after transfection, the cells were lysed for detecting the activity of polymerase, and the result showed that: compared with the empty vector, chANP32A, huANP32A and huANP32B can effectively promote the activity of polymerase with point mutations of A588V, Q591K, Q591R, V598I, D701N and E627K; in the absence of huANP32A and huANP32B, none of these point mutations allowed the polymerase to acquire the ability to replicate on 293T; these results indicated that: for the replication in humans of the human-derived influenza strain or mutant strain which was obtained by mutation of avian-derived influenza strain to adapt to the human body, huANP32A or huANP32B was a prerequisite for the replication of H7N9 polymerase in 293T. The result was shown in FIG. 14.

Example 9: Determination of Functional Domain of ANP32 Protein

According to the results in Example 5, it was shown that chANP32B protein did not support the activity of polymerase.

Figure 15A:
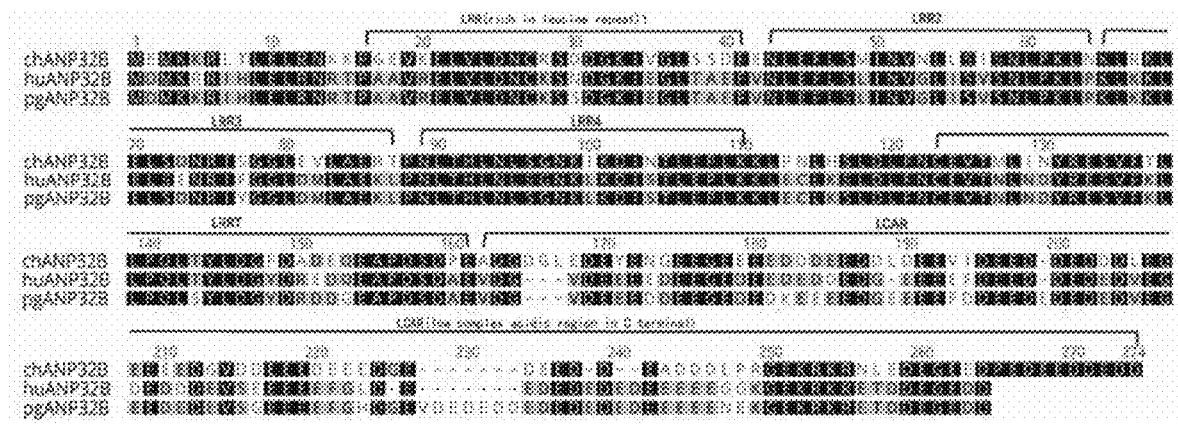
FIG. 15A is an alignment of ANP32B sequences(the aligned sequences of chANP32B, huANP32B, and pgANP32B are set forth in SEQ ID NO:395, 396, and 397, respectively)
Figure 15B:
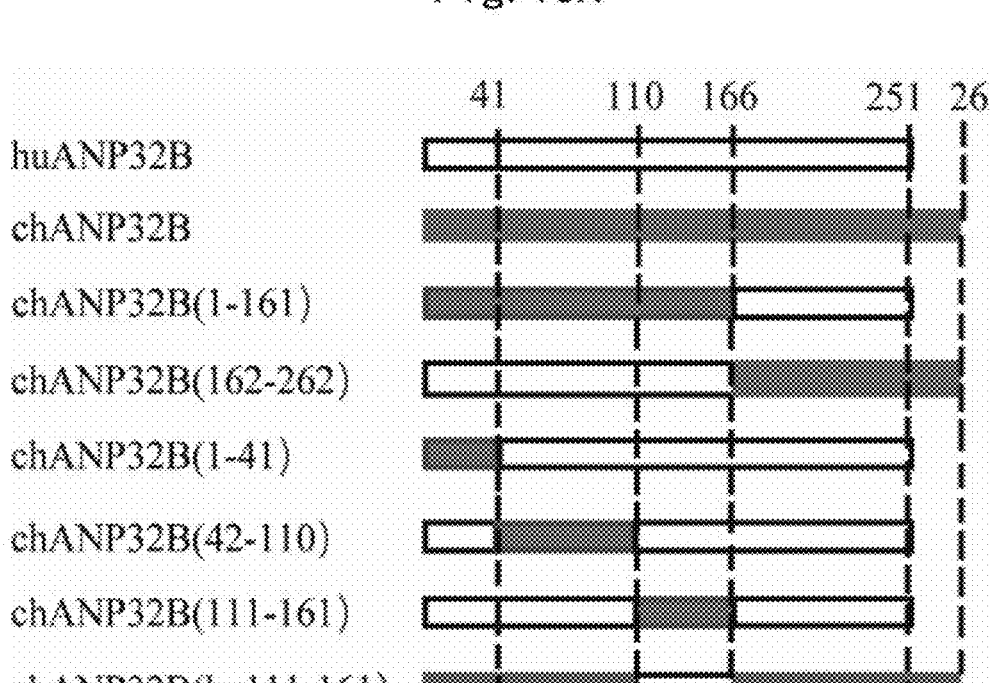
FIG. 15B shows an ANP32B truncation strategy.
Figure 15C:
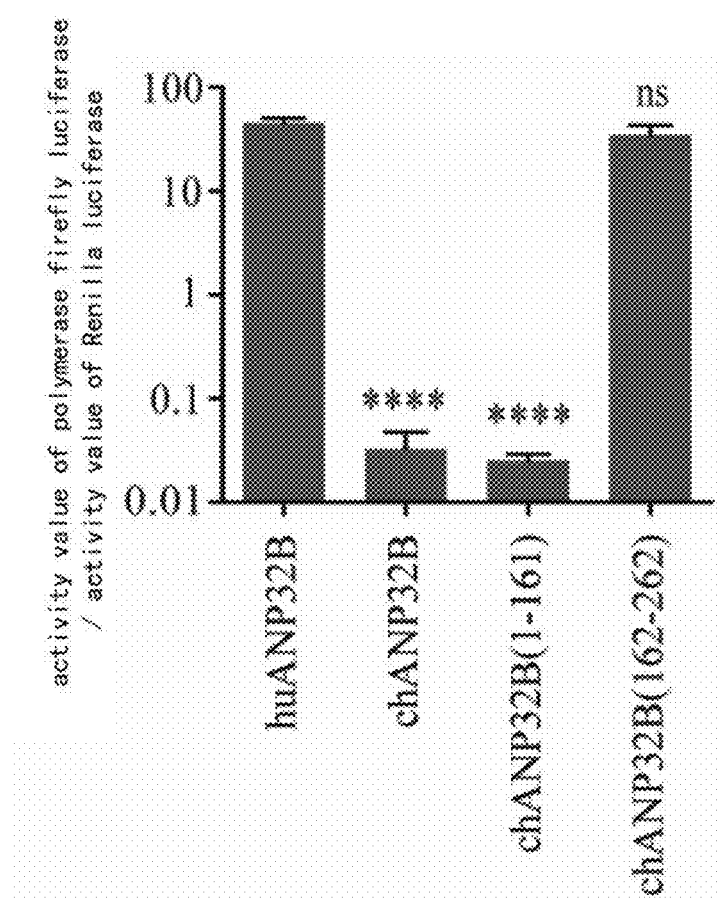
FIG. 15C shows the first round of interchanging huANP32B with chANP32B fragments.

By aligning the protein sequences of chANP32B, huANP32B and pgANP32B, it was found that there are differences in the sequence of ANP32B (FIG. 15A). According to the UniProtKB database, the functional domains of huANP32B protein were displayed: 1-41aa was the LRR1 region; 42-110aa was the LRR2, 3 &4 region; 111-161aa was the LRRCT region; and 162-251aa was the LCAR region. According to the functional domain of the huANP32B protein, the huANP32B gene fragment and the chANP32B gene fragment were replaced, and the replacement strategy of the gene fragment was shown in FIG. 15B.

Firstly, the huANP32B gene sequence was divided into two fragments: 1-161aa and 162-262aa; by using a homologous recombination PCR method, primers were designed to replace the corresponding fragment with a chANP32B fragment to construct a recombinant plasmid.

For example, the replacement of 1-161aa fragment was performed as follows: using a PCAGGS-chANP32B plasmid as a template, a PCAGGS-chANP32BΔ1-161 gene (SEQ ID NO:125 and SEQ ID NO:126 as primers) lacking the 1-161aa gene fragment was amplified by KOD-FX Neo high-efficiency DNA polymerase; then by using a PCAGGS-huANP32B plasmid as a template, a huANP32B (1-161) fragment was amplified (SEQ ID NO:127 and SEQ ID NO:128 as primers), wherein both ends of the primers amplifying the huANP32B (1-161) fragment respectively contain 15 bp bases which are the same as the left and right arms of the PCAGGS-chANP32BΔ1-161 gene. After the fragments were amplified and recovered, the two fragments were ligated by In-Fusion ligase (purchased from Clontech) according to the instructions, and then transformed into DH5α competent cells. The next day, a single clone was picked and sequenced, and the plasmid which was verified correct by sequencing was named as chANP32B(162-262) and was extracted in large-scale for later use. The primers were shown in Table 12.

The chANP32B(1-161) recombinant plasmid was constructed according to the method described above. By using a PCAGGS-chANP32B plasmid as a template, a PCAGGS-chANP32BΔ162-262 gene lacking the 162-262aa gene fragment was amplified by KOD-FX Neo high-efficiency DNA polymerase (ca #KFX-201, purchased from Toyobo) (SEQ ID NO:129 and SEQ ID NO:130 as primers); then by using a PCAGGS-huANP32B plasmid as a template, a huANP32B(162-262) fragment was amplified(SEQ ID NO:131 and SEQ ID NO:132 as primers), wherein both ends of the primers used for amplifying the huANP32B (162-262) fragment respectively contain 15 bp bases which are the same as the left and right arms of the PCAGGS-chANP32BΔ162-262 gene. After the fragments were amplified and recovered, the two fragments were ligated by In-Fusion ligase (purchased from Clontech) according to the instructions, and then transformed into DH5α competent cells. The next day, a single clone was picked and sequenced, and the plasmid which was verified correct by sequencing was named as chANP32B(1-161) and was extracted in large-scale for later use. The primers were shown in Table 12.

TABLE 12

| primers | |
|---|---|
| primer name | primer sequence |
| pCAGGS Vector_up, SEQ ID NO: 125 | GCGGCCGCGAGCTCGAATTCTTTGCCAAAA |
| pCAGGS_ch32B (162-262)-down SEQ ID NO: 126 | GAGGCAGATGGGGATGGACTGGAAGACGAG |
| hu32B(1-161)_F, SEQ ID NO: 127 | GAATTGTGCGGCCGCATGGACATGAAGAGGAGGATCCA |
| hu32B(1-161)_R, SEQ ID NO: 128 | ATCCCCATCTGCCTCGGCATCTGAGTCAGGTGCTTCCT |

TABLE 12-continued

| primers | |
|---|---|
| primer name | primer sequence |
| pCAGGS_ch32B (1-161)-vector up SEQ ID NO: 129 | AGGGTCTGAGTCAGGGGCTTCCTGCTCATC |
| pCAGGS Vector_down, SEQ ID NO: 130 | GGCAGCGGAGACTACAAGGATGACGATGAC |
| hu32B(162-262)_F, SEQ ID NO: 131 | CCTGACTCAGACCCTGAGGTGGATGGTGTGGATGAAGA |
| hu32B(162-262)_R. SEQ ID NO: 132 | GTAGTCTCCGCTGCCATCATCTTCTCCTTCATCATCTG |

Double-knockout cell lines (DKO) were plated in a 12-well plate at $3\times10^5$/well; after 20 hours, the plasmids of PCAGGS-huANP32B, PCAGGS-chANP32B, PCAGGS-chANP32B(1-161) and PCAGGS-chANP32B(162-262) were respectively co-transfected with the $H1N1_{SC09}$ polymerase reporter system into the DKO cell line. The transfection system was: PB1 plasmid (80 ng), PB2 plasmid (80 ng), PA plasmid (40 ng), NP plasmid (160 ng), pMD18T-vLuc plasmid (80 ng), pRL-TK plasmid (10 ng) and ANP32A protein plasmid (20 ng), and each group was provided with triplicate wells. 24 hours after transfection, the cells were lysed and the activity of polymerase was detected; the result was shown in FIG. 15C: the ability of chANP32B(1-161) to support $H1N1_{SC09}$ polymerase activity was lost, while chANP32B(162-262) retained the ability to support $H1N1_{SC09}$ polymerase activity. Therefore, the key region of the protein ANP32B that supports polymerase activity is located within 1-161aa.

The homologous recombination PCR was performed as described above; by using huANP32B as a backbone, chANP32B 1-161aa was further divided into three regions of 1-41aa, 42-110aa and 111-161aa to replace the corresponding fragments of PCAGGS-huANP32B, to construct the recombinant plasmid PCAGGS-chANP32B(1-41) (using plasmid PCAGGS-huANP32B as a template, using the primer pair SEQ ID NO:133 and SEQ ID NO: 134 to amplify the PCAGGS-hu32Δ(1-41) gene fragment; using the PCAGGS-chANP32B plasmid as a template, using the primer pair SEQ ID NO: 135 and SEQ ID NO: 136 to amplify the chANP32B (1-41) gene fragment), PCAGGS-chANP32B (42-110) (using the PCAGGS-huANP32B plasmid as a template, using the primer pair SEQ ID NO: 137 and SEQ ID NO: 138 to amplify the PCAGGS-hu32BΔ(42-110) gene fragment; using the PCAGGS-chANP32B plasmid as a template, using the primer pair SEQ ID NO: 139 and SEQ ID NO: 140 to amplify the chANP32B (42-110) gene fragment) and PCAGGS-chANP32B (111-161) (using the PCAGGS-huANP32B plasmid as a template, using primer pair SEQ ID NO: 141 and SEQ ID NO: 142 to amplify the PCAGGS-hu32BΔ(111-161) gene fragment; using the PCAGGS-chANP32B plasmid as a template; using the primer pair SEQ ID NO: 143 and SEQ ID NO: 144 to amplify the chANP32B (111-161) gene fragment). The primers were shown in Table 13.

TABLE 13 primers

| primer name | primer sequence |
| --- | --- |
| pCAGGS Vector_up, SEQ ID NO: 133 | GCGGCCGCGAGCTCGAATTCTTTGCCAA |
| pCAGGS_hu32B (42-262)-down SEQ ID NO: 134 | GTGAACTTAGAGTTCCTCAGTTTAATAAAT |
| ch32B(1-41)_F, SEQ ID NO: 135 | GAATTGTGCGGCCGCATGGAGATGAAAAAGCGGCTCAC |
| ch32B(1-41)_R, SEQ ID NO: 136 | GAACTCTAAGTTCACAAAATCTGAAGAGAGCCCAACGA |
| pCAGGS_hu32B (1-41)_up, SEQ ID NO: 137 | AAATTCAGCTGTTAAGCCCTCAATTTTTCC |
| pCAGGS_hu32B (111-262)_down SEQ ID NO: 138 | AAGTTAGAATGTCTGAAAAGCCTGGACCTC |
| ch32B(42-110)_F, SEQ ID NO: 139 | TTAACAGCTGAATTTGAGAACCTGGAGTTCCTCAGCAT |
| ch32B(42-110)_R, SEQ ID NO: 140 | CAGACATTCTAACTTTTTCAAGGGTTCCAGGGTATTGA |
| pCAGGS_hu32B (1-110)-up SEQ ID ID: 141 | TTTCAAAGGTTCCAAGGTGCTGATATCTTT |
| pCAGGS_hu32B (162-262)_down SEQ ID NO: 142 | CTCCTCCTCTTCATCCACACCATCCACCTC |
| ch32B(111-161)_F, SEQ ID NO: 143 | TTGGAACCTTTGAAAAAGTTGCCAAACCTGCATAGTCT |
| ch32B(111-161)_R, SEQ ID NO: 144 | CACACCATCCACCTCAGGGTCTGAGTCAGGGGCTTCCT |

Figure 15D:
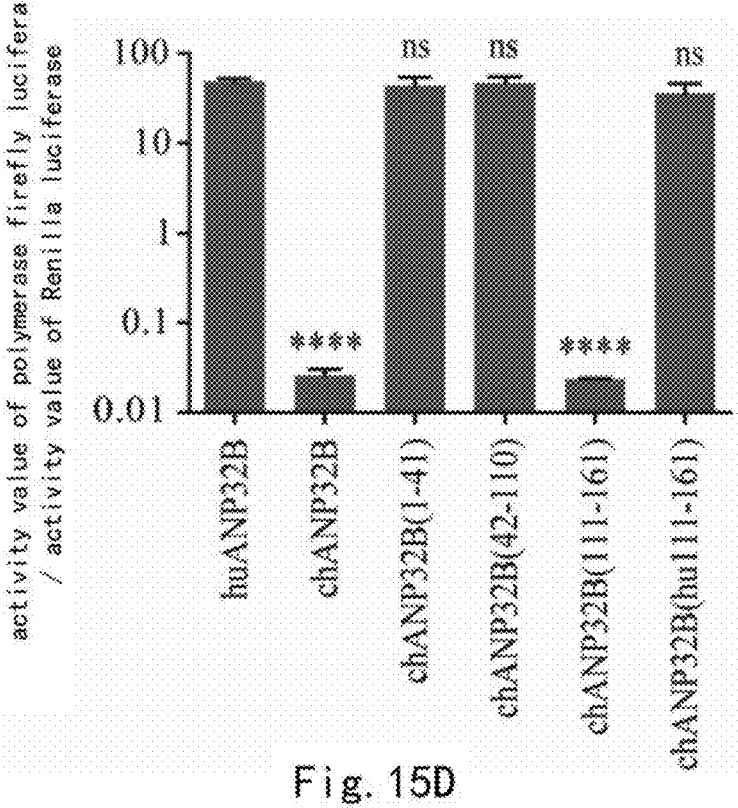
FIG. 15D shows the second round of interchanging huANP32B with chANP32B fragments.

Double-knockout cell lines (DKO) were plated in a 12-well plate at 3×10⁵/well; after 20 hours, the plasmids of PCAGGS-huANP32B, PCAGGS-chANP32B, PCAGGS-chANP32B(1-41), PCAGGS-chANP32B(42-110) and PCAGGS-chANP32B(111-161) were respectively co-transfected with the H1N1$_{SCO9}$ polymerase reporter system into the DKO cell line. The transfection system was: PB1 plasmid (80 ng), PB2 plasmid (80 ng), PA plasmid (40 ng), NP plasmid (160 ng), pMD18T-vLuc plasmid (80 ng), pRL-TK plasmid (10 ng) and ANP32A protein plasmid (20 ng), and each group was provided with triplicate wells. 24 hours after transfection, the cells were lysed as described in Example 3 and the activity of polymerase was detected; the result was shown in FIG. 15D: the recombinant plasmid PCAGGS-chANP32B(111-161) lost the ability to support the activity of H1N1$_{SCO9}$ polymerase, while the recombinant plasmids PCAGGS-chANP32B(1-41) and PCAGGS-chANP32B(42-110) still maintained the support for the activity of H1N1$_{SCO9}$ polymerase.

The homologous recombination PCR was performed as described above, and the corresponding fragment of PCAGGS-chANP32B was replaced with the corresponding 111-161aa sequence of PCAGGS-huANP32B (using the PCAGGS-huANP32B plasmid as a template and using the primer pair of SEQ ID NO: 145 and SEQ ID NO:146 to amplify the PCAGGS-ch32BΔ(111-161) gene fragment; using the PCAGGS-huANP32B plasmid as a template and using the primer pair of SEQ ID NO:147 and SEQ ID NO:148 to amplify the huANP32B (111-162) gene fragment), to construct the recombinant plasmid PCAGGS-chANP32B(hu111-161); the primers were shown in Table 14. DKO cell line was co-transfected with the H1N1$_{SCO9}$ polymerase reporter system according to the above system, and the polymerase activity was detected as described in Example 3; the result was shown in FIG. 15D (column of chANP32B (hu111-161)), indicating that chANP32B (hu111-161) acquired the ability to support the activity of H1N1$_{SCO9}$ polymerase, which further indicated that the key region of the ANP32B protein to support polymerase activity was located within 111-161aa.

TABLE 14 primers

| primer name | primer sequence |
| --- | --- |
| pCAGGS_ch32B (1-110)_up SEQ ID NO: 145 | CTTTTTCAAGGGTTCCAGGGTATTGATGTC |
| pCAGGS_ch32B (162-262)_down SEQ ID NO: 146 | GAGGCAGATGGGGATGGACTGGAAGACGAG |
| hu32B(111-161)_F SEQ ID NO: 147 | GAACCCTTGAAAAAGTTAGAATGTCTGAAAAGCCTGGA |
| hu32B(111-161)_R SEQ ID NO: 148 | ATCCCCATCTGCCTCGGCATCTGAGTCAGGTGCTTCCT |

Figures 16A, 16B:
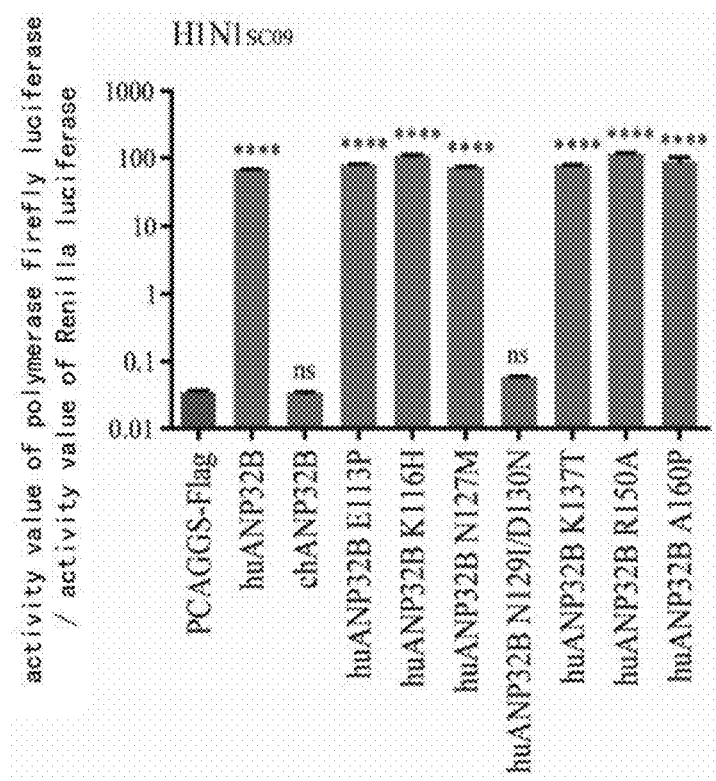
FIG. 16A is the sequence alignment of ANP32B 110-161 regions(the aligned chicken, human and pig sequences are set forth in SEQ ID NO:398, 399, and 400, respectively)
FIG. 16B shows the influence of the point mutation of huANP32B on $H1N1_{SC09}$ polymerase activity.

To further identify the key regions, alignment of the protein sequences of chANP32B, huANP32B and pgANP32B revealed that amino acids in the 111-161aa region of huANP32B and pgANP32B proteins were relatively conserved, while there were differences of mainly eight amino acids between chANP32B and the above two proteins (positions 113, 116, 127, 129, 130, 137, 150 and 160, respectively), as shown in FIG. 16A. Mutant primers were designed for these 8 amino acids in the huANP32B sequence (see Table 15 for the primers, and the mutant bases were underlined); by using the homologous recombination method as described above, the following point mutants were respectively constructed by using KOD FX Neo polymerase with PCAGGS-huANP32B plasmid as template: huANP32B E113P (using primer pair of SEQ ID NO: 149 and SEQ ID NO: 150), K116H (using primer pair of SEQ ID NO: 151 and SEQ ID NO: 152), N127M (using primer pair of SEQ ID NO: 153 and SEQ ID NO: 154), N129I/D130N (using primer pair SEQ ID NO: 155 and SEQ ID NO: 156), K137T (using primer pair of SEQ ID NO: 157 and SEQ ID NO: 158), R150A (using primer pair of SEQ ID NO: 159 and SEQ ID NO: 160), A160P (using primer pair of SEQ ID NO: 161 and SEQ ID NO: 162), which were respectively named as PCAGGS-huANP32B E113P, PCAGGS-huANP32B K116H, PCAGGS-huANP32B N127M, PCAGGS-huANP32B N129I/D130N PCAGGS-huANP32B K137T, PCAGGS-huANP32B R150A, PCAGGS-huANP32B A160P, for use in the next step of transfection after confirming by sequencing.

TABLE 15 primers for amino acid mutation

| primer name | primer sequence (5'-3') |
|---|---|
| huB_E113P_F SEQ ID NO: 149 | CCTTTGAAAAAGTTACCCTGTCTGAAAAGCCTG |
| huB_E113P_R SEQ ID NO: 150 | CAGGCTTTTCAGACAGGGTAACTTTTTCAAAGG |
| huB_K116H_F SEQ ID NO: 151 | AAGTTAGAATGTCTGCACAGCCTGGACCTCTTT |
| huB_K116H_R SEQ ID NO: 152 | AAAGAGGTCCAGGCTGTGCAGACATTCTAACTT |
| huB_N127M_F SEQ ID NO: 153 | AACTGTGAGGTTACCATGCTGAATGACTACCGA |
| huB_N127M_R SEQ ID NO: 154 | TCGGTAGTCATTCAGCATGGTAACCTCACAGTT |
| huB_N129I/ D130N_F SEQ ID NO: 155 | GAGGTTACCAACCTGATTAACTACCGAGAGAGTGTC |
| huB_N129I/ D130N_R SEQ ID NO: 156 | GACACTCTCTCGGTAGTTAATCAGGTTGGTAACCTC |
| huB_K137T_F SEQ ID NO: 157 | CGAGAGAGTGTCTTCACCCTCCTGCCCCAGCTT |
| huB_K137T_R SEQ ID NO: 158 | AAGCTGGGGCAGGAGGGTGAAGACACTCTCTCG |
| huB_R150A_F SEQ ID NO: 159 | TTGGATGGCTATGACGCTGAGGACCAGGAAGCA |
| huB_R150A_R SEQ ID NO: 160 | TGCTTCCTGGTCCTCAGCGTCATAGCCATCCAA |
| huB_A160P_F SEQ ID NO: 161 | GCACCTGACTCAGATCCGGAGGTGGATGGTGTG |
| huB_A160P_R SEQ ID NO: 162 | CACACCATCCACCTCCGGATCTGAGTCAGGTGC |

Double-knockout cell lines (DKO) were plated in a 12-well plate at 3×10⁵/well; after 20 hours, the point mutant plasmids of PCAGGS-Flag, PCAGGS-huANP32B, PCAGGS-chANP32B and PCAGGS-huANP32B, namely, PCAGGS-huANP32B E113P, PCAGGS-huANP32B K116H, PCAGGS-huANP32B N127M, PCAGGS-huANP32B N291/D130N, PCAGGS-huANP32B K137T, PCAGGS-huANP32B R150A, PCAGGS-huANP32B A160P were respectively co-transfected with the H1N1$_{SC09}$ polymerase reporter system into the DKO cell line. The transfection system was: PB1 plasmid (80 ng), PB2 plasmid (80 ng), PA plasmid (40 ng), NP plasmid (160 ng), pMD18T-vLuc plasmid (80 ng), pRL-TK plasmid (10 ng) and ANP32A mutant protein plasmid (20 ng), and each group was provided with triplicate wells. 24 hours after transfection, the cells were lysed as described in Example 3 and the polymerase activity were detected; the result was shown in FIG. 16B: compared to huANP32B, chANP32B and huANP32B N129I/D130N completely lost support for the activity of H1N1$_{SC09}$ polymerase, while the point mutants of huANP32B E113P, huANP32B K116H, huANP32B N127M, huANP32B K137T, huANP32B R150A and huANP32B A160P still retained support for the activity of H1N1$_{SC09}$ polymerase.

For the two sites 129/130, single point mutations of huANP32B N129I (using primer pair of SEQ ID NO:163 and SEQ ID NO: 164) and D130N (using primer pair of SEQ ID NO: 165 and SEQ ID NO: 166) were designed (see Table 16 for primers, and the mutated bases were underlined), and the resulting plasmids were named as PCAGGS-huANP32B N129I and PCAGGS-huANP32B D130N, wherein the PCAGGS-huANP32B plasmid was used as a template and the procedure was as described in this Example for the point mutation of 8 amino acids in the huANP32B sequence. After verification by sequencing, the plasmids were extracted in large amount for further transfection.

TABLE 16 primers for single point mutation huANP32B N129I and D130N

| primer name | primer sequence (5'-3') |
|---|---|
| huB_N129I_F SEQ ID NO: 163 | GAGGTTACCAACCTGATTGACTACCGAGAGAGT |
| huB_N129I_R SEQ ID NO: 164 | ACTCTCTCGGTAGTCAATCAGGTTGGTAACCTC |
| huB_D130N_F SEQ ID NO: 165 | GTTACCAACCTGAATAACTACCGAGAGAGTGTC |
| huB_D130N_R SEQ ID NO: 166 | GACACTCTCTCGGTAGTTATTCAGGTTGGTAAC |

Figures 17, 18:
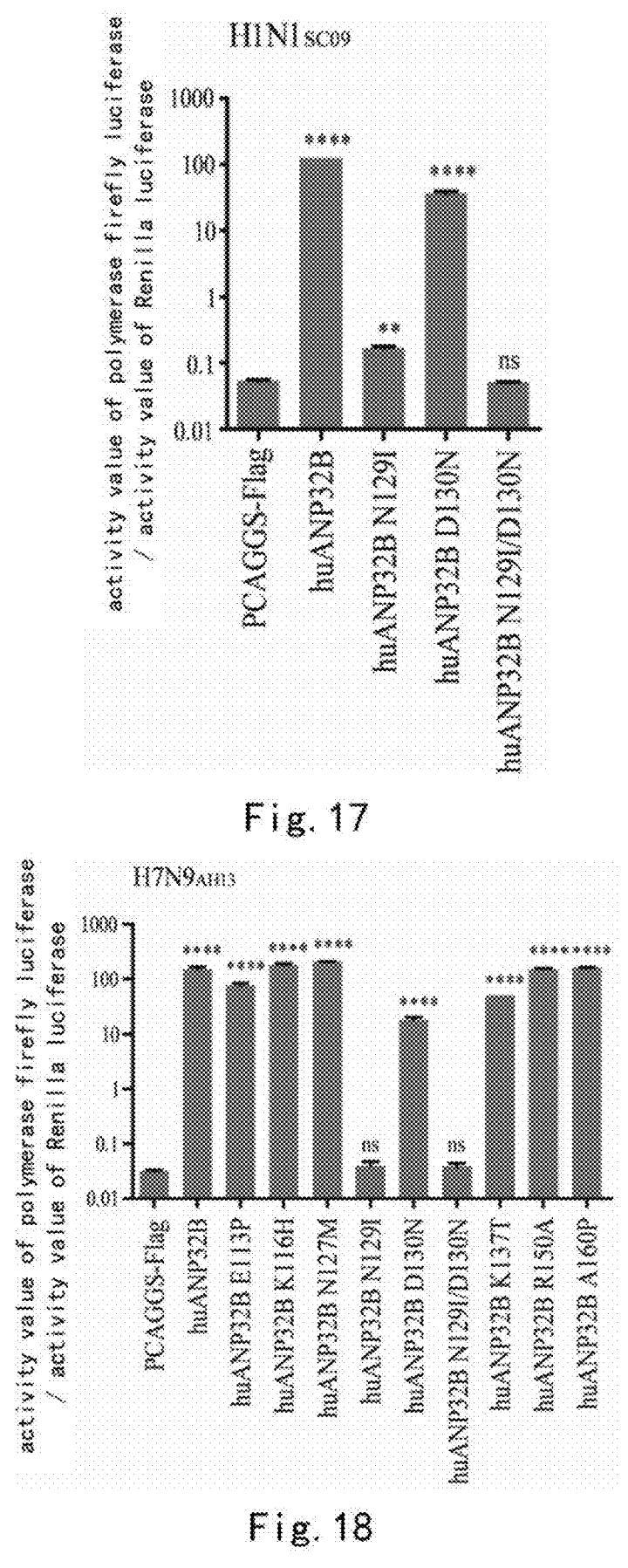

Double-knockout cell line (DKO) was plated in a 12-well plate at 3×10⁵/well and transfected as described above after 20 h, and the result showed that: compared to huANP32B, huANP32B N129I almost lost support for H1N1$_{SC09}$ polymerase activity, while the support of huANP32B D130N for H1N1$_{SC09}$ polymerase activity was reduced by about 5 times. This showed that the two sites of 129/130 were important for the activity of the ANP32 protein. The result was shown in FIG. 17.

Double-knockout cell lines (DKO) were plated in a 12-well plate at 3×10⁵/well; after 20 hours, the point mutation plasmids of PCAGGS-Flag empty vector, PCAGGS-huANP32B and PCAGGS-huANP32B were respectively co-transfected with the H7N9$_{AH13}$ polymerase reporter system into the DKO cell line. The transfection system was: PB1 plasmid (80 ng), PB2 plasmid (80 ng), PA plasmid (40 ng), NP plasmid (160 ng), pMD18T-vLuc plasmid (80 ng), pRL-TK plasmid (10 ng) and ANP32A mutant protein plasmid (20 ng), and each group was provided with triplicate wells. 24 hours after transfection, the cells were lysed as described in Example 3 and the polymerase activity were detected; the result showed that: compared to huANP32B, huANP32B N129I and huANP32B N129I/D130N completely lost support for the activity of H7N9$_{AH13}$ polymerase, while the point mutants of huANP32B K116H, huANP32B N127M, huANP32B R150A and huANP32B A160P still retained support for the activity of H7N9$_{AH13}$ polymerase, and the ability of huANP32B E113P, huANP32B D130N and huANP32B K137T to support the activity of H7N9$_{AH13}$ polymerase was reduced by about 3-8 times. The result was shown in FIG. 18.

According to the screening results of huANP32B point mutation, huANP32A was also subjected to the point mutant construction of N129I (using primer pair of SEQ ID NO: 167 and SEQ ID NO: 168), D130N (using primer pair of SEQ ID NO: 169 and SEQ ID NO: 170) and ND129/130IN (using primer pair of SEQ ID NO: 171 and SEQ ID NO: 172) (see Table 17 for primers, and mutated bases were underlined) by using overlapping PCR with the PCAGGS-huANP32A plasmid as a template, wherein the procedure is as described in the construction of a point mutant of 8 amino acids on the huANP32B sequence. As described above, the obtained plasmids were named as PCAGGS-huANP32A N129I, PCAGGS-huANP32A D130N and PCAGGS-huANP32A N129I/D130N. After verification by sequencing, the plasmids were extracted in large amount for further transfection.

TABLE 17

Primers for point mutations of N129I, D130N, N129I/D130N on huANP32A

| primer name | primer sequence (5'-3') |
| --- | --- |
| huA_N129I_F SEQ ID NO: 167 | GAGGTAACCAACCTG<u>ATT</u>GACTACCGAGAAA AT |
| huA_N129I_R SEQ ID NO: 168 | ATTTTCTCGGTAGTC<u>AAT</u>CAGGTTGGTTACCT C |
| huA_D130N_F SEQ ID NO: 169 | GTAACCAACCTGAAC<u>AAC</u>TACCGAGAAAATG TG |
| huA_D130N_R SEQ ID NO: 170 | CACATTTTCTCGGTA<u>GTT</u>GTTCAGGTTGGTTA C |
| huA_N129I/ D130N_F SEQ ID NO: 171 | GAGGTAACCAACCTG<u>ATTAAC</u>TACCGAGAAA ATGTG |
| huA_N129I/ D130N_R SEQ ID NO: 172 | CACATTTTCTCGGTA<u>GTTAAT</u>CAGGTTGGTTA CCTC |

Figure 19:
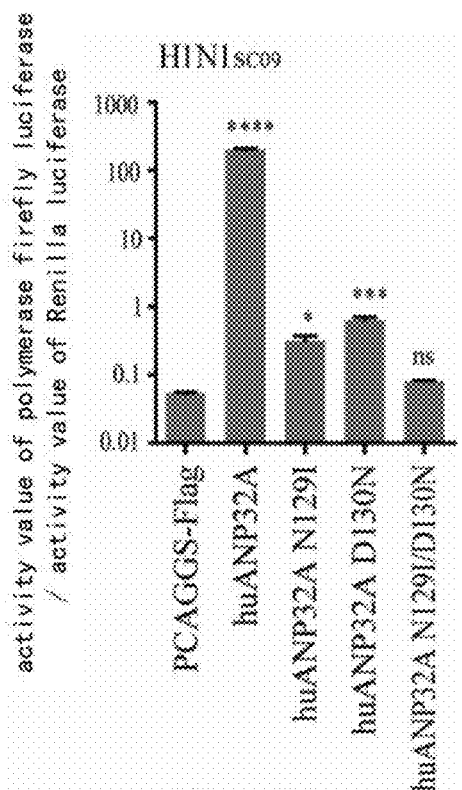
FIG. 19 shows the influence of point mutation at position 129 or 130 of huANP32A on $H1N1_{SC09}$ polymerase activity.

Double-knockout cell line (DKO) was plated in a 12-well plate at 3×10⁵/well and co-transfected with the H1N1$_{SC09}$ polymerase reporter system as described above after 20 h, and the result showed that: compared to huANP32A, huANP32A N129I/D130N completely lost support for H1N1$_{SC09}$ polymerase activity, huANP32A N129I almost lost support for H1N1$_{SC09}$ polymerase activity, while the ability of huANP32B D130N to support H1N1$_{SC09}$ polymerase activity was reduced by more than 100 times, as shown in FIG. 19.

Figure 20:
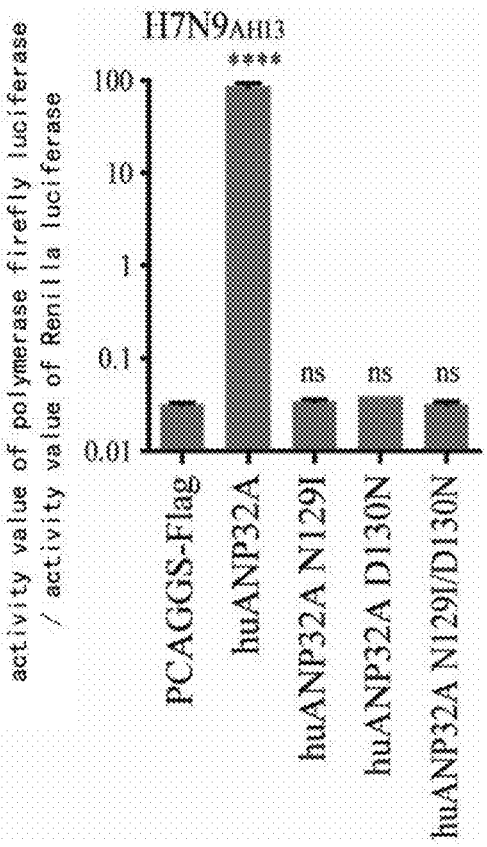
FIG. 20 shows the influence of point mutation of huANP32A on $H7N9_{AH13}$ polymerase activity.

Double-knockout cell line (DKO) was plated in a 12-well plate at 3×10⁵/well and after 20 h was co-transfected with the H7N9$_{SC09}$ polymerase reporter system as described above, and the result showed that: huANP32A N129I, huANP32A D130N and huANP32A N129I/D130N completely lost support for H7N9$_{AH13}$ polymerase activity as compared with huANP32A. The result was shown in FIG. 20.

According to the screening results of huANP32B point mutation, chANP32A was subjected to the point mutations of N129I (using primer pair of SEQ ID NO: 173 and SEQ ID NO: 174), D130N (using primer pair of SEQ ID NO: 175 and SEQ ID NO: 176) and N129I/D130N (using primer pair of SEQ ID NO: 177 and SEQ ID NO: 178) by overlapping PCR using PCAGGS-chANP32A plasmid as a template; at the same time, chANP32B was subjected to the point mutations of I129N (using primer pair of SEQ ID NO: 179 and SEQ ID NO: 180), N130D (using primer pair of SEQ ID NO: 181 and SEQ ID NO: 182) and I129N/N130D (using primer pair of SEQ ID NO: 183 and SEQ ID NO: 184) by using PCAGGS-chANP32B plasmid as a template (see Table 18 for primers, and the mutated bases were underlined.) After verification by sequencing, the plasmids were extracted in large amount for further transfection.

TABLE 18

Primers for point mutations of chANP32A and chANP32B

| primer name | primer sequence (5'-3') |
| --- | --- |
| chA_N129I_F SEQ ID NO: 173 | GAGGTAACCAACTTG<u>ATT</u>GATTATAGAGAAA AC |
| chA_N129I_R SEQ ID NO: 174 | GTTTTCTCTATAATC<u>AAT</u>CAAGTTGGTTACCTC |
| chA_D130N_F SEQ ID NO: 175 | GTAACCAACTTGAAT<u>AAC</u>TATAGAGAAAACG TA |
| chA_D130N_R SEQ ID NO: 176 | TACGTTTTCTCTATA<u>GTT</u>ATTCAAGTTGGTTAC |
| chA_ND129/ 130IN_F SEQ ID NO: 177 | GAGGTAACCAACTTG<u>ATTAAC</u>TATAGAGAAA ACGTA |
| chA_ND129/ 130IN_R SEQ ID NO: 178 | TACGTTTTCTCTATA<u>GTTAAT</u>CAAGTTGGTTAC CTC |
| chB_I129N_F SEQ ID NO: 179 | GAGGTGACGATGCTC<u>AAT</u>AACTACCGGGAGA GT |
| chB_I129N_R SEQ ID NO: 180 | ACTCTCCCGGTAGTT<u>ATT</u>GAGCATCGTCACCT C |
| chB_N130D_F SEQ ID NO: 181 | GTGACGATGCTCATC<u>GAC</u>TACCGGGAGAGTG TG |
| chB_N130D_R SEQ ID NO: 182 | CACACTCTCCCGGTA<u>GTC</u>GATGAGCATCGTC AC |
| chB_IN129/ 130ND_F SEQ ID NO: 183 | GAGGTGACGATGCTC<u>AATGAC</u>TACCGGGAGA GTGTG |
| chB_IN129/ 130ND_R SEQ ID NO: 184 | CACACTCTCCCGGTA<u>GTCATT</u>GAGCATCGTCA CCTC |

Figures 21, 22:
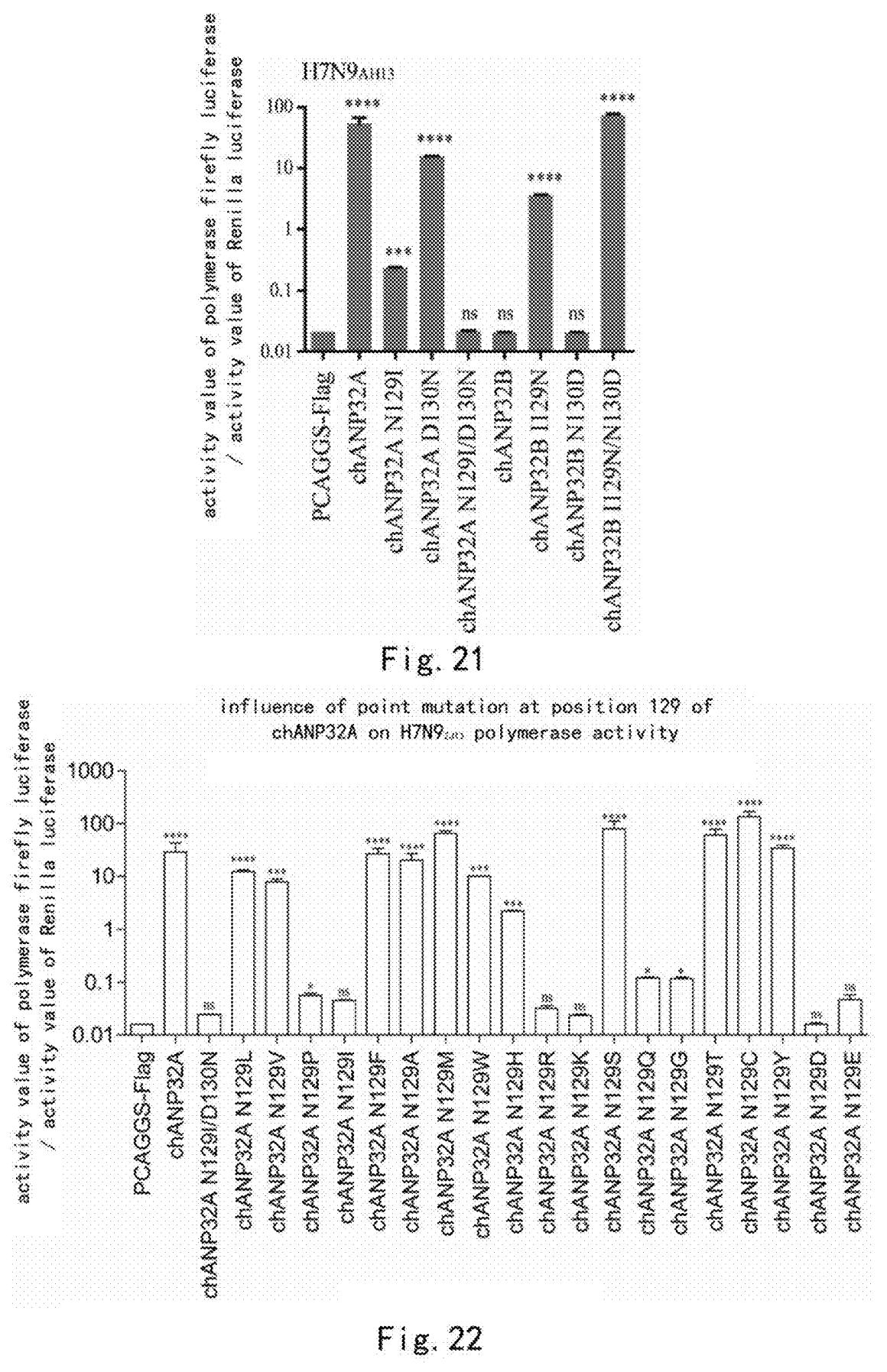

Double-knockout cell line (DKO) was plated in a 12-well plate at 3×10⁵/well and co-transfected with the H7N9$_{AH13}$polymerase reporter system as described above after 20 h, and the result showed that: compared with chANP32A, chANP32A N129I/D130N lost the support for H7N9$_{AH13}$ polymerase activity, the ability of chANP32A N129I to support H7N9$_{AH13}$ polymerase activity was decreased by more than 100 times, the ability of chANP32A D130N to support H7N9$_{AH13}$ polymerase activity was decreased by about 5 times; compared with chANP32B, chANP32B I129N and chANP32B I129N/N130D had the ability to support H7N9$_{AH13}$ polymerase activity, while chANP32B N130D still did not have the ability to support H7N9$_{AH13}$ polymerase activity. The result was shown in FIG. 21.

Example 10: Construction of the 129-Site Mutant of chANP32A Protein

Specifically, the primers for point mutation were shown in Table 19 (mutated bases were underlined), using PCAGGS-chANP32A plasmid as a template, the following point mutants of chANP32A were constructed by KOD-FX Neo high-efficiency DNA polymerase: N129A (using primer pair SEQ ID NO: 185 and SEQ ID NO: 186), N129C (using primer pair SEQ ID NO: 187 and SEQ ID NO: 188), N129D (using primer pair SEQ ID NO: 189 and SEQ ID NO: 190), N129E (using primer pair SEQ ID NO: 191 and SEQ ID NO: 192), N129F (using primer pair SEQ ID NO: 193 and SEQ ID NO: 194), N129G (using primer pair SEQ ID NO: 195 and SEQ ID NO: 196) N129H (using primer pair SEQ ID NO: 197 and SEQ ID NO: 198), N129K (using primer pair SEQ ID NO: 199 and SEQ ID NO: 200), N129L (using primer pair SEQ ID NO: 201 and SEQ ID NO: 202), N129M (using primer pair SEQ ID NO: 203 and SEQ ID NO: 204), N129I (using primer pair SEQ ID NO: 173 and SEQ ID NO: 174), N129P (using primer pair SEQ ID NO: 205 and SEQ ID NO: 206), N129Q (using primer pair SEQ ID NO: 207 and SEQ ID NO: 208), N129R (using primer pair SEQ ID NO: 209 and SEQ ID NO: 210), N129S (using primer pair SEQ ID NO: 211 and SEQ ID NO: 212), N129T (using primer pair SEQ ID NO: 213 and SEQ ID NO: 214), N129V (using primer pair SEQ ID NO: 215 and SEQ ID NO: 216), N129W (using primer pair SEQ ID NO: 217 and SEQ ID NO: 218), N129Y (using primer pair SEQ ID NO: 219 and SEQ ID NO: 220).

The obtained PCR product was digested with Dpn I in a 37° C. constant temperature water bath for 30 minutes, and then 5 ul of the digested product was taken and transformed into 20 ul of DH5α competent cells; the next day, a single clone was selected for sequencing, and the plasmid which was verified correct by sequencing was used for subsequent transfection experiment.

TABLE 19 primers for point mutation

| primer name | primer sequence (5'-3') |
|---|---|
| chA_N129A_F SEQ ID NO: 185 | GAGGTAACCAACTTGGCAGATTATAGAGAAAAC |
| chA_N129A_R SEQ ID NO: 186 | GTTTTCTCTATAATCTGCCAAGTTGGTTACCTC |
| chA_N129C_F SEQ ID NO: 187 | GAGGTAACCAACTTGTGTGATTATAGAGAAAAC |
| chA_N129C_R SEQ ID NO: 188 | GTTTTCTCTATAATCACACAAGTTGGTTACCTC |
| chA_N129D_F SEQ ID NO: 189 | GAGGTAACCAACTTGGACGATTATAGAGAAAAC |
| chA_N129D_R SEQ ID NO: 190 | GTTTTCTCTATAATCGTCCAAGTTGGTTACCTC |
| chA_N129E_F SEQ ID NO: 191 | GAGGTAACCAACTTGGAAGATTATAGAGAAAAC |
| chA_N129E_R SEQ ID NO: 192 | GTTTTCTCTATAATCTTCCAAGTTGGTTACCTC |
| chA_N129F_F SEQ ID NO: 193 | GAGGTAACCAACTTGTTCGATTATAGAGAAAAC |
| chA_N129F_R SEQ ID NO: 194 | GTTTTCTCTATAATCGAACAAGTTGGTTACCTC |
| chA_N129G_F SEQ ID NO: 195 | GAGGTAACCAACTTGGGAGATTATAGAGAAAAC |
| chA_N129G_R SEQ ID NO: 196 | GTTTTCTCTATAATCTCCCAAGTTGGTTACCTC |
| chA_N129H_F SEQ ID NO: 197 | GAGGTAACCAACTTGCACGATTATAGAGAAAAC |
| chA_N129H_R SEQ ID NO: 198 | GTTTTCTCTATAATCGTGCAAGTTGGTTACCTC |
| chA_N129K_F SEQ ID NO: 199 | GAGGTAACCAACTTGAAGGATTATAGAGAAAAC |

TABLE 19-continued primers for point mutation

| primer name | primer sequence (5'-3') |
|---|---|
| chA_N129K_R SEQ ID NO: 200 | GTTTTCTCTATAATCCTTCAAGTTGGTTACCTC |
| chA_N129L_F SEQ ID NO: 201 | GAGGTAACCAACTTGCTAGATTATAGAGAAAAC |
| chA_N129L_R SEQ ID NO: 202 | GTTTTCTCTATAATCTAGCAAGTTGGTTACCTC |
| chA_N129M_F SEQ ID NO: 203 | GAGGTAACCAACTTGATGGATTATAGAGAAAAC |
| chA_N129M_R SEQ ID NO: 204 | GTTTTCTCTATAATCCATCAAGTTGGTTACCTC |
| chA_N129P_F SEQ ID NO: 205 | GAGGTAACCAACTTGCCAGATTATAGAGAAAAC |
| chA_N129P_R SEQ ID NO: 206 | GTTTTCTCTATAATCTGGCAAGTTGGTTACCTC |
| chA_N129Q_F SEQ ID NO: 207 | GAGGTAACCAACTTGCAAGATTATAGAGAAAAC |
| chA_N129Q_R SEQ ID NO: 208 | GTTTTCTCTATAATCTTGCAAGTTGGTTACCTC |
| chA_N129R_F SEQ ID NO: 209 | GAGGTAACCAACTTGAGAGATTATAGAGAAAAC |
| chA_N129R_R SEQ ID NO: 210 | GTTTTCTCTATAATCTCTCAAGTTGGTTACCTC |
| chA_N129S_F SEQ ID NO: 211 | GAGGTAACCAACTTGAGCGATTATAGAGAAAAC |
| chA_N129S_R SEQ ID NO: 212 | GTTTTCTCTATAATCGCTCAAGTTGGTTACCTC |
| chA_N129T_F SEQ ID NO: 213 | GAGGTAACCAACTTGACAGATTATAGAGAAAAC |
| chA_N129T_R SEQ ID NO: 214 | GTTTTCTCTATAATCTGTCAAGTTGGTTACCTC |
| chA_N129V_F SEQ ID NO: 215 | GAGGTAACCAACTTGGTAGATTATAGAGAAAAC |
| chA_N129V_R SEQ ID NO: 216 | GTTTTCTCTATAATCTACCAAGTTGGTTACCTC |
| chA_N129W_F SEQ ID NO: 217 | GAGGTAACCAACTTGTGGGATTATAGAGAAAAC |
| chA_N129W_R SEQ ID NO: 218 | GTTTTCTCTATAATCCCACAAGTTGGTTACCTC |
| chA_N129Y_F SEQ ID NO: 219 | GAGGTAACCAACTTGTACGATTATAGAGAAAAC |
| chA_N129Y_R SEQ ID NO: 220 | GTTTTCTCTATAATCGTACAAGTTGGTTACCTC |

Example 11: Influence of the 129-Site Mutant of chANP32A Protein on the Replication of Influenza Virus H7N9$_{ZJ13}$ Double-knockout cell lines (DKO) were plated in a 12-well plate at 3×10⁵/well; after 20 hours, the 129-site mutant of chANP32A constructed in Example 10 were respectively co-transfected with the 6 plasmids of H7N9$_{ZJ13}$ polymerase reporter system. The transfection system was: PB1 (80 ng), PB2 (80 ng), PA (40 ng), NP (160 ng), pMD 18T-vLuc (80 ng), pRL-TK (10 ng) and the plasmid of ANP32 mutant protein (20 ng); and the empty vector (20 ng) was set as a negative control, chANP32A (20 ng) was set as positive control, and each group was provided with triplicate wells. 24 hours after transfection, the cells were lysed and the activity of polymerase was detected; The result showed that: compared with chANP32A, the two-point mutant of chANP32A N129I/D130N and the single-point mutants of chANP32A N129I, chANP32A N129R, chANP32A N129K, chANP32A N129D and chANP32A N129E did not have the ability to support H7N9$_{ZJ13}$ polymerase activity; chANP32A N129P, chANP32A N129Q, chANP32A N129G almost completely lost the ability to support H7N9$_{ZJ13}$ polymerase activity, while chANP32A N129L, chANP32A N129F, chANP32A N129A, chANP32A N129M, chANP32A N129S, chANP32A N129T, chANP32A N129C and chANP32A N129Y all supported H7N9$_{ZJ13}$ polymerase activity; the ability of chANP32A N129V, chANP32A N129W and chANP32A N129H to support H7N9$_{ZJ13}$ polymerase activity was reduced by approximately 100 times; the result was shown in FIG. 22.

Example 12: Influence of the 129-Site Mutant of chANP32A Protein on the Replication of Influenza Virus H7N9$_{AH13}$ Double-knockout cell lines (DKO) were plated in a 12-well plate at 3×10$^5$/well; after 20 hours, the 129-site mutant of chANP32A constructed in Example 10 were co-transfected with the 6 plasmids of H7N9$_{AH13}$ polymerase reporter system. The transfection system was: PB1 (80 ng), PB2 (80 ng), PA (40 ng), NP (160 ng), pMD 18T-vLuc (80 ng), pRL-TK (10 ng) and the plasmid of ANP32 mutant protein (20 ng); and the empty vector (20 ng) was set as a negative control, chANP32A (20 ng) was set as positive control, and each group was provided with triplicate wells. 24 hours after transfection, the cells were lysed and the activity of polymerase was detected; The result showed that: compared with chANP32A, the two-point mutant of chANP32A N129I/D130N and the single-point mutants of chANP32A N129P, chANP32A N129R, chANP32A N129K, chANP32A N129Q, chANP32A N129D and chANP32A N129E did not have the ability to support H7N9$_{AH13}$ polymerase activity; chANP32A N129I has little ability to support H7N9$_{AH13}$ polymerase activity; chANP32A N129F, chANP32A N129A, chANP32A N129M, chANP32A N129S, chANP32A N129G, chANP32A N129T, chANP32A N129C and chANP32A N129Y all supported H7N9$_{AH13}$ polymerase activity; the ability of chANP32A N129L and chANP32A N129W to support H7N9$_{AH13}$ polymerase activity was reduced by 3-10 times, and the ability of chANP32A N129V and chANP32A N129H to support H7N9$_{AH13}$ polymerase activity was reduced by approximately 20-100 times; the result was shown in FIG. 23.

Example 13: Influence of the 129-Site Mutant of chANP32A Protein on the Replication of Influenza Virus WSN Double-knockout cell lines (DKO) were plated in a 12-well plate at 3×10$^5$/well; after 20 hours, the chANP32A 129-site mutant constructed in Example 10 were co-transfected with the 6 plasmids of WSN polymerase reporter system. The transfection system was: PB1 (80 ng), PB2 (80 ng), PA (40 ng), NP (160 ng), pMD 18T-vLuc (80 ng), pRL-TK (10 ng) and the plasmid of ANP32 mutant protein (20 ng); and the empty vector (20 ng) was set as a negative control, chANP32A (20 ng) was set as positive control, and each group was provided with triplicate wells. 24 hours after transfection, the cells were lysed and the activity of polymerase was detected; The result showed that: compared with chANP32A, the two-point mutant of chANP32A N129I/D130N and the single-point mutants of chANP32A N129K and chANP32A N129D did not have the ability to support WSN polymerase activity; while chANP32A N129F, chANP32A N129A, chANP32A N129M, chANP32A N129S, chANP32A N129G, chANP32A N129T and chANP32A N129C all supported WSN polymerase activity; the ability of chANP32A N129P, chANP32A N129I, chANP32A N129H, chANP32A N129R, chANP32A N129Q and chANP32A N129E to support WSN polymerase activity was reduced by approximately 100 times; the ability of chANP32A N129L, chANP32A N129W, chANP32A N129Y and chANP32A N129V to support WSN polymerase activity was reduced by approximately 5-20 times; the result was shown in FIG. 24.

Example 14: Construction of the 130-Site Mutant of chANP32A Protein

The primers for point mutation were shown in Table 20 (mutated bases were underlined), using PCAGGS-chANP32A as a template, the following point mutants of chANP32A were constructed by KOD-FX Neo high-efficiency DNA polymerase amplification: N130A (using primer pair SEQ ID NO: 221 and SEQ ID NO: 222), D130C (using primer pair SEQ ID NO: 223 and SEQ ID NO: 224), D130E (using primer pair SEQ ID NO: 225 and SEQ ID NO: 226), D130F (using primer pair SEQ ID NO: 227 and SEQ ID NO: 228), D130G (using primer pair SEQ ID NO: 229 and SEQ ID NO: 230), D130H (using primer pair SEQ ID NO: 231 and SEQ ID NO: 232), D130K (using primer pair SEQ ID NO: 233 and SEQ ID NO: 234), D130L (using primer pair SEQ ID NO: 235 and SEQ ID NO: 236), D130M (using primer pair SEQ ID NO: 237 and SEQ ID NO: 238), D130N (using primer pair SEQ ID NO: 175 and SEQ ID NO: 176), D130P (using primer pair SEQ ID NO: 239 and SEQ ID NO: 240), D130Q (using primer pair SEQ ID NO: 241 and SEQ ID NO: 242), D130R (using primer pair SEQ ID NO: 243 and SEQ ID NO: 244), D130S (using primer pair SEQ ID NO: 245 and SEQ ID NO: 246), D130T (using primer pair SEQ ID NO: 247 and SEQ ID NO: 248), D130V (using primer pair SEQ ID NO: 249 and SEQ ID NO: 250), D130W (using primer pair SEQ ID NO: 251 and SEQ ID NO: 252), D130Y (using primer pair SEQ ID NO: 253 and SEQ ID NO: 254), D130I (using primer pair SEQ ID NO: 255 and SEQ ID NO: 256).

The obtained PCR product was digested with Dpn I in a 37° C. constant temperature water bath for 30 minutes, and then 5 ul of the digested product was taken and transformed into 20 ul of DH5α competent cells; the next day, a single clone was picked for sequencing, and the plasmids which were verified correct by sequencing were used for subsequent transfection experiment.

TABLE 20 primers of 130-site point mutation

| primer name | primer sequence (5'-3') |
|---|---|
| chA D130A-F, SEQ ID NO: 221 | GTAACCAACTTGAATGCATATAGAGAAAAC |
| chA D130A-R, SEQ ID NO: 222 | CGTTTTCTCTATATGCATTCAAGTTGGTTACC |
| chA D130C-F, SEQ ID NO: 223 | GTAACCAACTTGAATTGTTATAGAGAAAAC |
| chA D130C-R, SEQ ID NO: 224 | CGTTTTCTCTATAACAATTCAAGTTGGTTACCT |
| chA D130E-F, SEQ ID NO: 225 | GTAACCAACTTGAATGAATATAGAGAAAAC |
| chA D130E-R, SEQ ID NO: 226 | CGTTTTCTCTATATTCATTCAAGTTGGTTACC |
| chA D130F-F, SEQ ID NO: 227 | GTAACCAACTTGAATTTCTATAGAGAAAAC |
| chA D130F-R, SEQ ID NO: 228 | CGTTTTCTCTATAGAAATTCAAGTTGGTTACC |
| chA D130G-F, SEQ ID NO: 229 | GTAACCAACTTGAATGGCTATAGAGAAAAC |
| chA D130G-R, SEQ ID NO: 230 | CGTTTTCTCTATAGCCATTCAAGTTGGTTACC |
| chA D130H-F, SEQ ID NO: 231 | GTAACCAACTTGAATCACTATAGAGAAAAC |
| chA D130H-R, SEQ ID NO: 232 | CGTTTTCTCTATAGTGATTCAAGTTGGTTACC |
| chA D130K-F, SEQ ID NO: 233 | GTAACCAACTTGAATAAGTATAGAGAAAAC |
| chA D130K-R, SEQ ID NO: 234 | CGTTTTCTCTATACTTATTCAAGTTGGTTACC |
| chA D130L-F, SEQ ID NO: 235 | GTAACCAACTTGAATCTATATAGAGAAAAC |
| chA D130L-R, SEQ ID NO: 236 | CGTTTTCTCTATATAGATTCAAGTTGGTTACC |
| chA D130M-F, SEQ ID NO: 237 | GTAACCAACTTGAATATGTATAGAGAAAAC |
| chA D130M-R, SEQ ID NO: 238 | CGTTTTCTCTATACATATTCAAGTTGGTTACC |
| chA D130P-F, SEQ ID NO: 239 | GTAACCAACTTGAATCCATATAGAGAAAAC |
| chA D130P-R, SEQ ID NO: 240 | CGTTTTCTCTATATGGATTCAAGTTGGTTACC |
| chA D130Q-F, SEQ ID NO: 241 | GTAACCAACTTGAATCAATATAGAGAAAAC |
| chA D130Q-R, SEQ ID NO: 242 | CGTTTTCTCTATATTGATTCAAGTTGGTTACC |
| chA D130R-F, SEQ ID NO: 243 | GTAACCAACTTGAATAGATATAGAGAAAAC |
| chA D130R-R, SEQ ID NO: 244 | CGTTTTCTCTATATCTATTCAAGTTGGTTACC |
| chA D130S-F, SEQ ID NO: 245 | GTAACCAACTTGAATAGCTATAGAGAAAAC |
| chA D130S-R, SEQ ID NO: 246 | CGTTTTCTCTATAGCTATTCAAGTTGGTTACC |
| chA D130T-F, SEQ ID NO: 247 | GTAACCAACTTGAATACATATAGAGAAAAC |
| chA D130T-R, SEQ ID NO: 248 | CGTTTTCTCTATATGTATTCAAGTTGGTTACC |
| chA D130V-F, SEQ ID NO: 249 | GTAACCAACTTGAATGTATATAGAGAAAAC |
| chA D130V-R, SEQ ID NO: 250 | CGTTTTCTCTATATACATTCAAGTTGGTTACC |
| chA D130W-F, SEQ ID NO: 251 | GTAACCAACTTGAATTGGTATAGAGAAAAC |
| chA D130W-R, SEQ ID NO: 252 | CGTTTTCTCTATACCAATTCAAGTTGGTTACC |
| chA D130Y-F, SEQ ID NO: 253 | GTAACCAACTTGAATTACTATAGAGAAAAC |
| chA D130Y-R, SEQ ID NO: 254 | CGTTTTCTCTATAGTAATTCAAGTTGGTTACC |
| chA D130I-F, SEQ ID NO: 255 | GTAACCAACTTGAATATCTATAGAGAAAAC |
| chA D130I-R, SEQ ID NO: 256 | CGTTTTCTCTATAGATATTCAAGTTGGTTACC |

Figures 25, 26:
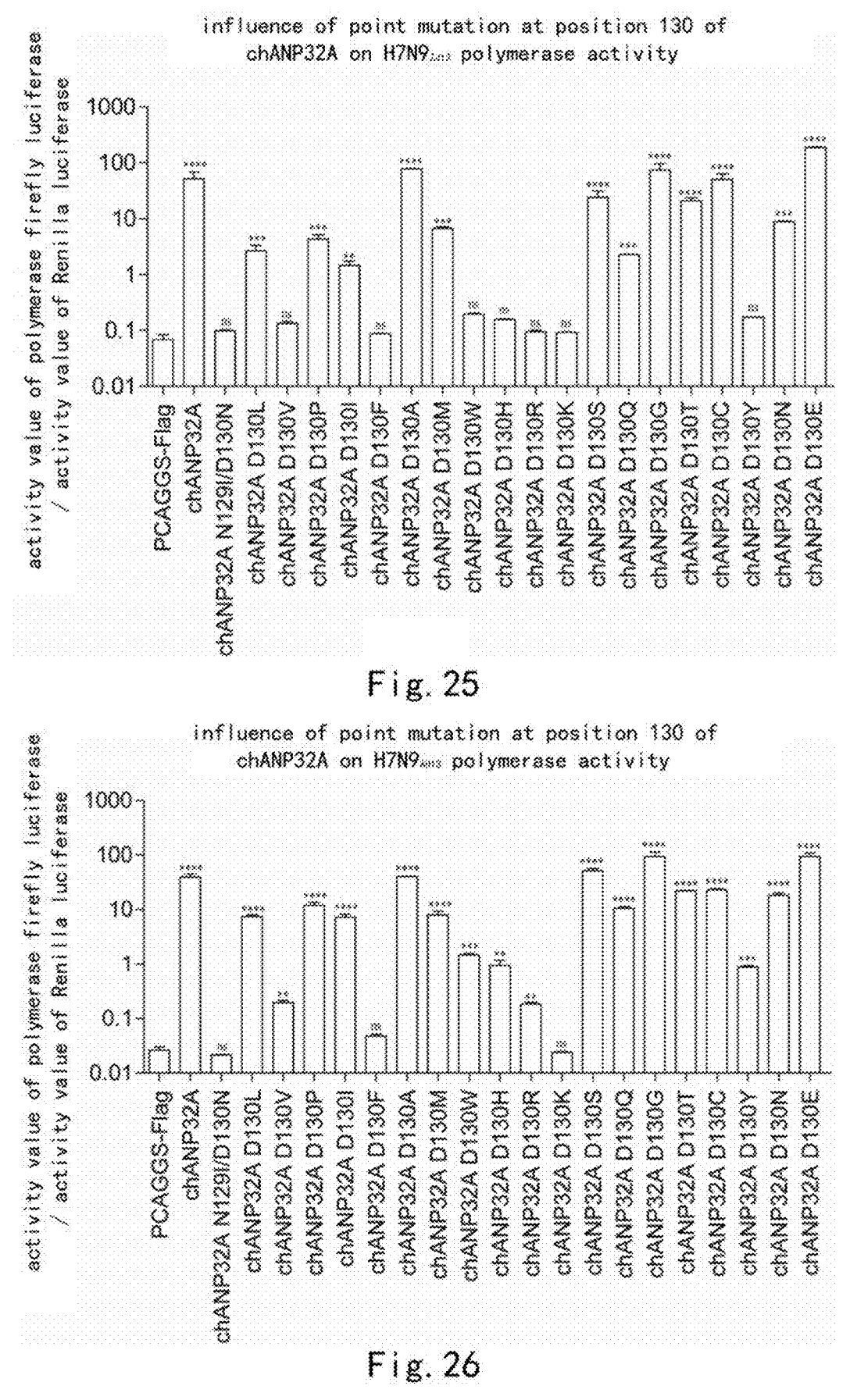

Example 15: Influence of the 130-Site Mutant of chANP32A Protein on the Replication of Influenza Virus H7N9$_{ZJ13}$ DKO cells constructed in Example 2 were plated in a 12-well plate at 3×10$^5$/well; after 20 hours, the 130-site mutant of chANP32A constructed in Example 14 were co-transfected with the 6 plasmids of H7N9$_{ZJ13}$ polymerase reporter system. The transfection system was: PB1 (80 ng), PB2 (80 ng), PA (40 ng), NP (160 ng), pMD 18T-vLuc (80 ng), pRL-TK (10 ng) and the plasmid of ANP32 mutant protein (20 ng); and the empty vector (20 ng) was set as a negative control, chANP32A (20 ng) was set as positive control, and each group was provided with triplicate wells. 24 hours after transfection, the cells were lysed and the activity of polymerase was detected; The result showed that: compared with chANP32A, the two-point mutant of chANP32A N129I/D130N and the single-point mutants of chANP32A D130V, chANP32A D130F, chANP32A D130W, chANP32A D130H, chANP32A D130R, chANP32A D130K and chANP32A D130Y did not have the ability to support H7N9$_{ZJ13}$ polymerase activity; while chANP32A D130A, chANP32A D130G, chANP32A D130C and chANP32A D130E all supported H7N9$_{ZJ13}$ polymerase activity; the ability of chANP32A D130S and chANP32A D130T to support polymerase activity was reduced by approximately 3 times; the ability of chANP32A D130L, chANP32A D130P, chANP32A D130I, chANP32A D130M, chANP32A D130Q and chANP32A D130N to support H7N9$_{113}$ polymerase activity was reduced by approximately 10-50 times; the result was shown in FIG. 25.

Example 16: Influence of the 130-Site Mutant of chANP32A Protein on the Replication of Influenza Virus H7N9$_{AH13}$ DKO cells constructed in Example 2 were plated in a 12-well plate at 3×10$^5$/well; after 20 hours, the 130-site mutant of chANP32A constructed in Example 14 were co-transfected with the 6 plasmids of H7N9$_{AH13}$ polymerase reporter system. The transfection system was: PB1 (80 ng), PB2 (80 ng), PA (40 ng), NP (160 ng), pMD18T-vLuc (80 ng), pRL-TK (10 ng) and the plasmid of ANP32 mutant protein (20 ng); and the empty vector (20 ng) was set as a negative control, chANP32A (20 ng) was set as positive control, and each group was provided with triplicate wells. 24 hours after transfection, the cells were lysed and the activity of polymerase was detected; The result showed that: compared with chANP32A, the two-point mutant of chANP32A N129I/D130N and the single-point mutants of chANP32A D130F and chANP32A D130K did not have the ability to support H7N9$_{AH13}$ polymerase activity; while chANP32A D130A, chANP32A D130S, chANP32A D130G and chANP32A D130E all supported H7N9$_{AH13}$ polymerase activity; the ability of chANP32A D130V and chANP32A D130R to support polymerase activity was reduced by more than 100 times, and almost did not have the ability to support polymerase activity; the ability of chANP32A D130L, chANP32A D130P, chANP32A D130I, chANP32A D130M, chANP32A D130W, chANP32A D130H, chANP32A D130Q and chANP32A D130Y to support H7N9$_{AH13}$ polymerase activity was reduced by approximately 10-100 times; the ability of chANP32A D130T, chANP32A D130C and chANP32A D130N to support H7N9$_{AH13}$ polymerase activity was reduced by approximately 3-5 times; the result was shown in FIG. 26.

Figure 27:
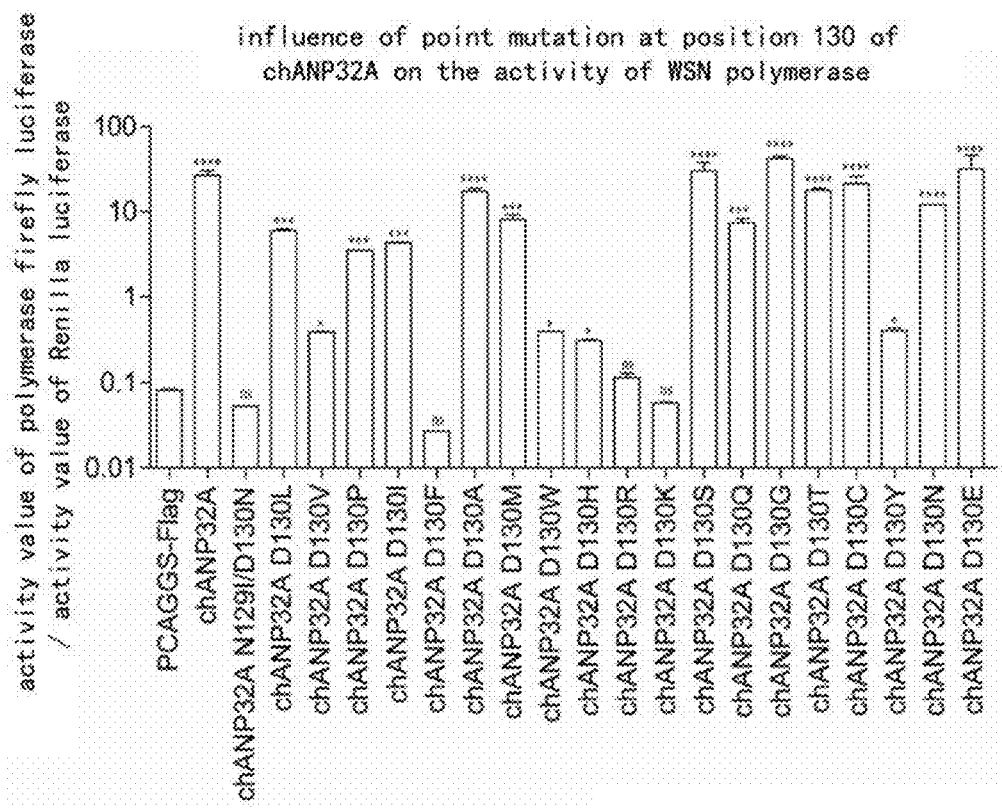
FIG. 27 shows the influence of point mutant at position 130 of chANP32A on the activity of WSN polymerase.

Example 17: Influence of the 130-Site Mutant of chANP32A Protein on the Replication of Influenza Virus WSN DKO cells constructed in Example 2 were plated in a 12-well plate at 3×10$^5$/well; after 20 hours, the 130-site mutant of chANP32A constructed in Example 14 was co-transfected with the 6 plasmids of WSN polymerase reporter system. The transfection system was: PB1 (80 ng), PB2 (80 ng), PA (40 ng), NP (160 ng), pMD18T-vLuc (80 ng), pRL-TK (10 ng) and the plasmid of ANP32 mutant protein (20 ng); and the empty vector (20 ng) was set as a negative control, chANP32A (20 ng) was set as positive control, and each group was provided with triplicate wells. 24 hours after transfection, the cells were lysed and the activity of polymerase was detected; The result showed that: compared with chANP32A, the two-point mutant of chANP32A N129I/D130N and the single-point mutants of chANP32A D130F, chANP32A D130R and chANP32A D130K did not have the ability to support WSN polymerase activity; while chANP32A D130S and chANP32A D130G, chANP32A D130E all supported WSN polymerase activity; chANP32A D130V, chANP32A D130W, chANP32A D130H and chANP32A D130Y almost did not have the ability to support polymerase activity; the ability of chANP32A D130L, chANP32A D130P, chANP32A D130I, chANP32A D130M, chANP32A D130Q and chANP32A D130N to support WSN polymerase activity was reduced by approximately 10-50 times; the ability of chANP32A D130A, chANP32A D130T and chANP32A D130C to support WSN polymerase activity was reduced by approximately 2-3 times; the result was shown in FIG. 27.

Example 18: Construction of the Vector of huANP32B Protein Segmented Mutation and Determination of Polymerase Activity

TABLE 21 primer sequences of huANP32B protein segmented mutation

| primer name | sequence (5'-3') |
|---|---|
| huANP_B1_F, SEQ ID NO: 257 | TCGCGGCCGCATGGCCGCCGCCGCCGCCGCC GCCGCCGCCCTGAGGAACCGGACCCCG |
| Human_B1_R, SEQ ID NO: 258 | GGTTCCTCAGGGCGGCGGCGGCGGCGGCGG CGGCGGCCATGCGGCCGCGAGCTCGAA |
| Human_B2_F, SEQ ID NO: 259 | CCACCTGGAGGCCGCCGCCGCCGCCGCCGCC GCCGCCGCCGAACTTGTCTTGGACAAT |
| Human_B2_R, SEQ ID NO: 260 | AGACAAGTTCGGCGGCGGCGGCGGCGGCGG CGGCGGCGGCCTCCAGGTGGATCCTCCT |
| Human_B3_F, SEQ ID NO: 261 | AGCTGTTCGAGCCGCCGCCGCCGCCGCCGCC GCCGCCGCCGATGGAAAAATTGAGGGC |
| Human_B3_R, SEQ ID NO: 262 | TTTTTCCATCGGCGGCGGCGGCGGCGGCGGC GGCGGCGGCTCGAACAGCTGCCGGGGT |
| Human_B4_F, SEQ ID NO: 263 | CAAATCAAATGCCGCCGCCGCCGCCGCCGCC GCCGCCGCCTTTGTGAACTTAGAGTTC |
| Human_B4_R, SEQ ID NO: 264 | AGTTCACAAAGGCGGCGGCGGCGGCGGCGG CGGCGGCGGCATTTGATTTGCAATTGTC |
| Human_B5_F, SEQ ID NO: 265 | AACAGCTGAAGCCGCCGCCGCCGCCGCCGC CGCCGCCGCCAATGTAGGCTTGATCTCA |
| Human_B5_R, SEQ ID NO: 266 | AGCCTACATTGGCGGCGGCGGCGGCGGCGGC GGCGGCGGCTTCAGCTGTTAAGCCCTC |
| Human_B6_F, SEQ ID NO: 267 | CAGTTTAATAGCCGCCGCCGCCGCCGCCGCC GCCGCCGCCCCAAGCTGCCTAAATTG |
| Human_B6_R, SEQ ID NO: 268 | GCAGCTTGGGGCGGCGGCGGCGGCGGCGG CGGCGGCGGCTATTAAACTGAGGAACTC |
| Human_B7_F, SEQ ID NO: 269 | TTCAAATCTCGCCGCCGCCGCCGCCGCCGCC GCCGCCGCCCTCAGTGAAAATAGAATC |
| Human_B7_R, SEQ ID NO: 270 | TTTCACTGAGGGCGGCGGCGGCGGCGGCGG CGGCGGCGGCGAGATTTGAAACTGAGAT |
| Human_B8_F, SEQ ID NO: 271 | AAAGCTTGAAGCCGCCGCCGCCGCCGCCGCC GCCGCCGCCGACATGTTAGCTGAAAAA |
| Human_B8_R, SEQ ID NO: 272 | CTAACATGTCGGCGGCGGCGGCGGCGGCGGC GGCGGCGGCTTCAAGCTTTTTCAATTT |

TABLE 21-continued primer sequences of huANP32B protein segmented mutation

| primer name | sequence (5'-3') |
|---|---|
| Human_B9_F, SEQ ID NO: 273 | TGGAGGTCTGGCCGCCGCCGCCGCCGCC GCCGCCGCCACACATCTAAACTTAAGT |
| Human_B9_R, SEQ ID NO: 274 | TTAGATGTGTGGCGGCGGCGGCGGCGGC GGCGGCGGCCAGACCTCCAAAGATTCT |
| Human_B10_F, SEQ ID NO: 275 | TCCAAATCTCGCCGCCGCCGCCGCCGCC GCCGCCGCCAAAGATATCAGCACCTTG |
| Human_B10_R, SEQ ID NO: 276 | TGATATCTTTGGCGGCGGCGGCGGCGGC GGCGGCGGCGAGATTTGGAAGTTTTTC |
| Human_B11_F, SEQ ID NO: 277 | AAATAAACTGGCCGCCGCCGCCGCCGCC GCCGCCGCCAAGTTAGAATGTCTGAAA |
| Human_B11_R, SEQ ID NO: 278 | ATTCTAACTTGGCGGCGGCGGCGGCGGC GGCGGCGGCCAGTTTATTTCCACTTAA |
| Human_B12_F, SEQ ID NO: 279 | ACCTTTGAAAGCCGCCGCCGCCGCCGCC GCCGCCGCCTTTAACTGTGAGGTTACC |
| Human_B12_R, SEQ ID NO: 280 | CACAGTTAAAGGCGGCGGCGGCGGCGG CGGCGGCGGCTTTCAAAGGTTCCAAGGT |
| Human_B13_F, SEQ ID NO: 281 | CCTGGACCTCGCCGCCGCCGCCGCCGCC GCCGCCGCCTACCGAGAGAGTGTCTTC |
| Human_B13_R, SEQ ID NO: 282 | TCTCTCGGTAGGCGGCGGCGGCGGCGGC GGCGGCGGCGAGGTCCAGGCTTTTCAG |
| Human_B14_F, SEQ ID NO: 283 | CCTGAATGACGCCGCCGCCGCCGCCGCC GCCGCCGCCCAGCTTACCTACTTGGAT |
| Human_B14_R, SEQ ID NO: 284 | AGGTAAGCTGGGCGGCGGCGGCGGCGGC CGGCGGCGGCGTCATTCAGGTTGGTAAC |
| Human_B15_F, SEQ ID NO: 285 | GCTCCTGCCCGCCGCCGCCGCCGCCGCC GCCGCCGCCGAGGACCAGGAAGCACCT |
| Human_B15_R, SEQ ID NO: 286 | CCTGGTCCTCGGCGGCGGCGGCGGCGGC CGGCGGCGGCGGGCAGGAGCTTGAAGAC |
| Human_B16_F, SEQ ID NO: 287 | CTATGACCGAGCCGCCGCCGCCGCCGCC GCCGCCGCCGAGGTGGATGGTGTGGAT |
| Human_B16_R, SEQ ID NO: 288 | CATCCACCTCGGCGGCGGCGGCGGCGGC GGCGGCGGCTCGGTCATAGCCATCCAA |
| Human_B17_F, SEQ ID NO: 289 | CTCAGATGCCGCCGCCGCCGCCGCCGCC GCCGCCGCCGACGAAGAAGGAGAAGAT |
| Human_B17_R, SEQ ID NO: 290 | CTTCTTCGTCGGCGGCGGCGGCGGCGGC GGCGGCGGCGGCATCTGAGTCAGGTGC |
| Human_B18_F, SEQ ID NO: 291 | AGAGGAGGAGGCCGCCGCCGCCGCCGC CGCCGCCGCCGACGATGAGGATGGTGAA |
| Human_B18_R, SEQ ID NO: 292 | CCTCATCGTCGGCGGCGGCGGCGGCGGC GGCGGCGGCCTCCTCCTCTTCATCCAC |
| Human_B19_F, SEQ ID NO: 293 | GGAAGACGAGGCCGCCGCCGCCGCCGC CGCCGCCGCCGATGAAGAAGATGATGAA |
| Human_B19_R, SEQ ID NO: 294 | CTTCTTCATCGGCGGCGGCGGCGGCGGC GGCGGCGGCCTCGTCTTCCTCATCTTC |
| Human_B20_F, SEQ ID NO: 295 | AGAGGAGTTTGCCGCCGCCGCCGCCGCC GCCGCCGCCGAAGGGGATGAGGACGAC |
| Human_B20_R, SEQ ID NO: 296 | CATCCCCTTCGGCGGCGGCGGCGGCGGC GGCGGCGGCAAACTCCTCTTCTTCACC |
| Human_B21_F, SEQ ID NO: 297 | TGAAGATGTAGCCGCCGCCGCCGCCGCC GCCGCCGCCGAGGAGGAAGAAGAATTT |
| Human_B21_R, SEQ ID NO: 298 | CTTCCTCCTCGGCGGCGGCGGCGGCGGC GGCGGCGGCTACATCTTCATCTTCATC |
| Human_B22_F, SEQ ID NO: 299 | TGAAGTCAGTGCCGCCGCCGCCGCCGCC GCCGCCGCCGAAGATGAAGATGAGGAT |
| Human_B22_R, SEQ ID NO: 300 | CTTCATCTTCGGCGGCGGCGGCGGCGGC GGCGGCGGCACTGACTTCATCGTCGTC |
| Human_B23_F, SEQ ID NO: 301 | ACTTGATGAAGCCGCCGCCGCCGCCGCC GCCGCCGCCGAGGAAGAAGGTGGGAAA |
| Human_B23_R, SEQ ID NO: 302 | CTTCTTCCTCGGCGGCGGCGGCGGCGGC GGCGGCGGCTTCATCAAGTCCAAATTC |
| Human_B24_F, SEQ ID NO: 303 | GGATGAAGAGGCCGCCGCCGCCGCCGC CGCCGCCGCCAAGAGAGAAACAGATGA |
| Human_B24_R, SEQ ID NO: 304 | TTTCTCTCTTGGCGGCGGCGGCGGCGGC GGCGGCGGCCTCTTCATCCTCATCCTC |
| Human_B25_F, SEQ ID NO: 305 | TGAAAAGAGGGCCGCCGCCGCCGCCGC CGCCGCCGCCGCCGGCAGCGGAGACTACA |
| Human_B25_R, SEQ ID NO: 306 | CTCCGCTGCCGGCGGCGGCGGCGGCGG CGGCGGCGGCGGCCCTCTTTTCACCTTT |

The huANP32B protein was subjected to a segmented mutation, wherein every 10 amino acids as a group were uniformly mutated to KOD-FX high-efficiency DNA polymerase and using PCAGGS-huANP32B as a template, the following segmented mutants were respectively constructed: huANP32B B1-10A (using primer pair SEQ ID NO: 257 and SEQ ID NO: 258), huANP32B B11-20A (using primer pair SEQ ID NO: 259 and SEQ ID NO: 260), huANP32B B21-30A (using primer pair SEQ ID NO: 261 and SEQ ID NO: 262), huANP32B B31-40A (using primer pair SEQ ID NO: 263 and SEQ ID NO: 264), huANP32B B41-50A (using primer pair SEQ ID NO: 265 and SEQ ID NO: 266), huANP32B B51-60A (using primer pair SEQ ID NO: 267 and SEQ ID NO: 268), huANP32B B61-70A (using primer pair SEQ ID NO: 269 and SEQ ID NO: 270), huANP32B B71-80A (using primer pair SEQ ID NO: 271 and SEQ ID NO: 272), huANP32B B81-90A (using primer pair SEQ ID NO: 273 and SEQ ID NO: 274), huANP32B B91-100A (using primer pair SEQ ID NO: 275 and SEQ ID NO: 276), huANP32B B101-110A (using primer pair SEQ ID NO: 277 and SEQ ID NO: 278), huANP32B B111-120A (using primer pair SEQ ID NO: 279 and SEQ ID NO: 280), huANP32B B121-130A (using primer pair SEQ ID NO: 281 and SEQ ID NO: 282), huANP32B B131-140A (using primer pair SEQ ID NO: 283 and SEQ ID NO: 284), huANP32B B141-150A (using primer pair SEQ ID NO: 285 and SEQ ID NO: 286), huANP32B B151-160tA (using primer pair SEQ ID NO: 287 and SEQ ID NO: 288), huANP32B B161-170A (using primer pair SEQ ID NO: 289 and SEQ ID NO: 290), huANP32B B171-180A (using primer pair SEQ ID NO: 291 and SEQ ID NO: 292), huANP32B B181-190A (using primer pairs SEQ ID NO: 293 and SEQ ID NO: 294), huANP32B B191-200A (using primer pair SEQ ID NO: 295 and SEQ ID NO: 296), huANP32B B201-210A (using primer pairs SEQ ID NO: 297 and SEQ ID NO: 298), huANP32B B211-220A (using primer pair SEQ ID NO: 299 and SEQ ID NO: 300), huANP32B B221-230A (using primer pair SEQ ID NO: 301 and SEQ ID NO: 302), huANP32B B231-240A (using primer pair SEQ ID NO: 303 and SEQ ID NO: 304), huANP32B B241-251A (using primer pair SEQ ID NO: 305 and SEQ ID NO: 306), and were respectively named as huANP32B B1-10A, huANP32B B11-20A, huANP32B B21-30A, huANP32B B31-40A, huANP32B B41-50A, huANP32B B51-60A, huANP32B B61-70A, huANP32B B71-80A, huANP32B B81-90A, huANP32B B91-100A, huANP32B B101-110A, huANP32B B 111-120A, huANP32B B 121-130A, huANP32B B 131-140A, huANP32B B141-150A, huANP32B B151-160A, huANP32B B161-170A, huANP32B B171-180A, huANP32B B181-190A, huANP32B B191-200A, huANP32B B201-210A, huANP32B B211-220A, huANP32B B221-230A, huANP32B B231-240A and huANP32B B241-251A. The obtained PCR product was digested with Dpn I in a 37° C. constant temperature water bath for 30 minutes, and then 2.5 ul of the digested product was taken and transformed into 20 ul of DH5α competent cells; the next day, a single clone was picked for sequencing, and the plasmid which was verified correct by sequencing was used for subsequent transfection experiment.

Figure 28:
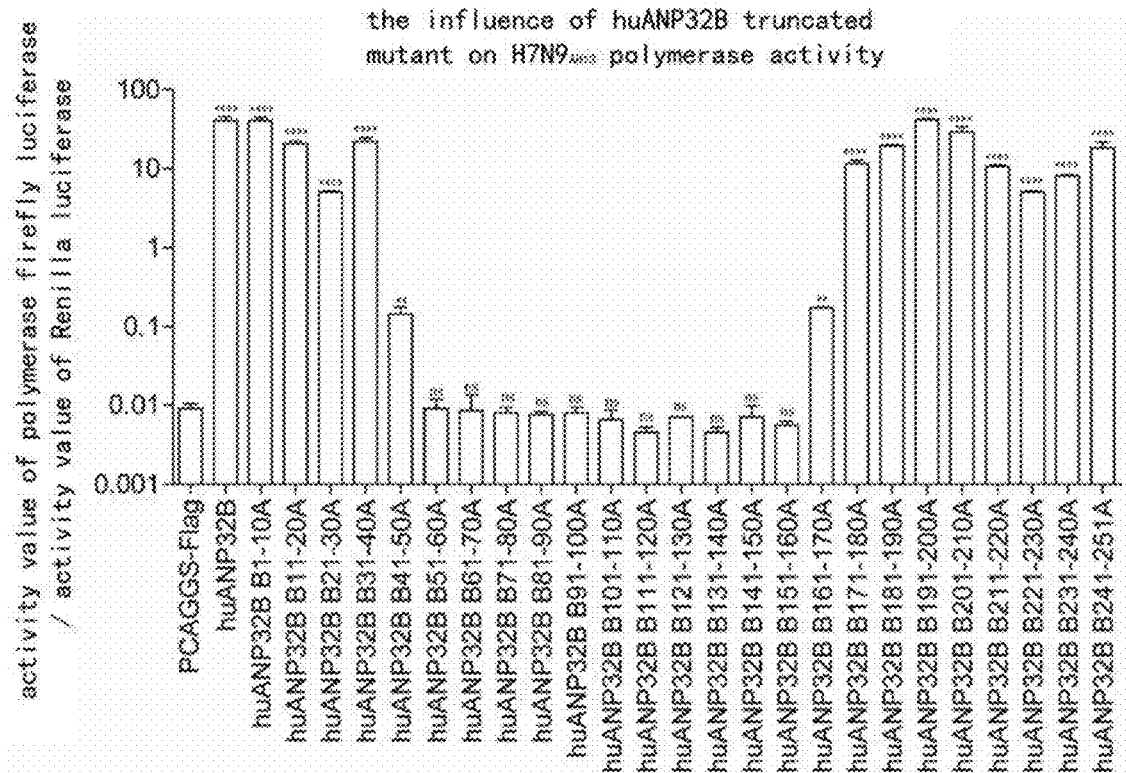
FIG. 28 shows the influence of huANP32B truncated mutant on $H7N9_{AH13}$ polymerase activity.
Figure 31:
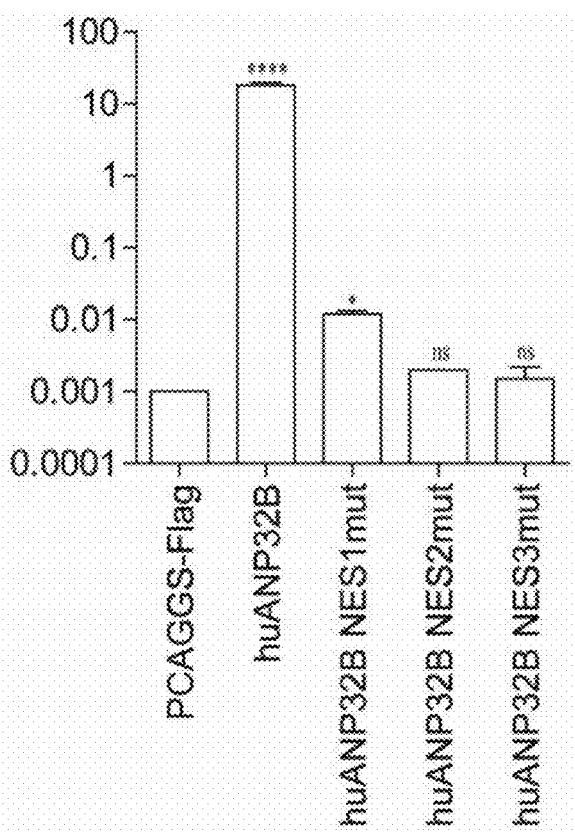
FIG. 31 shows the influence of huANP32B point mutant on H7N9AH13 polymerase activity.

Example 19: Influence of the Segmented Mutant of huANP32B Protein on the Replication of Influenza Virus H7N9$_{AH13}$ Double-knockout cell lines (DKO) were plated in a 24-well plate at 1×10$^5$/well; after 20 hours, the segmented mutant of huANP32B constructed in Example 18 were co-transfected with the 6 plasmids of H7N9$_{AH13}$ polymerase reporter system. The transfection system was: PB1 (40 ng), PB2 (40 ng), PA (20 ng), NP (80 ng), pMD18T-vLuc (40 ng), pRL-TK (5 ng) and the plasmid of ANP32 mutant protein (10 ng); and the empty vector (10 ng) was set as a negative control, huANP32B (10 ng) was set as positive control, and each group was provided with triplicate wells. 24 hours after transfection, the cells were lysed and the activity of polymerase was detected; the result showed that: compared with huANP32B, the segmented mutants of huANP32B B51-60A, huANP32B B61-70A, huANP32B B71-80A, huANP32B B81-90A, huANP32B B91-100A, huANP32B B101-110A, huANP32B B111-120A, huANP32B B121-130A, huANP32B B131-140A, huANP32B B141-150A and huANP32B B151-160A did not have the ability to support H7N9$_{AH13}$ polymerase activity; while huANP32B B1-10A, huANP32B B11-20A, huANP32B B21-30A, huANP32B B31-40A, huANP32B B 171-180A, huANP32B B 181-190A, huANP32B B 191-200A, huANP32B B201-210A, huANP32B B211-220A, huANP32B B221-230A, huANP32B B231-240A and huANP32B B241-251A all had the ability to support H7N9$_{AH13}$ polymerase activity; the ability of huANP32B B41-50A and huANP32B B161-170A to support H7N9$_{AH13}$ polymerase activity was reduced by about 200 times; the result was shown in FIG. 28.

Example 20: Construction of the Vector of chANP32A Protein Segmented Mutation and Determination of Polymerase Activity

TABLE 22 primer sequences used for chANP32A protein segmented mutation

| name | sequence (5'-3') |
|---|---|
| CK32A_B1_F, SEQ ID NO: 307 | TCGCGGCCGCATGGCCGCCGCCGCCG CCGCCGCCGCCGCCCTGCGGAACAGG ACGCCCT |
| CK32A_B1_R, SEQ ID NO: 308 | TCCTGTTCCGCAGGGCGGCGGCGGCG GCGGCGGCGGCGGCCATGCGGCCGCG AGCTCGAA |
| CK32A_B2_F, SEQ ID NO: 309 | GGATCCACTTAGAGGCCGCCGCCGCC GCCGCCGCCGCCGCCGCCGAACTTGTT CTTGAC |
| CK32A_B2_R, SEQ ID NO: 310 | AAGAACAAGTTCGGCGGCGGCGGCGG CGGCGGCGGCGCGGCCTCTAAGTGG ATCCTT |
| CK32A_B3_F, SEQ ID NO: 311 | CAGATGTTAAGGCCGCCGCCGCCGCC GCCGCCGCCGCCGCCGAAGGCAAAAT TGAAGG |
| CK32A_B3_R, SEQ ID NO: 312 | AATTTTGCCTTCGGCGGCGGCGGCGGC GGCGGCGGCGGCGGCCTTAACATCTG AGGGC |
| CK32A_B4_F, SEQ ID NO: 313 | CTGTAGGTCATACGCCGCCGCCGCCGC CGCCGCCGCCGCCGCCTTTGAAGAGC TGGAAT |
| CK32A_B4_R, SEQ ID NO: 314 | AGCTCTTCAAAGGCGGCGGCGGCGGC GGCGGCGGCGGCGGCGTATGACCTAC AGTTGT |
| CK32A_B5_F, SEQ ID NO: 315 | TTACAGATGAGGCCGCCGCCGCCGCC GCCGCCGCCGCCGCCAACGTAGGCTTA GCCTC |

TABLE 22-continued primer sequences used for chANP32A protein segmented mutation

| name | sequence (5'-3') |
|---|---|
| CK32A_B5_R, SEQ ID NO: 316 | TAAGCCTACGTTGGCGGCGGCGGCGGCGGCGGCGGCGGCGGCCTCATCTGTAAGGCCT |
| CK32A_B6_F, SEQ ID NO: 317 | TGAGTACAATCGCCGCCGCCGCCGCCGCCGCCGCCGCCGCCCCAAAGTTAAACAAACT |
| CK32A_B6_R, SEQ ID NO: 318 | TTAACTTTGGGGCGGCGGCGGCGGCGGCGGCGGCGGCGGCGATTGTACTCAAGAATTCC |
| CK32A_B7_F, SEQ ID NO: 319 | TGCAAACTTAGCCGCCGCCGCCGCCGCCGCCGCCGCCGCCCTAAGTGACAACAGAGTC |
| CK32A_B7_R, SEQ ID NO: 320 | TTGTCACTTAGGGCGGCGGCGGCGGCGGCGGCGGCGGCGGCTAAGTTTGCAACTGAGG |
| CK32A_B8_F, SEQ ID NO: 321 | GAAGCTCGAAGCCGCCGCCGCCGCCGCCGCCGCCGCCGCCGAAGTGTTGGCAGAAAAG |
| CK32A_B8_R, SEQ ID NO: 322 | CCAACACTTCGGCGGCGGCGGCGGCGGCGGCGGCGGCGGCTTCGAGCTTCTTAAGTTT |
| CK32A_B9_F, SEQ ID NO: 323 | AGGAGGACTGGCCGCCGCCGCCGCCGCCGCCGCCGCCGCCACGCATCTAAATCTAAGT |
| CK32A_B9_R, SEQ ID NO: 324 | TTTAGATGCGTGGCGGCGGCGGCGGCGGCGGCGGCGGCGGCCAGTCCTCCTGAGACT |
| CK32A_B10_F, SEQ ID NO: 325 | TCCAAACCTCGCCGCCGCCGCCGCCGCCGCCGCCGCCGCCAAAGATCTTGGTACAATA |
| CK32A_B10_R, SEQ ID NO: 326 | CCAAGATCTTTGGCGGCGGCGGCGGCGGCGGCGGCGGCGGCGAGGTTTGGACACTTTT |
| CK32A_B11_F, SEQ ID NO: 327 | GGCAACAAAATAGCCGCCGCCGCCGCCGCCGCCGCCGCCGCCAAGTTAGAAAACCTGA |
| CK32A_B11_R, SEQ ID NO: 328 | TTTTCTAACTTGGCGGCGGCGGCGGCGGCGGCGGCGGCGGCTATTTTGTTGCCACTTA |
| CK32A_B12_F, SEQ ID NO: 329 | ACCTCTGAAAGCCGCCGCCGCCGCCGCCGCCGCCGCCGCCTTCAATTGCGAGGTAACC |
| CK32A_B12_R, SEQ ID NO: 330 | CGCAATTGAAGGCGGCGGCGGCGGCGGCGGCGGCGGCGGCTTTCAGAGGTTCTATTGT |
| CK32A_B13_F, SEQ ID NO: 331 | TTTAGATCTTGCCGCCGCCGCCGCCGCCGCCGCCGCCGCCTATAGAGAAAACGTATTC |
| CK32A_B13_R, SEQ ID NO: 332 | TTTCTCTATAGGCGGCGGCGGCGGCGGCGGCGGCGGCGGCAAGATCTAAACTCTTCAG |
| CK32A_B14_F, SEQ ID NO: 333 | ACTTGAATGATGCCGCCGCCGCCGCCGCCGCCGCCGCCGCCCAACTCACATACCTCGA |
| CK32A_B14_R, SEQ ID NO: 334 | ATGTGAGTTGGGCGGCGGCGGCGGCGGCGGCGGCGGCGGCATCATTCAAGTTGGTTAC |
| CK32A_B15_F, SEQ ID NO: 335 | GCTCCTCCCAGCCGCCGCCGCCGCCGCCGCCGCCGCCGCCGATGACAAAGAAGCACCA |
| CK32A_B15_R, SEQ ID NO: 336 | TCTTTGTCATCGGCGGCGGCGGCGGCGGCGGCGGCGGCGGCTGGGAGGAGCTTGAATA |
| CK32A_B16_F, SEQ ID NO: 337 | CTACGATCGGGCCGCCGCCGCCGCCGCCGCCGCCGCCGCCGAGGGCTACGTGGAGGGC |
| CK32A_B16_R, SEQ ID NO: 338 | CGTAGCCCTCGGCGGCGGCGGCGGCGGCGGCGGCGGCGGCCCGATCGTAGCCATCGAG |
| CK32A_B17_F, SEQ ID NO: 339 | CTCTGATGCAGCCGCCGCCGCCGCCGCCGCCGCCGCCGCCGAGGAAGATGAAGATGTC |
| CK32A_B17_R, SEQ ID NO: 340 | CATCTTCCTCGGCGGCGGCGGCGGCGGCGGCGGCGGCGGCTGCATCAGAGTCTGGTGC |
| CK32A_B18_F, SEQ ID NO: 341 | AGACGATGAGGCCGCCGCCGCCGCCGCCGCCGCCGCCGCCAAAGATCGGGATGACAAA |
| CK32A_B18_R, SEQ ID NO: 342 | CCCGATCTTTGGCGGCGGCGGCGGCGGCGGCGGCGGCGGCCTCATCGTCTAAGCCCTC |
| CK32A_B19_F, SEQ ID NO: 343 | ATCTCTAGTGGCCGCCGCCGCCGCCGCCGCCGCCGCCGCCTCTGATGCAGAGGGCTAC |
| CK32A_B19_R, SEQ ID NO: 344 | CTGCATCAGAGGCGGCGGCGGCGGCGGCGGCGGCGGCGGCCACTAGAGATAAGACATC |
| CK32A_B20_F, SEQ ID NO: 345 | AGCACCGGACGCCGCCGCCGCCGCCGCCGCCGCCGCCGCCGACGACGAGGAGGAAGAT |
| CK32A_B20_R, SEQ ID NO: 346 | CCTCGTCGTCGGCGGCGGCGGCGGCGGCGGCGGCGGCGGCGTCCGGTGCTTCTTTGTC |
| CK32A_B21_F, SEQ ID NO: 347 | GGAAGGCTTAGCCGCCGCCGCCGCCGCCGCCGCCGCCGCCGAGTATGACGATGATGCT |
| CK32A_B21_R, SEQ ID NO: 348 | CGTCATACTCGGCGGCGGCGGCGGCGGCGGCGGCGGCGGCTAAGCCTTCCACGTAGCC |
| CK32A_B22_F, SEQ ID NO: 349 | AGACGAAGAGGCCGCCGCCGCCGCCGCCGCCGCCGCCGCCGATGAAGAGGATGAGGAG |
| CK32A_B22_R, SEQ ID NO: 350 | CCTCTTCATCGGCGGCGGCGGCGGCGGCGGCGGCGGCGGCCTCTTCGTCTTCATCTTC |
| CK32A_B23_F, SEQ ID NO: 351 | GGTAGTAGAAGCCGCCGCCGCCGCCGCCGCCGCCGCCGCCGGAGAAGAGGAGGACGTA |

TABLE 22-continued primer sequences used for chANP32A protein segmented mutation

| name | sequence (5'-3') |
|---|---|
| CK32A_B23_R, SEQ ID NO: 352 | CCTCTTCTCC<u>GGCGGCGGCGGCGGCG GCGGCGGCGGCGG</u>CTTCTACTACCTGA GCATC |
| CK32A_B24_F, SEQ ID NO: 353 | GGAAGAGGAAG<u>CCGCCGCCGCCGCCG CCGCCGCCGCCGCC</u>GAGGAGGATGAG GAAGGC |
| CK32A_B24_R, SEQ ID NO: 354 | CATCCTCCTC<u>GGCGGCGGCGGCGGCG GCGGCGGCGGCGG</u>CTTCCTCTTCCTCC TCCTC |
| CK32A_B25_F, SEQ ID NO: 355 | CGGAGAGGAAG<u>CCGCCGCCGCCGCCG CCGCCGCCGCCGCC</u>GACGTAGATGATG ATGAA |
| CK32A_B25_R, SEQ ID NO: 356 | CATCTACGTC<u>GGCGGCGGCGGCGGCG GCGGCGGCGGCGG</u>CTTCCTCTCCGCTT ACGTC |
| CK32A_B26_F, SEQ ID NO: 357 | TAATGATGGT<u>GCCGCCGCCGCCGCCGC CGCCGCCGCCGCCCC</u>GATGAAGAAC GGGGA |
| CK32A_B26_R, SEQ ID NO: 358 | CTTCATCGGGGGC<u>GGCGGCGGCGGCG GCGGCGGCGGCGG</u>CACCATCATTATAG CCTTC |
| CK32A_B27_F, SEQ ID NO: 359 | TGAAGAAGAAG<u>CCGCCGCCGCCGCCG CCGCCGCCGCCGCC</u>CGAGAACCCGAA GACGAA |
| CK32A_B27_R, SEQ ID NO: 360 | CGGGTTCTC<u>GGGCGGCGGCGGCGGCG GCGGCGGCGGCGG</u>CTTCTTCTTCATCT TCATC |
| CK32A_B28_F, SEQ ID NO: 361 | GAAGAGGAAA<u>GCCGCCGCCGCCGCCG CCGCCGCCGCCGCCGCC</u>GGCAGCGGA GACTAC |
| CK32A_B28_R, SEQ ID NO: 362 | CTCCGCTGCC<u>GGCGGCGGCGGCGGCG GCGGCGGCGGCGGCG</u>GCTTTCCTCTTC TGTCC |

The chANP32A protein was subjected to a segmented mutation, wherein every 10 amino acids as a group were uniformly mutated to alanine, and the primers for point mutation were shown in Table 22 (the mutated bases were underlined). For example, the chANP32A 1-10A mutant was resulted from the mutation of amino acid segment DMKKRIHLE (SEQ ID NO:432) at positions 2-9 of chANP32A protein to AAAAAAAAA (SEQ ID NO:429), and the chANP32A 11-20A mutant is the mutation of amino acid segment LRNRTPSDVK(SEQ ID NO:433) at positions 11-20 of chANP32A protein to AAAAAAAAAA (SEQ ID NO:431), and so on. Using KOD-FX high-efficiency DNA polymerase and using PCAGGS-chANP32A as a template, the following segmented mutants were respectively constructed: chANP32A 1-10 mutA (using primer pair SEQ ID NO: 307 and SEQ ID NO: 308), chANP32A 11-20 mutA (using primer pair SEQ ID NO: 309 and SEQ ID NO: 310), chANP32A 21-30mutA (using primer pair SEQ ID NO: 311 and SEQ ID NO: 312), chANP32A 31-40mutA (using primer pair SEQ ID NO: 313 and SEQ ID NO: 314), chANP32A 41-50mutA (using primer pair SEQ ID NO: 315 and SEQ ID NO: 316), chANP32A 51-60mutA (using primer pair SEQ ID NO: 317 and SEQ ID NO: 318), chANP32A 61-70mutA (using primer pair SEQ ID NO: 319 and SEQ ID NO: 320), chANP32A 71-80mutA (using primer pair SEQ ID NO: 321 and SEQ ID NO: 322), chANP32A 81-90mutA (using primer pair SEQ ID NO: 323 and SEQ ID NO: 324), chANP32A 91-100mutA (using primer pair SEQ ID NO: 325 and SEQ ID NO: 326), chANP32A 101-110mutA (using primer pair SEQ ID NO: 327 and SEQ ID NO: 328), chANP32A 111-120mutA (using primer pair SEQ ID NO: 329 and SEQ ID NO: 330), chANP32A 121-130mutA (using primer pair SEQ ID NO: 331 and SEQ ID NO: 332), chANP32A 131-140mutA (using primer pair SEQ ID NO: 333 and SEQ ID NO: 334), chANP32A 141-150mutA (using primer pair SEQ ID NO: 335 and SEQ ID NO: 336), chANP32A 151-160mutA (using primer pairs SEQ ID NO: 337 and SEQ ID NO: 338), chANP32A 161-170mutA (using primer pair SEQ ID NO: 339 and SEQ ID NO: 340), chANP32A 171-180mutA (using primer pair SEQ ID NO: 341 and SEQ ID NO: 342), chANP32A 181-190mutA (using primer pairs SEQ ID NO: 343 and SEQ ID NO: 344), chANP32A 191-200mutA (using primer pairs SEQ ID NO: 345 and SEQ ID NO: 346), chANP32A 201-210mutA (using primer pairs SEQ ID NO: 347 and SEQ ID NO: 348), chANP32A 211-220mutA (using primer pairs SEQ ID NO: 349 and SEQ ID NO: 350), chANP32A 221-230mutA (using primer pairs SEQ ID NO: 351 and SEQ ID NO: 352), chANP32A 231-240mutA (using primer pair SEQ ID NO: 353 and SEQ ID NO: 354), chANP32A 241-250mutA (using primer pair SEQ ID NO: 355 and SEQ ID NO: 356), chANP32A 251-260mutA (using primer pair SEQ ID NO: 357 and SEQ ID NO: 358), chANP32A 261-270mutA (using primer pair SEQ ID NO: 359 and SEQ ID NO: 360), chANP32A 271-281mutA (using primer pair SEQ ID NO: 361 and SEQ 1D NO: 362), and were respectively named as chANP32A 1-10mutA, chANP32A 11-20mutA, chANP32A 21-30mutA, chANP32A 31-40mutA, chANP32A 41-50mutA, chANP32A 51-60mutA, chANP32A 61-70mutA, chANP32A 71-80mutA, chANP32A 81-90mutA, chANP32A 91-100mutA, chANP32A 101-110mutA, chANP32A 111-120mutA, chANP32A 121-130mutA, chANP32A 131-140mutA, chANP32A 141-150mutA, chANP32A 151-160mutA, chANP32A 161-170mutA, chANP32A 171-180mutA, chANP32A 181-190mutA, chANP32A 191-200mutA, chANP32A 201-210mutA, chANP32A 211-220mutA, chANP32A 221-230mutA, chANP32A 231-240mutA, chANP32A 241-250mutA, chANP32A 251-260mutA, chANP32A 261-270mutA and chANP32A 271-281mutA. The obtained PCR product was digested with Dpn I in a 37° C. constant temperature water bath for 30 minutes, and then 2.5 ul of the digested product was taken and transformed into 20 ul of DH5α competent cells; the next day, a single clone was picked for sequencing, and the plasmid which was verified correct by sequencing was used for subsequent transfection experiment.

Figures 29, 30:
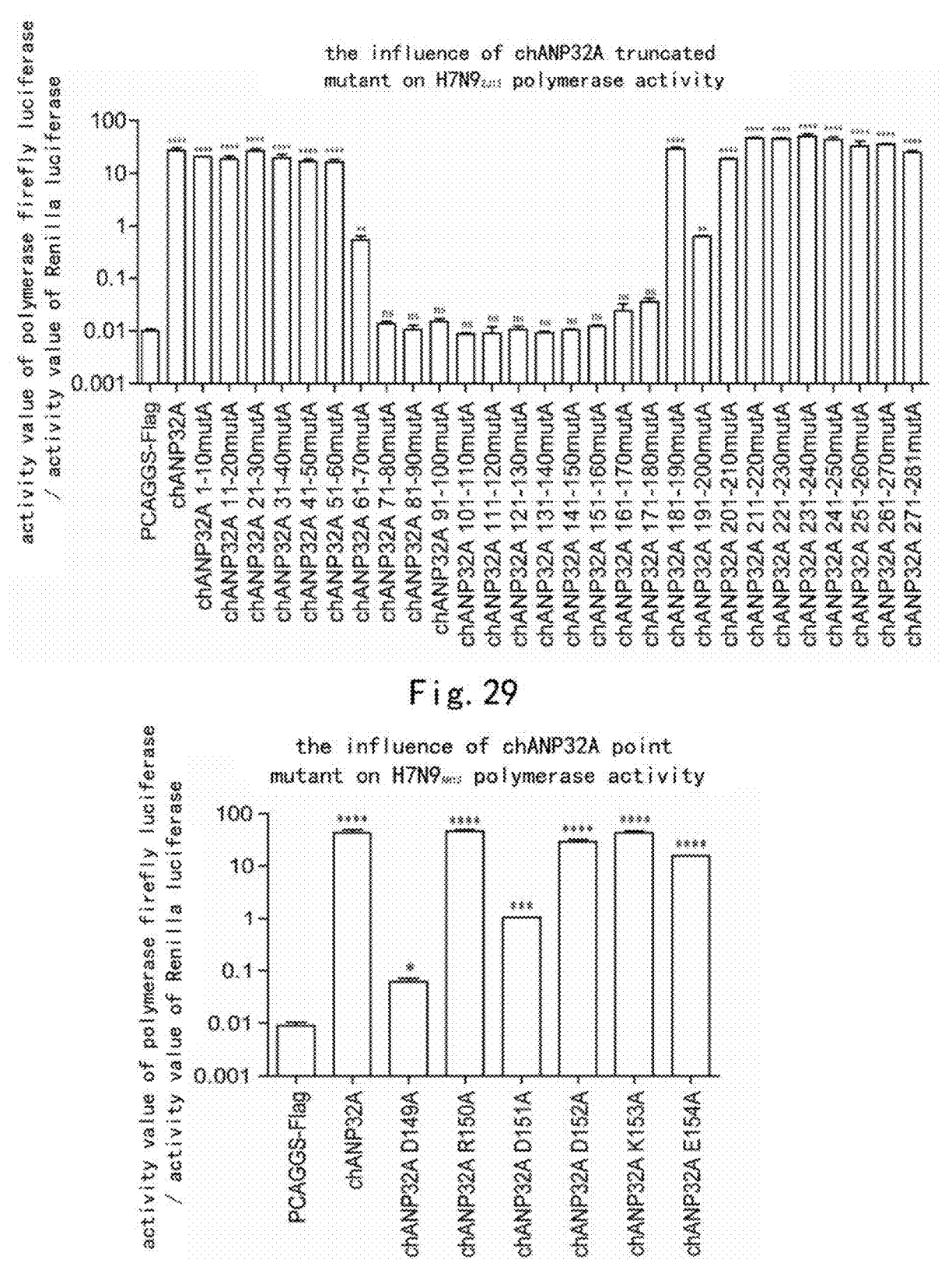

Example 21: Influence of the Segmented Mutant of chANP32A Protein on the Replication of Influenza Virus H7N9$_{ZJ13}$ Influence of the segmented mutant of chANP32A protein on the replication of influenza virus H7N9$_{ZJ13}$: double-knockout cell lines (DKO) were plated in a 24-well plate at 1×10⁵/well; after 20 hours, the segmented mutant of chANP32A constructed in Example 20 were co-transfected with the 6 plasmids of H7N9$_{ZJ13}$ polymerase reporter system. The transfection system was: PB1 (40 ng), PB2 (40 ng), PA (20 ng), NP (80 ng), pMD18T-vLuc (40 ng), pRL-TK (5 ng) and the plasmid of ANP32 mutant protein (10 ng); and the empty vector (10 ng) was set as a negative control, chANP32A (10 ng) was set as positive control, and each group was provided with triplicate wells.24 hours after transfection, the cells were lysed and the activity of polymerase was detected, and the results showed that: compared with chANP32A, the segmented mutants chANP32A 71-80mutA, chANP32A 81-90mutA, chANP32A 91-100mutA, chANP32A 101-110mutA, chANP32A 111-120mutA, chANP32A 121-130mutA, chANP32A 131-140mutA, chANP32A 141-150mutA, chANP32A 151-160mutA, chANP32A 161-170mutA and chANP32A 171-180mutA did not have the ability to support $H7N9_{ZJ13}$ polymerase activity; while chANP32A 1-10mutA, chANP32A11-20mutA, chANP32A 21-30mutA, chANP32A 31-40mutA, chANP32A 41-50mutA, chANP32A 51-60mutA, chANP32A 181-190mutA, chANP32A 201-210mutA, chANP32A 211-220mutA, chANP32A 221-230mutA, chANP32A 231-240mutA, chANP32A 241-250mutA, chANP32A 251-260mutA, chANP32A 261-270mutA, chANP32A 271-281mutA all supported $H7N9_{ZJ13}$ polymerase activity; the ability of chANP32A 61-70mutA and chANP32A 191-200mutA to support $H7N9_{ZJ13}$ polymerase activity was reduced by about 100 times; the result was shown in FIG. 29.

Example 22: Construction of the Amino Acid Site Mutation Vector of chANP32A Protein and Determination of Polymerase Activity

TABLE 23 primer sequences of chANP32A protein amino acid site mutation

| name | sequence (5'-3') |
|---|---|
| chA_D149A_F, SEQ ID NO: 363 | TTATCTCTAGTGAAA<u>GCC</u>CGGGATGACAAAGAA |
| chA_D149A_R, SEQ ID NO: 364 | TTCTTTGTCATCCCG<u>GGC</u>TTTCACTAGAGATAA |
| chA_R150A_F, SEQ ID NO: 365 | TCTCTAGTGAAAGAT<u>GCC</u>GATGACAAAGAAGCA |
| chA_R150A_R, SEQ ID NO: 366 | TGCTTCTTTGTCATC<u>GGC</u>ATCTTTCACTAGAGA |
| chA_D151A_F, SEQ ID NO: 367 | CTAGTGAAAGATCGG<u>GCC</u>GACAAAGAAGCACCG |
| chA_D151A_R, SEQ ID NO: 368 | CGGTGCTTCTTTGTC<u>GGC</u>CCGATCTTTCACTAG |
| chA_D152A_F, SEQ ID NO: 369 | GTGAAAGATCGGGAT<u>GCC</u>AAAGAAGCACCGGAC |
| chA_D152A_R, SEQ ID NO: 370 | GTCCGGTGCTTCTTT<u>GGC</u>ATCCCGATCTTTCAC |
| chA_K153A_F, SEQ ID NO: 371 | AAAGATCGGGATGAC<u>GCC</u>GAAGCACGGACTCT |
| chA_K153A_R, SEQ ID NO: 372 | AGAGTCCGGTGCTTC<u>GGC</u>GTCATCCCGATCTTT |
| chA_E154A_F, SEQ ID NO: 373 | GATCGGGATGACAAA<u>GCC</u>GCACCGGACTCTGAT |
| chA_E154A_R, SEQ ID NO: 374 | ATCAGAGTCCGGTGC<u>GGC</u>TTTGTCATCCCGATC |

The primers of point mutation were shown in Table 23 (mutated bases were underlined); using KOD-FX high-efficiency DNA polymerase and using PCAGGS-chANP32A as a template, the following point mutants of chANP32A were constructed: D149A (using primer pair SEQ ID NO: 363 and SEQ ID NO: 364), R150A (using primer pair SEQ ID NO: 365 and SEQ ID NO: 366), D151A (using primer pair SEQ ID NO: 367 and SEQ ID NO: 368), D152A (using primer pair SEQ ID NO: 369 and SEQ ID NO: 370), K153A (using primer pair SEQ ID NO: 371 and SEQ ID NO: 372) and E154A (using primer pair SEQ ID NO: 373 and SEQ ID NO: 374), and were respectively named as chANP32A D149A, chANP32A R150A, chANP32A D151A, chANP32A D152A, chANP32A K153A and chANP32A E154A. The obtained PCR product was digested with Dpn I in a 37° C. constant temperature water bath for 30 minutes, and then 2.5 ul of the digested product was taken and transformed into 20 ul of DH5α competent cells; the next day, a single clone was picked for sequencing, and the plasmid which was verified correct by sequencing was used for subsequent transfection experiment.

Example 23: Influence of the chANP32A Protein Point Mutant on the Replication of Influenza Virus $H7N9_{AH13}$ Double-knockout cell lines (DKO) were plated in a 24-well plate at $1 \times 10^5$/well; after 20 hours, the amino acid mutant of chANP32A constructed in Example 22 were co-transfected with the 6 plasmids of $H7N9_{AH13}$ polymerase reporter system. The transfection system was: PB1 (40 ng), PB2 (40 ng), PA (20 ng), NP (80 ng), pMD18T-vLuc (40 ng), pRL-TK (5 ng) and the plasmid of ANP32 mutant protein (10 ng); and the empty vector (10 ng) was set as a negative control, chANP32A (10 ng) was set as positive control, and each group was provided with triplicate wells.24 hours after transfection, the cells were lysed and the activity of polymerase was detected; the result showed that: compared with chANP32A, the ability of chANP32A D149A to support $H7N9_{AH13}$ polymerase activity was reduced by about 1000 times, and almost did not have the ability to support the polymerase activity; the ability of chANP32A D151A to support $H7N9_{AH13}$ polymerase activity was reduced by about 50 times; chANP32A R150A, chANP32A D152A and chANP32A K153A all supported the $H7N9_{AH13}$ polymerase activity; the ability of chANP32A E154A to support polymerase activity was reduced by about 5 times; the result was shown in FIG. 30.

Example 24: Construction of the Amino Acid Site Mutation Vector of huANP32B Protein and Determination of Polymerase Activity

TABLE 24 primer sequences of huANP32B protein amino acid site mutation

| name | sequence (5'-3') |
|---|---|
| huB_NES1_F, SEQ ID NO: 375 | TGATCTCAGTTTCAAAT<u>GCC</u>CCCAAGGCCCCTAAATTGAAAAAGCTTGAACTCAGTGA |
| huB_NES1_R, SEQ ID NO: 376 | AAGCTTTTTCAATTTAGG<u>GGC</u>CTTGGGGGCATTTGAAACTGAGATCAAGCCTACATTT |

TABLE 24-continued primer sequences of huANP32B protein amino acid site mutation

| name | sequence (5'-3') |
|---|---|
| huB_NES2_F, SEQ ID NO: 377 | AGCTGAAAAAGCCCCAAATGCCACAC ATGCCAACGCCAGTGGAAATAAACTG AAAGA |
| huB_NES2_R, SEQ ID NO: 378 | TTATTTCCACTGGCGTTGGCATGTGTG GCATTTGGGGCTTTTTCAGCTAACATG TCCA |
| huB_NES3_F, SEQ ID NO: 379 | GAACCTTTGAAAAAGGCCGAATGTGC CAAAAGCGCCGACCTCTTTAACTGTG AGGTT |
| huB_NES3_R, SEQ ID NO: 380 | TTAAAGAGGTCGGCGCTTTTGGCACAT TCGGCCTTTTTCAAAGGTTCCAAGGTG CTG |

The protein sequence of huANP32B was analyzed and it contained 3 known Nuclear Export Signals (NES), which were NSE1(LPKLPKLKKL(SEQ ID NO:434), located at positions 60-71), NSE2 (LPNLTHLNL(SEQ ID NO:435), located at positions 87-95) and NES3 (LEPLKKLE-CLKSLDL(SEQ ID NO:436), located at positions 106-120). To determine whether the nuclear export domain of huANP32B was correlated with its ability to support polymerase activity, mutations were made to these three nuclear export regions, respectively. For the NES1 region, leucines at positions 60 and 63 were both mutated to alanine, and the mutant was named as huANP32B NES1mut. For the NES2 region, leucines at positions 87, 90, 93 and 95 were all mutated to alanine, and the mutant was named as huANP32B NES2mut. For the NES3 region, leucines at positions 112, 115 and 118 were all mutated to alanine, and the mutant was named as huANP32B NES3mut. The primers of point mutation were shown in Table 24 (mutated bases were underlined); using KOD-FX high-efficiency DNA polymerase for amplification and using PCAGGS-huANP32B as a template, the following point mutants of huANP32B were constructed: NES1mut (using primer pair SEQ ID NO: 375 and SEQ ID NO: 376), NES2mut (using primer pair SEQ ID NO: 377 and SEQ ID NO: 378) and NES3mut (using primer pair SEQ ID NO: 379 and SEQ ID NO: 380), and were respectively named as huANP32B NES1mut, huANP32B NES2mut and huANP32B NES3mut. The obtained PCR product was digested with Dpn I in a 37° C. constant temperature water bath for 30 minutes, and then 2.5 ul of the digested product was taken and transformed into 20 ul of DH5α competent cells; the next day, a single clone was picked for sequencing, and the plasmid which was verified correct by sequencing was used for subsequent transfection experiment.

Example 25: Influence of the Point Mutant of huANP32B Protein on the Replication of Influenza Virus $H7N9_{AH13}$ Double-knockout cell lines (DKO) were plated in a 24-well plate at $1\times10^5$/well; after 20 hours, the amino acid mutant of huANP32B constructed in Example 24 were co-transfected with the 6 plasmids of $H7N9_{AH13}$ polymerase reporter system. The transfection system was: PB1 (40 ng), PB2 (40 ng), PA (20 ng), NP (80 ng), pMD18T-vLuc (40 ng), pRL-TK (5 ng) and the plasmid of ANP32 mutant protein (10 ng); and the empty vector (10 ng) was set as a negative control, huANP32B (10 ng) was set as positive control, and each group was provided with triplicate wells.24 hours after transfection, the cells were lysed and the activity of polymerase was detected; the result showed that: compared with huANP32B, the ability of huANP32B NES1mut to support $H7N9_{AH13}$ polymerase activity was reduced by about 1000 times, and almost did not have the ability to support the polymerase activity; huANP32B NES2mut and huANP32B NES3mut did not have the ability to support $H7N9_{AH13}$ polymerase activity; the result was shown in FIG. 31.

Example 26: Construction of a Site-Directed Mutant Cell Line

We performed the construction of a site-directed mutant cell line by using CRISPR-Cas9 technology. According to NCBI published reference nucleotide sequences human ANP32A (NM_006305.3) and human ANP32B (NM_006401.2), sgRNAs for positions 129/130 of the two proteins were designed by using the online software <<http://crispr.mit.edu/>> (see Table 25 for sequences).

TABLE 25

| sgRNA sequences | |
|---|---|
| primer name | primer sequence (5'-3') |
| huANP32A-129/130-sgRNA, SEQ ID NO: 381 | CCAACCTGAACGACTACCGA |
| huANP32B-129/130-sgRNA, SEQ ID NO: 382 | CTCTCGGTAGTCATTCAGGT | sgRNA primers for the huANP32A 129/130 amino acid site and the huANP32B 129/130 amino acid site were designed; using the recombinant plasmid pMD18T-U6-huANPsgRNA-1 constructed in Example 2 as a template and using KOD-FX Neo high-efficiency DNA polymerase (cat # KFX-201, purchased from Toyobo) for amplification, recombinant plasmids pMD18T-U6-huANP32A-129/130-sgRNA (using primer pair SEQ ID NO:383 and SEQ ID NO: 384) and pMD18T-U6-huANP32B-129/130-sgRNA (using primer pair SEQ ID NO:386 and SEQ ID NO: 387) were respectively constructed by a point mutation PCR method, and the obtained PCR product was digested with Dpn I in a 37° C. constant temperature water bath for 30 minutes, then 5 ul of the digested product was taken and transformed into 20 ul of DH5α competent cells; the next day, a single clone was picked for sequencing, and the plasmids which were verified correct by sequencing, pMD18T-U6-huaNP32A-129/130-sgRNA (containing huANP 32A-129/130-sgRNA) and pMD18T-U6-huANP32B-129/130-sgRNA (containing huANP 32B-129/130-sgRNA), were used for subsequent transfection experiment. At the same time, a donor sequence huANP32A-sgRNA-ssODN (SEQ ID NO: 385) for intracellular huANP32A N129I/D130N point mutation and a donor sequence huANP32B-sgRNA-ssODN (SEQ ID NO: 388) for huANP32B N129I/D130N point mutation were synthesized. The synthesized single nucleotide sequence was diluted to 10 uM with distilled water for future use.

TABLE 26

| primer sequences | |
|---|---|
| primer name | primer sequence (5'-3') |
| huANP32A-sgRNA-F, SEQ ID NO: 383 | TCTCGGTAGTCGTTCAGGTGTTT TAGAGCTAGAAAT |
| huANP32A-sgRNA-R, SEQ ID NO: 384 | ACCTGAACGACTACCGAGACGG TGTTTCGTCCTTTC |
| huANP32A-sgRNA-ssODN, SEQ ID NO: 385 | TGAGTTGCGGGAGGAGCTTGAA CACATTTTCTCGGTAGTTAATCA GGTTGGTTACCTCGCAATTGAA AAGGTCTAAGCTC |
| huANP32B-sgRNA-F, SEQ ID NO: 386 | TCTCGGTAGTCATTCAGGTGTTT TAGAGCTAGAAATAGC |
| huANP32B-sgRNA-R, SEQ ID NO: 387 | ACCTGAATGACTACCGAGACGG TGTTTCGTCCTTTC |
| huANP32B-sgRNA-ssODN, SEQ ID NO: 388 | TAAGCTGGGGCAGGAGCTTGAA GACACTCTCTCGGTAGTTAATCA GGTTGGTAACCTCACAGTTAAA GAGGTCCAGGCTT |

Figures 32, 33:
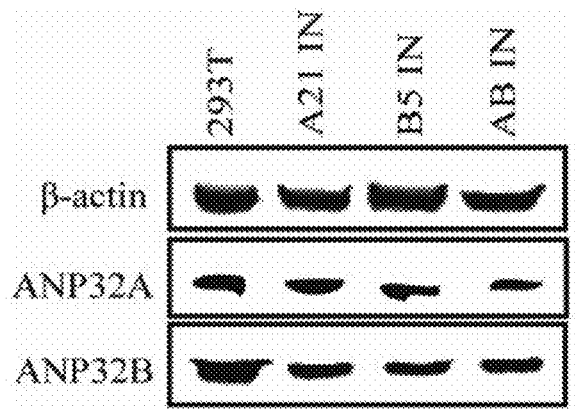
FIG. 32 shows the identification and sequencing result of site-directed mutant cell line of amino acid at position 129/130 of huANP32A and huANP32B, wherein gaggtaaccaacctgaacgactaccgagaaaatgtg is shown in SEQ ID NO:401, gaggtaaccaacctgattaactaccgagaaaatgtg is shown in SEQ ID NO:402, and EVTNLINYRENV is shown in SEQ ID NO:403;gaggttaccaacctgaatgactaccgagagagtgtc is shown in SEQ ID NO:404,gaggttaccaatctgaatgactaccgagagagtgtc is shown in SEQ ID NO:405), EVTNLNDYRENV is shown in SEQ ID NO:406); and gaggttaccaacctgattaactaccgagagagtgtc is shown in SEQ ID NO:407.
FIG. 33 shows the protein detection result of site-directed mutant cell line of amino acid at position 129/130 of huANP32A and huANP32B.
Figure 34:
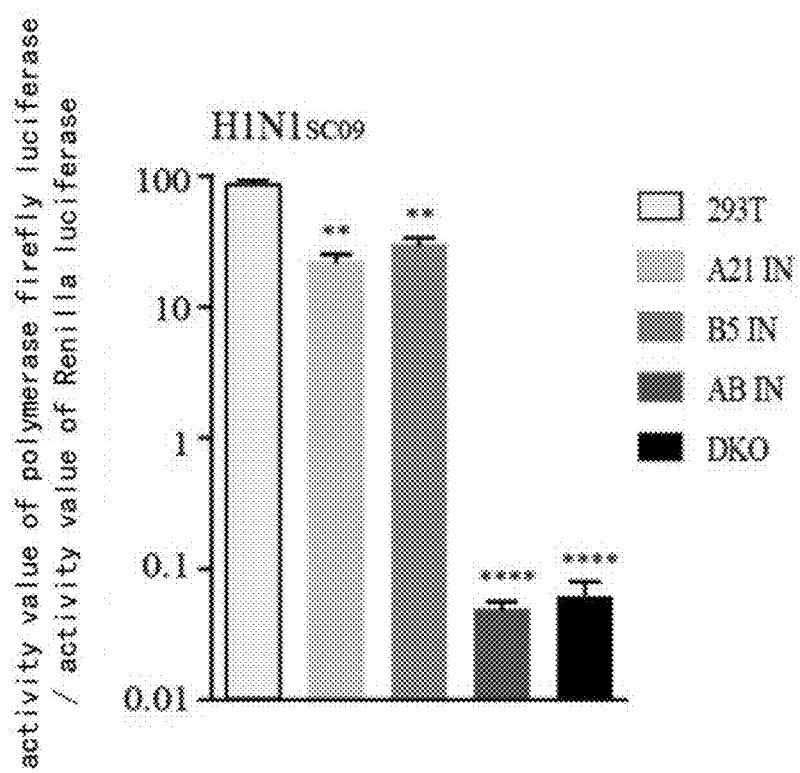
FIG. 34 shows the detection of activity of $H1N1_{SC09}$ polymerase on different cell lines.

1 ug of eukaryotic plasmid pMJ920 (Addge plasma #42234) expressing Cas9-GFP protein, 1 ug of pMD18T-U6-huANP32A-129/130-sgRNA recombinant plasmid and 0.5 µl, of diluted huANP32A-sgRNA-ssODN (SEQ ID NO: 385) were mixed with lipofectamine 2000 at a ratio of 1:2.5, and then transfected into 293T cells; 1 ug of eukaryotic plasmid pMJ920 (Addge plasma #42234) expressing Cas9-GFP protein, 1 ug of pMD18T-U6-huANP32B-129/130-sgRNA recombinant plasmid and 0.5 µL of diluted huANP32B-sgRNA-ssODN (SEQ ID NO: 388) were mixed with lipofectamine 2000 at a ratio of 1:2.5, and then transfected into 293T cells. After 48 hours, GFP-positive cells were screened by an ultra-speed flow cytometry sorting system, and plated in a 96-well plate at a single cell/well for about 10 days; single-cell clones were picked for expansion and culture, and then cellular RNA was extracted according to the procedure using a SimplyP total RNA extraction Kit (purchased from Bioflux, cat # BSC52M1), and cDNA was synthesized using a reverse transcription Kit of Takara Co., Ltd (PrimeScript™ RT reagent Kit with gDNA Eraser (Perfect read Time), Cat.RR047A); and sgRNA-targeting fragments of huANP32A (using primer pair SEQ ID NO:389 and SEQ ID NO: 390) and huANP32B (using primer pair SEQ ID NO:391 and SEQ ID NO: 392) were amplified by KOD Fx Neo polymerase using the cDNA as a template, and the amplification primers were shown in Table 27, wherein the size of huANP32A amplified fragment was 570 bp, and the size of huANP32B amplified fragment was 572 bp. Single-cell clones that were verified to have correct gene mutations by sequencing were subject to western blotting identification and subsequent experimental studies. The cell lines of mutations of both the 129/130 amino acid sites of huANP32A and huANP32B were obtained after the first round of obtaining the huANP32B single-knockout cell line, followed by another round of knockout screening, and the transfection system and screening steps were as described above. For the constructed cell lines, the fragments of interest of huANP32A and huANP32B were amplified; the effect of single mutation and double mutation were verified; the identification and sequencing results of cell lines were shown in FIG. 32, wherein FIG. 32A showed the sequencing results of huANP32A and huANP32B 129/130-site amino acids of the huANP32A N129I/D130N single-mutant cell line (named as A21 IN), FIG. 32B showed the sequencing results of huANP32A and huANP32B 129/130-site amino acids of the huANP32B N129I/D130N single-mutant cell line (named as B5 IN), and FIG. 32C showed the sequencing results of huANP32A and huANP32B 129/130-site amino acids of the double-mutant pall line (named as AB IN).

Figure 35:
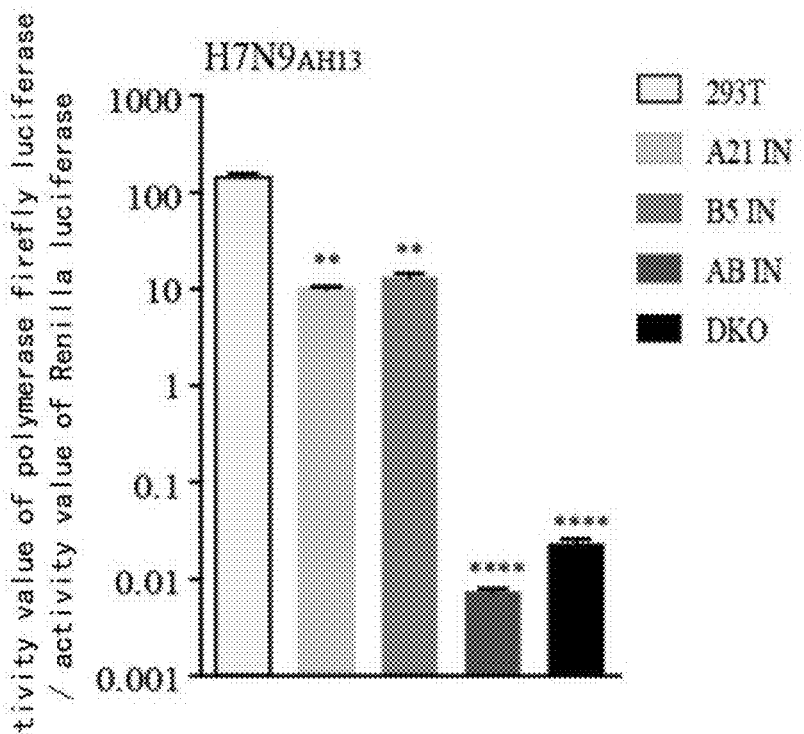
FIG. 35 shows the detection of activity of $H7N9_{AH13}$ polymerase on different cell lines.

TABLE 27

| the primer sequences for identification of huANP32A and huANP32B point-mutant cell line | |
|---|---|
| primer name | primer sequence (5'-3') |
| hu32A gRNA-F, SEQ ID NO: 389 | CCAAAGTTAAACAAACTTAAGAAGC TTGAACTAAGC |
| hu32A gRNA-R, SEQ ID NO: 390 | TTAGTCATCATCTTCTCCCTCATCTTC AGGTTCT |
| hu32B gRNA-F, SEQ ID NO: 391 | AGCTGCCTAAATTGAAAAAGCTTGAA CTC |
| hu32B gRNA-R, SEQ ID NO: 392 | TTAATCATCTTCTCCTTCATCATCTGTT TCTCTC |

Anti-PHAP1 antibody (purchased from Abcam, cat # ab51013) and Anti-PHAPI2/APRIL antibody [EPR14588] (purchased from Abcam, cat # ab200836) were used in Western blotting; β-actin is used as the internal control gene, and the antibody of Monoclonal Anti-β-Actin antibody produced in mouse (purchased from Sigma, cat # A1978-200UL) was used, and the results were shown in FIG. 33.

Based on the above, we successfully constructed a huANP32A N129I/D130N single-mutant cell line (named as A21 IN), a huANP32B N129I/D130N single-mutant cell line (named as B5 IN) and a huANP32A and huANP32B double-mutant cell line (named as AB IN), which were used for subsequent experiments.

Example 27: Influence of ANP32 Protein on the Replication of Influenza Virus

The double-knockout cell line (DKO) constructed in Example 2, the A21 IN cell line, B5 IN cell line and AB IN cell line constructed in Example 26, and the wild-type 293T cell line were plated in a 12-well plate at $3\times10^5$/well; after 20 hours, the 5 plasmids of $H1N1_{SC09}$ polymerase reporter system were co-transfected. The transfection system was: PB1 plasmid (80 ng), PB2 plasmid (80 ng), PA plasmid (40 ng), NP plasmid (160 ng), pMD18T-vLuc plasmid (80 ng) and pRL-TK plasmid (10 ng), and each group was provided with triplicate wells.24 h after transfection, the cells were lysed as described in Example 3 and the activity of polymerase was detected; the result showed that: the activity of $H1N1_{SC09}$ polymerase on the single-mutant cell line of A21 IN cell line and B5 IN cell line was slightly different from that of the wild type 293T cell, and was reduced by only 3-5 times, while the activity of the polymerase on the AB IN cell line and the DKO cell line was significantly reduced by about 3000-5000 times, and the result was shown in FIG. 34.

The above experiment was repeated with the $H7N9_{AH13}$ polymerase reporter system instead of the $H1N1_{SC09}$ polymerase reporter system; the result showed that: the activity of H7N9$_{AH13}$ polymerase on the single-mutant cell line of A21 IN cell line and B5 IN cell line was slightly different from that of the wild type 293T cell, and was reduced by only about 10 times, while the activity of the H7N9$_{AH13}$ polymerase on the AB IN cell line and the DKO cell line was significantly reduced by about 7000-10000 times, and the result was shown in FIG. 35.

Example 28: Alignment of Amino Acid Sequences of Avian-Derived ANP32A Proteins

The amino acid sequences of avian-derived ANP32A proteins (chANP32A, zfANP32A, dkANP32A and tyANP32A) were compared (see FIG. 36), wherein the corresponding relationship of amino acid positions 129, 130, 149, 151, and positions 60, 63, 87, 90, 93, 95, 112, 115 and 118 between each avian-derived ANP32A protein and chANP32A protein was shown in Table 28.

TABLE 28

| chANP32A | 129 | 130 | 149 | 151 | 60 | 63 | 87 | 90 | 93 | 95 | 112 | 115 | 118 |
|---|---|---|---|---|---|---|---|---|---|---|---|---|---|
| zfANP32A | 129 | 130 | 149 | 151 | 60 | 63 | 87 | 90 | 93 | 95 | 112 | 115 | 118 |
| dkANP32A | 119 | 120 | 139 | 141 | 50 | 53 | 77 | 80 | 83 | 85 | 102 | 105 | 108 |
| tyANP32A | 128 | 129 | 148 | 150 | 59 | 62 | 86 | 89 | 92 | 94 | 111 | 114 | 117 |

As demonstrated in Example 21, the mutation of amino acids in the amino acid segment 71-180 of chANP32A to alanine resulted in a complete loss of the ability of the protein to support polymerase activity, while the mutation of amino acids in the amino acid segments 61-70 and 191-200 to alanine resulted in a decrease of the ability of the protein to support polymerase activity.

Figures 36, 37:
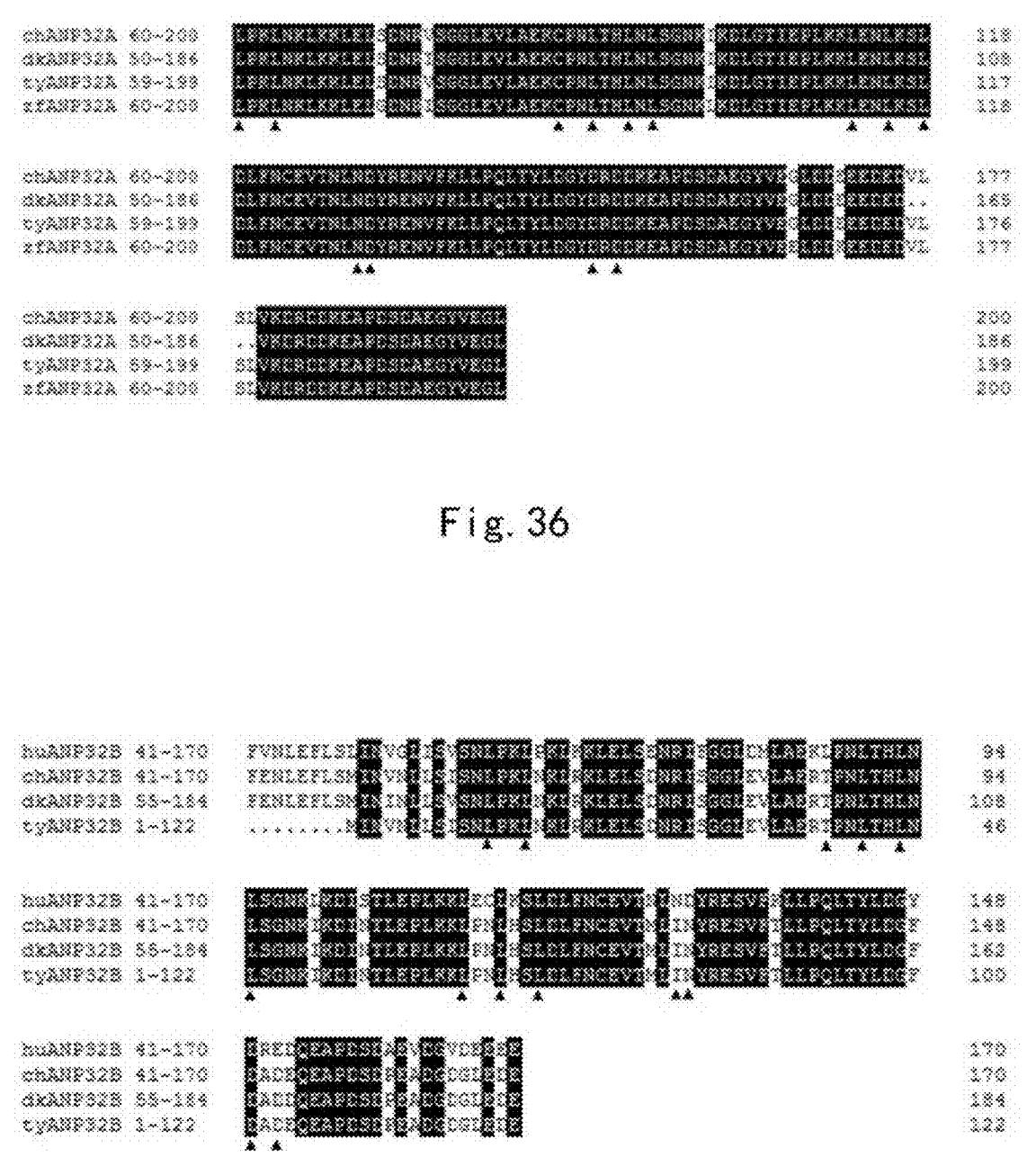

As can be seen from the alignment of the amino acid sequences of the zfANP32A protein and the chANP32A protein in FIG. 36, the sequences of the following amino acid segments of zfANP32A are completely identical to corresponding amino acid sequences in chANP32A: amino acid segment 61-71, amino acid segment 73-75, amino acid segment 77-99, amino acid segment 101-165, amino acid segment 167-169, amino acid segment 171-180 and amino acid segment 181-200, therefore, the mutation of amino acids in amino acid segment 61-71, amino acid segments 73-75, 77-99, 101-165, 167-169 and 171-180 of the zfANP32A protein to alanine also resulted in a complete loss of the ability of the protein to support the polymerase activity; the mutation of amino acids in amino acid segments 61-70 and 191-200 to alanine resulted in a decrease in the ability to support polymerase activity.

From the alignment of the amino acid sequences between the dkANP32A protein and the chANP32A protein in FIG. 36, it was found that the amino acid at position 66 of the dkANP32A protein was I, while the amino acid at position 76 of the chANP32A protein was V, and that the amino acids at positions 164-167 of dkANP32A were deleted (aligned with positions 176-179 of chANP32 protein). It can be seen that the mutation of amino acids in the amino acid segments 61-65 and 67-166 of the dkANP32A protein to alanine resulted in a complete loss of the ability of the protein to support polymerase activity, while the mutation of amino acids in the amino acid segments 51-60 and 177-186 to alanine resulted in a decrease of the ability of the protein to support polymerase activity.

From the alignment of the amino acid sequences between the tyANP32A protein and the chANP32A protein in FIG. 36, it can be seen that the amino acid sequence of the tyANP32A protein is completely identical to the amino acid sequence of the chANP32A protein. It can be seen that the mutation of amino acids in the amino acid segment 60-179 of the tyANP32A protein to alanine resulted in a complete loss of the ability of the protein to support polymerase activity, while the mutation of amino acids in the amino acid segments 60-69 and 190-199 to alanine resulted in a decrease of the ability of the protein to support polymerase activity.

Example 29: Alignment of Amino Acid Sequences Between Avian-Derived ANP32B Protein and huANP32B Protein

| huANP32B | 129 | 130 | 149 | 151 | 60 | 63 | 87 | 90 | 93 | 95 | 112 | 115 | 118 |
|---|---|---|---|---|---|---|---|---|---|---|---|---|---|
| chANP32B | 129 | 130 | 149 | 151 | 60 | 63 | 87 | 90 | 93 | 95 | 112 | 115 | 118 |
| dkANP32B | 143 | 144 | 163 | 165 | 74 | 77 | 101 | 103 | 107 | 109 | 126 | 129 | 132 |
| tyANP32B | 81 | 82 | 101 | 103 | 12 | 15 | 39 | 42 | 45 | 47 | 64 | 67 | 70 |

As demonstrated in Example 19, the mutation of amino acids in the amino acid segment 51-160 of huANP32B to alanine resulted in a complete loss of the ability of the protein to support polymerase activity, while the mutation of amino acids in the amino acid segments 41-50 and 161-170 to alanine resulted in a decrease of the ability of the protein to support polymerase activity.

As can be seen from the alignment of the amino acid sequences of the chANP32B protein and the huANP32B protein in FIG. 37, the sequences of the following amino acid segments of chANP32B are completely identical to corresponding amino acid sequences in huANP32B protein: amino acid segment 43-48, amino acid segment 50-52, amino acid segment 58-63, amino acid segment 68-72, amino acid segment 74-76, amino acid segment 78-80, amino acid segment 83-85, amino acid segment 88-99, amino acid segment 101-103, amino acid segment 105-112, amino acid segment 117-126, amino acid segment 131-136, amino acid segment 138-147 and amino acid segment 153-159, therefore, the mutation of amino acids in amino acid segments 50-52, 58-63, 68-72, 74-76, 78-80, 83-85, 88-99, 101-103, 105-112, 117-126, 131-136, 138-147 and 153-159 of the chANP32B protein to alanine also resulted in a complete loss of the ability of the protein to support the polymerase activity; the mutation of amino acids in amino acid segment 43-48 to alanine resulted in a decrease in the ability to support polymerase activity.

As can be seen from the alignment of the amino acid sequences of the dkANP32B protein and the huANP32B protein in FIG. 37, the sequences of the following amino acid segments of dkANP32B are completely identical to corresponding amino acid sequences in huANP32B protein: amino acid segment 57-62 (corresponding to the amino acid segment 43-48 of huANP32B), amino acid segment 70-77 (corresponding to the amino acid segment 56-63 of huANP32B), amino acid segment 82-86 (corresponding to amino acid segment 68-72 of huANP32B), amino acid segment 88-90 (corresponding to the amino acid segment 74-76 of huANP32B), amino acid segment 92-94 (corresponding to the amino acid segment 78-80 of huANP32B), amino acid segment 97-99 (corresponding to the amino acid segment 83-85 of huANP32B), amino acid segment 102-113 (corresponding to the amino acid segment 88-99 of huANP32B), amino acid segment 115-117 (corresponding to the amino acid segment 101-103 of huANP32B), amino acid segment 119-126 (corresponding to the amino acid segment 105-112 of huANP32B), amino acid segment 131-140 (corresponding to the amino acid segment 117-126 of huANP32B), amino acid segment 145-150 (corresponding to the amino acid segment 131-136 of huANP32B), amino acid segment 152-161 (corresponding to the amino acid segment 138-147 of huANP32B) and amino acid segment 166-173 (corresponding to the amino acid segments 152-159 of huANP32B), therefore, the mutation of amino acids in amino acid segments 70-77, 82-86, 88-90, 92-94, 97-99, 102-113, 115-117, 119-126, 131-140, 145-150, 152-161 and 166-173 of the dkANP32B protein to alanine also resulted in a complete loss of the ability of the protein to support the polymerase activity; the mutation of amino acids in amino acid segment 57-62 to alanine resulted in a decrease in the ability to support polymerase activity.

As can be seen from the alignment of the amino acid sequences of the tyANP32B protein and the huANP32B protein in FIG. 37, the sequences of the following amino acid segments of tyANP32B are completely identical to corresponding amino acid sequence in huANP32B protein: amino acid segment 10-15 (corresponding to the amino acid segment 58-63 of huANP32B), amino acid segment 20-24 (corresponding to amino acid segment 68-72 of huANP32B), amino acid segment 26-28 (corresponding to the amino acid segment 74-76 of huANP32B), amino acid segment 30-32 (corresponding to the amino acid segment 78-80 of huANP32B), amino acid segment 35-37 (corresponding to the amino acid segment 83-85 of huANP32B), amino acid segment 40-51 (corresponding to the amino acid segment 88-99 of huANP32B), amino acid segment 53-55 (corresponding to the amino acid segment 101-103 of huANP32B), amino acid segment 57-64 (corresponding to the amino acid segment 105-112 of huANP32B), amino acid segment 69-78 (corresponding to the amino acid segment 117-126 of huANP32B), amino acid segment 83-88 (corresponding to the amino acid segment 131-136 of huANP32B), amino acid segment 90-99 (corresponding to the amino acid segment 138-147 of huANP32B) and amino acid segment 105-111 (corresponding to the amino acid segments 153-159 of huANP32B), therefore, the mutation of amino acids in amino acid segments 20-24, 26-28, 30-32, 35-37, 40-51, 53-55, 57-64, 69-78, 83-88, 90-99 and 105-111 of the tyANP32B protein to alanine also resulted in a complete loss of the ability of the protein to support the polymerase activity.

corresponding amino acid sequences in chANP32A: amino acid segment 41-54, amino acid segment 56-75, amino acid segment 77-102 and amino acid segment 104-169, therefore, the mutation of amino acids in amino acid segments 77-102 and 104-169 of the dogANP32A protein to alanine also resulted in a complete loss of the ability of the protein to support the polymerase activity; the mutation of amino acids in amino acid segment 61-70 to alanine resulted in a decrease in the ability to support polymerase activity.

Figures 38, 39:
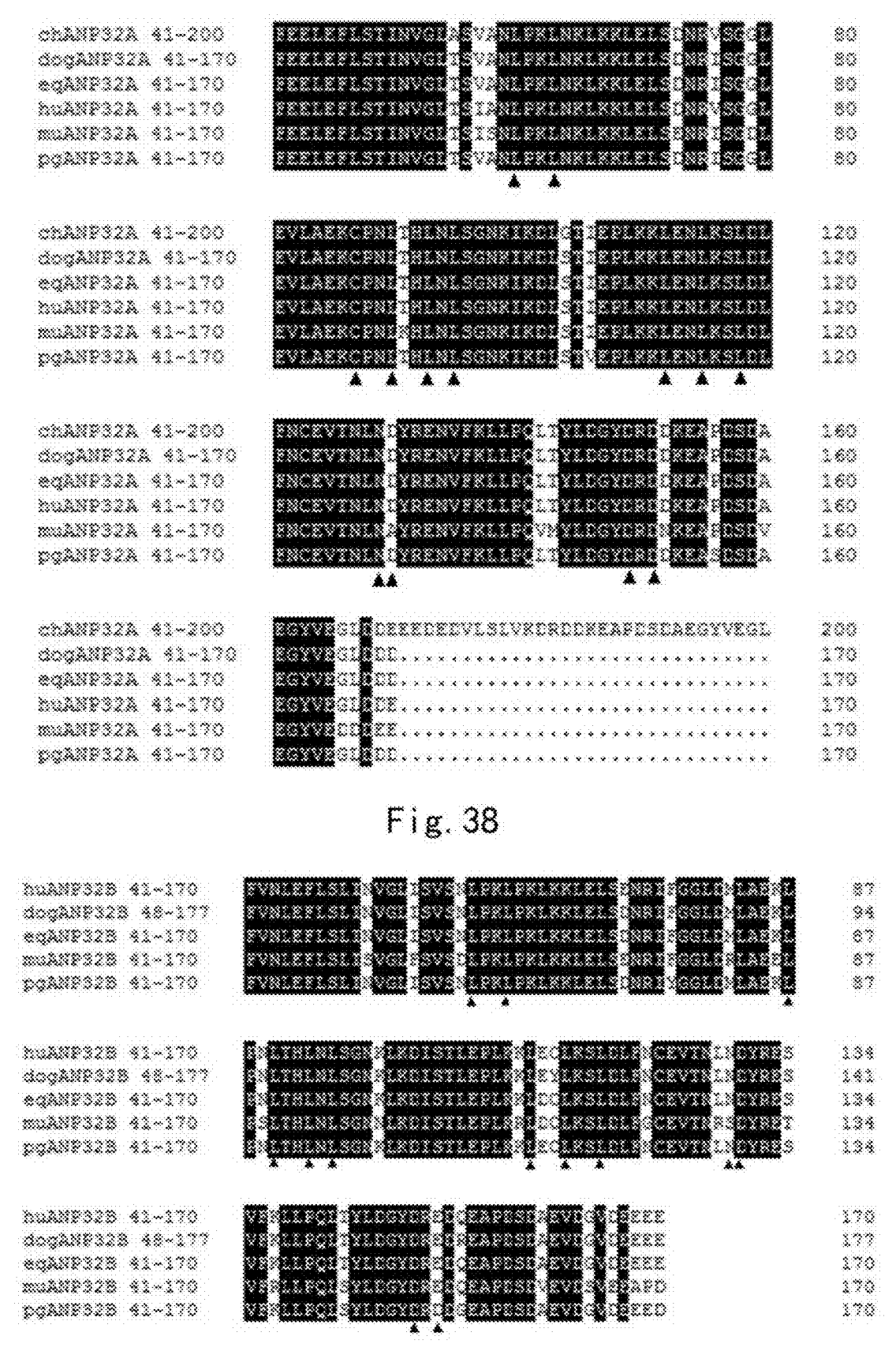

As can be seen from the alignment of the amino acid sequences of the pgANP32A protein and the chANP32A protein in FIG. 38, the sequences of the following amino acid segments of pgANP32A are completely identical to corresponding amino acid sequences in chANP32A: amino acid segment 41-54, amino acid segment 56-75, amino acid segment 77-102, amino acid segment 106-155 and amino acid segment 157-169, therefore, the mutation of amino acids in amino acid segments 77-102,106-155 and 157-169 of the pgANP32A protein to alanine also resulted in a complete loss of the ability of the protein to support the polymerase activity; the mutation of amino acids in amino acid segment 61-70 to alanine resulted in a decrease in the ability to support polymerase activity.

As can be seen from the alignment of the amino acid sequences of the muANP32A protein and the chANP32A protein in FIG. 38, the sequences of the following amino acid segments of muANP32A are completely identical to corresponding amino acid sequences in chANP32A: amino acid segment 41-54, amino acid segment 59-72, amino acid segment 80-90, amino acid segment 92-102, amino acid segment 104-129, amino acid segment 131-141, amino acid segment 144-151, amino acid segment 153-159 and amino acid segment 161-165, therefore, the mutation of amino acids in amino acid segments 80-90, 92-102, 104-129, 131-141, 144-151, 153-159 and 161-165 of the muANP32A protein to alanine also resulted in a complete loss of the ability of the protein to support the polymerase activity; the mutation of amino acids in amino acid segments 61-70 to alanine resulted in a decrease in the ability to support polymerase activity.

Example 31: Alignment of Amino Acid Sequence of Mammalian ANP32B Protein

The amino acid sequences of mammalian ANP32B proteins (huANP32B, dogANP32B (XP_013973354.1), eqANP32B (XP_023485491.1), muANP32B (NP_570959.1), pgANP32B(XP_020922136.1)) were compared (see FIG. 39), wherein the corresponding relationship of amino acid positions 129, 130, 149, 151, and positions 60, 63, 87, 90, 93, 95, 112, 115 and 118 among various mammalian ANP32B proteins was shown in Table 31.

to alanine resulted in a decrease of the ability of the protein to support polymerase activity.

As can be seen from the alignment of the amino acid sequences of the eqANP32B protein and the huANP32B protein in FIG. 39, the sequences of the following amino acid segments of eqANP32B are completely identical to corresponding amino acid sequences in huANP32B: amino acid segment 41-72, amino acid segment 74-112 and amino acid segment 115-170, therefore, the mutation of amino acids in amino acid segments 51-72, 74-112 and 115-160 of the eqANP32B protein to alanine also resulted in a complete loss of the ability of the protein to support the polymerase activity; the mutation of amino acids in amino acid segments 41-50 and 161-170 to alanine resulted in a decrease in the ability to support polymerase activity.

As can be seen from the alignment of the amino acid sequences of the pgANP32B protein and the huANP32B protein in FIG. 39, the sequences of the following amino acid segments of pgANP32B are completely identical to corresponding amino acid sequences in huANP32B: amino acid segment 41-72, amino acid segment 78-142, amino acid segment 144-150 and amino acid segment 154-169, therefore, the mutation of amino acids in amino acid segments 51-72, 78-142, 144-150 and 154-160 of the pgANP32B protein to alanine also resulted in a complete loss of the ability of the protein to support the polymerase activity; the mutation of amino acids in amino acid segments 41-50 and 161-169 to alanine resulted in a decrease in the ability to support polymerase activity.

As can be seen from the alignment of the amino acid sequences of the muANP32B protein and the huANP32B protein in FIG. 39, the sequences of the following amino acid segments of muANP32B are completely identical to corresponding amino acid sequences in huANP32B: amino acid segment 41-50, amino acid segment 60-81, amino acid segment 90-98, amino acid segment 100-110, amino acid segment 114-121, amino acid segment 123-127, amino acid segment 130-133, amino acid segment 138-142 and amino acid segment 144-159, therefore, the mutation of amino acids in amino acid segments 60-81, 90-98, 100-110, 114-121, 123-127, 130-133, 138-142 and 144-159 of the muANP32B protein to alanine also resulted in a complete loss of the ability of the protein to support the polymerase activity; the mutation of amino acids in amino acid segment 41-50 to alanine resulted in a decrease in the ability to support polymerase activity.

As can be seen from the alignment of the amino acid sequences of the dogANP32B protein and the huANP32B protein in FIG. 39, the sequences of the following amino acid segments of dogANP32B are completely identical to corresponding amino acid sequences in huANP32B: amino acid segment 48-79 (corresponding to the amino acid seg-

TABLE 31

| huANP32B | 129 | 130 | 149 | 151 | 60 | 63 | 87 | 90 | 93 | 95 | 112 | 115 | 118 |
| --- | --- | --- | --- | --- | --- | --- | --- | --- | --- | --- | --- | --- | --- |
| dogANP32B | 136 | 137 | 156 | 158 | 67 | 70 | 94 | 97 | 100 | 102 | 119 | 122 | 125 |
| eqANP32B | 129 | 130 | 149 | 151 | 60 | 63 | 87 | 90 | 93 | 95 | 112 | 115 | 118 |
| muANP32B | 129 | 130 | 149 | 151 | 60 | 63 | 87 | 90 | 93 | 95 | 112 | 115 | 118 |
| pgANP32B | 129 | 130 | 149 | 151 | 60 | 63 | 87 | 90 | 93 | 95 | 112 | 115 | 118 |

As demonstrated in Example 19, the mutation of amino acids in the amino acid segment 51-160 of huANP32B to alanine resulted in a complete loss of the ability of the protein to support polymerase activity, while the mutation of amino acids in the amino acid segments 41-50 and 161-170 ment 41-72 of the huANP32B protein), amino acid segment 81-120 (corresponding to the amino acid segment 74-113 of the huANP32B protein), amino acid segment 122-159 (corresponding to the amino acid segment 115-152 of the huANP32B protein), amino acid segment 161-177 (corresponding to amino acid segment 154-170 of the huANP32B protein), therefore, the mutation of amino acids in amino acid segments 58-79, 81-120, 122-159 and 161-167 of the dogANP32B protein to alanine also resulted in a complete loss of the ability of the protein to support the polymerase activity; the mutation of amino acids in amino acid segments 48-57 and 168-177 to alanine resulted in a decrease in the ability to support polymerase activity.

Figure 40:
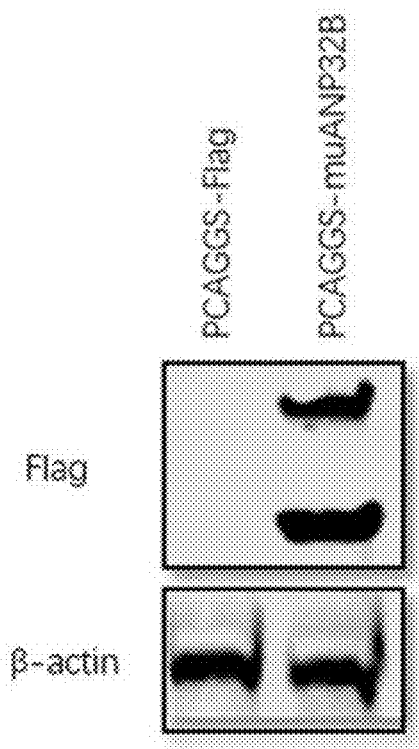
FIG. 40 shows the detection of murine ANP32B protein expression.

Example 32: Construction of Murine ANP32B Protein Expression Vector and Mutation Vector The nucleotide sequence of murine ANP32B (muANP32B) was shown in GenBank No. NM_130889.3, the amino acid sequence thereof was shown in GenBank No. NP_570959.1; the PCAGGS-muANP32B recombinant plasmid was constructed according to the construction method described in Example 1, and the protein expression was detected by Western blotting as the detection method described in Example 1, and the result was shown in FIG. 40.

According to the screening results of huANP32B point mutation described in Example 8, muANP32B was subjected to a point mutant construction of S129I/D130N (using primer pair of SEQ ID NO: 393 and SEQ ID NO: 394) (see Table 32 for primers, and mutated bases were underlined) by using overlapping PCR with the PCAGGS-muANP32B recombinant plasmid as a template, wherein the process was as described for the construction of a point mutant in Example 8. As described above, the obtained plasmid was named as PCAGGS-muANP32B S129I/D130N. After verification by sequencing, the plasmids were extracted in large amount for further transfection.

TABLE 32

Primers for point mutation of S129I/D130N on muANP32B

| primer name | primer sequence (5'-3') |
| --- | --- |
| muB_S129I/D130N_F SEQ ID NO: 393 | CTAACCGGATTAACTACCGAGAAACTGTCTT |
| muB_S129I/D130N_R SEQ ID NO: 394 | TCGGTAGTTAATCCGGTTAGTGACCTCACA |

Figure 41:
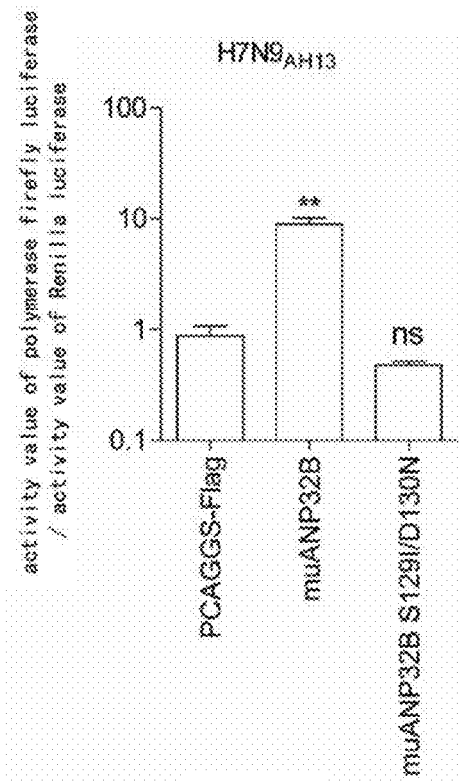
FIG. 41 shows the influence of murine ANP32B protein point mutant on $H7N9_{AH13}$ polymerase activity.

Example 33: Influence of Murine ANP32B Protein Mutant on Polymerase Activity Double-knockout cell line (DKO) was plated in a 12-well plate at $3\times10^5$/well and after 20 h was co-transfected with the H7N9$_{AH13}$ polymerase reporter system according to the transfection system described in Example 8, and the result showed that: muANP32B S129I/D130N completely lost its support for H7N9$_{AH13}$ polymerase activity as compared with muANP32B, as shown in FIG. 41.

The invention claimed is:

1. An isolated mutated acidic leucin-rich nuclear phosphoprotein 32 (ANP32) protein resulting from subjecting a wild type ANP32 protein to one or more mutations selected from the group consisting of:
  the amino acid at position 129 substituted with isoleucine (I), lysine (K), aspartic acid (D), valine (V), proline (P), tryptophan (W), histidine (H), arginine (R), glutamine (Q), glycine (G), or glutamic acid (E);
  the amino acid at position 130 substituted with asparagine (N), phenylalanine (F), lysine (K), leucine (L), valine (V), proline (P), isoleucine (I), methionine (M), tryptophan (W), histidine (H), arginine (R), glutamine (Q), or tyrosine (Y);
  the amino acids at positions 60 and 63 are both substituted with alanine (A);
  the amino acids at positions 87, 90, 93 and 95 are all substituted with alanine (A); and
  the amino acids at positions 112, 115 and 118 are all substituted with alanine (A);
  wherein:

the wild type ANP32 protein is wild type ANP32A or ANP32B derived from chicken, human, zebra finch, duck, turkey, pig, mouse or horse;

when the wild type ANP32 protein is chicken ANP32B protein, duck ANP32B protein or turkey ANP32B protein, the amino acid at position 129 of the mutated ANP32 protein is not isoleucine (I) and the amino acid at position 130 of the mutated ANP32 protein is not asparagine (N);

when the wild type ANP32 protein is human ANP32A protein, the amino acid at position 130 of the mutated ANP32 protein is not asparagine (N);

when the wild type ANP32 protein is mouse ANP32A protein, the amino acid at position 130 of the mutated ANP32 protein is not alanine (A);

when the wild type ANP32 protein is an ANP32A protein, the amino acid positions correspond to the amino acid positions of a chicken ANP32A protein of GenBank No. XP_413932.3; and when the wild type ANP32 protein is an ANP32B protein, the amino acid positions correspond to the amino acid positions of the human ANP32B protein of GenBank No. NP_006392.1.

* * * * *

UNITED STATES PATENT AND TRADEMARK OFFICE
CERTIFICATE OF CORRECTION

| | |
|---|---|
| PATENT NO. | : 11,597,948 B2 |
| APPLICATION NO. | : 16/755840 |
| DATED | : March 7, 2023 |
| INVENTOR(S) | : Xiaojun Wang |

It is certified that error appears in the above-identified patent and that said Letters Patent is hereby corrected as shown below:

In the Specification

In Column 2, Line 17, delete "importin a," and insert --importin α,--.

In Column 2, Line 56, delete "427)," and insert --427,--.

In Column 2, Line 61, delete "175," and insert --175;--.

In Column 5, Line 37, delete "ANP32A" and insert --ANP32A.--.

In Column 13, Line 11 (Approx.), delete "405)," and insert --405,--.

In Column 13, Line 12 (Approx.), delete "406);" and insert --406;--.

In Column 13, Line 45, delete "426)." and insert --4026.--.

In Column 15, Line 1, delete "DH5a" and insert --DH5α--.

In Column 15, Line 12 (Approx.), delete "the a" and insert --the--.

In Column 15, Line 24 (Approx.), delete "DH5a" and insert --DH5α--.

In Column 16, Line 43, delete "(Addge" and insert --(Addgene--.

In Column 19, Line 42 (Approx.), delete "Mice[J]," and insert --Mice[J].--.

In Column 22, Line 38 (Approx.), delete "Z112" and insert --ZJ12--.

In Column 22, Line 42 (Approx.), delete "Z112" and insert --ZJ12--.

Signed and Sealed this
Fourteenth Day of November, 2023

Katherine Kelly Vidal
*Director of the United States Patent and Trademark Office*

CERTIFICATE OF CORRECTION (continued)
U.S. Pat. No. 11,597,948 B2

In Column 22, Line 45, delete "Z112" and insert --ZJ12--.

In Column 22, Line 48 (Approx.), delete "Z112" and insert --ZJ12--.

In Column 22, Line 52 (Approx.), delete "Z112" and insert --ZJ12--.

In Column 22, Line 55, delete "Z112" and insert --ZJ12--.

In Column 22, Line 58 (Approx.), delete "Z112" and insert --ZJ12--.

In Column 23, Line 3, delete "polI" and insert --pol I--.

In Column 23, Line 3-4, delete "3 'end" and insert --3' end--.

In Column 24, Line 41, delete "pMD 18T-" and insert --pMD18T- --.

In Column 25, Line 38, delete "H1N1$_{SC09}$polymerase" and insert --H1N1$_{SC09}$ polymerase--.

In Column 31, Line 41 (Approx.), delete "DH5c" and insert --DH5α--.

In Column 32, Line 8, delete "V5981" and insert --V598I--.

In Column 32, Line 28, delete "H7N9$_{713}$" and insert --H7N9$_{ZJ13}$--.

In Column 35, Line 29 (Approx.), delete "ID ID" and insert --ID--.

In Column 40, Line 42 (Approx.), delete "H7N9$_{AH13}$polymerase" and insert --H7N9$_{AH13}$ polymerase--.

In Column 43, Line 7, delete "wells.24" and insert --wells. 24--.

In Column 43, Line 8, delete "The" and insert --the--.

In Column 43, Line 40, delete "wells.24" and insert --wells. 24--.

In Column 43, Line 41, delete "The" and insert --the--.

In Column 44, Line 10 (Approx.), delete "The" and insert --the--.

In Column 46, Line 50 (Approx.), delete "wells.24" and insert --wells. 24--.

In Column 46, Line 51 (Approx.), delete "The" and insert --the--.

In Column 46, Line 65, delete "H7N9$_{113}$" and insert --H7N9$_{ZJ13}$--.

In Column 47, Line 16 (Approx.), delete "wells.24" and insert --wells. 24--.

CERTIFICATE OF CORRECTION (continued)
U.S. Pat. No. 11,597,948 B2

In Column 47, Line 17 (Approx.), delete "The" and insert --the--.

In Column 47, Line 51, delete "wells.24" and insert --wells. 24--.

In Column 47, Line 53, delete "The" and insert --the--.

In Column 50, Line 64, delete "B 11" and insert --B11--.

In Column 51, Line 45, delete "B 111" and insert --B111--.

In Column 51, Line 45, delete "B 121" and insert --B121--.

In Column 51, Line 46, delete "B 131" and insert --B131--.

In Column 52, Line 6, delete "wells.24" and insert --wells. 24--.

In Column 52, Line 18, delete "B 171" and insert --B171--.

In Column 52, Line 18, delete "B 181" and insert --B181--.

In Column 52, Line 19, delete "B 191" and insert --B191--.

In Column 56, Line 32, delete "1D" and insert --ID--.

In Column 57, Line 3, delete "wells.24" and insert --wells. 24--.

In Column 58, Line 37 (Approx.), delete "wells.24" and insert --wells. 24--.

In Column 60, Line 2, delete "wells.24" and insert --wells. 24--.

In Column 61, Line 24 (Approx.), delete "(Addge" and insert --(Addgene--.

In Column 61, Line 28 (Approx.), delete "µl," and insert --µL,--.

In Column 61, Line 31, delete "(Addge" and insert --(Addgene--.

In Column 62, Line 11, delete "pall" and insert --cell--.

In Column 62, Line 56, delete "wells.24" and insert --wells. 24--.

In Column 64, Line 32, below "huANP32B Protein" insert --The amino acid sequences of avian-derived ANP32B proteins (chANP32B, dkANP32B(XP_012963723.1) and tyANP32B(XP_010723174.1)) were compared with the amino acid sequence of huANP32B protein (see Fig. 37), wherein the corresponding relationship of amino acid positions 129, 130, 149, 151, and positions 60, 63, 87, 90, 93, 95, 112, 115 and 118 between each avian-derived ANP32B protein and huANP32B protein was shown in Table 29.--.